(12) United States Patent
Fernandez Rodriguez et al.

(10) Patent No.: US 11,952,595 B2
(45) Date of Patent: Apr. 9, 2024

(54) PRODUCTION OF LYTIC PHAGES

(71) Applicant: Eligo Bioscience, Paris (FR)

(72) Inventors: Jesus Fernandez Rodriguez, Paris (FR); Antoine Decrulle, Paris (FR); Aymeric Leveau, Paris (FR); Ines Canadas Blasco, Paris (FR); Aurelie Mathieu, Paris (FR); Thibault Carlier, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 18/348,910

(22) Filed: Jul. 7, 2023

(65) Prior Publication Data

US 2024/0010994 A1    Jan. 11, 2024

Related U.S. Application Data

(62) Division of application No. 17/742,693, filed on May 12, 2022, now Pat. No. 11,739,304.

(60) Provisional application No. 63/187,532, filed on May 12, 2021, provisional application No. 63/187,531, filed on May 12, 2021.

(51) Int. Cl.
| | |
|---|---|
| *C12N 7/00* | (2006.01) |
| *C12N 1/20* | (2006.01) |
| *C12N 15/70* | (2006.01) |
| *C12N 15/74* | (2006.01) |

(52) U.S. Cl.
CPC ............... *C12N 7/00* (2013.01); *C12N 1/20* (2013.01); *C12N 15/70* (2013.01); *C12N 15/74* (2013.01); *C12N 2795/10322* (2013.01); *C12N 2795/10352* (2013.01); *C12N 2800/101* (2013.01); *C12N 2800/40* (2013.01)

(58) Field of Classification Search
None
See application file for complete search history.

(56) References Cited

U.S. PATENT DOCUMENTS

| | | |
|---|---|---|
| 4,920,048 A | 4/1990 | Diderichsen |
| 5,691,185 A | 11/1997 | Dickely et al. |
| 6,291,245 B1 | 9/2001 | Kopetzki et al. |

(Continued)

FOREIGN PATENT DOCUMENTS

| | | |
|---|---|---|
| WO | 94/17201 A1 | 8/1994 |
| WO | 2014/124226 A1 | 8/2014 |

(Continued)

OTHER PUBLICATIONS

Rajagopala et al. The protein interaction map of bacteriophage lambda. BMC Microbiology 2011, 11:213, 1-15.

(Continued)

*Primary Examiner* — Michelle S Horning
(74) *Attorney, Agent, or Firm* — Arrigo, Lee, Guttman & Mouta-Bellum LLP

(57) ABSTRACT

The present invention concerns a production bacterial cell for producing lytic phage particles or lytic phage-derived delivery vehicles, said production bacterial cell stably comprising at least one phage structural genes and at least one phage DNA packaging genes, said phage structural gene(s) and phage DNA packaging gene(s) being derived from a lytic bacteriophage, wherein the expression of at least one of said phage structural genes and/or at least one of said phage DNA packaging gene(s) in said production bacterial cell is controlled by an induction mechanism.

19 Claims, 8 Drawing Sheets

Specification includes a Sequence Listing.

(56) References Cited

U.S. PATENT DOCUMENTS

| | | |
|---|---|---|
| 6,413,768 B1 | 7/2002 | Galen |
| 6,752,994 B2 | 6/2004 | Jacobs, Jr. et al. |
| 10,113,163 B2 | 10/2018 | Liu et al. |
| 2005/0186666 A1 | 8/2005 | Schneider et al. |
| 2015/0064138 A1 | 3/2015 | Lu et al. |
| 2015/0166980 A1 | 6/2015 | Liu et al. |
| 2019/0160120 A1 | 5/2019 | Haaber |
| 2022/0135986 A1 | 5/2022 | Leveau et al. |
| 2022/0135987 A1 | 5/2022 | Leveau et al. |

FOREIGN PATENT DOCUMENTS

| | | |
|---|---|---|
| WO | 2017/141173 A2 | 8/2017 |
| WO | 2018/164988 A1 | 9/2018 |
| WO | 2018/236548 A1 | 12/2018 |
| WO | 2019/105821 A1 | 6/2019 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |

OTHER PUBLICATIONS

Auster et al. Optimizing DNA transduction by selection of mutations that evade bacterial defense systems. RNA Biology. 2019, 16 (4), 595-599.

Rees and Liu. Base editing: precision chemistry on the genome and transcriptome of living cells. Nat Rev Genet. Dec. 2018 ; 19(12): 770-788. doi:10.1038/s41576-018-0059-1.

Russel and Model. Genetic Analysis of the Filamentous Bacteriophage Packaging Signal and of the Proteins That Interact with It. Journal of Virology, Aug. 1989, 63 (8), 3284-3295.

Sharon et al. Functional genetic variants revealed by massively parallel precise genome editing. Cell. Oct. 4, 2018; 175(2): 544-557.e16. doi:10.1016/j.cell.2018.08.057.

Simon et al. Retrons and their applications in genome engineering. Nucleic Acids Research, 2019, vol. 47, No. 21 11007-11019 doi: 10.1093/nar/gkz86.

Sorensen et al. A Food-Grade Cloning System for Industrial Strains of Lactococcus lactis. Applied and Environmental Microbiology, Apr. 2000, 66(4), 1253-1258.

Stanton et al. Genomic Mining of Prokaryotic Repressors for Orthogonal Logic Gates. Nat Chem Biol. Feb. 2014 ; 10(2): 99-105. doi:10.1038/nchembio. 1411.

Struhl et al. Functional genetic expression of eukaryotic DNA in *Escherichia coli*. Proc. Natl. Acad. Sci. May 1976. 73 (5), 1471-1475.

Tomida et al. Pan-Genome and Comparative Genome Analyses of Propionibacterium acnes Reveal Its Genomic Diversity in the Healthy and Diseased Human Skin Microbiome. mBio. 4(3), e00003-13, 1-11. doi: 10.1128/mBio.00003-13.

Vo et al. CRISPR RNA-guided integrases for high-efficiency, multiplexed bacterial genome engineering. Nature Biotechnology, 2021, 39, 480-489. https://doi.org/10.1038/s41587-020-00745-y.

Wannier et al. Improved bacterial recombineering by parallelized protein discovery. PNAS, 2020, 117(24), 13689-13698.

Wannier et al. Recombineering and MAGE. Nat Rev Methods Primers. 2021, 1-51. doi: 10.1038/s43586-020-00006-x.

Weigele and Raleigh. Biosynthesis and Function of Modified Bases in Bacteria and Their Viruses. Chemical Reviews. 2016, 12655-12687.

Wu et al. The DNA site utilized by bacteriophage P22 for initiation of DNA packaging. Molecular Microbiology (2002) 45(6), 1631-1646.

Yan et al. Cas13d is a compact RNA-targeting type Vi Crispr effector positively modulated by a WYL domain- containing accessory protein. Mol Cell. Apr. 19, 2018; 70(2): 327-339.e5. doi:10.1016/j.molcel.2018.02.028.

Zhao et al. New base editors change C to A in bacteria and C to G in mammalian cells. Nat Biotechnol 2021, 39, 35-40. https://doi.org/10.1038/s41587-020-0592-2.

Fernandez Rodriguez and Voigt. Post-translational control of genetic circuits using Potyvirus proteases. Nucleic Acids Research, 2016, vol. 44, No. 13, 6493-6502. doi: 10.1093/nar/gkw537.

Studier.Processing of Bacteriophages T7 RNAs BY RNase III1. From Gene to Protein: Information Transfer in Normal and Abnormal Cells. 1979. Department of Biology Brookhaven National Laboratory. 261-269.

Abudayyeh et al RNA targeting with CRISPR-Cas13a. Nature. Oct. 12, 2017; 550(7675): 280-284. doi:10.1038/nature24049.

Anne et al. Protein Secretion in Gram-Positive Bacteria: From Multiple Pathways to Biotechnology. Current Topics in Microbiology and Immunology. Nov. 25, 2016. 267-308. DOI 10.1007/82_2016_49.

Anzalone et al. Search-and-replace genome editing without double-strand breaks or donor DNA. Nature. Dec. 2019 ; 576(7785): 149-157. doi:10.1038/s41586-019-1711-4.

Brede et al. Heterologous Production of Antimicrobial Peptides in Propionibacterium freudenreichii. Applied and Environmental Microbiology, Dec. 2005, 8077-8084. doi:10.1128/AEM.71.12.8077-8084.2005.

Brüggemann H, et al. A Janus-Faced Bacterium: Host-Beneficial and -Detrimental Roles of Cutibacterium acnes. Front. Microbiol. (2021)12:673845. 1-22. doi: 10.3389/fmicb.2021.673845.

Cambray G et al. Measurement and modeling of intrinsic transcription terminator. Nucleic Acids Research, 2013, vol. 41, No. 9 5139-5148 doi: 10.1093/nar/gkt163.

Dunn and Studier. Complete Nucleotide Sequence of Bacteriophage T7 DNA and the Locations of T7 Genetic Elements. J. Mol. Biol. (1983) 166, 477-535.

Chen et al. Characterization of 582 natural and synthetic terminators and quantification of their design constraints. 2013. Nature Methods, vol. 10, No. 7, 659-666.

Chen et al. Precise and programmable C:G to G:C base editing in genomic DNA.2020. 1-19. https://doi.org/10.1101/2020.07.21.213827.

Chen et al. Programmable C:G to G:C genome editing with CRISPR-Cas9-directed base excision repair proteins. Nature Communications, (2021) 12:1384. 1-7. https://doi.org/10.1038/s41467-021-21559-9.

Cheng et al. Complete genomic sequences of Propionibacterium freudenreichii phages from Swiss cheese reveal greater diversity than Cutibacterium (formerly Propionibacterium) acnes phages. BMC Microbiology (2018) 18:19, 1-13. https://doi.org/10.1186/s12866-018-1159-y.

Chung and Hinkle. Bacteriophage T7 DNA Packaging II. Analysis of the DNA Sequences Required for Packaging Using a Plasmid Transduction Assay. Journal of Molecular Biology. 1990, 216, 927-938.

Costa et al. Secretion systems in Gram-negative bacteria: structural and mechanistic insights. 2015. Nature Reviews Microbiology. vol. 13, 343-359.

Cotter et al. Bacteriocins—a viable alternative to antibiotics. 2013. Nature Reviews Microbiology. vol. 11, 95-105.

Cox et al. RNA Editing with CRISPR-Cas13. Science. Nov. 24, 2017; 358(6366): 1019-1027. doi:10.1126/science.aaq0180.

Del Solar et al. Replication and Control of Circular Bacterial Plasmids. Microbiology and Molecular Biology Reviews. 1998. vol. 62, No. 2, 434-4.

Dickely et al. Isolation of Lactococcus lactis nonsense suppressors and construction of a food-grade cloning vector. Molecular Microbiology (1992), 15 (5), 839-847.

Farzadfard and Lu. Genomically Encoded Analog Memory with Precise In vivo DNA Writing in Living Cell Population. Science. Nov. 14, 2014; 346(6211): 1256272. doi: 10.1126/science.1256272.

Fiedler and Skerra. proBA complementation of an auxotrophic *E. coli* strain improves plasmid stability and expression yield during fermenter production of a recombinant antibody fragment. 2001. Gene. 274, 111-118.

(56) References Cited

OTHER PUBLICATIONS

Fillol-Salom et al. Phage-inducible chromosomal islands are ubiquitous within the bacterial universe. The ISME Journal (2018) 12:2114-2128.
Fonfara et al. Phylogeny of Cas9 determines functional exchangeability of dual-RNA and Cas9 among orthologous type II CRISPR-Cas systems. Nucleic Acids Research, 2014, vol. 42, No. 4 2577-2590.
Gaudelli et al. Programmable base editing of A•T to G•C in genomic DNA without DNA cleavage. Nature. Nov. 23, 2017; 551(7681): 464-471. doi:10.1038/nature24644.
Gautier et al. Bacteriophages infecting dairy propionibacteria. Lait (1995) 75, 427-434.
Gautier et al. Occurrence of Propionibacterium freudenreichii Bacteriophages in Swiss Cheese. Applied and Environmental Microbiology, Jul. 1995, vol. 61, No. 7. p. 2572-2576.
Groenen and Van de Putte. Mapping of a Site for Packaging of Bacteriophage Mu DNA. Virology. 1985, 144, 520-522.
Grunewald et al. A dual-deaminase CRISPR base editor enables concurrent adenine and cytosine editing. Nat Biotechnol. Jul. 2020 ; 38(7): 861-864. doi:10.1038/s41587-020-0535-y.
Hashimoto and Fujisawa. DNA Sequences Necessary for Packaging Bacteriophage T3 DNA. Virology 1992, 187, 7,788-795.
Henkel et al. Toxins from Bacteria. EXS. 2010 ; 100: 1-29.
Hohn. DNA sequences necessary for packaging of bacteriophage A DNA (cosmid/in vivo packaging/in vitro packaging of restriction fragments). Dec. 1983. Proc. Nati. Acad. Sci. USA vol. 80, pp. 7456-7460.
Ioannidi et al. Drag-and-drop genome insertion without DNA cleavage with CRISPR directed integrases. 2021. bioRxiv 2021.11.01.466786; doi: https://doi.org/10.1101/2021.11.01.466786.
Jinek et al. A Programmable Dual-RNA-Guided DNA Endonuclease in Adaptive Bacterial Immunity. Science. Aug. 17, 2012. vol. 337, 6096, 816-821.
Kabashima et al. The immunological anatomy of the skin. Nature Reviews Immunology. 2019. vol. 19, 19-30.
Qimron et al. Genomewide screens for Escherichia coli genes affecting growth of T7 bacteriophage. PNAS. 2006. 103(50), 19039-19044.
Karberg et al. Group II introns as controllable gene targeting vectors for genetic manipulation of bacteria. Nature Biotechnology. 2001, 19, 1162-1167.
Kashaf et al. Integrating cultivation and metagenomics for a multi-kingdom view of skin microbiome diversity and functions. Nature Microbiology. 2022. 7, 169-191.
Komor et al. Programmable editing of a target base in genomic DNA without double-stranded DNA cleavage. Nature. 2016. 533(7603): 420-424. doi: 10.1038/nature17946.
Koonin et al. Diversity, classification and evolution of CRISPR-Cas systems. 2018. Curr Opin Microbiol. Jun. 2017 ; 37: 67-78. doi:10.1016/j.mib.2017.05.008.
Krupovic et al. A classification system for virophages and satellite viruses. 2016. Arch Virology. 161:233-247.
Kues and Stahl. Replication of Plasmids in Gram-Negative Bacteria. Microbiological Reviews, Dec. 1989, 53, 4, 491-516.
Kurt et al. CRISPR C-to-G base editors for inducing targeted DNA transversions in human cells. Nat Biotechnol. Jan. 2021 ; 39(1): 41-46. doi:10.1038/s41587-020-0609-x.
Li et al. Targeted, random mutagenesis of plant genes with dual cytosine and adenine base editors. Nature Biotechnology. 2020. 38, 875-882.
Ma et al. Transposon-Associated CRISPR-Cas System: A Powerful DNA Insertion Tool. Trends in Microbiology. 2021. 29, 7, 565-586.
MacCormick et al. Construction of a food-grade host/vector system for Lactococcus lactis based on the lactose operon. FEMS Microbiology Letters 127 (1995) 105-109.
Marinelli et al. Propionibacterium acnes Bacteriophages Display Limited Genetic Diversity and Broad Killing Activity against Bacterial Skin Isolates. mBio 2012, 3(5), 1-13.
Miwa and Matsubara. Identification of sequences necessary for packaging DNA into lambda phage heads (Recombinant DNA; cosmid; Ml3 dideoxynucleotide sequencing; h cohesive end; plasmid vector). Gene, 20(1982) 261-279.
Mutalik et al. Precise and reliable gene expression via standard transcription and translation initiation elements. Nature Methods. 2013, 10, 4, 354-368.
Petri and Schmieger. Isolation of fragments with pac function for phage P22 from phage LP7 DNA and comparison of packaging gene 3 sequences. Gene, 88 (1990) 47-55.
Quiles-Puchalt et al. *Staphylococcal* pathogenicity island DNA packaging system involving cos-site packaging and phage-encoded HNH endonucleases. PNAS. 2014. 111 (16), 6016-6021.
Bruggemann et al. Bacteriophages infecting Propionibacterium acnes. Biomed Res Int, 2013, 705741, 1-11. doi: 10.1155/2013/705741.
Rohde et al. Expert Opinion on Three Phage Therapy Related Topics: Bacterial Phage Resistance, Phage Training and Prophaged in Bacterial Production Strains. Viruses, 2018, 10(178), 1-15.
Brown et al. Phage engineering: how advances in molecular biology and synthetic biology are being utilized to enhance the therapeutic potential of bacteriophages. Quantitative Biology, 2017, 5(1), 42-54.
Pires et al. Current challenges and future opportunities of phage therapy. FEMS Microbiology Reviews, 2020, 44(6), 684-700.
Monteiro et al. Phage Therapy: Going Temperate? Trends in Microbiology, 2019, 27(4), 368-377.

Production from Pf1s22904 colonies 1-8

SLST PCR
Expected size 612bp pAN594 specific PCR
Expected size 769bp

```
                              SEQUENCE LISTING

Sequence total quantity: 27
SEQ ID NO: 1            moltype = DNA  length = 282
FEATURE                 Location/Qualifiers
misc_feature            1..282
                        note = primase ori from the PICI of the Escherichia coli
                          strain CFT073
source                  1..282
                        mol_type = other DNA
                        note = primase ori from the PICI of the Escherichia coli
                          strain CFT073
                        organism = synthetic construct
SEQUENCE: 1
tttgttgcaa tggctgtcta ccctgtctac ctgagtaaag aaaaatacat ttaattcagt   60
acattaactt gggtagacag cctttttta ctgtctacct actatctacc ctctctacct  120
gattttacct gaatcagaca gggaggtaga tacggggtag atagtggata aaagcactct  180
accccactga aagccgcgcc attactgcca tggtggccag taaggtagat aaggtagaca  240
aggggaggca caactcaaaa ctttttaaac gaggggtaa aa                      282

SEQ ID NO: 2            moltype =   length =
SEQUENCE: 2
000

SEQ ID NO: 3            moltype = DNA  length = 282
FEATURE                 Location/Qualifiers
source                  1..282
                        mol_type = other DNA
                        note = Primase ori deltaGAAABCC
                        organism = synthetic construct
SEQUENCE: 3
tttgttgcaa tggctgtcta ccctgtctac ctgagtaaag aaaaatacat ttaattcagt   60
acattaactt gggtagacag cctttttta ctgtctacct actatctacc ctctctacct  120
gattttacct gaatcagaca gggaggtaga tacggggtag atagtggata aaagcactct  180
accccactga aagcagcgcc attactgcca tggtggccag taaggtagat aaggtagaca  240
aggggaggca caactcaaaa ctttttaaac gaggggtaa aa                      282

SEQ ID NO: 4            moltype = DNA  length = 282
FEATURE                 Location/Qualifiers
source                  1..282
                        mol_type = other DNA
                        note = Primase ori devoid of restriction sites
                        organism = synthetic construct
SEQUENCE: 4
tttgttgcaa tggctgtcta ccctgtctac ctgagtaaag aaaaatacat ttaattcagt   60
atattaactt gggtagacag cctttttta ctgtctacct tctgtctacc ctctctacct  120
gattttacct gaatcagaca gggaggtaga cacggggtag acagtggata aaagcactct  180
accccactga aagcagtgcc attactggca tggttgccag taaggttgat aaggtagaca  240
aggggaggga caactcaaaa ctttttaaac gaggggtaa aa                      282

SEQ ID NO: 5            moltype = AA  length = 584
FEATURE                 Location/Qualifiers
source                  1..584
                        mol_type = protein
                        note = PICI primase-helicase
                        organism = synthetic construct
SEQUENCE: 5
MKLAPNVKQQ SRGIKHKETE VIIFAGSDAW SHAKQWQEHD ARMAGDNEPP VWLGEQQLSE   60
LDKLQIVPEG RKSVRIFRAG YLAPVMIKAI GQKLAAAGVQ DANFYPDGMH GQKVENWREY  120
LARERQNLSD GLVIELPVKQ KAQLSQMADS ERAQLLADRF DGVCVHPESE IVHVWCGGVW  180
CPVSTMELSR EMVAIYSEHR ATFSKRVINN AVEALKVIAE PMGEPSGDLL PFANGALDLK  240
TGEFSPHTPE NWITTHNGIE YTPPAPGENI RDNAPNFHKW LEHAAGKDPR KMMRICAALY  300
MIMANRYDWQ MFIEATGDGG SGKSTFTHIA SLLAGKQNTV SAEMTSLDDA GGRAQVVGSR  360
LIVLADQPKY TGEGTGIKKI TGGDPVEINP KYEKRFTAVI RAVVLATNNN PMIFTERAGG  420
VARRRVIFRF DNIVSEAEKD RELPEKIAAE IPVIIRRLLA NFADPEKARA LLIEQRDGDE  480
ALAIKQQTDP VIEFCQFLNF LEEARGLMMG GGGDSVKYTT RNSLYRVYLA FMAYAGRSKP  540
LNVNDFGKAM KPAAKVYGHE YITRKVKGVT QTNAITTDDC DAFL                   584

SEQ ID NO: 6            moltype = DNA  length = 1752
FEATURE                 Location/Qualifiers
source                  1..1752
                        mol_type = other DNA
                        note = PICI primase-helicase
```

```
                 organism = synthetic construct
SEQUENCE: 6
atgaaactgg caccgaacgt aaaacagcag tcacgcggca taaaacacaa agaaacagaa    60
gtcattattt ttgcgggtag tgatgcctgg tcacacgcaa aacaatggca ggaacatgac   120
gcgcgtatgg ccggagataa tgagcctcct gtgtggcttg gggagcagca gttatccgaa   180
ctggataagc tgcaaattgt gccggaaggc agaaaatccg tgcgcatatt cagggccgga   240
tatcttgcgc cagtaatgat aaaggcgatt ggtcagaagc tggcggcggc aggcgtacag   300
gatgcaaatt tttaccctga tggtatgcac ggtcagaagg tggagaactg cgcgaatat   360
ctggcccgtg agcgccagaa tctttctgat ggtctggtca ttgagcttcc ggtaaagcaa   420
aaggcgcaac tttcgcagat ggcggacagt gagcgcgcgc agctgcttgc cgatcgcttt   480
gatgcgtttt gcgtacatcc tgaaagtgaa atcgttcacg tatggtgcgg cggggtatgg   540
tgtccggtca gcacaatgga gctgagccgc gaaatggtgg cgatctattc agagcacagg   600
gccactttca gcaagcgcgt aatcaataac gccgtgaaag cgttaaaagt tattgccgaa   660
ccaatgggcg agccgtccgg cgatttgctg ccgttcgcca atggtgcgct tgacctgaaa   720
acggggggaat tttccccgca cacgccgag aactggatca ccacgcacaa cggcattgag   780
tacacgccac cagcacccgg ggagaacatc gcgataacg cgccaaactt tcataaatgg   840
cttgagcacg cagccggaaa agacccgcgc aagatgatgc gtatatgtgc cgcgctgtac   900
atgattatgg cgaaccggta cgactggcag atgtttattg aggccaccgg agacggcggg   960
agcggtaaaa gtacattcac acacatagcc agccttctgg cagggaaaca aaacacggta  1020
agcgctgaaa tgacatcgct tgatgatgct ggtgggcgtg cgcaggttgt cgggagtcgt  1080
cttatcgtcc tggcagacca gccgaaatat acaggcgaag aacgggcat caagaaaatc  1140
acgggcggcg accccgtgga aattaacccg aaatatgaaa agcgttttac cggtgataatc  1200
agggcggtgg tgctggcaac caataacaat ccgatgatat tcaccgaacg ggccggaggt  1260
gtggcacgtc gtcgggtgat attccggttc gataacatcg taagcgaggc agaaaaagac  1320
agggagctac cggaaaagat cgcggctgaa atccctgtca ttatccgccg cttgctggcg  1380
aactttgccg accctgaaaa ggcacgggct ttactactga acagcgtga cggtgatgaa  1440
gcactggcaa taaagcaaca gacggatccg gttattgagt tttgccagtt cctgaatttt  1500
ctggaggaag cacgcggcct gatgatgggc ggcggtggcg attcagtgaa gtacacgacc  1560
agaaacagcc tttaccgcgt ctatctggcg tttatgcgt acgcaggcag gagcaaaccg  1620
ctaaacgtaa atgactttgg caaggctatg aagccagccg cgaaagttta cggacatgaa  1680
tatattacgc ggaaagttaa aggagtaacg cagactaacg caataacaac agacgattgc  1740
gacgcgtttt ta                                                      1752

SEQ ID NO: 7        moltype = DNA  length = 22368
FEATURE             Location/Qualifiers
source              1..22368
                    mol_type = other DNA
                    note = Lambda prophage structural operon
                    organism = synthetic construct
SEQUENCE: 7
atggaagtca acaaaaagca gctggctgac attttcggtg cgagtatccg taccattcag    60
aactggcagg aacagggaat gcccgttctg cgaggcggtg gcaagggtaa tgaggtgctt   120
tatgactctg ccgccgtcat aaaatgtat gccgaaaggg atgctgaaat tgagaacgaa   180
aagctgcgcc gggaggttga agaactgcgc caggccagcg aggcagatct ccagccagga   240
actattgagt acgaacgcca tcgacttacg cgtgcgcagg ccgacgcaca ggaactgaag   300
aatgccagag actccgctga agtggtgaa accgcattct gtactttcgt gctgtcgcgg   360
atcgcaggtg aaattgccag tattctgac gggctcccc tgtcggtgca gcggcgtttt   420
ccggaactgg aaaaccgaca tgttgatttc ctgaaacggg atatcatcaa agccatgaac   480
aaagcagccg cgctcgatga actgataccg gggttgctga gtgaatatat cgaacagtca   540
ggttaacagg ctgcggcatt ttgtccgcgc cgggcttcgc tcactgttca ggccggagcc   600
acagccgccg gttgaatggg cggatgctaa ttactatctc ccgaaagaat ccgcatacca   660
ggaagggcgc tgggaaacac tgccccttca gcgggccatc atgaatgcga tgggcagcga   720
ctacatccgt gaggtgaatg tggtgaagtc tgcccgtgtc ggttattcca aaatgctgct   780
gggtgtttat gcctactta tagagcataa gcagcgcaac accctatct ggttgccgac   840
ggatggtgat gccgagaact ttatgaaaac ccacgttgga ccgactattc gtgatattcc   900
gtcgctgctg gcgctggccc gtggtatgg caaaaagcac cgggataaca cgctcaccat   960
gaagcgtttc actaatgggc gtggcttct gtgcctgggc ggtaaagcgg caaaaaacta  1020
ccgtgaaaag tcggtggatg tggcgggtta tgatgaactt gctgcttttg atgatgtat  1080
tgaacaggaa ggctctccga cgttcctggg tgacaagcgt attgaaggct cggtctggcc  1140
aaagtccatc cgtggcctcca cgccaaaagt gagaggcacc tgtcagattg agcgtgcagc  1200
cagtgaatcc ccgcatttta tgcgttttca tgttgcctgc ccgcattgcg gggaggagca  1260
gtatcttaaa tttggcgaca agagacgcc gtttggcctc aaatgacgc cggatgaccc  1320
ctccagcgtg ttttatctct gcgagcataa tgcctgcgtc atccgccagc aggagctgga  1380
ctttactgat gcccgttata tctgcgaaaa gaccgggatc tggaccgtga atggcattct  1440
ctggtttttcg tcatccggtg aagagattga gccaactgac agtgtgacct ttcacatctg  1500
gacagcgtac agcccgttca ccacctgggt gcagattgtc aaagactgga tgaaaacgaa  1560
aggggatacg ggaaaacgta aaccttcgt aaacaccacg ctcggtgaga cgtgggaggc  1620
gaaaattggc gaacgtccgg atgctgaagt gatggcagag cggaaagagc attattcagc  1680
gcccgttcct gaccgtgtgg cttacctgac cgccggttac gactcccagc tggaccgcta  1740
cgaaatgcgc gtatgggat gggggccggg tgaggaaagc tggctgattg accggcagat  1800
tattatgggc cgccacacg atgaacagac gctgctgcgt gtggatgagg ccatcaataa  1860
aacctatacc cgccggaatg tgcagaaat tcgatatcc cgtatctgct gggatactgg  1920
cgggattgac ccgaccattg tgtatgaacg ctcgaaaaa catgggctgt tccgggtgat  1980
ccccattaaa ggggcatccg tctacggaaa gccggtgcgc gaaccgtg ataagcgaaa  2040
caaaaacggg gtttacctta ccgaaatcgg tacggatacc gcgaaagagc agatttataa  2100
ccgcttcaca ctgacgccgg aaggggatga accgcttccc ggtgccgttc acttcccgaa  2160
taccccggat ttttgatc tgaccgaagc gcagcagctg actgctgaag gcaggtcga  2220
aaatgggtg gatggcagga aaaaatact gtgggacagc aaaagcgac gcaatgaggc  2280
actcgactgc ttcgttatg cgctggcgg gctgcgcatc agtatttccc gctggcagct  2340
```

```
ggatctcagt gcgctgctgg cgagcctgca ggaagaggat ggtgcagcaa ccaacaagaa   2400
aacactggca gattacgccc gtgccttatc cggagaggat gaatgacgcg acaggaagaa   2460
cttgccgctg cccgtgcggc actgcatgac ctgatgacag gtaaacgggt ggcaacagta   2520
cagaaagacg gacgaagggt ggagtttacg gccacttccg tgtctgacct gaaaaaatat   2580
attgcagagc tggaagtgca gaccggcatg acacagcgac tgcagggacc tgcaggattt   2640
tatgtatgaa aacgcccacc attcccaccc ttctggggcc ggacggcatg acatcgctgc   2700
gcgaatatgc cggttatcac ggcggtggca gcggatttgg agggcagttg cggtcgtgga   2760
acccaccgag tgaaagtgtg gatgcagccc tgttgcccaa ctttacccgt ggcaatgccc   2820
gcgcagacga tctggtacgc aataacggct atgccgccaa cgccatccag ctgcatcagg   2880
atcatatcgt cgggtctttt ttccggctca gtcatcgccc aagctggcgc tatctgggca   2940
tcggggagga agaagcccgt gcctttccc gcgaggttga agcggcatgg aaagagtttg   3000
ccgaggatga ctgctgctgc attgacgttg agcgaaaacg cacgtttacc atgatgattc   3060
gggaaggtgt ggccatgcac gcctttaacg tgaactgtt cgttcaggcc acctgggata   3120
ccagttcgtc gcggcttttc cggacacagt tccggatggt cagcccgaag cgcatcagca   3180
acccgaacaa taccgcgac agccggaact gccgtgccgg tgtgcagatt aatgacagcg   3240
gtgcggcgct gggatattac gtcagcgagg acgggtatcc tggctggatg ccgcagaaat   3300
ggacatggat accccgtgag ttaccccggcg gcgcgcctc gttcattcac gttttttgaac   3360
ccgtggagga cgggcagact cgcggtgcaa atgtgtttta cagcgtgatg gagcagatga   3420
agatgctcga cacgctgcag aacacgcagc tgcagagcgc cattgtgaag gcgatgtatg   3480
ccgccaccat tgagagtgag ctggatacgc agtcagcgat ggatttatt ctgggcgcga   3540
acagtcagga gcagcgggaa aggctgaccg gctggattgt tgaaattgcc gcgtattacg   3600
ccgcagcgcc ggtccggctg ggaggcgcaa aagtaccgca cctgatgccg ggtgactcac   3660
tgaacctgca gacggctcag gatacggata acgctactc cgtgtttgag cagtcactgc   3720
tgcggtatat cgctgccggg ctgggtgtct cgtatgagca gctttccgg aattacgccc   3780
agatgagcta ctccacggca cgggccagtg cgaacgagtc gtgggcgtac tttatgggc   3840
ggcgaaaatt cgtcgcatcc cgtcaggcga gccagatgtt tctgtgctgg ctggaagagg   3900
ccatcgttcg ccgcgtggtg acgttacctt caaaagcgcg cttcagtttt caggaagccc   3960
gcagtgcctg ggggaactgc gactggatag gctccggtcg tatggccatc gatggtctga   4020
aagaagttca ggaagcggtg atgctgatag aagccggact gagtacctac gagaaagagt   4080
gcgcaaaacg cggtgacgac tatcaggaaa tttttgccca gcaggtccgt gaaacgatga   4140
agcgccgtgc agccggtctt aaaccgcccc cctgggcggc tgcagcattt gaatccggc   4200
tgcgacaatc aacagaggag gagaagagtg acagcagagc tgcgtaatct cccgcatatt   4260
gccagcatgg cctttaatga gccgctgatg cttgaacccg cctatgcgcg ggttttcttt   4320
tgtgcgcttg caggccagct tggatcagc agcctgacgg atgcggtgtc cggcgacagc   4380
ctgactgccc aggaggcact cgccgacgct gcattatccg gtgatgatga cggaccacga   4440
caggcccgca gttatcaggt catgaacggc atcgccgtgc tgccggtgtc cggcacgctg   4500
gtcagccgga cgcgggcgct gcagccgtac tcggggatga ccggttacaa cggcattatc   4560
gcccgtctgc aacaggctgc cagcgatccg atggtggacg gcattctgct cgatatggac   4620
acgccgggcg ggatggtggc gggggcattt gactgcgctg acatcatcgc ccgtgtgcgt   4680
gacataaaac cggtatgggc gcttgccaac gacatgaact gcagtgcagg tcagttgctt   4740
gccagtgccg cctcccggcg tctggtcacg cagaccgccc ggacaggctc catcggcgtc   4800
atgatggctc acagtaatta cggtgctgcg ctggagaaac agggtgtgga aatcacgctg   4860
atttacacgg gcagccataa ggtgagtggc aaccctaca gccatcttcc ggatgacgtc   4920
cgggagacac tgcagtcccg gatggacgca acccgccaga tgtttgcgca gaaggtgtcg   4980
gcatataccg gcctgtccgt gcaggttgtg ctggataccg aggctgcagt gtacagcggt   5040
caggaggcca ttgatgccgg actggctgat gaacttgtta acagcaccga tcgcatcacc   5100
gtcatgcgtg atgcactgga tgcacgtaaa tcccgtctct caggagggca aatgaccaaa   5160
gagactcaat caacaactgt ttcagccact gcttcgcagg ctgacgttac tgacgtggtg   5220
ccagcgacgg agggcgagaa cgccagcgcg gcgcagccgg acgtgaacgc gcagatcacc   5280
gcagcggttg cggcagaaaa cagccgcatt atggggatcc tcaactgtga ggaggctcac   5340
ggacgcgaag aacaggcacg cgtgctggca gaaaccccg gtatgaccgt gaaaacggct   5400
cgccgcattc tggccgcagc accacagagt gcacaggcgc gcagtgacac tgcgctggat   5460
cgtctgatgc aggggcacc ggcaccgctg gctgcaggta accggcatc tgatgccgtt   5520
aacgatttgc tgaacacacc agtgtaaggg atgtttatga cgagcaaaga aaccttacc   5580
cattaccagc cgcagggcaa cagtgacccg gctcataccg caaccgcgcc cggcggattg   5640
agtgcgaaag cgcctgcaat gaccccgctg atgctggaca cctccagccg taagctggtt   5700
gcgtgggatg gcaccaccga cggtgctgcc gttggcattc ttgcggttgc tgctgaccag   5760
accagcacca cgctgacgtt ctacaagtcc ggcacgttcc gttatgagga tgtgctctgg   5820
ccggaggctg ccagcgacga gacgaaaaaa cggaccgcgt ttgccgaac ggcaatcaga   5880
atcgtttaac tttaccccttc atcactaaag gccgcctgtg cggctttttt tacgggattt   5940
ttttatgtcg atgtacacaa ccgcccaact gctggcggca aatgagcaga aatttaagtt   6000
tgatccgctg tttctgcgtc tcttttttccg tgagagctat cccttcacca cggagaaagt   6060
ctatctctca caaattccgg gactggtaaa catgcgctg tacgtttcgc cgattgtttc   6120
cggtgaggtt atccgttccc gtggcgggctc cacctcgtaa tttacgccgg gatatgtcaa   6180
gccgaagcat gaagtgaatc cgcagatgac cctgcgtcgc ctgccggatg aagatccgca   6240
gaatctggcg gaccccggctt accgccgccg tcgcatcatc atgcagaaca tgcgtgacga   6300
agagctggcc attgctcagg tcgaagagat gcaggcagtt tctgccgtgc ttaagggcaa   6360
atacaccatg accggtgaag ccttcgatcc ggttgaggtg gatatgggcc gcagtgagga   6420
gaataacatc acgcagtccg gcggcacgga gtgagcaag cgtgacaagt ccacgtatga   6480
cccgaccgac gatatcgaag cctacgcgct gaacgccagc ggtgtggtga atatcatcgt   6540
gttcgatccg aaaggctggg cgctgttccg ttccttcaaa gccgtcaagg agaagctgga   6600
tacccgtcgt ggctctaatt ccgagctgga gacagcggtg aaagacctgg gcaaagcggt   6660
gtcctataag gggatgtatg cgatgtggc catcgtcgtg tattccggac agtacgtgga   6720
aaacggcgtc aaaaagaact tcctgccgga caacagccga ccaacaggtc   6780
acgcggtctg cgcacctatg gctgcattca ggatgcggac gcacagcgcg aaggcattaa   6840
cgcctctgcc cgttacccga aaaactgggg gaccaccggc gatccggcgc gtgagttcac   6900
catgattcag tcagcaccgc tgatgctgct ggctgaccct gatgagttcg tgtccgtaca   6960
actggcgtaa tcatgcccct tcggggcat tgttttctctg tggaggagtc catgacgaaa   7020
gatgaactga ttgcccgtct ccgctcgctg ggtgaacaac tgaaccgtga tgtcagcctg   7080
```

```
acggggacga aagaagaact ggcgctccgt gtggcagagc tgaaagagga gcttgatgac   7140
acggatgaaa ctgccggtca ggacacccct ctcagccggg aaaatgtgct gaccggacat   7200
gaaaatgagg tgggatcagc gcagccggat accgtgattc tggatacgtc tgaactggtc   7260
acggtcgtgg cactggtgaa gctgcatact gatgcacttc acgccacgcg ggatgaacct   7320
gtggcatttg tgctgccggg aacggcgttt cgtgtctctg ccggtgtggc agccgaaatg   7380
acagagcgcg gcctgccag aatgcaataa cgggaggcgc tgtggctgat ttcgataacc   7440
tgttcgatgc tgccattgcc cgcgccgatg aaacgatacg cgggtacatg ggaacgtcag   7500
ccaccattac atccggtgag cagtcaggtg cggtgatacg tggtgttttt gatgaccctg   7560
aaaatatcag ctatgccgga cagggcgtgc gcgttgaagg ctccagcccg tccctgtttg   7620
tccggactga tgaggtgcgg cagctgcggc gtggagacac gctgaccatc ggtgaggaaa   7680
atttctgggt agatcgggtt tcgccggatg atggcggaag ttgtcatctc tggcttggac   7740
ggggcgtacc gcctgccgtt aaccgtcgcc gctgaaaggg ggatgtatgg ccataaaagg   7800
tcttgagcag gccgttgaaa acctcagccg tatcagcaaa acggcggtgc ctggtgccgc   7860
cgcaatggcc attaaccgcg ttgcttcatc cgcgatatcg cagtcggcgt cacaggttgc   7920
ccgtgagaca aaggtacgcc ggaaactggt aaaggaaagg gccaggctga aaagggccac   7980
ggtcaaaaat ccgcaggcca gaatcaaagt taaccggggg gatttgcccg taatcaagct   8040
gggtaatgcg cgggttgtcc tttcgcgccg caggcgtcgt aaaaaggggc agcgttcatc   8100
cctgaaaggt ggcggcagcg tgcttgtggt gggtaaccgt cgtattcccg gcgcgtttat   8160
tcagcaactg aaaaatggcc ggtggcatgt catgcagccgt gtggctggga aaaaccgtta   8220
ccccattgat gtggtgaaaa tcccgatggc ggtgccgctg accacggcgt ttaaacaaaa   8280
tattgagcgg atacggcgtg aacgtcttcc gaaagagctg ggctatgcgc tgcagcatca   8340
actgaggatg gtaataaagc gatgaaacat actgaactcc gtgcagcgat actgatgca   8400
ctggagaagc atgacaccgg ggcgacgttt tttgatggtc gccccgctgt ttttgatgag   8460
gcggattttc cggcagttgc cgtttatctc accggcgctg aatacacggg cgaagagctg   8520
gacagcgata cctggcaggc ggagctgcat atcgaagttt tcctgcctgc tcaggtgccg   8580
gattcagagc tggatgcgg gatggagtcc cggatttatc cggtgatgag cgatatcccg   8640
gcactgtcag atttgatcac cagtatggtg gccagcggct atgactaccg gcgcgacgat   8700
gatgcgggct tgtggagttc agccgatctg acttatgtca ttacctatga aatgtgagga   8760
cgctatgcct gtaccaaatc ctacaatgcc ggtgaaaggt gccgggacca ccctgtgggt   8820
ttataagggg agcggtgacc cttacgcgaa tccgcttca gacgttgact ggtcgcgtt   8880
ggcaaaagtt aaagacctga cgcccggcga actgaccgct gagtcctatg acgacagcta   8940
tctcgatgat gaagatgcag actgactgc gaccgggcag gggcagaaat ctgccggaga   9000
taccagcttc acgctggcgt ggatgccgg agagcagggg cagcaggcgc tgctggcgtg   9060
gtttaatgaa ggcgatgccc gtgccgaata aatccgcttc ccgaaacgac cggtcgatgt   9120
gttccgtggc tgggtcagca gtatcggtaa ggcggtgacg gcgaaggaag tgatcacccg   9180
cacggtgaaa gtcaccaatg tgggacgtcc gtcgatggca gaagatcgca gcacggtaac   9240
agcggcaacc ggcatgaccg tgacgcctgc cagcaccctcg gtggtgaaag gcagagcac   9300
cacgctgacc gtggccttcc agccggaggg cgtaaccgac aagagctttc gtgcggtgtc   9360
tgccgataaa acaaaagcca ccgtgtcggt cagtggtatg accatcaccg tgaacggcgt   9420
tgctgcaggc aaggtcaaca ttccggttgt atccggtaat ggtgagtttg ctgcggttgc   9480
agaaattacc gtcaccgcca gttaatccgg agagtcagcg atgttcctga aaccgaatc   9540
atttgaacat aacggtgtga ccgtcacgct ttctgaactg tcagccctgc agcgcattga   9600
gcatctccgc ctgatgaaac ggcaggcaga acaggcggga tcagacagca accggaagtt   9660
tactgtggaa gacgccatca gaaccggcgc gtttctggtg gcgatgtccc tgtggcataa   9720
ccatccgcag aagacgcaga tgccgtccat gaatgaagcc gttaaacaga ttgagcagga   9780
agtgcttacc acctggccca cggaggcaat ttctcatgct gaaaacgtgg tgtaccggct   9840
gtctggtatg tatgagtttg tggtgaataa tgccccctgaa cagacagagg acgccgggcc   9900
cgcagagcct gtttctgcgg gaaagtgttc gacggtgagc tgagttttgc cctgaaactg   9960
gcgcgtgaga tggggcgacc cgactggcgt gccatgcttg ccgggatgtc atccacggag  10020
tatgccgact ggcaccgctt ttacagtacc cattattttc atgatgttct gctggatatg  10080
cacttttccg ggctgacgta caccgtgctc agcctgtttt tcagcgatcc ggatatgcat  10140
ccgctggatt tcagtctgct gaaccggcgc gaggctgacg aagagcctga agatgatgtg  10200
ctgatgcaga aagcggcagg gcttgccgga ggtgtccgct ttggcccgga cgggaatgaa  10260
gttatccccg cttccccgga tgtggcggac atgacggagg atgacgtaat gctgatgaca  10320
gtatcagaag ggatcgcagg aggagtccgg tatggctgaa ccggtaggcg atctggtcgt  10380
tgatttgagt ctggatgcgg ccagatttga cgagcagatg gccagagtca ggcgtcattt  10440
ttctggtacg gaaagtgatg cgaaaaaaac agcggcagtc gttgaacagt cgctgagccg  10500
acaggcgctg gctgcacaga aagcggggat ttccgtcggg cagtataaag ccgccatgcg  10560
tatgctgcct gcacagttca ccgacgtggc tcaggcgcag aaagtccgtg  10620
gctgatcctg ctgcaacagg ggggcaggt gaaggactcc ttcggcggga tgatccccat  10680
gttcagggggg cttgccggtg cgatcaccct gccgatggtg ggggcacct cgctggcggt  10740
ggcgaccggt gcgctggcgt atgcctggta tcagggcaac tcaaccctgt ccgatttcaa  10800
caaaacgctg gtccttttcg gcaatcaggc gggactgacg cagatcgta tgctggtcct  10860
gtccagagcc gggctgcgg cagggctgac gtttaaccag accagcggt cactcagcgc  10920
actggttaag gcggggtaa gcggtgaggc tcagattgcg tccatcagcc agagtggc  10980
gcgtttctcc tctgcatccg gcgtggaggt ggacaaggtc gctgaagcct cgggaagct  11040
gaccacagac ccgacgtcgg ggctgacggc gatggctcgc cagttccata acgtgtcggc  11100
ggagcagatt gcgtatgttg ctcagttgca gcgttccggc gatgaagccg gggcattgca  11160
ggcggcgaac gaggccgcaa cgaaaggggtt tgatgaccag acccgccgcc tgaaagagaa  11220
catgggcacg ctgagacct gggcagacag gactgcgcgg gcattcaaat ccatgtggga  11280
tgcggtgctg gatattggtc gtcctgatac cgcgcaggag atgctgatta aggcagaggc  11340
tgcgtataag aaagcagacg acatctgaa tctgcgcaag gatgattatt ttgttaacga  11400
tgaagcgcgg gcgcgttact gggatgatcg tgaaaaggcc cgtcttgcgc ttgaagccgc  11460
ccgaaagagg gctgagcagg agactcaaca ggacaaaat gcagacgaac agagcgatac  11520
cgaagcgtca cggctgaaat ataccgaaga ggcgcagaag gcttacgaac ggctgcagac  11580
gccgctggag aaatataccg cccgtcagga agaactgaac aaggcactga agacgggaa  11640
aatcctgcag gcgattaca acacgctgat ggcggcggcg aaaaaggatt atgaagcgac  11700
gctgaaaaag ccgaaacagt ccagcgtgaa ggtgtctgcg ggcgatcgtc aggaagacag  11760
tgctcatgct gccctgctga cgcttcaggc agaactccgg acgctggaga agcatgccgg  11820
```

```
agcaaatgag aaaatcagcc agcagcgccg ggatttgtgg aaggcggaga gtcagttcgc  11880
ggtactggag gaggcggcgc aacgtcgcca gctgtctgca caggagaaat ccctgctggc  11940
gcataaagat gagacgctgg agtacaaacg ccagctggct gcacttggcg acaaggttac  12000
gtatcaggag cgcctgaacg cgctggcgca gcaggcggat aaattcgcac agcagcaacg  12060
ggcaaaacgg gccgccattg atgcgaaaag ccgggggctg actgaccggc aggcagaacg  12120
ggaagccacg gaacagcgcc tgaaggaaca gtatgcgat aatccgctgg cgctgaataa  12180
cgtcatgtca gagcagaaaa agacctgggc ggctgaagac cagcttcgcg ggaactggat  12240
ggcaggcctg aagtccggct ggagtgagtg ggaagagagc gccacggaca gtatgtcgca  12300
ggtaaaaagt gcagccacgc agacctttga tggtattgca cagaatatgg cggcgatgct  12360
gaccggcagt gagcagaact ggcgcagctt cacccgttcc gtgctgtcca tgatgacaga  12420
aattctgctt aagcaggcaa tggtggggat tgtcgggagt atcggcagcg ccattggcgg  12480
ggctgttggt ggcggcgcat ccgcgtcagg cggtacagcc attcaggccg ctgcggcgaa  12540
attccatttt gcaaccggag gatttacggg aaccggcggc aaatatgagc cagcggggat  12600
tgttcaccgt ggtgagtttg tcttcacgaa ggaggcaacc agccggattg gcgtggggaa  12660
tctttaccgg ctgatgcgcg gctatgccac cggcggttat gtcggtacac cgggcagcat  12720
ggcagacagc cggtcgcagg cgtccggac gtttgagcag aataaccatg tggtgattaa  12780
caacgacggc acgaacgggc agataggtcc ggctgctctg aaggcggtgt atgacatggc  12840
ccgcaagggt gcccgtgatg aaattcagac acagatgcgt gatggtggcc tgttctccgg  12900
aggtggacga tgaagacctt ccgctggaaa gtgaaacccg gtatggatgt ggcttcggtc  12960
ccttctgtaa gaaaggtgcg cttttggtgat ggctattctc agcagcgcc tgccgggctg  13020
aatgccaacc tgaaaacgta cagcgtgacg ctttctgtcc cccgtgagga ggccacggta  13080
ctggagtcgt ttctggaaga gcacgggggc tggaaatcct ttctgtggac gccgccttat  13140
gagtggcggc agataaaggt gacctgcgca aaatgtcgt cgcgggtcag tatgctgcgt  13200
gttgagttca gcgcagagtt tgaacaggtg gtgaactgat gcaggatatc cggcaggaaa  13260
cactgaatga atgcacccgt gcggagcagt cggccagcgt ggtgctctgg gaaatcgacc  13320
tgacagaggt cggtggagaa cgttattttt tctgtaatga cagaacgaa aaaggtgagc  13380
cggtcacctg gcaggggcga cagtatcagc cgtatcccat tcaggggagc ggttttgaac  13440
tgaatggcaa aggcaccagt acgcgcccca cgctgacggt ttctaacctg tacggtatgg  13500
tcaccgggat ggcggaagat atgcagagtc tggtcggcgg aacggtggtc cggcgtaagg  13560
tttacgccgg ttttctggat gcggtgaact tcgtcaacgg aaacagttac gccgatccgg  13620
agcaggaggt gatcagccgc tggcgcattg agcagtgcag cgaactgagc gcggtgagtg  13680
cctcctttgt actgtccacg ccgacggaaa cggatggcgc tgttttccg ggacgtatca  13740
tgctggccaa cacctgcacc tggacctatc gcggtgacga gtgcggttat agcggtccgg  13800
ctgtcgcgga tgaatatgac cagccaacgt ccgatatcac gaaggataaa tgcagcaaat  13860
gcctgagcgg ttgtaagttc cgcaataacg tcggcaactt tggcggcttc ctttccatta  13920
acaaactttc gcagtaaatc ccatgacaca gacagaatca gcgattctgg cgcacgcccg  13980
gcgatgtgcg ccagcggagt cgtgcggctt cgtggtaagc acgccggagg gggaaagata  14040
tttccctgc gtgaatatct ccggtgagcc ggaggcgtat ttccgtatgt cgccggaaga  14100
ctggctgcag gcagaaatgc agggtgagat tgtggccgtg gtccacagcc acccggtgg  14160
tctgccctgg ctgagtgagg ccgaccggcg gctgcaggtg cagagtgatt tgccgtggtg  14220
gctggtctgc cggggacga ttcataagtt ccgctgtgtg ccgcatctca ccgggcggcg  14280
ctttgagcac ggtgtgacgg actgttacac actgttccgg gatgcttatc atctggcggg  14340
gattgagatg ccggactttc atcgtgagga tgactgtgag cgtaacggcc agaatctcta  14400
tctggataat ctggaggcga cggggctgta tcaggtgccg ttgtcagcgg cacagccggg  14460
cgatgtgctg ctgtgctgtt ttggttcatc agtgccgaat cacgccgcaa tttactgcgg  14520
cgacggcgag ctgctgcacc atattcctga caactgagc aaacgagaga ggtacaccga  14580
caaatggcag cgacgcacac actccctctg gcgtcaccgg gcatggcgcg catctgcctt  14640
tacggggatt tacaacgatt tggtcgccgc atcgaccttc gtgtgaaaac ggggcctgaa  14700
gccatccggg cactggccac acagctcccg gcgtttcgtc agaaactgag cgacggctgg  14760
tatcaggtac ggattgccgg gcgggacgtc agcacgtccg ggttaacggc gcagttacat  14820
gagactctgc ctgatggccg tgtaattcat attgttccca gagtcgccgg ggccaagtca  14880
ggtggcgtat tccagattgt cctgggggct gccgccattg ccggatcatt ctttaccgcc  14940
ggagccaccc ttgcagcatg gggggcagcc atttgggccg gtggtatgac cggcatcctg  15000
ttttctctcg gtgccagtat ggtgctcggt ggtgtggcgc agatgctggc accgaaagcc  15060
agaactcccc gtatacagac aacgataac ggtaagcaga acacctattt ctcctcactg  15120
gataacatgg ttgcccaggg caatgttctg cctgttctgt acggggaaat gcgcgtggtg  15180
tcacgcgtgg tttctcagga gatcagcacg cagacgaag gggacggtgg tcaggttgtg  15240
gtgattggtc gctgatgcaa aatgttttat gtgaaaccgc ctgcgggcgg ttttgtcatt  15300
tatggagcgt gaggaatggg taaaggaagc agtaaggggc ataccccgcg cgaagcgaag  15360
gacaacctga agtccacgca gttgctgagt gtgatcgata ccatcagcga agggccgatt  15420
gaaggtccgg tggatggctt aaaaagcgtg ctgctgaaca gtacgccggt gctggacact  15480
gaggggaata ccaacatatc cggtgtcacg gtggtgttcc gggctggtga gcaggagcag  15540
actccgccgg agggatttga atcctccggc tccgagacgg tgctgggtac ggaagtgaaa  15600
tatgacacgc cgatcacccg caccattacg tctgcaaaca tcgaccgtct gcgctttacc  15660
ttcggtgtac aggcactggt ggaaaccacc tcaaagggtg acaggaatcc gtcggaagtc  15720
cgcctgctgg ttcagataca acgtaacggt ggctgggtga cggaaaaaga catcaccatt  15780
aagggcaaaa ccacctcgca gtatctgcc tcggtggtga tgggtaacct gccgccgcgc  15840
ccgtttaata tccggatgcg caggatgacg ccggacagca ccacagacca gctgcagaa  15900
aaaacgctct ggtcgtcata cactgaaatc atcgatgtgct aacagtgcta cccgaacacg  15960
gcactggtcg gcgtgcaggt ggactcggag cagttcggca gccagcaggt gagccgtaat  16020
tatcatctgc gcgggcgtat tctgcaggtg ccgtcgaact ataaccggca gacgcggcaa  16080
tacagcggta tctgggacgg aacgtttaaa ccggcataca gcaacaacat ggcctggtgt  16140
ctgtgggata tgctgaccca tccgcgctac ggcatgggga acgtcttgg tgcggcggat  16200
gtggataaat gggcgctgta tgtcatcggc cagtactgcg accagtcagt gccggacggc  16260
tttggcggca cggagccgcg catcacctgt aatgcgtacc tgaccacaca cgtaaggcg  16320
tgggatgtgc tcagcgattt ctgctcggcg atgcgctgta tgccggtatg aacgggcag  16380
acgctgacgt tcgtgcagga ccgaccgtcg gataagacgt ggacctataa ccgcagtaat  16440
gtggtgatgc cggatgatgg cgcgccgttc cgctacagct tcagcgccct gaaggaccgc  16500
cataatgccg ttgaggtgaa ctggattgac ccgaacaacg gctgggagac ggcgacagag  16560
```

```
cttgttgaag atacgcaggc cattgcccgt tacggtcgta atgttacgaa gatggatgcc   16620
tttggctgta ccagccgggg gcaggcacac cgcgccgggc tgtggctgat taaaacagaa   16680
ctgctggaaa cgcagaccgt ggatttcagc gtcggcgcag aagggcttcg ccatgtaccg   16740
ggcgatgtta ttgaaatctg cgatgatgac tatgccggta tcagcaccgg tggtcgtgtg   16800
ctggcggtga acagccagac ccggacgctg acgctcgacc gtgaaatcac gctgccatcc   16860
tccggtaccg cgctgataag cctggttgac ggaagtggca atccggtcag cgtggaggtt   16920
cagtccgtca ccgacggcgt gaaggtaaaa gtgagccgtg ttcctgacgg tgttgctgaa   16980
tacagcgtat gggagctgaa gctgccgacg ctgcgccagc gactgttccg ctgcgtgagt   17040
atccgtgaga acgacgacgg cacgtatgcc atcaccgccg tgcagcatgt gccggaaaaa   17100
gaggccatcg tggataacgg ggcgcacttt gacggcgaac agagtggcac ggtgaatggt   17160
gtcacgccgc cagcggtgca gcacctgacc gcagaagtca ctgcagacag cggggaatat   17220
caggtgctgg cgcgatggga cacaccgaag gtggtgaagg cgtgagtttt cctgctccgt   17280
ctgaccgtaa cagcggacga cggcagtgag cggctggtca gcacggcccg gacgacggaa   17340
accacatacc gcttcacgca actggcgctg gggaactaca ggctgacagt ccgggcggta   17400
aatgcgtggg ggcagcaggg cgatccggcg tcggtatcgt tccggattgc cgcaccggca   17460
gcaccgtcga ggattgagct gacgccgggc tattttcaga taaccgccac gccgcatctt   17520
gccgtttatg acccgacggt acagtttgag ttctggttct cggaaaagca gattgcggat   17580
atcagacagg ttgaaaccag cacgcgttat cttggtacgg cgctgtactg gatagccgcc   17640
agtatcaata tcaaaccggg ccatgattat tactttttata tccgcagtgt gaacaccgtt   17700
ggcaaatcgg cattcgtgga ggccgtcggt cgggcgagcg atgatgcgga aggttacctg   17760
gattttttca aaggcaagat aaccgaatcc catctcggca aggagctgct ggaaaaagtc   17820
gagctgacgg aggataacgc cagcagactg gaggagtttt cgaaagagtg aaggggatgcc   17880
agtgataagt ggaatgccat gtgggctgtc aaaattgagc agaccaaaga cggcaaacat   17940
tatgtcgcgg gtattggcct cagcatggag gacacggagg aaggcaaact gagccagttt   18000
ctggttgccg ccaatcgtat cgcatttatt gacccggcaa acgggaatga aacgccgatg   18060
tttgtgcgc agggcaacca gatattcatg aacgacgtgt tcctgaagcg cctgacggcc   18120
cccaccatta ccagcggcgg caatcctccg gccttttccc tgacaccgga cggaaagctg   18180
accgctaaaa atgcggatat cagtggcagt gtgaatgcga actccgggac gctcagtaat   18240
gtgacgatag ctgaaaactg tacgataaac ggtacgctga gggcggaaaa aatcgtcggg   18300
gacattgtaa aggcggcgag cgcggcttt ccgcgccagc gtgaaagcag tgtggactgg   18360
ccgtcaggta cccgtactgt caccgtgacc gatgaccatc cttttgatcg ccagatagtg   18420
gtgcttccgc tgacgtttcg cggaagtaag cgtactgtca gcggcaggac aacgtattcg   18480
atgtgttatc tgaaagtact gatgaacggt gcggtgattt atgatggcgc ggcgaacgag   18540
gcggtacagg tgttctcccg tattgttgac atgccagcgg gtcggggaaa cgtgatccg   18600
acgttcacgc ttacgtccac acggcattcg gcagatattc cgccgtatac gtttgccagc   18660
gatgtgcagg ttatggtgat taagaaacag gcgctgggca tcagcgtggt ctgagtgtgt   18720
tacagaggtt cgtccgggaa cgggcgtttt attataaaac agtgagaggt gaacgatgcg   18780
taatgtgtgt attgccgttg ctgtctttgc cgcacttgcg gtgacagtca ctccggcccg   18840
tgccgaaggt ggacatggta cgtttacggt gggctatttt caagtgaaac cgggtacatt   18900
gccgtcgttg tcgggcgggg ataccggtgt gagtcatctg aaaggggata acgtgaagta   18960
ccgttatgag ctgacggaca gtgtgggggt gatggcttcc ctggggttcg ccgcgtcgaa   19020
aaagagcagc acagtgatga ccggggagga tacgtttcac tatgagagcc tgcgtggacg   19080
ttatgtgacg gtgatggccg gaccggtttt acaaatcagt aagcaggtca gtgcgtacgc   19140
catggccgga gtggctcaca gtcggtggtc cggcagtaca atggattacc gtaagacgag   19200
aatcactccc gggtatatga agagacgac cactgccagg gacgaaagtg caatgcggca   19260
tacctcagtg gcgtggagtg caggtataca gattaatccg gcagcgtccg tcgttgttga   19320
tattcttat gaaggctccg gcagtggcga ctggcatcga gcggattca tcgttggggt   19380
cggttataaa ttctgattag ccaggtaaca cagtgttatg acagcccgcc ggaaccggtg   19440
ggctttttttg tggggtgaat atggcagtaa agatttcagg agtcctgaaa gacggcacag   19500
gaaaaccggt acagaactgc accattcagc tgaaagccag acgtaacagc accacggtgg   19560
tggtgaacac ggtgggctca gagaatccgg atgaagccgg gcgttacgc atggatgtgg   19620
agtacggtca gtacagtgtc atcctgcagg ttgacggttt tccaccatcg cacgccggga   19680
ccatcaccgt gtatgaagat tcacaaccgg ggacgctgaa tgatttttctc tgtgccatga   19740
cggaggatga tgcccggccg gaggtgctgc gtcgtcttga actgatggtg gaagaggtgg   19800
cgcgtaacgc gtccgtggtg gcacagagta cggcagacgc gaagaaatca gccggcgatg   19860
ccagtgcatc agctgctcag gtcgcggccc ttgtgactga tgcaactgac tcagcacgcg   19920
ccgcagcac gtccgccgga caggctcat cgtcagctca ggaagcgtcc tccggcgcag   19980
aagcggcatc agcaaaggcc actgaagcgg aaaaaagtgc cgcagccgca gagtcctcaa   20040
aaaacgcggc ggccaccagt gccggtcgg cgaaaacgtc agaaacgaat gctgcagcgt   20100
cacaacaatc agccgccacg tctgcctcca ccgcggccac gaaagcgtca gaggccgcca   20160
cttcagcacg agatgcggtg gcctcaaaag aggcagcaaa atcatcagaa acgaacgcat   20220
catcaagtgc cggtcgtgca gcttcctcgg caacggcggc agaaaattct gccagggcgg   20280
caaaaacgtc cgagacgaat gccaggtcat ctgaaacagc agcggaacgg agcgcctctg   20340
ccgcggcaga cgcaaaaaca gcggcggcgg ggagtcgctc aacggcatcc acgaaggcga   20400
cagaggctgc gggaagtgcg gtatcagcat cgcagagcaa aagtgcggca aagcggcgg   20460
caatacgtgc aaaaaattcg gcaaaacgtg cagaagatat agcttcagct gtcgcgcttg   20520
aggatgcgga cacaacgaga aagggggatag tgcagctcag cagtgcaacc aacagcacgt   20580
ctgaaacgct tgctgcaacg ccaaaggcgg ttaaggtggt aatggatgaa acgaacagaa   20640
aagcccactg gacagtccgg cactgaccgg aacgccaacc gccaaaccg cgctcagggg   20700
aacaaacaat acccagattg cgaacaccgc ttttgtactg gccgcgattg cagatgttat   20760
cgacgcgtca cctgacgcac tgaatacgct gaatgaactg gccgcagcgc tcgggaatga   20820
tccagatttt gctaccacca tgactaacgc gcttgcgggg aaacaaccga agaatgcgac   20880
actgacggcg ctgcagggc tttccacggc gaaaaataaa ttaccgtatt ttgcggaaaa   20940
tgatgcgaag acggctgcac aactgactca ggttggcagg gatattctgg caaaaattc   21000
cgttgcagat gttcttgaat accttgggggc cggtgagaat tcggcctttc cggcaggtgc   21060
gccgatcccg tggccatcag atatcgttcc gtctggctac gtcctgatgc aggggcaggc   21120
gtttgacaaa tcagcctacc caaaacttgc tgtcgcgtat ccatcgggtg tgcttcctga   21180
tatgcgaggc tggacaatca aggggaaacc cgccagcggt cgtgctgtat tgtctcagga   21240
acaggatgga attaagtcgc acaccccacag tgccagtgca tccggtacgg atttgggac   21300
```

```
gaaaaccaca tcgtcgtttg attacgggac gaaaacaaca ggcagtttcg attacggcac  21360
caaatcgacg aataacacgg gggctcatgc tcacagtctg agcggttcaa caggggccgc  21420
gggtgctcat gcccacacaa gtggtttaag gatgaacagt tctggctgga gtcagtatgg  21480
aacagcaacc attacaggaa gtttatccac agttaaagga accagcacac agggtattgc  21540
ttatttatcg aaaacggaca gtcagggcag ccacagtcac tcattgtccg gtacagccgt  21600
gagtgccggt gcacatgcgc atacagttgg tattggtgcg caccagcatc cggttgttat  21660
cggtgctcat gcccattctt tcagtattgg ttcacacgga cacaccatca ccgttaacgc  21720
tgcgggtaac gcgaaaaca ccgtcaaaaa cattgcattt aactatattg tgaggcttgc  21780
ataatggcat tcagaatgag tgaacaacca cggaccataa aaatttataa tctgctggcc  21840
ggaactaatg aatttattgg tgaaggtgac gcatatattc cgcctcatac cggtctgcct  21900
gcaaacagta ccgatattgc accgccagat attccggctg gctttgtggc tgttttcaac  21960
agtgatgagg catcgtggca tctcgttgaa gaccatcggg gtaaaaccgt ctatgacgtg  22020
gcttccggcg acgcgttatt tatttctgaa ctcggtccgt taccgaaaaa ttttacctgg  22080
ttatcgccgg gagggaata tcagaagtgg aacggcacag cctggtgaa ggatacggaa  22140
gcagaaaaac tgttccggat ccgggaggcg gaagaaacaa aaaaaagcct gatgcaggta  22200
gccagtgagc atattgcgcc gcttcaggat gctgcagatc tggaaattgc aacgaaggaa  22260
gaaacctcgt tgctggaagc ctggaagaag tatcgggtgt gctgaaccg tgttgataca  22320
tcaactgcac ctgatattga gtggcctgct gtccctgtta tggagtaa             22368

SEQ ID NO: 8               moltype = DNA   length = 20330
FEATURE                    Location/Qualifiers
source                     1..20330
                           mol_type = genomic DNA
                           organism = Lambdavirus lambda
SEQUENCE: 8
tcaaggtccc taaattaata cgactcacta tagggagata ggggcccttta cgattattac  60
tttaagattt aactctaaga ggaatctttta ttatgttaac acctattaac caattactta  120
agaaccctaa cgtatattcca gatgtaccttc gtgcaaccgc tgagtatcta caggttcgat  180
tcaactatgc gtacctcgaa gcgtctggtc atataggact tatgcgtgct aatggttgta  240
gtgaggccca catcttgggt ttcattcagg gcctacagta tgcctctaac gtcattgacg  300
agattgagtt acgcaaggaa caactaagag atgatgggga ggattgacac tatgtgtttc  360
tcaccgaaaa ttaaaactcc gaagatggat accaatcaga ttcgagccgt tgagccagcg  420
cctctgaccc aagaagtgtc aagcgtggag ttcggtgggt cttctgatga gacggatacc  480
gagggcaccg aagtgtctgg acgcaaaggc ctcaaggtcg aacgtgatga ttccgtagcg  540
aagtctaaag ccagcggcaa tggctccgct cgtatgaaat cttccatccg taagtccgca  600
tttggaggta agaagtgatg tctgagttca catgtgtgga ggctaagagt cgcttccgtg  660
caatccggtg gactgtggaa caccttgggt tgcctaaagg attcgaagga cactttgtgg  720
gctacagcct ctacgtagac gaagtgatgg acatgtctgg ttgccgtgaa gagtacattc  780
tggactctac cggaaaacat gtagcgtact tcgcgtagcg cgtaagctgt gcattcacc  840
acaaaggaga cattctggat gtaacgtccg ttgtcattaa tcctgaggca gactctaagg  900
gcttacagcg attcctagcg aaacgcttta agtaccttgc ggaactccac gattgcgatt  960
gggtgtctcg ttgtaagcat gaaggcgaga caatgcgtgt atactttaag gaggtataag  1020
ttatggtgtaa gaaagttaag aaggccgtga cagaaagtcac caagtccgtt aagaaagtcg  1080
ttaaggaagg ggctcgtccg gttaaacagg ttgctggcgg tctagctggt ctggctggtg  1140
gtactggtga agcacagatg gtggaagtac cacaagctgc cgcacagatt gttgacgtac  1200
ctgagaaaga ggtttccact gaggacgaag cacagacaga aagcggacgc aagaaagctc  1260
gtgctgcgg taagaaatcc ttgagtgtag cccgtagctc cggtggcgtg atcaacattt  1320
aatcaggagg ttatcgtgga agactgcatt gaatgaccg gaggtgtcaa ctctaagggt  1380
tatggtcgta agtgggttaa tgtaaactt gtgactccac ataggcacat ctatgaggag  1440
acatatggtc cagttccaac aggaattgtg gtgatgcata tctgcgataa ccctaggtgc  1500
tataacataa agcaccttac gcttggaact ccaaaggata attccgagga catggttacc  1560
aaaggtagac aggctaaagg agaggaacta agcaagaaac ttacagagtc agacgttctc  1620
gctatacgct cttcaacctt aagccaccgc tccttaggag aactgtatgg agtcagtcaa  1680
tcaaccataa cgcgaatact acagcgtaag acatggagac acatttaatg gctgagaaac  1740
gaacaggact tgcggaggat ggcgcaaagt ctgtctatga gcgtttaaag aacgaccgtg  1800
ctccctatga gacacgcgct cagaattgcg ctcaatatac catccatca ttgttccta   1860
aggactccga taacgcctct acagattatc aaactccgtg gcaagccgtg ggcgctcgtg  1920
gtctgaacaa tctagcctct aagctcatgc tggctctatt ccctatgcag acttggatgc  1980
gacttactat atctgaatat gaagcaaagc agttactgag cgaccccgat ggactcgcta  2040
aggtcgatga gggcctctcg atggtagagc gtatcatcat gaactacatt gagtctaaca  2100
gttaccgcgt gactctcttt gaggctctca acagttagt cgtagctggt aacgtcctgc  2160
tgtacctacc ggaaccggaa gggtcaaact ataatcccat gaagctgtac cgattgtctt  2220
cttatgtggt ccaacgagac gcattcggca acgttctgca aatggtgact cgtgaccaga  2280
tagcttttgg tgctctccct gaggacatcc gtaaggctgt agaaggtcaa ggtggtgaca  2340
agaaagctga tgagacaatc gacgtgtaca ctcacatcta tctggatgag gactcaggtg  2400
aataccttccg atacgaagag gtcgaggtga tggaagtcca aggctccgat gggacttatc  2460
ctaaagaggc ttgcccatac atcccgattc ggatggtcag actagatggt gaatcctacg  2520
gtcgttcgta cattgaggaa tacttaggtg acttacggtc ccttgaaaat ctccaagagg  2580
ctatcgtcaa gatgtccatg attagctcta aggttatcgg cttagtgaat cctgctggta  2640
tcacccagcc acgccgactg accaaagctc agactggtga cttcgttact ggtcgtccag  2700
aagacatctc gttcctccaa ctggagaagc aagcagactt tactgtagct aaagccgtaa  2760
gtgacgctat cgaggctcgc ctttcgtttg cctttatgtt gaactctgcg gttcagcgta  2820
caggtgaacg tgtgaccgcc gaagagattc ggtatgtagc ttctgaactt gaagatactt  2880
taggtggtgt ctactcatc cttttctcaag aattacaatt gcctctggta cgagtgctct  2940
tgaagcaact acaagccacg caacagattc tgagttacc taaggaagcc gtagagccaa  3000
ccattagtac aggtctggaa gcaattggtc gaggacaaga ccttgataag ctggagcggt  3060
gtgtcactgc gtgggctgca ctggcacctta tgcgggacga ccctgatatt aaccttgcga  3120
tgattaagtt acgtattgcc aacgctatcg gtattgacac ttctggtatt ctactcaccg  3180
aagaacagaa gcaacagaag atgggcccaac agtctatgca aatgggtatg gataatggtg  3240
```

```
ctgctgcgct ggctcaaggt atggctgcac aagctacagc ttcacctgag gctatggctg  3300
ctgccgctga ttccgtaggt ttacagccgg gaatttaata cgactcacta tagggagacc  3360
tcatctttga aatgagcgat gacaagaggt tggagtcctc ggtcttcctg tagttcaact  3420
ttaaggagac aataataatg gctgaatcta atgcagacgt atatgcatct tttggcgtga  3480
actccgctgt gatgtctggt ggttccgttg aggaacatga gcagaacatg ctggctcttg  3540
atgttgctgc ccgtgatggc gatgatgcaa tcgagttagc gtcagacgaa gtggaaacag  3600
aacgtgacct gtatgacaac tctgacccgt tcggtcaaga ggatgacgaa ggccgcattc  3660
aggttcgtat cggtgatggc tctgagccga ccgatgtgga cactggagaa gaaggcgttg  3720
agggcaccga aggttccgaa gagtttaccc cactgggcga gactccagaa gaactggtag  3780
ctgcctctga gcaacttggt gagcacgaag agggcttcca agagatgatt aacattgctg  3840
ctgagcgtgg catgagtgtc gagaccattg aggctatcca gcgtgagtac gaggagaacg  3900
aagagttgtc cgccgagtcc tacgctaagc tggctgaaat tggctacacg aaggctttca  3960
ttgactcgta tatccgtggt caagaagctc tggtggagca gtacgtaaac agtgtcattg  4020
agtacgctgg tggtcgtgaa cgttttgatg cactgtataa ccaccttgag acgcacaacc  4080
ctgaggctgc acagtcgctg gataatgcgt tgaccaatcg tgacttagcg accgttaagg  4140
ctatcatcaa cttggctggt gagtctcgcg ctaaggcgtt cggtcgtaag ccaactcgta  4200
gtgtgactaa tcgtgctatt ccggctaaac ctcaggctac caagcgtgaa ggctttgcgg  4260
accgtagcga gatgattaaa gctatgagtg accctcggta tcgcacagat gccaactatc  4320
gtcgtcaagt cgaacagaaa gtaatcgatt cgaacttctg atagacttcg aaattaatac  4380
gactcactat agggagacca caacggtttc cctctagaaa taattttgtt taactttaag  4440
aaggagatat acatatggct agcatgactg gtggacagca aatgggtact aaccaaggta  4500
aaggtgtagt tgctgctgga gataaactgg cgttgttctt gaaggtattt ggcggtgaag  4560
tcctgactgc gttcgctcgt acctccgtga ccacttctcg ccacatggta cgttccatct  4620
ccagcggtaa atccgctcag ttccctgttc tgggtcgcac tcaggcagcg tatctggctc  4680
cgggcgagaa cctcgacgat aaacgtaagg acatcaaaca caccgagaag gtaatcacca  4740
ttgacgtct cctgacggct gacgttctga tttatgatat tgaggacgcg atgaaccact  4800
acgacgttcg ctctgagtat acctctcagt tgggtgaatc tctggcgatg gctgcggatg  4860
gtgcggttct ggctgagatt gccggtcgt gtaacgtgga aagcaaatat aatgagaaca  4920
tcgagggctt aggtactgct accgtaattg agaccactca gaacaaggcc gcacttaccg  4980
accaagttgc gctgggtaag gagattattg cggctctgac taaggctcgt ggcgctctga  5040
ccaagaacta tgttccggct gctgaccgtg tgttctactg tgacccagat agctactctg  5100
cgattctggc agcactgatg ccgaacgcag caaactacgc tgctctgatt gaccctgaga  5160
agggttctat ccgcaacgtt atgggctttg aggttgtaga agttccgcac ctcaccgctg  5220
gtggtgctgc taccgctcgt gagggcacta ctggtcagaa gcacgtcttc cctgccaata  5280
aaggtgaggg taatgtcaag gttgctaagg acaacgttat cggcctgttc atgcaccgct  5340
ctgcggtagg tactgttaag ctgcgtgact ggctctggaa gcgcgctcgc cgtgctaact  5400
tccaagcgga ccagattatc gctaagtacg caatgggcca cggtggtctt cgcccagaag  5460
ctgctggtgc agtggttttc aaagtggagt aatgctgggg gtggcctcaa cggtcgctgc  5520
tagtcccgaa gaggcgagtg ttacttcaac agaagaaacc ttaacgccag cacaggaggc  5580
cgcacgcacc cgcgctgcta acaaagcccg aaaggaagct gagttggctg ctgccaccgc  5640
tgagcaataa ctagcataac cccttggggc ctctaaacgg gtcttgaggg gttttttgct  5700
gaaaggagga actatatgcg ctcatacgat atgaacgttg agactgccgc tgagttatca  5760
gctgtgaacg acattctggc gtctatcggt gaacctcgtg tatcaacgct ggaaggtgac  5820
gctaacgcag atgcagcgaa cgctcggcgt attctcaaca agattaaccg acagattcaa  5880
tctcgtggat ggacgttcaa cattgaggaa ggcataacgc tactacctga tgtttactcc  5940
aacctgattg tatacagtga cgactattta tccctaatgt ctacttccgg tcaatccatc  6000
tacgttaacc gaggtggcta tgtgtatgac cgaacgagtc aatcagaccg ctttgactct  6060
ggtattactg tgaacattat tcgtctccgc gactacgatg agatgcctga gtgcttccgt  6120
tactggattg tcaccaaggc tttcccgtcag ttcaacaacc gattctttgg ggcaccggaa  6180
gtagagggtg tactccaaga agaggaagat gaggctagac gtctctgcat ggagtatgag  6240
atggactacg gtgggtacaa tatgctggat ggagatgcgt tcacttctgg tctactgact  6300
cgctaacatt aataaataag gaggctctaa tggcactcat tagccaatca atcaagaact  6360
tgaagggtgg tatcagccaa cagcctgaca tccttcgtta tccagaccaa gggtcacgcc  6420
aagttaacgg ttggtcttcg gagaccgagg gcctccaaaa gcgtccacct cttgttttct  6480
taaatacact tggagacaac ggtgcgttag gtcaagctcc gtacatccac ctgattaacc  6540
gagatgagca cgaacagtat tacgctgtgt tcactggtag cggaatccga tgtgttcgacc  6600
tttctggtaa cgagaagcaa gttaggtatc taacggttc caactacatc aagaccgcta  6660
atccacgtaa cgacctgcga atggttactg tagcagacta tacgttcatc gttaaccgta  6720
acgttgttgc acagaagaac acaaagtctg tcaacttacc gaattacaac cctaatcaag  6780
acggattgat taacgttcgt ggtggtcagt atggtaggga actaattgta cacattaacg  6840
gtaaagacgt tgcgaagtat aagataccag atggtagtca acctgaacac gtaaacaata  6900
cggatgccca atgttagct gaagagttag ccaagcagat gcgcactaac ttgtctgatt  6960
ggactgtaaa tgtagggcaa gggttcatcc atgtgaccgc acctagtggt caacagattg  7020
actccttcac gactaaagat ggctacgcag accagttgat taaccctgtg aacccactacg  7080
ctcagtcgtt ctctaagctg ccacctaatg ctcctaacgg ctacatggta aaaatcgtag  7140
gggacgcctc taagtctgcc gaccagtatt acgttcggta tgacgctgag cggaaagttt  7200
ggactgagac tttaggttgg aacactgagg accaagttct atgggaaacc atgccacacg  7260
ctcttgtgcg agccgctgac ggtaatttcg acttcaagtg gcttgagtgg tctcctaagt  7320
cttgtggtga cgttgacacc aacccttggc cttcttttgt tggttcaagt attaacgctg  7380
tgttcttctt ccgtaaccgc ttaggattcc ttagtggga gaacatcata ttgagtcgta  7440
cagccaaata cttcaacttc taccctgcgt ccattgcgaa cctagtgat gacgacccta  7500
tagacgtagc tgtgagtacc aaccgaatag caatccttaa gtacgccgtt ccgttctcag  7560
aagagttact catctggtcc gatgaagcac aattcgtcct gactgcctcg ggtactctca  7620
catctcaagtc ggttgagttg aacctaacga cccttgggc cgtacaggac cgagcgagac  7680
cttttgggat tgggcgtaat gtctactttg ctagtccgag gtccagcttc acgtccatcc  7740
acaggtacta cgctgtgcag gatgtcagtt ccgttaagaa tgctgaggac attacatcac  7800
acgttcctaa ctacatccct aatggtgtgt tcagtatttg cggaagtggt acggaaaact  7860
tctgttcggt actatctcac ggggacccta gtaaaatctt catgtacaaa ttcctgtacc  7920
tgaacgaaga gttaaggcaa cagtcgtggt ctcattggga ctttggggaa aacgtacagg  7980
```

```
ttctagcttg tcagagtatc agctcagata tgtatgtgat tcttcgcaat gagttcaata   8040
cgttcctagc tagaatctct ttcactaaga acgccattga cttacaggga gaaccctatc   8100
gtgcctttat ggacatgaag attcgataca cgattcctag tggaacatac aacgatgaca   8160
cattcactac ctctattcat attccaacaa tttatggtgc aaacttcggg aggggcaaaa   8220
tcactgtatt ggagcctgat ggtaagataa ccgtgtttga gcaacctacg gctgggtgga   8280
atagcgaccc ttggctgaga ctcagccgta acttggaggg acgcatggtg tacattgggt   8340
tcaacattaa cttcgtatat gagttctcta agttcctcat caagcagact gccgacgacg   8400
ggtctacctc cacggaagac attgggcgct tacagttacg ccgagcgtgg gttaactacg   8460
agaactctgg tacgtttgac attatgttg agaaccaatc gtctaactgg aagtacacaa    8520
tggctggtgc ccgattaggc tctaacactc tgagggctgg gagactgaac ttagggaccg   8580
gacaatatcg attccctgtg gttggtaacg ccaagttcaa cactgtatac atcttgtcag   8640
atgagactac ccctctgaac atcattgggt gtggctggga aggtaactac ttacggagaa   8700
gttccggtat ttaattaaat attctccctg tggtggctcg aaattaatac gactcactat   8760
agggagaaca atacgactac gggagggttt tcttatgatg actataagac tactaaaag   8820
tacagacttt gaggtattca ctccggctca ccatgacatt cttgaagcta aggctgctgg   8880
tattgagccg agtttccctg atgcttccga gtgtgtcacg ttgagcctct atgggttccc   8940
tctagctatc ggtggtaact gcggggacca gtgctggttc gttacgagcg accaagtgtg   9000
gcgacttagt ggaaaggcta agcgaaagtt ccgtaagtta atcatggagt atcgcgataa   9060
gatgcttgag aagtatgata ctcttttgaa ttacgtatgg gtaggcaata cgtcccacat   9120
tcgtttcctc aagactatcg gtgcggtatt ccatgaagag tacacacgag atggtcaatt   9180
tcagttattt acaatcacga aaggaggata accatatgtg ttgggcagcc gcaataccta   9240
tcgctatatc tggcgctcag gctatcagtg gtcagaaccg tcaggccaaa atgattgccg   9300
ctcagaccgc tgctggtcgt cgtcaagcta tggaaatcat gaggcagacg aacatccaga   9360
atgctgacct atcgttgcaa gctcgaagta aacttgagga agcgtccgcc gagttgacct   9420
cacagaacat gcagaaggtc caagctattg ggtctatccg agcggctatc ggagagagta   9480
tgcttgaagg ttcctcaatg gaccgcatta agcgagtcac agaaggacag ttcattcggg   9540
aagccaatat ggtaactgag aactatcgcc gtgactacca agcaatcttc cacacagcaac   9600
ttggtggtac tcaaagtgct gcaagtcaga ttgacgaaat ctataagagc gaacagaaac   9660
agaagagtaa gctacagatg gttctggacc cactggctat catgggtct tccgctgcga    9720
gtgcttacgc atccggtgcg ttcgactcta agtccacaac taaggcacct attgttgccg   9780
ctaaaggaac caagacgggg aggtaatgag ctatgagtaa aattgaatct gcccttcaag   9840
cggcacaacc gggactctct cggttacgtg gtggtgctgg aggtatgggc tatcgtgcag   9900
caaccactca ggccgaacag ccaaggtcaa gcctattgga caccattggt cggttcgcta   9960
aggctggtgc cgatatgtat accgctaagg aacaacgagc acgagaccta gctgatgaac   10020
gctctaacga gattatccgt aagctgaccc ctgagcaacg tcgaaagct ctcaacaacg    10080
ggacccttct gtatcaggat gacccatacg ctatggaagc actccgagtc aagactggtc   10140
gtaacgctgc gtatcttgtg gacgatgacg ttatcgagaa gataaagag ggtgtcttcc    10200
gtactcgcga agagatggaa gagtatcgcc atagtcgcct tcaagagggc gctaaggtat   10260
acgctggaca gttcggcatc gaccctgagg acgttgatta tcagcgtgt ttcaacgggg    10320
acattaccga gcgtaacatc tcgctgtatg gtgcgcatga taacttcttg agccagcaag   10380
ctcagaaggg cgctatcatg aacagccgag tggaactcaa cggtgtcctt caagaccctg   10440
atatgctgcg tcgtccagac tctgctgact tcttttgagaa gtatatcgac aacggtctgg   10500
ttactgccga aatccatct gatgctcaag ccacacagct tataagccaa ggcttcagtg    10560
acgcttctag ccgtgctggt ggtgctgact tcctgatgcg agtcggtgac aagaaggtaa   10620
cacttaacgg agccactacg acttaccgag agttgattgg tgaggaacag tggaacgctc   10680
tcatggtcac agcacaacgt tctcagtttg agactgacgc gaagctgaac gagcagtatc   10740
gcttgaagat taactctgcg ctgaaccaag aggaccaaag gacagcttgg gagatgcttc   10800
aaggtatcaa ggctgaacta gataaggtcc aacctgatga gcagatgaca ccacaacgtg   10860
agtggctaat ctccgcacag gaacaagttc agaatcagat gaacgcatgg acgaaagctc   10920
aggccaaggc tctggacgat tccatgaagt caatgaacaa acttgacgta atcgacaagc   10980
aattccagaa gcgaatcaac ggtgagtggg tctcaacgga ttttaaggat atgccagtca   11040
acgagaacac tggtgagttc aagcatagcg atatggttaa ctacgccaat aagaagctcg   11100
ctgagattga cagtatggac attcagacg gtgccaagga tgctatgaag ttgaagtacc    11160
ttcaagcgga ctctaaggac ggagcattcc gtacagccat cggaaccatg gtcactgacg   11220
ctggtcaaga gtggtctgcc gctgtgatta acggtaagtt accagaacga accccagcta   11280
tggatgctct gcgcagaatc cgcaatgctg accctcagtt gattgctgcg ctataccag    11340
accaagctga gctattcctg acgatggaca tgatgacaa gcagggtatt gaccctcagg    11400
ttattcttga tgccgaccga ctgactgtta agcggtccaa agagcaacgc tttgaggatg   11460
ataaagcatt cgagtctgca tcaaggctcc tgaaattgcc tgagattgcc cgtatgccag   11520
cgtcactgcg cgaatctgca cgtaagattt atgactccgt taagtatcgc tcggggaacg   11580
aaagcatggc tatggagcag atgaccaagt tccttaagga atctacctac acgttcactg   11640
gtgatgatgt tgacggtgat accgttggtg tgattcctaa gaatatgatg caggttaact   11700
ctgacccgaa atcatgggag caaggtcggg atattctgga ggaagcacgt aagggaatca   11760
ttgcgagcaa cccttggata accaataagc aactgaccat gtattctcaa ggtgactcca   11820
tttaccttat ggacaccaca ggtcaagtca gagtccgata cgacaaagag ttactctcga   11880
aggtctggag tgagaaccag aagaaactcg aagagaaagc tcgtgagaag gctctggctg   11940
atgtgaacaa gcgagcacct atagttgccg ctacgaaggc ccgtgaagct gctgctaaac   12000
gagtccgaga gaaacgtaaa cagactccta gttcatcta cggacgtaag gagtaactaa    12060
aggctacata aggaggccct aaatggataa gtacgataag aacgtaccaa gtgattatga   12120
tggtctgttc caaaaggctg ctgatgccaa cggggtctct tatgacccttt tacgtaaagt   12180
cgcttggaca gaatcacgat ttgtgcctac agcaaaatct aagactggac cattaggcat   12240
gatgcaattt accaaggcaa ccgctaaggc cctcggtctg cgagttaccg atggtccaga   12300
cgacgaccga ctgaaccctg agtagctat taatgctgcc gctaagcaac ttgcaggtct    12360
ggtagggaag tttgatgcg tgaactcaa agctgccctt gcgtacaacc aaggcgaggg    12420
acgcttgggt aatccacaac ttgaggcgta ctctaaggga gacttcgcat caatctctga   12480
ggagggacgt aactacatgc gtaaccttct ggatgttgct aagtcaccta ggctggaca    12540
gttgaaaact tttggtggca taaccccaaa gggtaaggc attccggctg aggtaggatt    12600
ggctggaatt ggtcacaagc agaaagtaac acaggaactt cctgagtcca caagtttga    12660
cgttaagggt atcgaacagg aggctacggc gaaaccattc gccaaggact tgggagac    12720
```

```
ccacggagaa acacttgacg agtacaacag tcgttcaacc ttcttcggat tcaaaaatgc  12780
tgccgaagct gaactctcca actcagtcgc tgggatggct ttccgtgctg gtcgtctcga  12840
taatggtttt gatgtgttta aagacaccat tacgccgact cgctggaact ctcacatctg  12900
gactccagag gagttagaga agattcgaac agaggttaag aaccctgcgt acatcaacgt  12960
tgtaactggt ggttcccctg agaacctcga tgacctcatt aaattggcta acgagaactt  13020
tgagaatgac tcccgcgctg ccgaggctgc cctaggtgcc aaactgagtg ctggtattat  13080
tggtgctggt gtggaccgcc ttagctatgt tcctatggtc ggtgtcactg gtaagggctt  13140
taagttaatc aataaggctc ttgtagttgg tgccgaaagt gctgctctga cgttgcatc   13200
cgaaggtctc cgtacctccg tagctggtgg tgacgcagac tatgcgggtg ctgccttagg  13260
tggctttgtg tttggcgcag gcatgtctgc aatcagtgac gctgtagctg ctggactgaa  13320
acgcagtaaa ccagaagctg agttcgacaa tgagttcatc ggtcctatga tgcgattgga  13380
agcccgtgag acagcacgaa acgccaactc tgcggacctc tctcggatga acactgaaga  13440
catgaagttt gaaggtgaac ataatggtgt cccttatgag gacttaccaa cagagagagg  13500
tgccgtggtg ttacatgatg gctccgttct aagtgcaagc aacccaatca acctaagac   13560
tctaaaagag ttctccgagg ttgaccctga gaaggctgcg cgaggaatca aactggctgg  13620
gttcaccgag attggcttga agaccttggg gtctgacgat gctgacatcc gtagagtggc  13680
tatcgaccte gttcgctctc ctactggtat gcagtctggt gcctcaggta agttcggtgc  13740
aacagcttct gacatccatg agagacttca tggtactgac cagcgtactt ataatgactt  13800
gtacaaagca atgtctgacg ctatgaaaga ccctgagttc tctactggcg gcgctaagat  13860
gtcccgtgaa gaaactcgat acactatcta ccgtagagcg gcactagcta ttgagcgtcc  13920
agaactacag aaggcactca ctccgtctga gagaatcgtt atggacatca ttaagcgtca  13980
ctttgacacc aagcgtgaac ttatggaaaa cccagcaata ttcggtaaca caaaggctgt  14040
gagtatcttc cctgagagtc gccacaaagg tacttacgtt cctcacgtat atgaccgtca  14100
tgccaaggcg ctgatgattc aacgctacg tgccgaaggt ttgcaggaag ggattgcccg   14160
ctcatggatg aacagctacg tctccagacc tgaggtcaag gccagagtcg atgagatgct  14220
taaggaatta cacggggtga aggaagtaac accagagatg gtagaaggt acgctatgga  14280
taaggcttat ggtatctccc actcagacca gttcaccaac agttccataa tagaagagaa  14340
cattgagggc ttagtaggta tcgagaataa ctcattcctt gaggcacgta acttgtttga  14400
ttcggaccta tccatcacta tgccagacgg acagcaattc tcagtgaatg acctaaggga  14460
cttcgatatg ttccgcatca tgccagcgta tgaccgccgt gtcaatggtg acatcgccat  14520
catgggtgtct actggtaaaa ccactaagga acttaaggat gagattttgg ctctcaaagc  14580
gaaagctgag ggagacggta agaagactgg cgaggtacat gctttaatgg ataccgttaa  14640
gattcttact ggtcgtgcta gacgcaatca ggacactgtg tgggaaacct cactgcgtgc  14700
catcaatgac ctagggttct tcgctaagaa cgcctacatg ggtgctcaga acattacgga  14760
gattgctggg atgattgtca tcggtaacgt tcgtgctcta gggcatggta tcccaattct  14820
gcgtgataca ctctacaagt ctaaaccagt ttcagctaag gaactcaagg aactccatgc  14880
gtctctgttc gggaaggagg tggaccagtt gattcggcct aaacgtgctg acattgtgca  14940
gcgcctaagg gaagcaactg ataccggacc tgccgtggcg aacatcgtag ggaccttgaa  15000
gtattcaaca caggaactgg ctgctcgctc tccgtggact aagctactga acggaaccac  15060
taactacctt ctggatgctg cgcgtcaagg tatgcttggg gatgttatta gtgccaccct  15120
aacaggtaag actacccgct gggagaaaga aggcttcctt cgtggtgcct ccgtaactcc  15180
tgagcagatg gctggcatca agtctctcat caaggaacat atggtacgcg gtgaggacgg  15240
gaagtttacc gttaaggaca agcaagcgtt ctctatggac ccagggcgta tggacttatg  15300
gagactggct gacaaggtag ctgatgaggc aatgctgcgt ccacataagg tgtccttaca  15360
ggattcccat gcgttcggag cactaggtaa gatggttatg cagtttaagt ctttcactat  15420
caagtccctt aactctaagt tcctgcgaac cttctatgat ggatacaaga caaccgagc   15480
gattgacgct gcgctgagca tcatcaccct tatgggtctc gctggtgttt tctatgctat  15540
ggctgcacac gtcaaagcat acgctctgcc taaggagaaa cgtaaggagt acttggagcg  15600
tgcactggac ccaaccatga ttgcccacgc tgcgttatct cgtagttctc aattgggtgc  15660
tcctttggct atggttgacc tagttggtgg tgttttaggg ttcgagtcct ccaagatggc  15720
tcgctctacg attctaccta aggacaccgt gaaggaacgt gacccaaaca aaccgtacac  15780
ctctagagag gtaatgggcg ctatgggttc aaaccttctg gaacagatgc cttcggctgc  15840
ctttgtggct aacgtaggg ctaccttaat gaatgctgct ggcgtggtca actcacctaa   15900
taaagcaacc gagcaggact tcatgactgg tcttatgaac tccacaaaag agttagtacc  15960
gaacgaccca ttgactcaac agcttgtgtt gaagatttat gaggcgaacg gtgttaactt  16020
gagggagcgt aggaaataat acgactcact atagggagag gcgaaataat cttctccctg  16080
tagtctctta gatttacttt aaggaggtca aatggctaac gtaattaaaa ccgttttgac  16140
ttaccagtta gatggctcca atcgtgattt taatatcccg tttgagtatc tagcccgtaa  16200
gttcgtaggt gtaactctta ttggtgtaga ccgaaaggtc cttacgatta atacagacta  16260
tcgctttgct acacgtacta ctatctctct gacaaaggct tggggtccag ccgatggcta  16320
cacgaccatc gagttacgtc gagtaacctc cactaccgac cgattggttg actttacgga  16380
tggttcaatc ctccgcgcgt atgaccttaa cgtcgctcag attcaaacga tgcacgtagc  16440
ggaagaggcc cgtgacctca ctacggatac tatcggtgtc aataacgatg gtcacttgga  16500
tgctcgtggt cgtcgaattg tgaacctagc gaacgccgtg gtgaccgcg atgctgttcc   16560
gtttggtcaa ctaaagacca tgaaccagaa ctcatggcaa gcacgtaatg aagccttaca  16620
gttccgtaat gaggctgaga cttttcagaaa ccaagcggag gcttaaggaa acgagtccag  16680
taccaacgct acgaacacaa agcagtggcg cgatgagacc aagggtttcc gagacgaagc  16740
caagcggttc aagaatacgg ctggtcaata cgctacatct gctgggaact ctgcttccgc  16800
tgcgcatcaa tctgaggtaa tctgccaca gcatccgcta actctgctca   16860
tttggcagaa cagcaagcag accgtgcgga acgtgaggca gacaagctgg aaaattacaa  16920
tggattggct ggtgcaattg ataaggtaga tggaaccaat gtgtactgga aaggaaatat  16980
tcacgctaac gggcgccttt acatgaccac aaacggtttt gactgtggcc agtatcaaca  17040
gttctttggt ggtgtcacta atcgttactc tgtcatggag tggggagatg agaacggatg  17100
gctgatgtat gttcaacgta gagttggac aacagcgata tccagttagt                17160
agtaaacgga cagatcatca cccaaggtgg agccatgacc ggtcagctaa aattgcagaa  17220
tgggcatgtt cttcaattag agtccgcatc cgacaaggcg cactatattc tatctaaaga  17280
tggtaacagg aataactggt acattggtag agggtcagat aacaacaatg actgtaccct  17340
ccactccatat gtacatggta cgaccttaac actcaagcag gactatgcag tagttaacaa  17400
acacttccac gtaggtcagg ccgttgtggc cactgatggt aatattcaag gtactaagtg  17460
```

```
gggaggtaaa tggctggatg cttacctacg tgacagcttc gttgcgaagt ccaaggcgtg    17520
gactcaggtg tggtctggta gtgctggcgg tggggtaagt gtgactgttt cacaggatct    17580
ccgcttccgc aatatctgga ttaagtgtgc caacaactct tggaacttct tccgtactgg    17640
ccccgatgga atctacttca tagcctctga tggtggatgg ttacgattcc aaatacactc    17700
caacggtctc ggattcaaga atattgcaga cagtcgttca gtacctaatg caatcatggt    17760
ggagaacgag taattggtaa atcacaagga aagacgtgta gtccacggat ggactctcaa    17820
ggaggtacaa gtatgtatgg aaaaggataa gagccttatt acattcttag agatgttgga    17880
cactgcgatg gctcagcgta tgcttgcgga ccttccggac catgagcgtc gctctccgca    17940
actctataat gctattaaca aactgttaga ccgccacaag ttccagattg gtaagttgca    18000
gccggatgtt cacatcttag gtggccttgc tggtgctctt gaagagtaca aagagaaagt    18060
cggtgataac ggtcttacgg atgatgatat ttacacatta cagtgatata ctcaaggcag    18120
atagtggtct ttatggatgt cattgtctat acgagatgct cctacgtgaa atctgaaagt    18180
taacgggagg cattgaaatc aagtaaggag gcaatgtgtc tactcaatcc aatcgtaatg    18240
cgctcgtagt ggcgcaactg aaaggagact tcgtggccgt cctattcgtc ttatggaagg    18300
cgctaaacct accggtgccc actaagtgtc agattgacat ggctaaggtg ctggcgaatg    18360
gagacaacaa gaagttcatc ttacaggctt tccgtggtat cggtaagtcg ttcatcacat    18420
gtgcgttcgt tgtgtggtcc ttatggagag accctcagtt gaagatactt atcgtatcag    18480
cctctaagga gcgtgcagac gctaactcca tctttattaa gaacatcatt gacctgctgc    18540
cattcctatc tgagttaaag ccaagacccg gacagcgtga ctcggtaatc agctttgatg    18600
taggcccagc caatcctgac cactctccta gtgtgaaatc agtaggtatc actggtcagt    18660
taactggtag ccgtgctgac attatcattg cggatgacgt tgagattccg tctaacagcg    18720
caactatggg tgcccgtgag aagctatgga ctctggttca ggagttcgct gcgttactta    18780
aaccgctgcc ttcctctcgc gttatctacc ttggtacacc tcagacagag atgactctct    18840
ataaggaact tgaggataac cgtgggtaca caaccattat ctggcctgct ctgtacccaa    18900
ggacacgtga agagaacctc tattactcac agcgtcttgc tcctatgtta cgcgctgagt    18960
acgatgagaa ccctgaggca cttgctggga ctccaacaga cccagtgcgc tttgaccgtg    19020
atgacctgcg cgagcgtgag ttggaatacg gtaaggctgg cttacgcta cagttcatgc    19080
ttaaccctaa ccttagtgat gccgagaagt acccgctgag gcttcgtgac gctatcgtag    19140
cggccttaga cttagagaag gccccaatgc attaccagtg gcttccgaac cgtcagaaca    19200
tcattgagga ccttcctaac gttggcctta agggtgataa cctgcatacg taccacgatt    19260
gttccaacaa ctcaggtcag taccaacaga agattctggt cattgaccct agtggtcgcg    19320
gtaaggacga aacaggttac gctgtgctgt acacactgaa cggttacatc taccttatgg    19380
aagctggagg tttccgtgat ggctactccg ataagaccct tgagttactc gctaagaagg    19440
caaagcaatg gggagtccag acggttgtct acgagagtca cttcggtgac ggtatgttcg    19500
gtaaggtatt cagtcctatc cttcttaaac accacaactg tgcgatggaa gagttcgtg    19560
cccgtggtat gaaagagatg cgtatttgcg atacccttga gccagtcatg cagactcacc    19620
gccttgtaat tcgtgatgag gtcattaggg ccgactacca gtccgctcgt gacgtagacg    19680
gtaagcatga cgttaagtac tcgttgttct accagatgac ccgtatcact cgtgagaaag    19740
gcgctctggc tcatgatgac cgattggatg ccctgccgtt aggcattgag tatctccgtg    19800
agtccatgca gttggattcc gttaagtag aaggcgaggt tttagcagat ttttagaag    19860
agcatatgat gcgcccaacc gtagcagcaa cccacattat cgaaatgagc gttggtggtg    19920
tggacgttta tagtgaagat gacgaaggct atggcaccag ctttatcgaa tggtaaggac    19980
caacataaag ggaggagact catgttccgc ttattgttga acctactgcg gcatagagtc    20040
acctaccgat ttcttgtggt actttgtgct gcccttgggt acgcatctct tactgggac    20100
ctcagttcac tggagtctgt cgtttgctct atactcactt gtagcgatta gggtcttcct    20160
gaccgactga tggctcaccg agggattcag cggtatgatt gcatcacacc acttcatccc    20220
tatagagtca agtcctaagg tatacccata aagagcctct aatggtctat cctaaggtct    20280
atacctaaag ataggccatc ctatcagtgt cacctaaaga gggtcttaga                20330

SEQ ID NO: 9          moltype = DNA   length = 3555
FEATURE               Location/Qualifiers
source                1..3555
                      mol_type = other DNA
                      note = Payload pJ23115-GFP T7 cos 2.0
                      organism = synthetic construct
SEQUENCE: 9
cctttaggga aatatgctaa gttttcaccg taacacgcca catcttgact atatatgtgt      60
agaaactgcc ggaaatcgtc gtggtattct gaccagagcg atgaaaacgt tcagtttgc     120
tcatggaaaa cggtgtaaca agggtgaaca ctatcccata tcaccagctc accgtctttc    180
attgccatac gaaactccgg atgtgcattc atcaggcggg caagaatgtg aataaaggcc    240
ggataaaact tgtgcttatt tttctttacg gttttttaaaa aggccgtaat atccagctga    300
acggtttggt tataggtgca ctgagcaact gactggaatg cctcaaaatg ttctttacga    360
tgccattgac ttatatcaac tgtagtatat ccagtgattt ttttctccat tttagcttcc    420
ttagcttgcg aaatctcgat aactcaaaaa atagtagtga tctttattca ttatggtgaa    480
agttgtctta cgtgcaacat tttcgcaaaa agttggcgct tgatttcagt gcaattatc    540
tcttcaaatg tagcacttta tagctagctc agcccttggt acaatgctag cgttttcatt    600
aaagaggaga aggaagcca tgagtaaagg tgaggaatta tttactggtg ttgttccgat    660
cttagttgaa ctggacggcg atgttaacgg tcataaattc agtgttcgtg gtgaaggtga    720
aggtgatgca accaacggta agctgaccct gaaattcatc tgcactactg gtaaattacc    780
agtaccgtgg cctactctgg tgactaccct gacctatggt gttcagtgtt tttctcgtta    840
ccctgaccac atgaagcaac atgatttctt caaatctgca atgccggaag ttatgtaca    900
ggagcgcacc atttctttca aagacgatgg cacgtataaa acccgtgcag aggttaaatt    960
tgaaggtgac actctggtga atcgtattga actgaaaggc attgatttca agaggacgg    1020
caatatttta ggccacaaca tggaatataa cttcaactgc cataacgttt gaagacgtt    1080
agacaaacaa aagaacggta tcaaagctaa cttcaaaatt cgccataacg ttgaagacgt    1140
tagcgtacag ctgcggatc attaccaaca gaacactccg attggagatg ctcctgttt    1200
actgccggat aaccactacc tgtccaccca gtctaaactg tcgaaggatc cgaacgaaaa    1260
gcgcgaccac atggtgttat tagagttcgt taccgctagt ggtatcacgc acggtatgga    1320
tgaactctac aaataagtca gttcacctg ttttacgtta aaacccgctt cggcgggttt    1380
```

```
ttacttttgg gtttagccga acgccatagt acatgtaggt cgagggtgaa gtacttgctg   1440
acttccttga ggaacacatg atgcgtccta cggttgctgc tacgcatatc attgagatgt   1500
ctgtgggagg agttgatgtg tactctgagg acgatgaggg ttacggtacg tctttcattg   1560
agtggtgatt tatgcattag gactgcatag ggatgcacta tagaccacgg atggtcagtt   1620
ctttaagtta ctgaaaagac acgataaatt aatacgactc actatagggg gaggagggac   1680
gaaaggttac tatatagata ctgaatgaat acttatagag tgcataaagt atgcataatg   1740
gtgtacctag agtgacctct aagaatggtg attatattgt attagtatca ccttaactta   1800
aggcgggatc gtcaccctca gcagcgaaag acagctgtcg gtcagagcgt cattgcgaag   1860
ctgagtgtga tcgatgccat cagcgaaggg cccaaactcc gagcgattaa gcgtttgctg   1920
gctgtcacgc ctgcctgttg cttgcttgga cttgcgatgt acgtgctcag ctgtctttcg   1980
ctgctgaggg tgacgatccc gcgagggcct atggagttcc tatagggtcc tttaaaatat   2040
accataaaaa tctgagtgac tatctcacag tgtacggacc taaagttccc ccatagggg    2100
tacctaaagc ccagccaatc acctaaagtc aaccttcggt tgaccttgag ggttccctaa   2160
gggttgggga tgacccttgg gtttgtcttt gggtgttgtc ttgagtgtct ctctgtgtcc   2220
ctatctgtta cagtctccta aagtatcctc ctaaagtcac ctcctaacgt agaaatattt   2280
tatctgatta ataagatgat cttcttgaga tcgttttggt ctgcgcgtaa tctcttgctc   2340
tgaaaacgaa aaaccgcct tgcagggcgg ttttcgaag gttctctgag ctaccaactc    2400
tttgaaccga ggtaactggc ttggaggagc gcagtcgcca aaacttgtcc tttcagttta   2460
gccttatccg gcgcatgact tcaagactaa ctcctctaaa tcaattacca gtggctgctg   2520
ccagtggtgc ttttgcatgt cttttccggg tggactcaag acgatagtta ccggataagg   2580
cgcagcggtc ggactgaacg gggggttcgt gcatacagtc cagcttggag cgaactgcct   2640
acccggaact gagtgtcagg cgtggaatga gacaaactcg gccgtaacag aggaatgaca   2700
ccggcaaacc gaaaggcagg aacaggagag cgcacgaggg agccgccagg gggaaacgcc   2760
tggtatcttt atagtcctgt caggtttcgc caccactgat ttgagcgtca gatttcgtga   2820
tgcttgtcag gggggcggag cctatggaaa acggctttg ccgcgaccct ctcacttccc    2880
tgttaagtat cttcctggca tcttccagga aatctccgcc ccgttcgtaa gccatttccg   2940
ctcgccacag tcgaacgacc gagcgtagcg agtcagtgag cgaggaagcg gaatatatcc   3000
tgtatcacat attctgctga cgcaccgatg cagccttttt tctcctgcca catgaagcac   3060
ttcacttaca ccctcatcag tgccaacata gtaagccagt atacactccg ctagcgcaga   3120
tgtccggcgg tgcttttgcc gttacgcact acttagtca gttccgcagt accgtcagta    3180
gctgaacagg agggacagtg ttgatatcgg gtagccaccag aagtctatag catgtgcata   3240
cctttggtcg aaaaaaaaag cccgcactgt caggtgcggg cttttttcag tgtttccttg   3300
ccggattacg ccccgccctg ccactcatcg cagtattgtt gtaattcatt aagcattctg   3360
ccgacatgga agccatcaca aacggcatga tgaacttgga tcgccagtgg cattaacacc   3420
ttgtcgcctt gcgtataata ttttcccata gtgaaaacgg gggcgaagaa gttgtccata   3480
tttgctacgt ttaaatcaaa actggtgaaa ctcacccagg gattggcact gacgaaaaac   3540
atattttcga taaac                                                    3555
```

SEQ ID NO: 10         moltype = DNA   length = 6594
FEATURE               Location/Qualifiers
source                1..6594
                      mol_type = other DNA
                      note = p1884 plasmid
                      organism = synthetic construct
SEQUENCE: 10

```
tcagatcctt ccgtatttag ccagtatgtt ctctagtgtg gttcgttgtt tttgcgtgag    60
ccatgagaac gaaccattga gatcatactt actttgatgt tcactcaaaa attttgcctc   120
aaaactggtg agctgaattt ttgcagttaa agcatcgtgt agtgttttc ttagtccgtt    180
acgtaggtag gaatctgatg taatggttgt tggtattttg tcaccattca tttttatctg   240
gttgttctca agttcggtta cgagatccat ttgtctatct agttcaactt ggaaaatcaa   300
cgtatcagtc gggcggcctc gcttatcaac caccaatttc atattgctgt aagtgtttaa   360
atctttactt attggtttca aaacccattg gttaagcctt ttaaactcat ggtagttatt   420
tcaagcatt aacatgaact taaattcatc aaggctaatc tctatatttg ccttgtgagt    480
tttcttttgt gttagttctt ttaataacca ctcataaatc ctcatagagt atttgttttc   540
aaaagactta acatgttcca gattatattt tatgaatttt tttaactgga aaagataagg   600
caatatctct tcactaaaaa ctaattctaa ttttttcgctt gagaacttgg catagtttgt   660
ccactggaaa atctcaaagc ctttaaccaa aggattcctg atttccacag ttctcgtcat   720
cagctctctg gttgctttag ctaatacacc ataagcattt ccctactga tgttcatcat    780
ctgagcgtat tggttataag tgaacgatac cgtccgttct ttccttgtag ggttttcaat   840
cgtgggggttg agtagtgcca cacagcataa aattgcttg gtttcatgct ccgttaagtc    900
atagcgacta atcgctagtt catttgcttt gaaaacaact aattcagaca tacatctcaa   960
ttggtctagg tgattttaat cactatacca attgagatgg gctagtcaat gataattact   1020
agtccttttc ctttgagttg tgggtatctg taaattctgc tagaccttg ctggaaaact    1080
tgtaaattct gctagaccct ctgtaaattc cgctagcct ttgtgtgttt ttttgtta     1140
tattcaagtg gttataattt atagaataaa gaaagaataa aaagaataga                1200
tcccagccct gtgtataact cactacttta gtcagttccg cagtattaca aaaggatgtc   1260
gcaaacgctg tttgctcctc tacaaaacag acccttaaaac cctaaaggct taagtagcac   1320
cctcgcaagc tcggttgcgg ccgcaatcgg gcaaatcgct gaatattcct tttgtctccg   1380
accatcaggc acctgagtcg ctgtcttttt cgtgacattc agttcgctgc gctcacgtct   1440
ctggcagtga atgggggtaa atggcactac aggcgccttt tatgggattca tgcaaggaaa   1500
ctacccataa tacaagaaaa gcccgtcacg ggcttctcag ggcgttttat ggcgggtctg   1560
ctatgtggtc ctatctgact ttttgctgtt cagcagttcc tgccctctga ttttccagtc   1620
tgaccacttc ggattatccc gtgacaggtc attcagactg gctaatgcac ccagtaaggc   1680
agcggatca tcaacgggt ctgacgctca gtggaacgaa aactcacgtt aagggatttt    1740
ggtcatgaga ttatcaaaaa ggatcttcac ctagatcctt taaattaaa aatgaagttt    1800
taaatcaatc taaagtatat atgagtaaac ttggtctgac agttacgttt ccacaaccaa   1860
ttaaccaatt ctgatttaga aaactcatcg agcatcaaa tgaaactgca atttattcat    1920
atcaggatta tcaataccat attttgaaa aagccgtttc tgtaatgaag gagaaaaactc    1980
accgaggcag ttccatagga tggcaagatc ctggtatcgg tctgcgattc cgactcgtcc   2040
```

```
aacatcaata caacctatta atttcccctc gtcaaaaata aggttatcaa gtgagaaatc   2100
accatgagtg acgactgaat ccggtgagaa tggcaaaagc ttatgcattt ctttccagac   2160
ttgttcaaca ggccagccat tacgctcgtc atcaaaatca ctcgcatcaa ccaaaccgtt   2220
attcattcgt gattgcgcct gagcgagacg aaatacgcga tcgctgttaa aaggacaatt   2280
acaaacagga atcgaatgca accggcgcag gaacactgcc agcgcatcaa caatattttc   2340
acctgaatca ggatattctt ctaatacctg gaatgctgtt ttcccgggga tcgcagtggt   2400
gagtaaccat gcatcatcag gagtacggat aaaatgcttg atggtcggaa gaggcataaa   2460
ttccgtcagc cagtttagtc tgaccatctc atctgtaaca tcattggcaa cgctacctt    2520
gccatgtttc agaaacaact ctggcgcatc gggcttccca tacaatcgat agattgtcgc   2580
acctgattgc ccgacattat cgcgagccca tttatacccca tataaatcag catccatgtt  2640
ggaatttaat cgcggcctcg agcaagacgt ttcccgttga atatggctca taacacccct   2700
tgtattactg tttatgtaag cagacagttt tattgttcat gatgatatat ttttatcttg   2760
tgcaatgtaa catcagagat tttgagacac aacgtggctt tccctgcagg atttcggagg   2820
cctgcgttat cccctgattc tgtgataac cgtattaccg cctttgagtg agctgatacc    2880
gctcgccgca gccgaacgcc gactagtgga ttttacggct agctcagtcc taggtacaat   2940
gctagcgaat tcattaaaga ggagaaaggt acccatggca cgtaccccga gccgtagcag   3000
cattggtagc ctgcgtagtc cgcatacccta taaagcaatt ctgaccagca ccattgaaat  3060
cctgaaagaa tgtggttata gcggtctgag cattgaaagc gttgcacgtc gtgccggtgc   3120
aagcaaaccg accattatc gttggtggac caataaagca gcactgattg ccgaagtgta    3180
tgaaaatgaa agcgaacagg tgcgtaaatt tccggatctg ggtagcttta aagccgatct   3240
ggatttttctg ctgcgtaatc tgtggaaagt ttggcgtgaa accatttgtg gtgaagcatt  3300
tcgttgtgtt attgcagaag cacagctgga ccctgacccag ctgacccagc tgaaagatca  3360
gtttatggaa cgtcgtcgtg agatgccgaa aaaactggtt gaaaatgcca ttagcaatgg   3420
tgaactgccg aaagatacca atcgtgaact gctgctggat atgatttttg gtttttgttg   3480
gtatcgcctg ctgaccgaac agctgaccgt tgaacaggat attgaagaat ttaccttcct   3540
gctaattaat ggtgtttgtc cgggtacaca gcgttaacta gggcccatac cccaattat    3600
tgaaggccgc taacgcggcc ttttttttgtt tctggtctgc ccgacgtacg gtgaatctga  3660
ttcgttacca attgacatga tacgaaacgt accgtatcgt taaggtatt actaactgga    3720
agaggcacta aatgaacacg attaacatcg ctaagaacga cttctctgac atcgaactgg   3780
ctgctatccc gttcaacact ctggctgacc attacggtga gcgtttagct cgcgaacagt   3840
tggcccttga gcatgagtct tacgagatgg gtgaagcacg cttccgcaag atgtttgagc   3900
gtcaacttaa agctggtgag gttgcggata acgctgccgc caagcctctc atcactaccc   3960
tactccctaa gatgattgca cgcatcaacg actggtttga ggaagtgaaa gctaagcgcg   4020
gcaagcgccc gacagccttc cagttcctgc aagaaatcaa gccggaagcc gtagcgtaca   4080
tcaccattaa gaccactctg gcttgcctaa ccagtgctga caatacaacc gttcaggctg   4140
tagcaagcgc aatcggtcgg gccattgagg acgaggctcg cttcggtcgt atccgtgacc   4200
ttgaagctaa gcacttcaag aaaaacgttg aggaacaact caacaagcgc gtagggcacg   4260
tctacaagaa agcatttatg caagttgtcg aggctgacat gctctctaag ggtactactg   4320
gtggcgaggc gtggtcttcg tggcataagg aagactctat tcatgtagga gtacgctgca   4380
tcgagatgct cattgagtca accggaatgg ttagcttaca ccgccaaaat gctggcgtag   4440
taggtcaaga ctctgagact atcgaactcg cacctgaata cgctgaggct atcgcaaccc   4500
gtgcaggtgc gctggctggc atctctccga tgttccaacc ttgcgtagtt cctcctaagc   4560
cgtggactgg cattactggt ggtggctatt gggctaacgg tcgtcgtcct ctggcgctgg   4620
tgcgtactca cagtaagaaa gcactgatgc gctacgaaga cgtttacatg cctgaggtgt   4680
acaaagcgat taacattgcg caaaacaccg catggaaaat caacaagaaa gtcctagcgg   4740
tcgccaacgt aatcaccaag tggaagcatt gtccggtcga ggacatccct gcgattgagc   4800
gtgaagaact cccgatgaaa ccggaagaca tcgacatgaa tcctgaggct ctcaccgcgt   4860
ggaaacgtgc tgccgctgct gtgtaccgca aggacaaggc tcgcaagtct cgccgtatca   4920
gccttgagtt catgcttgag caagccaata agtttgctaa ccataaggcc atctggttcc   4980
cttacaacat ggactggcgc ggtcgtgttt acgctgtgtc aatgttcaac ccgcaaggta   5040
acgatatgac caaaggactg cttacgctgg cgaaaggtaa accaatcggt aaggaaggtt   5100
actactggct gaaaatccac ggtgcaaact gtgcgggtgt cgataaggtt ccgttccctg   5160
agcgcatcaa gttcattgag gaaaaccacg agaacatcat ggcttgcgct aagtctccac   5220
tggagaacac ttggtgggct gagcaagatt ctccgttctg cttccttgcg ttctgctttg   5280
agtacgctgg gtacagcac cacggcctga gctataactg ctcccttcg ctggcgtttg    5340
acggtgtcttg ctctggcatc cagcacttct ccgcgatgct ccgagatgag gtaggtggtc  5400
gcgcggttaa cttgcttcct agtgaaaccg ttcaggacat ctacgggatt gttgctaaga   5460
aagtcaacga gattctacaa gcagacgcaa tcaatgggac cgataacgaa gtagttaccg   5520
tgaccgatga gaacactggt gaaatctctg agaaagtcaa gctgggcact aaggcactgg   5580
ctgtccaatg gctggcttac ggtgttactc gcagtgtgac taagcgttca gtcatgacgc   5640
tggcttacgg gtccaaagag ttcggcttcc gtcaacaagt gctggaagat accattcagc   5700
cagctattga ttccggcaag ggtctgatgt tcactcagcc gaatcaggct gctggataca   5760
tggctaagct gatttgggaa tctgtgagcg tgacggtggt agctgcggtt gaagcaatga   5820
actggcttaa gtctgctgct aagctgctgg ctgctgaggt caaagataag aagactggag   5880
agattcttcg caagcgttgc gctgtgcatt gggtaactcc tgatggtttc cctgtgtggc   5940
aggaatacaa gaagccatt cagacgcgct tgaacctgat gttcctcggt cagttccgct    6000
tacagcctac cattaacacc aacaaagata gcgagattga tgcacacaaa caggagtctg   6060
gtatcgctcc taactttgta cacagccaag acggtagcca ccttcgtaag actgtagtgt   6120
gggcacacga gaagtacgga atcgaatctt ttgcactgat tcacgactcc ttcggtacca   6180
ttccggctga cgctgcgaac ctgttcaaag cagtgcgcga aactatggtt gacacatatg   6240
agtcttgtga tgtactggct gatttctacg accagttcgc tgaccagttg cacgagtctc   6300
aattggacaa aatgccagca cttccggcta aggtaacttt gaacctccgt gacatcttag   6360
agtcggactt cgcgttcgcg gcggctaacg acgagaacta cgctgcggca gtgtaataat   6420
gacgcatcct cacgataata tccgggtagg acgaacaata aggccgcaaa tcgcggcctt   6480
ttttattgat aacaaaagga cagttttccc tttgatatgt aacggtgaac agttgttcta   6540
cttttgtttg ttagtcttga tgcttcactg atagatacaa gagccataag aacc          6594
SEQ ID NO: 11      moltype = DNA   length = 6594
FEATURE            Location/Qualifiers
```

| source | 1..6594 |
| --- | --- |
| | mol_type = other DNA |
| | note = p1885 plasmid |
| | organism = synthetic construct |

SEQUENCE: 11

```
tcagatcctt ccgtatttag ccagtatgtt ctctagtgtg gttcgttgtt tttgcgtgag    60
ccatgagaac gaaccattga gatcatactt actttgcatg tcactcaaaa attttgcctc   120
aaaactggtg agctgaattt ttgcagttaa agcatcgtgt agtgttttttc ttagtccgtt   180
acgtaggtag gaatctgatg taatggttgt tggtatttttg tcaccattca tttttatctg   240
gttgttctca agttcggtta cgagatccat ttgtctatct agttcaactt ggaaaatcaa   300
cgtatcagtc gggcggcctc gcttatcaac caccaatttc atattgctgt aagtgtttaa   360
atctttactt attggtttca aacccattg gttaagcctt ttaaactcat ggtagttatt   420
ttcaagcatt aacatgaact taaattcatc aaggctaatc tctatatttg ccttgtgagt   480
tttcttttgt gttagttctt ttaataacca ctcataaatc ctcatagagt atttgttttc   540
aaaagactta acatgttcca gattatattt tatgaatttt tttaactgga aaagataagg   600
caatatctct tcactaaaaa ctaattctaa tttttcgctt gagaacttgg catagtttgt   660
ccactggaaa atctcaaagc ctttaaccaa aggattcctg atttcacag ttctcgtcat   720
cagctctctg gttgctttag ctaatacacc ataagcattt tccctactga tgttcatcat   780
ctgagcgtat tggttataag tgaacgatac cgtccgttct ttccttgtag ggttttcaat   840
cgtgggggttg agtagtgcca cacagcataa aattagcttg gttcatgct ccgttaagtc   900
atagcgacta atcgctagtt catttgcttt gaaaacaact aattcagaca tacatctcaa   960
ttggtctagg tgattttaat cactatacca attgagatgg gctagtcaat gataattact  1020
agtcctttttc ctttgagttg tgggtatctg taaattctgc tagaccttttg ctggaaaact  1080
tgtaaattct gctagaccct ctgtaaattc cgctagacct ttgtgtgttt ttttttgttta  1140
tattcaagtg gttataattt atagaataaa gaaagaataa aaaagataa aagaataga  1200
tcccagccct gtgtataact cactacttta gtcagttccg cagtattaca aaaggatgtc  1260
gcaaacgctg tttgctcctc tacaaaacag accttaaaac cctaaaggct taagtagcac  1320
cctcgcaagc tcggttgcgg ccgcaatcgg gcaaatcgct gaatattcct tttgtctccg  1380
accatcaggc acctgagtcg ctgtctttttt cgtgacattc agttcgctgc gctcacggct  1440
ctggcagtga atgggggtaa atggcactac aggcgccttt tatggattca tgcaaggaaa  1500
ctacccataa tacaagaaaa gcccgtcacg ggcttctcag ggcgttttat ggcgggtctg  1560
ctatgtggtg ctatctgact ttttgctgtt cagcagttcc tgccctctga ttttccagtc  1620
tgaccacttc ggattatccc gtgacaggtc attcagactg gctaatgcac ccagtaaggc  1680
agcggtatca tcaacggggt ctgacgctca gtggaacgaa aactcacgtt aagggatttt  1740
ggtcatgaga ttatcaaaaa ggatcttcac ctagatcctt ttaaattaaa aatgaagttt  1800
taaatcaatc taaagtatat atgagtaaac ttggtctgac agttacgttt ccacaaccaa  1860
ttaaccaatt ctgatttaga aaactcatc gagcatcaaa tgaaactgca atttattcat  1920
atcaggatta tcaataccat attttttgaaa aagccgtttc tgtaatgaag gagaaaactc  1980
accgaggcag ttccatagga tggcaagatc ctggtatcgg tctgcgattc cgactcgtcc  2040
aacatcaata caacctatta atttcccctc gtcaaaaata aggttatcaa gtgagaaatc  2100
accatgagtg acgactgaat ccggtgagaa tggcaaaagc ttatgcattt ctttccagac  2160
ttgttcaaca ggccagccat tacgctcgtc atcaaaatca ctcgcatcaa ccaaaccgtt  2220
attcattcgt gattgcgcct gagcgagacg aaatacgcga tcgctgttaa aaggacaatt  2280
acaaacagga atcgaatgca accggcgcag gaacactgcc agcgcatcaa caatatttttc  2340
acctgaatca ggatattctt ctaatacctg gaatgctgtt ttcccgggga tcgcagtggt  2400
gagtaaccat gcatcatcag gagtacggat aaaatgcttg atggtcggaa gaggcataaa  2460
ttccgtcagc cagtttagtc tgaccatctc atctgtaaca tcattggcaa cgctacctttt  2520
gccatgtttc agaaacaact ctggcgcatc gggcttccca tacaatcgat agattgtcgc  2580
acctgattgc ccgacattat cgcgagccca tttatacccca tataatcag catccatgtt  2640
ggaatttaat cgcggcctcg agcaagacgt ttcccgttga atatggctca taacaccccct  2700
tgtattactg ttatgtaag cagacagttt tattgttcat gatgatatat tttttatcttg  2760
tgcaatgtaa catcagagat tttgagacac aacgtggctt tccctgcagg atttcggagg  2820
cctgcgttat cccctgattc tgtggataac cgtattaccg cctttgagtg agctgatacc  2880
gctcgccgca gccgaacgcc gactagtgga ttttacggct agctcagtcc taggtacaat  2940
gctagcgaat tcattaaaga ggagaaaggt acccatggca cgtaccccga gccgtagcag  3000
cattggtagc ctgcgtagtc cgcataccca taaagcaatt ctgaccagca ccattgaaat  3060
cctgaaagaa tgtggttata gcggtctgag cattgaaagc gttcacgtc gtgccggtgc  3120
aagcaaaccg accatttatc gttggtggac caataaagca gcactgattg ccgaagtgta  3180
tgaaaatgaa agcgaacagg tcgtaaatt tccggatctg ggtagcttta aagccgatct  3240
ggattttctg ctgcgtaatc tgtggaaagt ttggcgtgaa accatttgtg gtgaagcatt  3300
tcgttgtgtt attgcagaag cacagctgga ccctgcaacc ctgacccagc tgaaagatca  3360
gtttatggaa cgtcgtcgtg agatgccgaa aaaactggtt gaaatgcca ttagcaatgg  3420
tgaactgccg aaagatacca atcgtgaact gctgctggat atgattttttg gtttttgttg  3480
gtatccgctg ctgaccgaac agctgaccgt tgaacaggat attgaagaat ttaccttcct  3540
gctaattaat ggtgttttgtc cgggtacaca gcgttaacta gggccccatac ccccaattat  3600
tgaaggccgc taacgcggcc tttttttttgtt tctggtctgc ccgacgtacg gtgaatctga  3660
ttcgttacca attgacatga tacgaaacgt accgtatcgt taagtattttt actaactgga  3720
agaggcacta aatgaacacg attaacatcg ctaagaacga cttctctgac atcgaactgg  3780
ctgctatccc gttcaacact ctggctgacc attacggtga gcgtttagct cgcgaacagt  3840
tggcccttga gcatgagtct tacgagatgg tgaagcacg cttccgcaag atgtttgagc  3900
gtcaacttaa agctggtgag gttgcggata cgctgccgc caagcctctc atcactaccc  3960
tactccctaa gatgattgca cgcatcaacg actggtttga ggaagtgaaa gctaagcgcg  4020
gcaagcgccc gacagccttc cagttcctgc aagaaatcaa gccggaagcc gtagcgtaca  4080
tcaccactct gcttgccta ccagtgctga ataacaacc gtcaggctg  4140
tagcaagcgc aatcggtcgg gccattgagg acgaggctcg cttcgtcgt atccgtgacc  4200
ttgaagctaa gcacttcaag aaaaacgttg aggaacaact caacaagcgc gtagggcacg  4260
tctacaagaa agcatttatg caagttgtcg aggctgacat gctctctaag ggtctactcg  4320
gtggcgagc gtggtcttcg tggcataagg aagactctat tcatgtagga gtacgctgca  4380
tcgagatgct cattgagtca accggaatgg ttagcttaca ccgccaaaat gctggcgtag  4440
```

```
taggtcaaga ctctgagact atcgaactcg cacctgaata cgctgaggct atcgcaaccc    4500
gtgcaggtgc gctggctggc atctctccga tgttccaacc ttgcgtagtt cctcctaagc    4560
cgtggactgg cattactggt ggtggctatt gggctaacgg tcgtcgtcct ctggcgctgg    4620
tgcgtactca cagtaagaaa gcactgatgc gctacgaaga cgtttacatg cctgaggtgt    4680
acaaagcgat taacattgcg caaaacaccg catggaaaat caacaagaaa gtcctagcgg    4740
tcgccaacgt aatcaccaag tggaagcatt gtccggtcga ggacatccct gcgattgagc    4800
gtgaagaact cccgatgaaa ccggaagaca tcgacatgaa tcctgaggct ctcaccgcgt    4860
ggaaacgtgc tgccgctgct gtgtaccgca aggacaaggc tcgcaagtct cgccgtatca    4920
gccttgagtt catgcttgag caagccaata agtttgctaa ccataaggcc atctggttcc    4980
cttacaacat ggactggcgc ggtcgtgttt acgctgtgtc aatgttcaac ccgcaaggta    5040
acgtatatga caaaggactg cttacgctgg cgaaaggtaa accaatcggt aaggaaggtt    5100
actactggct gaaaatccac ggtgcaaact gtgcgggtgt cgataaggtt ccgttccctg    5160
agcgcatcaa gttcattgag gaaaaccacg agaacatcat ggcttgcgct aagtctccac    5220
tggagaacac ttggtgggct gagcaagatt ccccgttctg cttccttgcg ttctgcttta    5280
agtacgctgg ggtacagcac cacggcctga gctataactg ctcccttccg ctggcgtttg    5340
acgggtcttg ctctggcatc cagcacttct ccgcgatgct ccgagatgag gtaggtggtc    5400
gcgcggttaa cttgcttcct agtgaaaccg ttcaggacat ctacgggatt gttgctaaga    5460
aagtcaacga gattctacaa gcagacgcaa tcaatgggac gataacgaa tagttaccg     5520
tgaccgatga gaacactggt gaaatctctg agaagtcaa gctgggcact aaggcactgg    5580
ctggtcaatg gctggcttac ggtgttactg cagtgtgact aagcgttca gtcatgacgc    5640
tggcttacgg gtccaaagag ttcggcttcc gtcaacaagt gctggaagat accattcagc    5700
cagctattga ttccgcaagg gtctgatgt tcactcagcc aatcaggct gctggataca    5760
tggctaagct gatttgggaa tctgtgagcg tgacggtggt agctgcggtt gaagcaatga    5820
actggcttaa gtctgctgct aagctgctgg ctgctgaggt caaagataag aagactggag    5880
agattcttcg caagcgttgc gctgtgcatt gggtaactcc tgatgtttc cctgtgtggc    5940
aggaatacaa gaagcctatt cagacgcgct tgaacctgat gttcctcggt cagttccgct    6000
tacagcctac cattaacacc aacaaagata gcgagattga tgcacacaaa caggagtctg    6060
gtatcgctcc taactttgta cacagccaag acggtagcca ccttcgtaag actgtagtgt    6120
gggcacacga gaagtacgga atcgaatctt ttgcactgat tcacgactcc ttcggtacca    6180
ttccggctga cgctgcgaac ctgttcaaag cagtgcgcga aactatggct gacacatatg    6240
agtcttgtga tgtactggct gatttctacg accagttcgc tgaccagttg cacgagtctc    6300
aattggacaa aatgccagca cttccggcta aaggtaactt gaacctccgt gacatcttag    6360
agtcggactt cgccgttcgcg gcagcgaacg acgaaaacta tgccctggta gcctaataat    6420
gacgcatcct cacgataata tccgggtagg acgaacaata aggccgcaaa tcgcggcctt    6480
tttattgat aacaaaagga cagttttccc tttgatatgt aacggtgaac agttgttcta    6540
cttttgtttg ttagtcttga tgcttcactg atagatacaa gagccataag aacc          6594
SEQ ID NO: 12            moltype = DNA  length = 2682
FEATURE                  Location/Qualifiers
source                   1..2682
                         mol_type = other DNA
                         note = T7 RNA polymerase version AAV
                         organism = synthetic construct
SEQUENCE: 12
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcgataaa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactgga cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg tctactcgg tggcgaggcg    600
tggtcttcgt ggcataagga agactctatt catgtagaga tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc ccgttctgc ttccttgcgt tctgctttaa gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaa tagttaccg tgaccgatga    1800
aacactggtg aaatctctga gaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagatc cattcagcc agctattgat   1980
tccgcaaggg tctgatgtt cactcagccg aatcaggctg ctggatacat ggctaagctg   2040
atttgggaat ctgtgagcgt gacggtggta gctgcggttg aagcaatgaa ctggcttaag   2100
```

```
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct    2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgg cggctaacga cgagaactac gctgcggcag tg                     2682

SEQ ID NO: 13         moltype = AA  length = 894
FEATURE               Location/Qualifiers
source                1..894
                      mol_type = protein
                      note = T7 RNA polymerase version AAV
                      organism = synthetic construct
SEQUENCE: 13
MNTINIAKND FSDIELAAIP FNTLADHYGE RLAREQLALE HESYEMGEAR FRKMFERQLK    60
AGEVADNAAA KPLITTLLPK MIARINDWFE EVKAKRGKRP TAFQFLQEIK PEAVAYITIK   120
TTLACLTSAD NTTVQAVASA IGRAIEDEAR FGRIRDLEAK HFKKNVEEQL NKRVGHVYKK   180
AFMQVVEADM LSKGLLGGEA WSSWHKEDSI HVGVRCIEML IESTGMVSLH RQNAGVVGQD   240
SETIELAPEY AEAIATRAGA LAGISPMFQP CVVPPKPWTG ITGGGYWANG RRPLALVRTH   300
SKKALMRYED VYMPEVYKAI NIAQNTAWKI NKKVLAVANV ITKWKHCPVE DIPAIEREEL   360
PMKPEDIDMN PEALTAWKRA AAAVYRKDKA RKSRRISLEF MLEQANKFAN HKAIWFPYNM   420
DWRGRVYAVS MFNPQGNDMT KGLLTLAKGK PIGKEGYWL KIHGANCAGV DKVPFPERIK    480
FIEENHENIM ACAKSPLENT WWAEQDSPFC FLAFCFEYAG VQHHGLSYNC SLPLAFDGSC   540
SGIQHFSAML RDEVGGRAVN LLPSETVQDI YGIVAKKVNE ILQADAINGT DNEVVTVTDE   600
NTGEISEKVK LGTKALAGQW LAYGVTRSVT KRSVMTLAYG SKEFGFRQQV LEDTIQPAID   660
SGKGLMFTQP NQAAGYMAKL IWESVSVTVV AAVEAMNWLK SAAKLLAAEV KDKKTGEILR   720
KRCAVHWVTP DGFPVWQEYK KPIQTRLNLM FLGQFRLQPT INTNKDSEID AHKQESGIAP   780
NFVHSQDGSH LRKTVVWAHE KYGIESFALI HDSFGTIPAD AANLFKAVRE TMVDTYESCD   840
VLADFYDQFA DQLHESQLDK MPALPAKGNL NLRDILESDF AFAAANDENY AAAV         894

SEQ ID NO: 14         moltype = DNA  length = 2682
FEATURE               Location/Qualifiers
source                1..2682
                      mol_type = other DNA
                      note = T7 RNA polymerase version LVA
                      organism = synthetic construct
SEQUENCE: 14
atgaacacga ttaacatcgc taagaacgac ttctctgaca tcgaactggc tgctatcccg     60
ttcaacactc tggctgacca ttacggtgag cgtttagctc gcgaacagtt ggccttgga    120
catgagtctt acgagatggg tgaagcacgc ttccgcaaga tgtttgagcg tcaacttaaa   180
gctggtgagg ttgcggataa cgctgccgcc aagcctctca tcactaccct actccctaag   240
atgattgcac gcatcaacga ctggtttgag gaagtgaaag ctaagcgcgg caagcgcccg   300
acagccttcc agttcctgca agaaatcaag ccggaagccg tagcgtacat caccattaag   360
accactctgg cttgcctaac cagtgctgac aatacaaccg ttcaggctgt agcaagcgca   420
atcggtcggg ccattgagga cgaggctcgc ttcggtcgta tccgtgacct tgaagctaag   480
cacttcaaga aaaacgttga ggaacaactc aacaagcgcg tagggcacgt ctacaagaaa   540
gcatttatgc aagttgtcga ggctgacatg ctctctaagg gtctactcgg tggcgaggcg   600
tggtcttcgt ggcataagga agactctatt catgtaggag tacgctgcat cgagatgctc   660
attgagtcaa ccggaatggt tagcttacac cgccaaaatg ctggcgtagt aggtcaagac   720
tctgagacta tcgaactcgc acctgaatac gctgaggcta tcgcaacccg tgcaggtgcg   780
ctggctggca tctctccgat gttccaacct tgcgtagttc ctcctaagcc gtggactggc   840
attactggtg gtggctattg ggctaacggt cgtcgtcctc tggcgctggt gcgtactcac   900
agtaagaaag cactgatgcg ctacgaagac gtttacatgc ctgaggtgta caaagcgatt   960
aacattgcgc aaaacaccgc atggaaaatc aacaagaaag tcctagcggt cgccaacgta  1020
atcaccaagt ggaagcattg tccggtcgag gacatccctg cgattgagcg tgaagaactc  1080
ccgatgaaac cggaagacat cgacatgaat cctgaggctg tcaccgcgtg gaaacgtgct  1140
gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg gtcgtgttta cgctgtgtca atgttcaacc cgcaaggtaa cgatatgacc  1320
aaaggactgc ttacgctggc gaaaggtaaa ccaatcggta aggaagtta ctactggcg   1380
aaaatccacg gtgcaaactg tgcgggtgtc gataaggttc cgttccctga gcgcatcaag  1440
ttcattgagg aaaaccacga gaacatcatg gcttgcgcta agtctccact ggagaacact  1500
tggtgggctg agcaagattc tccgttctgc ttccttgcgt tctgctttga gtacgctggg  1560
gtacagcacc accgcctgag ctataactgc tcccttccgc tggcgttttga cgggtcttgc  1620
tctggcatcc agcacttctc cgcgatgctc cgagatgaga tagggtcg cgcggttaac  1680
ttgcttccta gtgaaaccgt tcaggacatc tacgggattg ttgctaagaa agtcaacgag  1740
attctacaag cagacgcaat caatgggacc gataacgaag tagttaccgt gaccgatgag  1800
aacactggtg aaatctctga aaagtcaag ctgggcacta aggcactggc tggtcaatgg  1860
ctggcttacg gtgttactcg cagtgtgact aagcgttcag tcatgacgct ggcttacggg  1920
tccaaagagt tcgggcttcg tcaacaagtg ctggaagata ccattcagcc agctattgat  1980
tccggcaagg gtctgatgtt cactcagccg aatcaggctg ctggatacat ggctaagctg  2040
atttgggaat ctgtgagcgt gacggtggta gctgcggttg aagcaatgaa ctggcttaag  2100
tctgctgcta agctgctggc tgctgaggtc aaagataaga agactggaga gattcttcgc  2160
aagcgttgcg ctgtgcattg ggtaactcct gatggtttcc ctgtgtggca ggaatacaag  2220
aagcctattc agacgcgctt gaacctgatg ttcctcggtc agttccgctt acagcctacc  2280
```

```
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgg cagcgaacga cgaaaactat gccctggtag cc                      2682
```

SEQ ID NO: 15             moltype = AA   length = 894
FEATURE                   Location/Qualifiers
source                    1..894
                          mol_type = protein
                          note = T7 RNA polymerase version LVA
                          organism = synthetic construct
SEQUENCE: 15
```
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLEAK HFKKNVEEQL NKRVGHVYKK    180
AFMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAAANDENY ALVA          894
```

SEQ ID NO: 16             moltype = DNA   length = 20
FEATURE                   Location/Qualifiers
source                    1..20
                          mol_type = other DNA
                          note = AD1334 primer
                          organism = synthetic construct
SEQUENCE: 16
ggacctccca ccattccaag                                                 20

SEQ ID NO: 17             moltype = DNA   length = 20
FEATURE                   Location/Qualifiers
source                    1..20
                          mol_type = other DNA
                          note = AD1335 primer
                          organism = synthetic construct
SEQUENCE: 17
acggcgatgt tcaggttctt                                                 20

SEQ ID NO: 18             moltype = DNA   length = 20
FEATURE                   Location/Qualifiers
source                    1..20
                          mol_type = other DNA
                          note = AD1336 primer
                          organism = synthetic construct
SEQUENCE: 18
ggcgaaagaa gacctggtca                                                 20

SEQ ID NO: 19             moltype = DNA   length = 20
FEATURE                   Location/Qualifiers
source                    1..20
                          mol_type = other DNA
                          note = AD1337 primer
                          organism = synthetic construct
SEQUENCE: 19
tagccggcga aatggatgtt                                                 20

SEQ ID NO: 20             moltype = DNA   length = 20
FEATURE                   Location/Qualifiers
source                    1..20
                          mol_type = other DNA
                          note = AD1322 primer
                          organism = synthetic construct
SEQUENCE: 20
catcagaccg cattcgcttg                                                 20

SEQ ID NO: 21             moltype = DNA   length = 20
FEATURE                   Location/Qualifiers
source                    1..20

```
                        mol_type = other DNA
                        note = AD1323 primer
                        organism = synthetic construct
SEQUENCE: 21
ggacgaagat gtggaagcca                                           20

SEQ ID NO: 22           moltype = DNA  length = 32767
FEATURE                 Location/Qualifiers
source                  1..32767
                        mol_type = genomic DNA
                        organism = unidentified
SEQUENCE: 22
agcgatatct cccgggtttt ttccacaggg tgtccgccca gggcgtcgct gtcgagctca   60
cagcgcacgc tgaacgcccg ccagcactcg aggcgatccg aacagcctcg ctccgagtgc  120
gtcgggcctg tgtggatcgc tcatgagttt cgtaacaagc ccctagccac agcccgattc  180
agatagaata ggagcatgga agggcagtgc ggatggtgcg gtcgggcatt cgatcgtgcc  240
cggacgggtc gcccgcgacg cttctgctcg gcccgctgtc gggtcgccgc gtcccggtgt  300
gcgatcccgc tggccatgag gtcccgcact gcgtgggtcg gctgcgacgg caagcgcccc  360
atcaccctgg ctggcgctcc ggcctcatcc acggacccgg gcacatggtc tggctggtcg  420
caggtgcgac gcgcacggc cggcgatggc ttcgggacca tgctcggtga cgggctgggg   480
tgctgggatc tcgaccactt cgacgatcag ggcgcccggg ccttcatcga ccggatcgat  540
aagccgatca tcttcgccga gcggtcggtg tcggggcatg gcttccacat cttcgtccgg  600
actgacgagg cccccggacg ccgcaccgga aacatcgagt tctactcacg ccatcggttc  660
atcagggtca caggagacca gttcgtctga agaaggggt gcgccatggc tgcacaggtc  720
agggccgtgg accccgatga gcgcccaccc gcccgcaagc gggccaagac catcacccag  780
gccgcgaagt ccggcactga ggttgaactg ttggaggcac tgcaggctcg cgtggcccgg  840
gccgtgcagg accgtgacac tccgccgcgc gatctggcag cgctgacgaa gcggctgatg  900
gacatcaccc gggagctcga gcggccccgg gtcaaggatc aggaggcggg atctgatggt  960
gccgtcaccg cagacgaaac atggcgaccg caagctctct gaggtcgcca agcacctgat 1020
ccttcctgaa gggatcgtct cgacgggctg gccggccgtg cgtgaccggt gtggcgagtg 1080
gggtgtggtc ttcgaccgtt ggcaggacgg catgggccgg gtgatcctgt cgaagcgcgg 1140
cagcggcctg ttcgccgctg gtgtgggcgg ggtcggcatg tcgatcccgc gccagaccgg 1200
caagaccttc accgtcggca tgatcatcct cgggctgtgc tcgctgagcg aggagctcac 1260
ggtgctgtgg acctcccacc attccaagac gaccaccaag actttcgagt cgctgcgggg 1320
catggcccag cgtaagaagg tcgccccgtt gatccgtcag gtccgaacag gaaacggtga 1380
ccagcagatc atttcagca acggttcgag gatctacttc ggtgcccggg aacagggctt   1440
cgggcgtggc ttcgacgacg tggacatcga gatctttgac gaggcgcaga tcctgtccga 1500
gcaggccctc tccgacatgg ttcccgcggc gaatgtgagc accaatccgc tgatcatctt 1560
catgggcacc ccgccgcgtc cctcggaccc gtcggaggcg ttcgcgaacc gccgcgccga 1620
agctctggcg ggcgacgccc cggacgccgc ctgatcgaa ttcggagcgg acgagcacgc  1680
cgacccgacc agccgcgccc aatggcgtaa ggcaaaccca tccttcctc accgcacgtc   1740
ggagacctcc attctgcgga tgaagaagat gctcgggccc gagtccttca aacgcgaggg 1800
cttgggcatc tgggatgaga cggcatcggt ccgcgcgatc ccagccgagg ggtggcgcgt 1860
cctgaccgtc aaggaaccac ccgccgacgc gatccagtcc ttcggcatca agttcgccat 1920
cgacgggagt gcggtcgccc tggcagccgc cctgaaaccc aaggacgggc cgatctatgt 1980
cgaaggaatc gagcagcgct cggcatccga cggcatcgaa tggctcgccg actacctgac 2040
gccctgtgg cgcaacacgg cccagatcgt catcgatgcc aagtccggcc cggtgcccct  2100
ggttgatgcg ctgcgccgtg gtggcgtggc tgcgaaggtg atcctcaccc cgagcgtcgc 2160
cgacgtgatc accgcccaca gcctgactct ggaggccatc aagaccggtg gactgtcgca 2220
cctggctgac ccggagctgg atcggcaggt ccgcatcgcc acgaagcgaa agatcggggc 2280
cgccgggggc ttcggctggc aggccccga aggcgacacc gtcgccctcc tcgacgcgat 2340
cacgcttgcc cactgggcgg ccctcaccac gaagcgacat cccggcagga aggcggtggc 2400
actggcatga gcctcctcgt caaccccat gcgtcgccgt ccttcttctc gtccccgtcc  2460
gtggtcggac tcgagcagag cgagcaggag ctcctgacg agctggtggc cctgtgggca  2520
cgcaagaagc cccgcaacgt gctgcgcggc ctgtaccttg acggcaagca gcagatcaag 2580
aacctgaaca tcgccgtgcc cgacgagatc gccgacagtc tccagatcgt ggtcggctgc 2640
cccgagaagg ccgtcttcgg gctatcgaac ctgtgcatgt gggatggcgt cgtcactccc 2700
acaggcgacg agaatcccct cgggcttgac gatctcctgt cggccaaccg cttcgacgtc 2760
gagatcaatg aaacgatcac ctcggcgatg cgaactccg tggccttcct gaccgtatcg  2820
gcgggcaacg tgtccatagg tgagccgccg gtggtgatca tgccgttctc cgccgaatgg 2880
gcctcagccc tgtgggaccg gcgcaccccg tcaatcaagg cgggactgac catcggcgac 2940
atcgactacc tgggccgccc caccagcctc tcgctcttca cccgcaccgc caccatcacc 3000
tgcgtggggt cccggctggg atggatgatc gaagatcgcg ccgagcacgg gctgaaccgc 3060
gtcccgatgg agccggtccc gttccgccca acccttcgg gcccctttcgg cacggtccgg  3120
atctcgcgcc aggtgatgac catcgtggac cgcgccatgc gcgcggccct gcgcatggac 3180
atctcctcag agctgttcac cgcacccggc ctgctcctca acggaatcac cccggagcag 3240
tgggcagaga tccagaagtg gacatggaag ctcggcacgg tgcgcggcct gactcgcgac 3300
gaggatggcg agaccgcatc ggtcgagacg atccccage agtcgatgga accgttcatc 3360
gcgcagctgc gcgagctggc gcaggaattc gcctcagcca catccatgcc gctgtctgca 3420
ttggggggtcg tccaagacaa cccctcctcg gctgacgcca tctacgcggc gaaagaagc   3480
ctggtcatcg aggccaccaa cgccaaccgg atcaccggct acgcgctatc ccgggtcttc 3540
caagacgcgt tgatgatgcg cgacggcctg accgagatgc ccgacgagct cggcggggtc 3600
gccgccaagt ggcgcaaccc ggcgatgccg tcgatcgtgt cccagtccga cgcgatggtc 3660
aagcagattt cccgcgatcc cggctggcc gctaccgacg tccgcttcga acagctcggc  3720
tattcggcgg ctgacatcgt gcggattcgt acccagatgc gccgagccca ggctgcggac 3780
ggcctgactt cgttgctggc caaaccagcc acgtcgtcaa cgcctggcgc ggagccctct 3840
cagtccgcaa gtcgacggga gccagctgca agcactccgc tgccggacct cgaagggggc 3900
cctggtgacc gatcgtgatg acctgaacca tttccacgag gccaatgacg cgatccagcg 3960
gcgcgcaatc aacgacctga acaagttttg ggcgcggcctt gccaagtcag acccgaaagc 4020
```

```
cgttcgcgca gccatggact tattcgtccc ccagctcatc gcctcctacg gagagttggc  4080
cgccgaagcc gctgcccgtt ggtatgagga actacggccc gccgacaaga agaacttcca  4140
ggccgaactc gcggaccctg tgtccgacga catcatcgag gcagatgtgg ctgaggccct  4200
ggggaccagc ggcgcctggg acaccgaggc ggtgcgaggg agcctggccg atgcgatcag  4260
gcgtcagatc ttctacatgg cgcgggcgac tgtcgcacgc aacatcgctc acgacccgaa  4320
gcgtccaagg tttgcacgag ttcctcgggg cgcggtcacg tgcgcgttct gcaccatgct  4380
cgcctccagg gggtgggtgt actacaccgc gaagactgcc gggatcacac gaccctggca  4440
tcgcaagtgc gactgccaga tcgtgcctga gtggaaacgc ggcaacatcc atttcgccgg  4500
ctacgacccct gacaagatgt tcgagcagta tgccgaatcg gtcgatgcgg tggggtcgag  4560
cttcgacacg aaggcaatcc tcgccgacat gcgccgacgc catcccgaag cgctgaccga  4620
cggggtcgtc aacatgagtg aaggacaggg tccggtgacc agtgattaga cagtcggtga  4680
acggatgact acgccgtcgg cgctgcgccg ccgcctggaa tggctactgg agaaccgtga  4740
acggcttctc aggagccatg gcgagtcgga ctttgccgag atgctggatg gcgcccgtca  4800
cgagccttgat gaggccgcg agcaggcagg cctggccgca gtgagggcca caatctgtag  4860
caagccccgt tccaccttcg ggtgggcggg gctttgtcat gcccgcatcc gggcatccaa  4920
ttccgtccca ccgcgagggt ggggcgtcga cctggtggcg cgatgccgcc gaactaatcc  4980
ctggaagggg aaactgctat gcacaagaag ctcatgccgt gggtccgtct catcgaggcg  5040
gtcgagactc ctgctggagc cgccccccacg cccgcgatcg atccgaagga tccggcgagcc  5100
aatcccacca ctgagccgaa gccggccgac gcgacgtcgg agaagcctct cggcgaggcg  5160
ggcaaggttg cgttggatcg cgagccgag gctcgccgca gcgccgacaa gcgcgccagt  5220
gagttggagg cccgtgtgca ccagctcgag gacgcgggca agaccgaggc ccagaagcag  5280
gccgacgaac tcaagcgcac ccagtccgag ctggagacgc tgaggggcga gaaggcaccgg  5340
ctggaggtgg cgtccgcgac gggcgtcccg gtcgatctgc tcgctggccc cggcgacgat  5400
ctggatgcct acgcgcaggc cctgaacgcc tggcgcgaca agcagtccga aaagccagcc  5460
gcccctgcgg tggacacccc ttcccccttcg ccgtccgggg tgaccggaca gcccgtgcag  5520
ccgaaccgga cggtcgatga actcatcgcg gccgccgaga agaacggtcg tctgccaacc  5580
gcgaagcaac tcaaattgat gaagctcgac gcactgcgtc ggacgtcctg atcagaaagg  5640
caccactatg ccgggcatta ccggacaggg caccaccctac aaccttccga actatgtggg  5700
ggagcttttt gcggcatctc ccgaagcacac cccgctgctg tcggcgatcg ggggactgac  5760
cggcggcgag tcggtcggcg cccgccagtt cgaatgcgag ggctacgacc tgcgcgacgc  5820
cgacggttcg cgccagcgcc tcgagggagc caacgccccc gacggtgagg agcgcacccg  5880
ctactccgcc tccaatgtgg tcgagatcca ccaggagtcg gtggaggtgt cctacaccaa  5940
gcaggccgcg aaccgtgagc gggctaccaa cggtgccgcc acggtccagc tggcgggctc  6000
cgtgctgccg gccgatgagc tcacctggca gatcgaccag cagctcaagc aggtcgccg  6060
cgatgtcgag aagtccttca tcgcggggcac ctaccagtcg cccaccgaca acgccaagcc  6120
gcgccgcacg cgtggcctgc tggaggcgac caccacgaac gtggccgcct cgacccacac  6180
cgcaaaggaa ctcaccgtgg aggagatcct cgacctgttc cagaaggtgt gggagaacgg  6240
cggcatccag gaagccgaga cccgccaccgt cattgtcggt gccgccctga agcggaccct  6300
gacgcgtccg ttcatcaccg acgtcaagta ccaggaagaa tcccgcaacg ttggcggtgt  6360
gaacctgcag accttcgaaa ccgacttcgg caaggcgaac atcatgctcg accgcttcat  6420
gccgagcgac accctcgtgg tcgcgtcgct ggaggacctg aagccggcct tcctcgacat  6480
ccccggcaag ggcacttct tcgccgagcc gctcgccaag accggtgcag ccgacaaggt  6540
gcagatttac ggcgaggtcg ggctgcagta cgggaaccag gccaagcacg gaaagctcac  6600
tgtcgcaccc gcaaccccg ccaagtaatc acgatcggt ttgaggttgc ctgatgaaag  6660
tcacctcgac catcccgaac ctgactgttc tcgacctgga catccagttc gttgacggtc  6720
aggccgatgt ggaccgcat ctcgccgaga ggctgcgtcg cctcgagcct ctcggcgtgc  6780
gggtccccac agccagccgc aagcccca cgcggtcggg cgtaaggcag ggggtcagcc  6840
atggtcgcac ctgatccgga actgccgttc gccaccgtct ccgatatgga gagccggtgc  6900
cgttctttgt ctaaggacga gcacacgcgg gccgaggcc ttctggacga tgcgagcggg  6960
ttgatcgttg atacctgccc gcgctgggaa caggcctcac cggccaccct gcggcgtgtg  7020
acgtgctctg tcgtgcgccg ggcgatggcc gcagacgatg aggacatcgg cgcaacctcg  7080
ctcatggaca cgacgggccc cttcaccact cagcgcgcct actcatcacc ggccgggat  7140
ctcttcttga ccaaggccga gaaggccgcg ctcggcgggg tcaccggcgc attcgagacg  7200
agccttctgg ggctgacatg aagcgctcat ggccgacacc cgtggaacgt ctccgcgagg  7260
gtccgccga gattgaccgt gacggtgatc cgattgccgg ctccggagtg atcaccaagg  7320
atcctctccc tgatgccctg ttcgcgccgg gcggctcgca gatctcgtc gcccccggcc  7380
tggcggcagt cgtggacgaa cccacccctct actggcgcgg atcagaagtg atcgatgtgg  7440
tggccaccga caaggtccgg atagccggcc gagtctggac ccctgaagga atcctgcgc  7500
gatggccgaa gggcgtcgtg ctcaagctca aggccagga ggcaaagaat cgtggctaat  7560
ttccgtttcg aacccaatac gaaggcgttc accgagtggg cgcagcgcga ctgcgacgg  7620
cacctgatcg ccggcatcac ggcctcgatg ggggccaagg cgggcgaggg ttttctcgacg  7680
atggtctcca acaatggcga ccgcaccgc ggttatctcg cgacgccctc cacgaagggc  7740
cgtatgcggc aggcgcaggg gcatgtcatc gagcgggtca tcggatcgag cggcgtgtga  7800
aaccgccga cctccacacg ctcgtcgccc accatctggc tgagctccac gacctgcgac  7860
tcgtctccac ccgccccgag ggagagacg cgccgtccaa gttcgttcgg atcatctcga  7920
ccggcggagc gggccgctat ggcgggtct tccagggcat ccagctgacg atcggctcct  7980
acgcgggatc ggcggcgacc gcccgtgatc tcgcgatgca ggtggacgag gccatgaatg  8040
ggctgccggt ctcgccgttg ccggtctcca aggtcaccgg caacacccg tcggacgacc  8100
ccgatcccga cactcagcag cccgccaca cggccaccta ccaactcacc aacccttatct  8160
cttaggagtc attcatggct gtcaattccg tcaacgtgca cgtcttcggg tccgatgacg  8220
acgtgctcta cctgggcccg tcaggtctga atctgggcaa catttcgctg gaaaccgcga  8280
tcccgaagga gatgatcgac accggctggc tcactgatga cggtgtgacc ctcggcatga  8340
aggactctgt caaggccatc cagggccacc agggccacgg gaatgtgctt cagttcatgg  8400
actcgtccgga taccacccctc gaggcgaccc tcatggacga tcagctgacg accttcctgt  8460
ggaacctcga cgcggacgct gaggacatcg acggggtcac caagatcacc gcggccagct  8520
cccgcaaggt cctcaacctg tgcgcgatct gggacacctt cgacacccag cacagcggca  8580
tccattggcg ctacgtcttc ccctcgctca ccctgggcga gcgcgatgac atcccctcca  8640
aggtgggcga agccagcgct tacaagtatt cgctgggtgt gctggagaag ttcttcgtct  8700
tcaccaacgc ggcagcgatg aaggccggtg gagcatccgc caagacggtg accggtgtga  8760
```

```
agatcaccac caccgacggt gcgaccgtgg gcctcccgtc gtcgctgaag gtggggagga  8820
aggtgtccct cgccgccgag atctcctaca gcgacgggac gaaggcggtc aagcagacca  8880
atgccgtggg cctcacctgg acgtcctcgg acaaggccaa ggccaccatc gatggcggcg  8940
tggtcaccgg agtctcggca ggcaaggccg acatcaccgc ctcgatcgac ggcaagactt  9000
ccgaagcgct gtcgctgacc atcaacaccg ccgcctgacc aaccctcaaa ccctccgccc  9060
cggtcgtcct ctcgcgccgg ggcggagcct tgccacaccc gcgagaggtc aactttctg   9120
cgagaggaaa ccatcatggc cgaggccaag aagatcagcg ccgccgagaa ggcgcgccgc  9180
gagacccagt ccgcgaagga caccggcacg atcaccgaca ccaccgtgca gatcggcgat  9240
atcgagttga ccgtgcccgc cgccgtcttc gaagacgact gggaattcca ggaggcgatc  9300
ctgatggcca acgatcccga tgccaccgac gaggatcggg ccagggcaag catgacgctg  9360
ttccgtcgtc tggtcggaaa ccgccaccgc gaagtgcttg accagctgcg cgacgagtcg  9420
gggcgtgtgc cggtgtctaa ggtcaccgag accgtcaaga aggtcatgga cgcggtcaac  9480
ccaaactgat gagcctcttc cagctcctcg ccacacattg gaggagctg gaggggact    9540
tccaagaggc ctaccgcgtc gacctgcggg acttgtgggt tggtcggctg agcccggcgc  9600
gctgctgggt gctgctgaca caactgccac ccgggtctcg gctctggcgg atgctcggcg  9660
gccccatggc gtggggcatg gtcgagcgcg ccgtccgtga agagggctgg cgactcgcct  9720
cccagaacgc tggtaaggaa ctgcctcggc cggagccgcc tgcgccggga tggcgcgaca  9780
agcaggacga cctgcgacgc cgcgaagagc gccgtcttgc ccgcttcatg caacgccacg  9840
cagaacgcaa caactgaaca gtgcaccgtc ccgggaggtt tccatggctc tagatctcgg  9900
taccgcctgg gtgcaggtgt ctccgtcctt caggggcttc gcctccacgg tgaacaaaga  9960
ggtcggttcg gcagtgggcg gggccttcaa gtctgcggcc aaggtcggca ccaccgcgat 10020
cgccacgatc ggtgcggccg tcggtgggct ggcgctcaag gcgcgcatcg accgcgccct 10080
gtcgatcgag caggcgcagg ccaagctgaa gggcctgggc cacgacgcag ggtcgatcac 10140
cgagatcatg aacgacgccc tcgcctcggt gaagggcacc gccttcggtc tgggcgatgc 10200
cgcgacggtt gccgcgtcga tgtcggctgc cggcgtcaag tcgggcgagc agatgaccgg 10260
tgtgctgaag acggttgccg acaccgccca gatttcgggg cgctcgctca ccgatatccg 10320
tgcgatcttc gggtcggtgg cggcccgcgg caagctgcag ggcgacgaca tgctgcagct 10380
catgagctcc ggcgtgccgg tgctccaatt cctttccgac cagctcggcg tcaccaccgc 10440
cgacgtgtcg gacatggtgt ccaaggggca gatcgacttc gccactttct ccgccgccat 10500
gcagaagggt cttggtggtg cggcactggc tggcggcgaa accttcaccg gtgccatggc 10560
caacgtccgc gccgccctgt cccggctggg tgaggctgcc gccaagcctg ccctggacgg 10620
gctgcgcaat gtcttcaacg cgctgatccc ggcgattgat gccgcacaa atgcgctcaa  10680
gcccatcgcc agcgccctgg cgaaccgaat ttcgcaagca gcagaggcgg cttccgcctc 10740
gatcgggcgc ctcaccggct ccctcacgag catcacgaat ctcaatacga ggatgctcag 10800
cgcggccttc tcatcgatgc tgccgatcat cggagcactg tcggggcagc ttggctcctt 10860
gcttggcggg atcccggtcg tcgggcaggc cttcgcaggg atcactgggc cggtgggatt 10920
ggctgccggc gtgctggtcg agatcgtggc ggcttcatcg tcgctgcgtc aggccctggg 10980
cacgctggtc ggggtcgtcg ggtctcagtt gtccggtgtg atgacgggca tcgtcgcggt 11040
gtttgccggc ttcaggtccg tgcttggtgc cgtcggtgac gttctggccc cgttcgtgga 11100
ccgtgcggcg gacgccgcca atgtggtcct gcccttgctg gggggtgcgc tgtcggctgc 11160
cggtggcatc ctgcagtctt ttgcgggttt catcgagcgc aaccatgtgg cgctctccat 11220
tcttgcgggt gcggtggttg cggccgcgac gagttgaag atctataccg gcgcgcaaga  11280
tcttgccaac ga cgaagctcgg gctcgcgaca acggtcctga agggcaagct 11340
gtcatcgatg gggcggcgt tcaagacgaa tccgttcggt gtcatcctca tggcgatctc 11400
ggcgctggtg ggggcgttct cgattgccta ccagtcctct gagacgttcc gcaacggtgt 11460
gcaggggatt ctcggctcgc tggcgccggt gttttcctcc ctgatgggga cgctgtcggg 11520
gctattccag caggtcgcgg gcgctgtcgg gccggtcgtg tcgtcgatcg tctcgacgct 11580
ggcgtcggtg ttctcggcga tcggtcccgt cctgtcgcag ctggccggca ccatcggatc 11640
tgtcttctcg gcgatcggtc ccgtcctggc gtcggtcttc gggtcgatcg ggtcggttct 11700
ggcgagtgtc ttctccgggg tgatgagtgt cgtggcgccg atgctcaccg cgttgcagcc 11760
gctgttcacg cagctgtcgg cttcggcggg gcagatcggt gccggcgttcg gtcctgttgg 11820
tcaggcgctg tcgtcgtcct tccagcaggt cggtgccgcg ctggcgccgc tgctgccgat 11880
gcttggtcag cagttcgggg cgatcctgtc tcagctggct gcggcccctgg ctccggtcat 11940
gggtcagttc ctggctgcgg ctgctcaggt gttgccgacg ttggcgcagg ccttcgggca 12000
ggtcgccggg gtgctgatcg ggtcgctggg tcaggctctg acccagatcg ctccgctgat 12060
aggccagctg gtgggggtgc tgatcggggtc gctgggtcag gctctgacgc agattgcccc 12120
gctggtgggc accctggtcg gggtggtcgc gcagctgttc gcccagctgg cccctttggt 12180
gggtcagctg ctggtgcagc ttgttccggt tgtcgcggga atccttgtgg cgatcgtgcc 12240
gatcgtcggg atgctgatta gtcagtcgt tccggtgatc gtcacgctgc tccaggtgat 12300
caccccgatt atcaccatgc taatcagcgc gctggtgccg gtgatccagg tcgtgaccca 12360
gctggtgctg gcgatcatcc aggcggtgat cccgttgatc tcggcgatcc tgccggcgat 12420
ctcggcactc atctcggcgc tgctgccggt gatcgtcatg atcatccagg tggtggcgca 12480
ggtgctgcag tggctggcgc cgctgatctc caccctgatc acggcactga ttccggtgat 12540
caccagcggca atccaggtgg tcatcacggt cgtgtcgaca atttggtcgg tgctcgggc   12600
ggtcattggc tggttccagt ccacggttgt gcccatcatc ggcaccgttg ttggtcgcat 12660
cgcgaacgct ttcggttggg tgcgcgaccg tatttccgat gcctggaact ggattaagga  12720
ccgcattgtc gccccggttg tcgagtggtt ccagtccacg gtggtgccga agttcgaggc 12780
ggtgcgcgac tccgtggtgc gggccttcga gacgctgaag gatggcgttg gtcgcgcctg  12840
ggatgcgttg aaggatctcg caaagaagcc ggtcgaattc gtcgtgaaca cggtggctgc 12900
cgggttggtg cggcctaca actgggtggc gacgaagttc ggtgcgacg aggtcaagga   12960
gcctcatgtc gagttcgcca acggcgggtt cgcgggacgt gaggccggct tcgcgtcgtc 13020
gccgatcctg tgggccgagg ccggcccgga agcctatatc ccgttggatc cggccaagcg 13080
gacacgctcg ctggggatct gggccaagac cgggcagatg ctcggcgctc tacccatggc 13140
tgacgcggga atcatcggga acatcattgg cgggatccgc aacgccgtcg cggcgatcgg 13200
caatttcatc aagtcaccga tcgagtggct catgggccgg gtccgggacc tgatcgatga 13260
tgtgggcagc tcaccgttcg cccagatcgc cgcgaagatc cccggcaaga tccgcgacga 13320
tatcggcgcc tgggtcaagg aacacatggc ctccatattc ggcggcggcg gttccggatc 13380
ggaagcgttc gacggctggt ggaacgcggc tgtcgccatc aatcctgata tggcccccctt  13440
caagcagatc gccgccacgg tcgcccagaa cgaatccgga ttcaacccga acgtcatgaa 13500
```

```
caactgggat tcgaacgctg cggcgggcac gccgtcgggt gggctgatgc agttcatcca    13560
gcccaccttc gaggcctaca agtgcccgg attcgacaat tggatgggtg cggtcgatca    13620
gatcctcgcc tggtggaagt acgtgaatgc ccgctatggc gggccgttca atattcccgg    13680
aattgcctcg ctggcgggtg gcggcggata tgtcggctac gccggaggca ccctgaacgc    13740
ggctgccggc acggcatggg tgggggagaa cggccccgag ctggtcgatt tcggtggcgg    13800
cgagtcggtc tacaaccgct cccagattga cggtctggag gatcggatcg ctgaccggac    13860
gatttccccgg ctgcagcagc tgagggtggc gctgatcgtg gacggacatc agatgggtca    13920
ggtcatcgac ggccgcatct ccatggctgg cgctgctgca cacggatcga ggtggtgaca    13980
tggcgatcat tgcgacgcgc cgcgactggc ctgaggctcc gcaacgcttc cagtccgcca    14040
atgggcggct ggtggcggag ctggaccctg accggtgcgg agtgcgactg cgcggcaccg    14100
acctggaggc gtggagcgtc accctcaccg tgatggcga ggtgatccac accggcgacc    14160
ccatggtcac accgggagga acaggaatcg cctacgacct gtctgcaccg ttggatgctg    14220
atgtcgtcta cgaggcgcac gcgggtgggg cggtgctcac gcaggtggcc gtccacaccg    14280
cggcttgcc tttcgagtgg gggatggtga ccccgctggc cgaccccgac aagggcctga    14340
tgctacggac cgtcgccgac accccacgc tgggcaggtc ggcacgccag aagctgtctg    14400
cggtgccctc atcgaggctg caggcaggtg gctgggacgt ccccaccgac gcggcacagg    14460
gatgacgtg gctcgcggga ttccccgacg cctccaaagc gctcgccgag cgcgacgcga    14520
tcatggaggc cctatcgctg gggcgtgtct acttccggcc cgaaacctcg atcggcttcc    14580
cgcccatgtg ggcactgccc ggcgacgtgt cagcgaccaa gcagggcgac gcctggacgg    14640
tgtcgtcac gctgacgccg atcaccgctc ccgcgaccgc cgacctgccc gcctgggcgc    14700
ccggcaacag ctatgcgcgt gtggcggcca cccggggggag cctcgccgag ctcgcccgca    14760
catccaagac attcctcgag ctagtggggt tctgatgatt gaagtatcca agcgatgggc    14820
ctcctcagta ggggccggtg cacgctggtc ggtgatggtc tcctggtcct ccgacggagg    14880
ccagacctgg catgacgtgg tgcccaccgc ctgctcggtg gacgagtcta ccggccagca    14940
ggtgcggtgc aagctgtcct gcaccctgcg caaggccgac gccgagggcc tgaccgtctt    15000
cggttgcagg gcgcgcgtct tcgtgtcgat gcatcacacc gacagctggcg aggagacgat    15060
ccagctcggc gaattccgca ttgacaccac ctctgacacc accctcgccg ggccgtccgg    15120
tgcgcaggtc gcggcagttc aggtgagcgg ttcgagctgg gagcagcagc tgatggactc    15180
gcggctggtt gagccgcgtg aggtgtcggg tgccgcgatc gatgtgctcg gcggcctgat    15240
ccgggaggtg ctccctgacg cagagatcgt ctttcgacggc gggatcgatc ggccgcaa    15300
cattccgcag acgtggtgg agcgtgaccg gtgggccttc attgacggct cgaattcgtc    15360
ggagacgtcg gtgtcgcgga tgctcggcgc ccaggtctcg accgacgcac ggggcgtgtg    15420
gcatgtggcc ccgcctccgg tgctggacgg acggcggcg tggacgatcg aggcggcaa    15480
gggcggtgcg ctcctgtcgg cggtggccag cgaggaccgc tccacgatcc gtaacgcgt    15540
catcgcgcgc ggcgagtcaa ccgataagag cgtgccggtg ttgggtccgg tgaccgtggc    15600
tgatcacaat gcgtggtcac caaccaacgt ggacactccg gtctccaggg gcggcttcgg    15660
cacagtcccg atcttctaca cttcgagcct tttcaccgac acgacgcagg tggaggcggc    15720
agcgaaggcg atgctgcagc cgcgcctggg cgtcaaacgc accctggacc tgacaacgct    15780
cttcgaccct gccaaacgcg ccggggatgt gggtgtggtg cagaccactg atggtccgat    15840
caccgtcgtg ctcgaatcag tgtcgtgcga cctggtggcg gcgtcgatga cctgccagac    15900
gcgcggcacg accggcaccg agctgatcac gaccgaaacc acgacaacca ctggggagaa    15960
gatctcatga gtgcaccaga cattgccctg caaggactga tcggggaaga caccgagcag    16020
gtggcgttcg cccaggtgct cggcgtgggc gtcgacgggc ggtcggtgcg tgtccagcgc    16080
ggcactctca cccacgaggt ccgccggctc gatagctaca agccttcagc gggagaccgg    16140
gcgctgctgt tacggctatc tggcggcgaa tgggtgctga tcggcgccct cgcctgacct    16200
tgacgaccta acctctgaca acctgaaaag gagccctcca tggcaaccgt ctatggccct    16260
gacaaattca ccgtcccgac tggtccggac gcaccggacg tgccgcgcac gatcatcacg    16320
ctgctggact cgatgcgtcc ctcgctgatc gggcatgcgt cttcgatcgc tgaccgcacc    16380
gcgaaatatg ggcggcatc cgcgtcgagc attcaggcgc cgaagggcac agtggtggtg    16440
tctgccgagc tgaacgcaat ttgggtgaaa acatcggaca cgctgatgga gtgggcgacg    16500
atcattcagc actcggatga ggtggcgacc gtgtcggtgg tgtccaccca gtccgaccag    16560
gtgaccacgg tccagaagtt cacgattccc gagtcgggca tctatgcgct gtatgcatcg    16620
atgaatgacc agaacggctt ggatgtcgat gggtcgatcc gtgagataca tgttctggtg    16680
aacgggacct ggaagttcgg tgggatcttc ccggcgagca agttctggct ctggtcgggt    16740
tcgcggacga cctttcctcaa taagggcgac acctatcaga tcgactttat gcaacgctca    16800
ggcgggggaga ggtccctgaa ggtaacgctg tcttatcaaa ggatttttgta atggcgactt    16860
gggattacgg gtatgcgccg gctgatgtgg tgaccgatgc ggccggggat gtgctggccg    16920
gcatcgaact gcgggtgtgg gacgccgagg tggcagggaa agccgtcgcc gtccagcagg    16980
accgtggcga cggatggaaa cccgcgtcaa gagtcctcac cgacgacgtg ggccgctacc    17040
gatttcgtgc gcaagcgggc ccacggtgt gggtggagga cgtgtcaggg cggcgctggc    17100
ggatggatgc ctggcagacg ctcggcacga tgatcgactc cgcacagagc gccaccgccg    17160
cggccgagtc ggccaactca atcgcccacg aagccatgtc agtcgcccaa caagccagaa    17220
cgtcggcgaa ggccgccgcc gactccgccg ccgccgtgca gggggttgcc ccgtccgacg    17280
cgaatgtgtc gccgatcatc accggcgggg cgaagactgc tgaggcggtg cggagcggtg    17340
cgctggctgc tttccgacg accgggccga cgatcttcac gcacttcttg acgcgcgacg    17400
aggccctgca tgtggcgatc tccaccgacg gtgtgacggt ggaggacacc ggcctgcggt    17460
ggaagccgaa gaacgacacc accctgggg agtgcttcgt gcgcgaccca tcggtgtgtt    17520
tctgaaggg tgcctattgg gtcgccttca cccgcccac gaaggggcgg ggtgacgttc    17580
tcgggacgac caagtcgttc ggactgatga agaccaggac ctggcggaac ttccaggagc    17640
tcccgcggt cgtgatgccg agtcaattc agcagacgtg ggccgcgcag tggttcatcg    17700
gctccgacgg ggtgccgcat atctttgtgg ccctcggcac caccaccacg cccaacgcgt    17760
acttcacccca gtatgagctg cggccgctcg atgacgcgat gacgtcctgg tcggacccgg    17820
tggtcatgtc tggactgcca gcgaattgca tcgatgtcgc ggtgatcgag gacgccggta    17880
ccttccacgt ctttcgctcc aaccagaaga cgtcaaccgt acgtcagtgg acgtcacggg    17940
ggctcaccgg cccctacacg aagctggcgg ccagcgactt tcccggtgcc ggtgtcgaag    18000
gaccccagcc agtgccgctg aagacggcg gctggcggat ctacgtcgac aattacgcgg    18060
agaccgactc gatctatttc gccgagagca cggacttgct gcattggtcg cgctcaggcc    18120
cggtcaccct gccgatgcgt cacgtcggcg cggtcggcgg ggactccttc ggtgcgctac    18180
gcacccgcga gctgtggcag ccgaacatcc cgggcatgag ggggatgggg gcacccttct    18240
```

```
ggggcgtacc cttcgccgcg gggaacgtgc tgaaggaatt cgcgcagatc gtgtccatgc   18300
gcaccgacgg cggcggcgaa atcgatctgc caaaggcggc cacgctgggc ttcaccggca   18360
tcgattacat ctcggcgacg gctgtcgcga acgtcgagat tctgcagatc gagcccgaca   18420
ttcgcgctgt cgacagcatg atccacgcg  tcgccctgcg aggaccgagt acgccgcaga   18480
tcgatacaga cgtgaaggtc gcctggcagg tgctcggctg gggcgatccg agcacgccat   18540
gagcagggac gctgacgtga ccaagcaggg atccttgcct cggcgggtct gggacatgct   18600
ggcagagccg aagtcggtga cggtcctcat gacgattgcc tacgcggcgc tcgtcgcgct   18660
cggcttctgg gcgatcgacg acgcctccac gatgggggtc cgcgacatga tgggcggcct   18720
gctcatcgct ggtggcgtgt gcgggctgat cggatgcccg tggggccagt ggtggatcga   18780
gcgcgccggt ctggtggcga tcggtgccgc tttcgcggta cacctgtctt tcgtcgtggc   18840
gatctccccg cccgacggac cgtgggaagt ggcctcggcg ctggggctgc tgcttctcgt   18900
ggcgacacgc tggatcagga tcaggacgct gccagccgac ccgacgctgc ctcggcccgg   18960
gcctccagag gcgggggatg aatgaatgac ttccagacct ggatcacagt gctgggcgga   19020
gccggattcc ttggcgcgct cgtcacgctc atcaagggg  tggttgggtg gcgcaccggc   19080
aagtccggcc gcaaaatgag ggccgcccac gacgccatcg actgctgaa  tctggcgggc   19140
ttgtgggctg aagcctactg gcacgctcgc ggctattgcc gcagccacca tgaatggacc   19200
agcgattacg ccgacggcta tccaccccca cccgacgaca ccaacacccc tgactgagcc   19260
ccgccttgtg cggggctttc tcattcctca aagacttgga gacattcatg gactggacca   19320
atctgaacgc tgacgtgacg aagctgatgg gcgtgcactt cacccccgga cgtgaaggca   19380
ggacgatcga caagatcgtg atccaccaca acggcggcaa cctgagcatc gaccagatct   19440
ggaatgtgtg gcagacccgt gaagcctccg cgcattatca ggtggaggcg ggtggccgta   19500
tcggccagct cgtcaacgat ttggacaccg cgtggcactg gactgacca  19560
tgacctcgat cggcatcgag catgccgacg actcgaccga cccgtggcat gtgtctgatg   19620
ctgccgtcga tgccgcgcg  cacctggtgg ctgcactgtg tcgcggctac aaccttggcc   19680
ggccggagtg gatgcgcaac gtcttcccgc actctcagtt cacgtccacg tcgtgcccgg   19740
cgtcgctgcc ccgggaccag ctcggcgact acatgggggg cgcacaagcc tacttcgatg   19800
gcgcgccggt ggctgcggtc catcagtcgg tccctgcccc cgcccccagcg cccagccgtc   19860
atgtggacct gcccgcgtgg aatctccccg agggcaactt ctacggcctc gtcagcggcg   19920
gaaacgactc ccacgcggc  ttctatcccg ccgagcgtcc cgctgtgagg gccatccagc   19980
tgtggctcat ccgtcacggc tacgccggcg cggtgcctga cagttgggcg gacggcatct   20040
acgagcagcc gaccgccgac gccgtgaccg ctttccagca cgccgagcgc cccaacagca   20100
cggaccggtg gggcgaggtc tgggccgacg acctggccac catggccgcc aacaactgac   20160
aaggagctga tgccaagtga tctggactct cgcattctgg aagggcgcag gcgagcgcgc   20220
catcaaaacc gccgcgcaga ccgcgcgtcg cctcatgggt acctcgacgc tcatcgaaca   20280
ggtgccgtgg actgtcgtcg cctccggcac cgccatgcct gtggtgctgt cgctcgatcac   20340
ctcgatcggc aacgccgact tcaccgccgg cgtcccccact accgccaagg ggctcgaggc   20400
gacgaccgtg ggcaagacgg acaccacgcc cgtcacgcca ccggcgcgcg tcgccgaaga   20460
ggtcccagcc ggcttcgtcc cggacacggc cccggatccc gtgccgaccg tctgacctga   20520
ggggtgacg  gcgacccctgc gccgatagc cactcaagca acctgagcga cacaagacca   20580
cccactctga ccttcgcggg tcggagtggg cggccttttt gcgtctcagg ggcgcagatg   20640
atgactcgtc gtctttaatt ctagcagtac gcgttcagcg tcgccagacc atgactttct   20700
cggctgcctg gagcggcgca ccttcgggc  cttttgaggta ggggggcgatg tagatgagct   20760
tgcgcagtcc atgcttgggg ccgtgcgcct ggtgggtccg gtgccgcggg accatgaacc   20820
gcacggtgag cttgtgcccg gttccgtcgt cgccggtcgg gaccacggtg cgcacgggac   20880
gcagatcgac cagggtgacg tgacggtcgg ggcgtggcgt gcggggcctg tgctcggtgc   20940
ccggggcctt gccggtgcgg gagtcgatcg tgcgccgctc ggcgacggtg ggggtgtcca   21000
tgagcacgct catcgccatc agcagcgacg cggacatgcc ggcctcgggg ctcagcgtgg   21060
catccagatc ggattcgggg cggatgagaa tcgacaggat ctcgacaagg gaccgtcca   21120
cgtcagcgaa gccgggcgga tagtcgccca gccgccccag cagctggatc atggtgcccc   21180
caccgggagc gggaagccag gcgatggccc acacgggagg attccctgc  caggtgcggc   21240
cgccggacag gtcgaaggtg cgcggcttgg gccccgacgg gggtttggcg aagcaggcca   21300
gtccggtcgg ggtgatcagc tggctcgggc tccactcggg cacgtccagg gcagcatcca   21360
gagcgagcgc cgccatctcg ccactcaccc agaacagcga cgcattaccg agccgctcgg   21420
cactccaccc gaagccggac atcggcagtg ccttgtcgcc catggcttca gccaccgcat   21480
cagggtgggt ggcggccagt tgctccaggc gctcgtcgag gtggcgggag tcccgcacaa   21540
agcggcgacg cagcccgggc actccgcggg gtgtccacgt ccagctctcc ggggctgcca   21600
tgtcaggcga cgactcgaat gcccaggctc cgccacgcct cggcggtgtg gtcgagcccc   21660
agatcccacc actgggtcag cgcgtgttcc atggcgatcg tggcgcaggc cgacagctgc   21720
gaggccttgt cgcgagccga cagcaggtcg gcgctcgg   tgccgtcggg cgtgaagtcc   21780
tgcagggcga tagtgatgtc tccgccggga agctgggaga ccgtgtcggc ggtcatgcct   21840
gcctgggtgg cgtcggcgat gatgcccagc tcgaccagcg tccagccggt gcgggccagg   21900
tcgatgcgct gggcctcgcg ccacaggtcc atctcggtgc gggtgcgtgc cgacaggctc   21960
ggggtgcgg  ccacatcggc tccgcgtcgg gccatccatg cggccatgtc gtcggtgggc   22020
cgccaggtga ttgtgctggc catgaagatc ctcctcggaa tggaaagtgg aaaggggagg   22080
ggccggagcc cctcccctga tggttgatgt ggtcagcgga tccaggtgaa gggctggtcg   22140
ccgatgatca agcggaccgc gaggtcgtag ggggcctcgt cctcgctgga ctcgacatcg   22200
accgcgtcga gctcgacacc gtcgcgggtg atggtgatgg tgtcggtcgt ggtggcccga   22260
ccgtcgatca ccgtcggagt gttgatgctg gtgaactctg ccggtcgatgcc gaccagtcga   22320
tggtcggcga ccgcttccca gaaggcgtcc tcgtcggctt cgatggagaa gtgcacgctg   22380
gaggcgatcg tcgcaccctc ggaggtctcc tcgctgtgga gcgtgaccag ctcgtcggcg   22440
atggcgtcga ggtcatactc ggcgcgggcg tcggcgactg cacctccggc ctcgatggca   22500
tcgatgatag aggcgatggc ctcgccgcgg gtggagaagg tagtgtcggt agaatcggtc   22560
atgatcctgt ccctttcagg gtcttggcct catcgggtg  cttccggtg  gggcctcttg   22620
ctcctt gtgacaccca ctgtcgtcac agtgttgaa  catgtcaagc cagtgggagg   22680
cctttcttta aagagatttc agcgggcgac cgcgccgcct cggacacctg gcccagtag   22740
ccctggaggg cgcactgaat caattggttg tcaattggtt gtcaaacctg acccgtcgac   22800
gggagtgag  gaggtggtac cggctgatct acgcctgaaa cagatggagc gggcgacggg   22860
aatcgaaccc gcgtgtctag cttgggaaac gggcatcgtg ctagtctggg gaccgccgaa   22920
atgacgattt caggcgtaaa ccggcctccg gtgtcttacc ctgatagctg ggtgatagca   22980
```

```
ccgaattggt tgtcagattg gttgtcagat cgccccagga ggatggtcgc attgtcacgc   23040
gcaagctacg gggacggcac ccagccgacc cggcgttccg acgggcgctg ggcagcatcg   23100
gcctatgacg gctggcaggc gaacgggaac cgccggcgcc gatgggtgta cggccgcacc   23160
caggccgaat gcaagcggaa gctgcgcgac ctgaagcggg agatctggtc agacacccag   23220
cagatgaatg tgaacccccag ggagaccgtc aagagctgga cggcatcatg gctggacgac   23280
taccgatcga ttgccagacc aacaaccttc gccaccgacg agtccatggt cgcgcaactgg   23340
atcgtcccag ccatcggtgc ccggcgcctg tccgaactga cagcgcgcga cgcctcgaag   23400
ctgcaacggg tctgccgaga cggggggactg tcggcgacaa cgtctcacta tgccgggctg   23460
ctcctgcggc gcatcctgaa ggctgcccgc gcgaacggct accgcatccc cgactccgtc   23520
atgctggccc ggatcccggg catcggcgca tccaacaggt ccgccctgag cgccatccag   23580
gcggccaacc tgctctcgac ggcaaacgca cgcgacacct ggccggagcc gcccagcctt   23640
cccgacctgc cctacgggc catctcgaag ctcgcaccag cagaagcgca gaagcgtgaa   23700
caactcaaga tggagcggtt ggaatggact gccgcccaaa acacggaccc ctccaggtgg   23760
gctgccgcac tcatgcaggg acttcggtca ggagaggctc gaggcctcac gtggggatcgt   23820
gtcgatctcg ataaggggac gatcaccatt gatcgtcaac tccagcgcat caagcccgac   23880
gcggcgcttc caccgggata caaggtcacc cggctgaagg cagccactg cctcgtggca   23940
ccgaaatctc gatcagggat ccgccgcgtc ccgatcgtcc cctggatggg ccaggctctc   24000
acccgctggc gcgacataca gggcgacagc cccttcggtc tcgtgtggcc gctgcccacc   24060
ggggcgccgc ccacgcgggt ccatgacctg cgggcatgcg gtggactcca gcgcgtcgcc   24120
ggggtccaca aggaggatgg aaacctctac gtcctccacg aagcacgaca ctccaccgtg   24180
tcgctgctgc ttgctgccgg ggtcccgaaa tcagtggtca tcgcgatcgt cgggcatgca   24240
agcttcgcgg cgaccgagca ctacgcccac accgacctcg aagcagcagc cgccgccctc   24300
atgaaggtgc aggaccgcct cgggctggag ctcgagagct gagcatgcaa agagccgccc   24360
accgaccaa tcgcggtctg gtgggcggct cttttgcgcc ttagagcacg tccgtcacca   24420
cgcctggaag ttgctgacga cgggtgcctg gtcggtgccg gtcacgtcgc agtgaaccgt   24480
gtatttggcg gagccgacgt cggccgcgat gttgacgttc cacagatcgt cggtcttatt   24540
gagggcggcg accgaatcga cggttgagtg gaccttgatc ttaagcgatg ggtattgctt   24600
gcccaaggca tccctcgcat aggtgccaca gccagaggtt gcgccggtca tggtgagtcc   24660
agtggtcgtt gcctcgacgg gtgtgggcgt ggcggacgca gtgggcgtct tcgtggccgt   24720
cggcgtcttc gccgctttcg gagtcttgga ggctgatgat gacgatcctg atgtctgggg   24780
atcgcacgcg gtcagcgcgc cggcgaggca gagtgacgca agcagggcga tgggacgag   24840
cgccttgcgg cgcatggtgt gggtcattcg ggttccttgg ttggttggtt cacatgctgt   24900
ccacagcaac ctagccgcgg aacctgcccg cctgggggtg atgagggcaa gtggcaagaa   24960
ttacatcgat gggattctcg ccacccctg aagagcgtgg gtggcgaggt ctacattcgt   25020
acgcatgtac gaaacatgga agcctctcgg acacggctcg atctctggtg gatcggccg   25080
cacaatggag tgcactgaag tagccggagtg ggcagagcgt cgtgcgcgtg ggtggggctc   25140
agcgctggta tcgcgcctgc gcggcgtcca tgaagacgcc gggttcaaag tcgagcacgc   25200
gagcaagctc aaagaggagt gcgacaggga gatcccgctt gccctgctcg atcctgatga   25260
tggtggattc gctgactcca gcgagtcgag cggtctcgac ctgggttaag cccttggcgg   25320
ctcgctcggc tcgaagctgg gcggcgatcg cggcgcgaat tgcatcacgc ttgctggcct   25380
ggttctggtc catgctgtca gcatagccgc cacattggac agttttccgg tccgattggg   25440
atgctcggca cttgcatctg gccatatggc atggcaagct gtccatatgg ccagttcaga   25500
catcaacctg gaggctgcgg acatgatctc cgccgccatc ggcggcaagcg acaccagtcg   25560
ggctgaagtc gccacgctga cgggaatccc gttgaccact ctgcgtcgga agctcatggg   25620
ccgatcgccc gtcaacatcg aggacatctt cctgatcgcc ggcgcgctcg ggataccgcc   25680
tgtgagtatc acgcccgacg ttctcacgag tgaagccgcc gcctagcccc caaacagaag   25740
aagccccgc ctgctgtcac agacgggagc caaccaaagg agtttccaat gagcattcta   25800
cccttcgact accacggtca ggaagtccgg ttcatcaccg atgagtccgg cgagcctcag   25860
gtcgtcgcgt cagatctcgc gaaggccctc aactatcgga acgcacccga catgatgcgt   25920
tccatcgacc tagaggaaag gggtacgcgt ccggtgcgta cccctggcgg tgagcaggag   25980
atgctcacgc tgaccgaggc cggcatgtac caagccatcc tgcaacgcca gacaggccgg   26040
atggtcgacg tcgcccaacg agccgctgtg aagcgattcc agcattgggt tacccacgag   26100
gtgattccct cgatccgcaa gcgcggcatg tatgccactc cggatgcagt cgaggcgatg   26160
ctggccgatc cggacgttat gatcggacg ctcaccgagc tgaaggccca gcgggccagg   26220
gtggccagc tgcagcccaa ggccgactac gttgacgcct tcgtggccga gaggatctg   26280
cggctcctgc gcaatgtggc caagtcgatc ggagtgcagg agggcgccat tcgcgacgcc   26340
ttgctcgcac acgagtggat ctacgcggag gagtcctcgc gctggtcgaa ctctcagggc   26400
tgcaaggtca tcgagcaccg ctattcaccg cgctctgaca aggcccgata ctttcgcccg   26460
gtcccgaatc accaggcacc ccgatttaag ggcgaggtaa tgcacaccct gaaggtcact   26520
ccggcagggg ctgaggcgat ctccaagatg gcaaagcgct ggggcctcgt cgtccaggag   26580
gtggcggcat gacctcgact ctcaccggca acatcatcgc cctgctgatc gtggccggcg   26640
tgatcgtcct cgcgatgggg gtgcgccgtg aaggtcgatg acttcgacga tgtgcgcccc   26700
ctgacgcaga aggacgtcgc cgagctactc cacgcaagcg tcggttacgt gcgctcctgc   26760
cgcctggcga gcaagccgaa aggccggtc ttcccgatgc ccggctggaa gaccgacgga   26820
aagcgctatc tgcttcccgc ttggcggttc cgcgagtggg tcgaaagctt gcccgatgcc   26880
tagcccgcgc cgcttcctaa tcctgatcgc cctgggtgcc gccgccgtcg tttcgcgcc   26940
ctcctcaatt caattctct tcatggccgc gcttgtgctc ggcctcacca tcacatgcct   27000
caaggagtcc aacatgcct gacacacagc cccgtcgtgc gcgtcgtcgc acgctgtccg   27060
agatcctcgc ccccgccgcg gcgcccagca gagcggaggc aacggcatga ggccaccagc   27120
cgttgaaacc cctgatgtga aggcgccggc cacgcctgct ggttcccggc tcttcaaggc   27180
tgtccgtcct gacggcttcg acttccacag cgggactgtc cggtggctcc ctgctgatgg   27240
cgcaccgatc ccggagggcg ggtggcttgt cgagcatccg catcctggtg aggttggcag   27300
ctgggatgca gcttttatc tgtcggcgtc gtcggtggag acggactgca caggtttcca   27360
gtggcctcca tcctcctgt ccgtggagcc cgtaggtgcc atgtgaccc ctcgcccga   27420
caaatttcct cgcaagcggg ccgcgcacgc gtggcgcgtc atagaagagc tcccgcatg   27480
gcggcttttc ggtccccagg ggcggacggt cctggacatc atcgagcaaa ccgctcatct   27540
gaccaaacgc cagatcgcgg ccctgaacag ggctctggac gccgcacggg acaccgtttg   27600
ggacgttgct tggaacgccg cgtggcacgc cgctcgggtc gctgctcggg tcgctgctcg   27660
gggcgctgct cggggcgctg ctcggtacgc cgcttgggac gctgctcggg gcgctgcttg   27720
```

```
gtacgccact tgggtcgctg ctcggggcgc tgctctcgga tggctcgtca aggacctgat  27780
ctccgtcgag gacttccgca ccctgacggg cccgtgggag caggtcatgg gtccgatcga  27840
ggtggcggca tgaaccgcac ctatttcaag gccgttaggg cggacggcac tgacttctac  27900
accggcaagg tccgctggct gcccgatgat ggcgcaccga tccctgccgg gggttgggtc  27960
gttgagcatc cgacgagcga acgcgtgggg gacgacgccc gcacctatct ctcggtttcg  28020
acggtggaaa ccgactcgcg cgggatgggc tggccgtgcc gtctcctgcg ggtcgtcccc  28080
gacggcagac aggtgagcat ccctgaaccc gtggggctgc ccagcacgag ggcctcgatc  28140
aggtggcgcg tcatcgaaga gctccccgca tggcaggcgc ttggacccca ggggcgcgag  28200
attgaggcgc tgctcggaca ggttgagagt ctcacggagg accagaccct cgaaatgtct  28260
gccgctcggg gcttcgctcg gggcttcgct cgggacgtcg cgcggttcgc cgctctggtc  28320
gcctctcggg gcggtgctct gaacgctgcc cagggcggtg ctttgggcac tgctctgaac  28380
gctgttcggg acgctgttct cggatggctc gtcaaagatt ttatctctga tgaggaattc  28440
cgcaccctcg tgggccgtgt ggagcaggtc atgggtcggg tgatcgcatg atgccgatca  28500
ccaagccgtg cgcggttaag gacatgccgg agggcgagta tcactcggat ccctgcctcg  28560
agccgtccct gtcgtccacg atggcgaaaa ccattgtttc gggtgaggct ggcccggccc  28620
gtctgcgaga gatcatgtct cacgggcagg aacataaggc cgtcttcgat ttcggcagcg  28680
ccgcgcacga gaaggtgctg ggacgcgcg ccggtgtcga ggtgctggat ttccctgcct  28740
ggaccacgaa ggcttcgcgt gaggcgcgtc aggccgtgtg ggatgccggc ggaactcccg  28800
tgctggcgaa ggattccgcc caggtggatg cgatgcgtca ggcgatcctg tccaatcctg  28860
tggcaggtga gctgttcacg cgcggggctg gttctcctga attgtcgatg ttcaccattg  28920
acgaggagac gggacgctgg cagcggggac ggctcgactt cctggcggac cgcaagacca  28980
tcgtcgactt caagacatct ggacagtccg tcgagctgcc cgactggatc aagcacagct  29040
ggcagttcgg ctaccacatc caagccgccg cctatatgga ccaggcgatc tcgctggatc  29100
tggtcgatga ggacgccatc ttcctgcatg tcgtcagga gacgaagccg cccttcttgc  29160
tcgcgatcta tcaggtttca gctgaccagc tggccgaggg caggcgtcag atgcgtcgtg  29220
ccctggacct gtgggaccgc tgcctgaccc tcgacgaatg gcccgcatc cctgcggtga  29280
tccaactatc caagctgccc gattgggtgc acaccactga tgacgaaaag gactcctgac  29340
atgaccgaaa ccacacctag caccgacatt gaaaccaccg cccccacccc gtcgggggtcg  29400
atcgcggcgg tcggctccga gacggcaggc ctgacgcttc agcagaagct cgactatgcc  29460
tctgccctgg ccgactccga gctcctgccc gccgcctaca agggcaagcc cgcgaatgtg  29520
ttggtggcga tggagtacgg cggcgagctg ggcatcggca cgctcgtcgc ggtgaaccag  29580
atcacggtga tcaacggcgg cgtctccatg gaggcgaagc tcatgatgac gctcgcccgc  29640
cgagccgggc acatcgtgcg cctgtccggc gacgacaagc aggccacctg catcatcatc  29700
cgcgccgacg atcccgggca cgaatcggtc gtcacttggg acgaggccaa ggcgaagacc  29760
gccggactgt ggggcaaggg ccactggcag aagaacccgg gcttgatgtt gaagtaccgg  29820
gcggcctcgg agaacatccg gctcacctgc cctgaggtgc tggcggggat tgtctacaca  29880
cccgaagagc tcgatgagcg caccgagcgt gcaggccggt ccacgatgcg tgtccatcag  29940
gtcgtggccg agcggagaa gaccgctgcc tacttcatga aggccctcca cctgaacggc  30000
ggccagttca aggagtttgc ccagccgtcg ctggacatcc cgttgaagag ctcgggaatcg  30060
ctggccaagg cagacaagca gcgtgtcctg ggcgctctcg ccagctggga gaacagcggg  30120
gccgatccca ccactggcga ggtcctcgac gccgagccgg tcgagggcgg tgcggcatga  30180
gcaccttgcc tgcggatgct gccgagaggt ggcagcagtg ggatggcctg gcccgcacga  30240
tcctcgccct tcatctcggc ctgactgatc ttgagatggt cgagctggtg ggcgggctgg  30300
tcggtgccgg ctggcatcag gatgggccgg tggagtcatg agctcggccg aggagcacca  30360
cgacgtgtgg gcgggtgtcg aggacgccat ccctgagtgg gtgagcgaca aggtggcctg  30420
ctcggtgcgg tcggatgccg attggaatgc cgacgaggac agccgcaagg ccgtggcggc  30480
ggtgaggatc tgcgagcggt gcgccttaac cgagcagtgc ctggattggg cgctggccca  30540
ccacgaggcc ggcatctggg gtgggctcac cgcctccgac cgcgagcgca tcgagcgtgg  30600
cgcgccggtg cggcgggtcc gcgagattcg tcggcgtcgc acgcggtta ggcaggtgca  30660
ggagtcatga gcgcaccact gaccaaggcc cagaaggtcg cggcggtcgt cgagcagctg  30720
ttgcgtgcgg gcgccgacac cagcacgctc ctggaggcga cggggccga ccggcccgga  30780
cgattgcggg acaccttcg ccgcgctggc cgtgacgacc tcgccgcccg gatcatcacc  30840
accgaccggg cagcccagcg cagacgggaa gtcatcgagg cggtcgagaa gctggtctgg  30900
gtggacaggg ccgacgagat cgccgccgaa ctcggctaca gctcgcgcta cggcctgcaa  30960
cagtccttgc gcggctgggg gcgtcgggac cttgccgatc agatcgtgct gacccgcgag  31020
acgcaccgcg acagggtcat cgctgacgtg gaatggatcg ccggtacacg gggcccgag  31080
gatgtcgccc gggcgaccgg ataccgcaac gcggcggcgc tgcaggccgc cctgaccggg  31140
tggggccgca aggacctcgc cgaccggatc gtcggagcat cacgcaacga cacgggccgc  31200
ttccgcttca catggagggc cgcatgagcg ccaaccgctc cggccgcgcc acgtacaacc  31260
acacggggat cttcgtccat ctgcgcgaag ccgccgagcc gtccacacag ccaccctccg  31320
accagacatg cccagccctg catgtcatcg ccggactgac accctgggcc gaccaccagc  31380
cccgccacgc cctcggcgtc gacgggcgat gccggcactg ccacaccacc atcaaaggaa  31440
acccatgatc ttcaaagaca ccacgatcgg gccgctcgaa acacggttca cctggtcgat  31500
gggtcggac cgctgcggga cgccgctcga ctggctcgtc gccgcttcgt caagaccga  31560
gcgtagtgag gtaatcgccg tcaagttcct gagggagcgt gccgcgatg cgggggcct  31620
cagagagtgg ggggagctgg acctttgccc ttcatgcttc tcgtgatgg acgcatgatt  31680
accaccacac aactcggaga agcagaccgg tggggccgtg gcctccaagt ccgctcgatc  31740
ctgtgcaacg gctgcggcat agctctggcg accgacatcg gccttcgtgg agacgccacc  31800
gccctccaag tgcaatccga cctgcacgcc cgagcacgcc ccgccggtcg gacacacccc  31860
gcctggcgcg tcgacctctg cccgcaatgc accaccacaa ccaaaggagc atgaccatga  31920
aggccaccca gtacgccaaa tcgaccgacc ctgaagtcat cgccaccatc gaagagaacg  31980
agctgtcacg acgggcatgg atcgacgaca ccaaggcgtg gttcggcaag acgatccgga  32040
caggaatccc gggcgccaaa ttgttcctct tttccacccg gaccgctatc aggctgttgg  32100
ggatcgtgac gtcggacgag aagaagcctg ccgggtgaga gttctgctcg cgttcacgct  32160
ctcggttcga gccacgaaag aacaatccct tgcgcgccac atgggacgca cgccggtggc  32220
aagcagcgtc gatcccaggt ctgccgtgg ttctcacgtc ctccgtgtcg ggagagttac  32280
agagctggtt gaggatgtat ccctgccct tcatctctag tggtgccgca tggctggacc  32340
tggagcacat gcctgaccct gacagtccgc acttcggacc gcagtggact gaagtccgtg  32400
catcgcaggc aatggcagcc aaggaagcat tgaaggacgc gtcatgagca ctccgggatc  32460
```

```
actgcgcgcc gcgctcgacc agctggacga gatcggcatc gccgaccatg tgcagtcctt   32520
ggaatgggat cgggccggcg cccgcaccac agcctggctc gagacctgcg gcgacttcgc   32580
tgcggcctgc cagtggggcg atgccgcggg cgaatgggtc acgtgggaca tcaccgacgt   32640
ggccgaggcg gacgtcagcc cccggctgcg cgtcaagcac atgcacctgc gagccaggcc   32700
ctgtgctgat gcgcccgcga aggcggtggc ggcatgagca aggcccttga cccactggat   32760
caccttc                                                              32767
```

| SEQ ID NO: 23 | moltype = DNA  length = 29768 |
|---|---|
| FEATURE | Location/Qualifiers |
| source | 1..29768 |
| | mol_type = genomic DNA |
| | organism = unidentified |

SEQUENCE: 23

```
tcgtacggct tagtgaaata cctcccttt gttgtttat cgttttgtcg acttttgtt       60
tggtggtgtg tgtggtgcag cctgagcttc ctgatagtcg tgattggtgt ggggagacgc   120
gtcggtggtg gtgtgtgtgg ggcgaggatc cgcgtgccgg gtttgtgtct gatgaggagt   180
ggttgtttct catggatgct gcggtgattc atgatgtggt gtggcgtgag ggtcgcgcgg   240
atttggtggc ttcgttgcgt gctcatgtga aggcttttat gggtatgttg gataggtatt   300
cggttgatgt ggcgtctggt ggccgtggtg ggggttctgc ggtagcgatg attgaccggt   360
ataggaagcg tagggggggct tgagtaggtg tctggtgttg ttgggtctca ggttcctcgt   420
caccgggtgg ctgtggcgta ttcggtgtct gctggcgggg atgctgggga gcttggtagg   480
gcttatgggt tgacgcctga tccgtggcag cagcaggtgt tggatgattg gcttgctgtg   540
ggtggtaatg gcaggcttgc ttcgggtgtg tgtggggtgt ttgttccgcg gcagaatggc   600
aagaatgcta tttggagat tgtggagttg tttaaggcga ctattcaggg tcgccgtatt    660
ttgcatacgc ctcacgagtt gaagtcggct cgtaaggcgt ttatgcggtt gcggtcgttt   720
tttgagaatg agcggcagtt tcctgacttg tatcgtatgg tgaagtcgat tcgtgcgacg   780
aatggccagg aggctattgt gttgcatcat ccgattgtg ccacgtttga aagaagtgt    840
ggttgtccgg gttgggttc ggttgagttt gtggctcgta gccggggttc tgctcgcggg    900
tttacggttg atgatttggt gtgtgatgag gctcaggagt tgtcggatga gcagttggag   960
gctttgcttc ctaccgtgag cgctgccccg tctggtgatc ctcagcagat ttttttgggt  1020
acgccgccgg ggccgttggc tgacgggtct gtggtgttgc gtcttcgcgg gcaggctttg  1080
tcgggtggta aacggtttgc gtggacggag ttttcgattc ctgacgagtc tgatccggat  1140
gatgtgtcgc ggcagtggcg gaagttggcg ggtgacacta atccggcgtt ggggcgccgc  1200
ctgaattccg ggacagtctc ggatgagcat gagtcgatgt ctgctgccgg gtttgctcgg  1260
gagcggcttg gctggtggga tcgtggccag tctgcttcgt ctgtgattcc ggcggataag  1320
tgggttcagt cggctgtggt tgaggcggct ctggttggcg ggaaggtttt tggtgtctcg  1380
tttttctcgct cggggggatcg tgtcgcgttg gctggtgctg gtaaaacgga ttctggtgtg  1440
catgttgagg ttattgatgg cctgtctggg acgattgttg atggtgtggg ccagctggct  1500
gattggttgg cgttgcgttg gggtgacact gaaaaggtta tggttgcagg gtctggtgcg  1560
gtgttgttgc agaaggcttt gacgatcgt ggtgttccgg gtcgtggcgt gattgtggct   1620
gatactgggg tgtatgtgga ggcgtgtcaa gccttcctgg agggtgtcag gtctgggagc  1680
gtgtctcatc ctcgtgccga ttcgaggcgt gacatgttgg atattgctgt gaggtcggct  1740
gtgcagaaga agaagggttc tgcgtgggt tgggttcct cgtttaagga tggttctgag    1800
gttcctttgg aggctgtgtc tttggcgtat cttggtgcga agatggcgaa agcgaagcgg  1860
cgtgaacggt ctggtaggaa gcgggtgtct gtggtatgaa ctcggatgag ttggctctga  1920
ttgagggcat gtacgatcgt attcaaggg tgtcttcgtg gcattgccgt attgagggct  1980
actatgaagg ctctaatcgg gtgcgtgatt tgggggttgc tattccttcg gagttgcagc  2040
gggtgcagac ggtggtgtca tggcctggga ttgcggtgga tgctttggag gagcgtctgg  2100
attggcttgg ctggactaat ggtgacggct acggtttgga tggtgtgtat gctgcgaatc  2160
ggcttgctac ggcgtcgtgt gatgttcacc ttgatgcact gattttggg ttgtcgtttg   2220
tggcgatcat tccccaagag gatgggtcgg tgttggttcg tcctcagtcg ccgaagaatt  2280
gtactgccg gtttctgcc gatgggtctt gtttggatcg tggccttgtg gtgcagcaga    2340
cgtgtgatcc tgaggttgtt gaggcggagt gtttgcttcc tgatgtgatt gttcaggtgg  2400
agcggcgggg ttcgcgtgag tgggttgaga cgggccgtat cgagaatgtg ttgggtgcgg  2460
ttccgttggt gcctgtttg aatcgtcgcc gtacttctag gattgatgcc cgttcggaga   2520
ttacgaggtc tattagggct tacacggatg aggctgttcg cacactgttg gggcagtctg  2580
tgaatcgtga ttttatgcg tatcctcagc gttgggtgac tggcgtgagc gcggatgagt   2640
tttcgcagcc gggttgggtt ctgtcgatgg cttctgtgtg ggctgtggat aaggatgatg  2700
atggtgacac tccgaatgtg gggtcgtttc ctgtgaattc tcctacaccg tattctgatc  2760
agatgcgttt gttggcgcag ttgactgcgg gtgaggcggc tgttccggaa cgctatttcg  2820
ggtttatcac ttctaaacccg ccttctgggg aggctttggc tgcggaggag tctcggcttg  2880
tgaagcgtgc tgaacgcagg cagacgtcgt ttggtcaggg ctggctgtcg gttgtttcc    2940
tggctgcccg ggcgttggat tcgagtgttg atgaggccgc gttttttggt gatgttggtt  3000
tgcgttggcg tgatgcgtcg acgccgactc gggcggctac ggctgatgct gtgacgaagc  3060
ttgtgggtgc tggtattttg cctgctgatt ctcggacggt gttggagatg ttgggtttgg  3120
atgatgtgca ggttgaggct gtgatgcgtc atcgtgccga gtcttcggat ccgttggcgg  3180
cactggctgg ggctatttcc cgtcaaacta acgaggttg ataggcgatg gcttcgggtg   3240
ctgtgtcgag gcttgctgcg actgagtatc agcgtgaggc tgtcaggttt gctgggaagt  3300
atgcggcta ttatgccgag ttgggtcgtt tgtggcgtgc cggcaggatg agtgacacgc   3360
agtatgtgcg tttgtgtgtg gagttggagc gtgccggcca tgacggttca gcagctatgg  3420
cgggcaaatt cgtttcagat tttgccggt tgaatggtgt cgatcctggt ttgatcgtgt   3480
atgacgagtt tgatgctgcg gcggctttgg ctaggtcgtt ttcgactatg aagattatga  3540
atagtgaccc ggataggggcg aatgatacga ttgatgcgat ggctgcgggt gttaatcggg  3600
ctgttatgaa tgctggtcgt gacacggttg agtggtgcgc aggtaggtcgt              3660
ggcgtcgggt gactgatggt gatccgtgtg ctttttgtgc catgttggct acgaggtcgg  3720
attatacgac taaagagcgg gcgcttacta ctggtcatac gcggcgtcat aagcgtgccg  3780
gtaggcgtcc gtttggttcg aagtatcatg atcattgtgg ttgtacggtg gttgaggttg  3840
ttggtccttg ggaaccgaat agggctgatg ccgagtcatca gaggacgtat gagaaggctc  3900
gtgagtgggt tgatgatcat gggttgcagc agtcgtctgg caatatttg aaggctatgc    3960
```

-continued

```
gtactgttgg tggcatgaga taatttgatg tggtttccgg ttgtgtgccg ccggttatcg   4020
gtgcacaggg ttgtctcccg cacggggtc aacaatgttg tgttgttttc cgcaaggagt    4080
gtaggggttag gctatggccg atcagagtat tgaggaacag aatgttgaca atgatgttgt  4140
ggagtccgga aaggataacg gcattgttga tacagtaaaa gacgatggcg ggcaggaggt   4200
agccgacaat cagttgaaga atgaaggcga gggtaaatcg ccggggactg attggaaggc   4260
ggaggcccgt aagtgggagt ctcgtgctaa aagtaatttc gccgagttgg agaagcttcg   4320
tacatcgagt gacgattctg gatctactat tgatgagctt cgccgcaaga atgaggaact   4380
cgaagaccgg attaacgggt ttgttcttga gggtgtgaag cgcgaggtgg ctgccgagtg   4440
tggcctgtcg ggtgatgcga tcgctttctct tcacgtgtagc gataaggagt cgcttgccga  4500
gtctgctaag gctttgaagg gtttgatcga ccatagtagt ggtggtggcg cgggtgtgcg   4560
ccgtcttgcg gggagtgccc ccgttgatga tgttaaacga cgtgtgaggtg tcgcgtttgt  4620
ggatgctctt gtcaataatt ctaggagatg atttatcatg gctgacgatt ttctttctgc   4680
agggaagctt gagcttcctg gttctatgat tggtgcggtt cgtgaccgtg ctatcgattc   4740
tggtgtttctt gctaaactgt caccggagca gccgactatt ttcgggcctg ttaagggcgc  4800
cgttttttagt ggtgttccgc gcgctaagat tgttggcgag ggcgatgtta agccttccgc  4860
tagcgttgat gtttctgcgt ttactgcgca gcctatcaag gttgtgactc agcagcgtgt   4920
ctcggacgag tttatgtggg ctgacgccga ttaccgtctg ggtgtgcttc aggatctgat   4980
ttcccccggcc ctgggtgctt ctattggtcg cgccgttgat cttattgctt tccatgctat  5040
tgatcctgct acgggtaagc ctgctgcggc tgtcaaggtg tcgctggata agacgaataa   5100
gacgttgat gccaccgatt ccgctacggc tgatcttgtt aaggctgttg gtctgattgc    5160
tggtgctggt ttgcaggttc ctaacggtgt tgctttggat ccggcgttct cgtttgctct   5220
gtcaactgag gtgtatccga agggtcgcc gcttgccggt cagccaatgt atcctgccgc    5280
cgggttcgcc ggcctggata attggcgcg cctaaatgtt ggttcttctt cgactgtttc    5340
tggtgccccg gagatgtcgc ctgcttctgg tgttaaggct attgttgtg atttctctcg    5400
tgtccattgg gggttccagc gtaacttccc gattgagctg atcgagtatg gtgacccgga   5460
tcagacgggg cgtgacttga agggccataa tgaggttgtg gttcgtgccg aggctgtgat   5520
gtatgttgga attgagtcgc ttgattcgtt tgctgtcgtg aaggagaagg ctgccccgaa   5580
gcctaatccg ccgccggta actgattcat ttgttgcgat aatgtttatg ctgtgtgcag    5640
ggggtggtgt tgatgggtat cattttgaag cctgaggata ttgagccttt cgccgatatt   5700
cctagagaga agcttgaggc gatgatgcc gatgtggcag ctgtggctgt cagtgtcgcc    5760
ccctgtatcg ctaaaccgga tttcaaatat agggatgccg ctaaggctat tctgcgtagg   5820
gctttgttgc gctggaatga tactggcgtg tcgggtcagg tgcagtatga gtctgcgggc   5880
ccgtttgctc agactacacg gtcgaatact cctacgaatt tgttgtggcc ttctgagatt   5940
gccgcgttga agaagttgtg tgagggtgat agtggggctg gtaaggcgtt cactattaca   6000
ccgaccatga ggagtagtgt gaatcattct gaggtgtgtt ccacggttgg gggtgagggt   6060
tgctcgtgcg ggtcgaatat taacggctat gctggcccgt tgtgggagat atgatatgac   6120
cggttttcct tacggtgaaa cggttgtgat gcttcagccg actgttcgtg tcgatgatct   6180
tggtgacaag gtggaggatt ggtctaagcc tgtcgagact gtgtaccata acgtggccat   6240
ctatgcttcc gtttcgcagg aggatgaggc cgcgggcgt gactcggatt atgagcattg    6300
gacactgctg ttcaagcagc ctgtcaaggc tgctggttat cggtgtcgtt ggcgtattcg   6360
gggtgttgtg tgggaggctg acgggtctcc tatggtgtgg catcatccga tgtctggctg   6420
ggatgctggt acgcaggtta atgtgaagcg taagaagggc tgatgggttg tggcacgtga   6480
tgttgatgtg aagctgaact tgccgggtat tcgtgaggtg ttgaagtctt ctgggggtca   6540
gggcatgttg gctgagcgtg gtgagcgtgt caagcgtgcg gcctcggcga atgtgggcgg   6600
taacgcttac gatagggccc agtatcgtgc cgggttgtcg tctgaggtgc aggttcaccg   6660
tgttgaggct gtggcgcgta ttggcaccac ctataagggg ggtaaaagga ttgaggctaa   6720
gcatgcacg ttggcgaggt cgattggggc tgcgtcgtga tcgtttacgg tgatcctcga    6780
atatgggcta aacgtgtgtt ggcggatgat ggttggctgt ctgatgtacc gtgcacgggt   6840
actgtgccgg atacatttga gggtgatctg atttggttgg cgttggatgg tggcccggag   6900
ttgcatgttc gtgagcgtgt ttttttgcgt gtgaatgtgt tttcggatac gccggatcgt   6960
gctatgtctt tggctcgccg ggttgaggct gtgctggctga tggtgtgga tggtgatccg   7020
gtggtgtttt gcaggcgttc gactgggcct gatttgctgg tggatggtgc acgttttgat   7080
gtgtattcgc ttttttgagct gatatgtagg cctgcggagt ctgaataagc ttattgtttt   7140
tgttttaatg taattgtttg atatttaatg ggggttgtga tggctgctac acgtaaagcg   7200
tctaatgttc gttcagcggt tactggcgac gtttatattg gtgacgcgca gcggggtgat   7260
tctattaagg gtgtggaggc ggttccttcc gggcttacag cttttgggta tctgtctgat   7320
gacgggttta agattaagcc tgagcgtaaa acggatgatt tgaaggcttg gcagaatgcg   7380
gatgttgttc gcactgtggc tacggagtcg tctatcgaga tttctttcca gctgattgag   7440
tcgaagaagg aggttatcga actgttttgg cagtcgaagg ttactgccgg atctgattcg   7500
ggttcgttcg atatttctcc tggtgccaca acaggtgttc acgccctgtt gatggatatt   7560
gttgatggcg atcaggttat tcgctactat ttccctgagg ttgagctcat tgatcgtgac   7620
gagattaagg gcaagaatgg cgaagtgtac gggtatggtg tgacgttgaa ggcgtatcct   7680
gcccagatta ataagactgg taatgcggtg tcgggtcggg ggtggatgac ggctttaaaa   7740
gctgatactc ctccgactcc tccgccggcc ccggttccctc cgaagcctca gccggatccg   7800
aatccgccgt ccggtaactg atacacgatt ttagggggatt gttaatagat gagtgacact   7860
ggtttcacgt tgaagattgg tgatcgtagc tgggtgttgg cggatgcgga ggagacggct   7920
caggctgttc ctgcccgcgt tttccgtcgt gccgccagga ttgcccagtc gggggagtct   7980
gcggatttcg cccaggttga ggtgatgttt tctatgttga aggctgccgc cccagctgac   8040
gcggtggagg ccctggaggg gcttcctatg gttcgtgtgg ttgcttccat ccgtgagtgg   8100
atggaataca agcctgacgg taagggtgcc tcgctggggg aatagtttgg ctccacggcc   8160
tgattgatga ttatcgtggg gccatcgaat acgatttccg caccaagttt ggtgtttctg   8220
tttatagtgt tggtggcccg cagatgtgtt ggggtgaggc tgtccggctg gctgcgtgt    8280
tgtgtaccga tacgtctagc cagttggcgg cccaccttaa tggttggcag cgcccgtttg   8340
agtggtgcga gttgggctgg ttggacatgt tggatcatta caggtctgct aatagtgagg   8400
ggcagccgga gcctgtggcg aggccgactg atgagcgtcg ggcaaggttt acgtctgggc   8460
aggtggacga tattttggcg cgtgttcgtg ccggtggcgg ggtgtctcgc gagattgata   8520
ttatggggtg aatagtgtat gtctggtgag attgcttccg catatgtgtc gttgtatacg   8580
aagatgcctg gccttaaaag tgatgttggt aaacagttgt cgggtgttat gcctgctgag   8640
gggcagcgtt cgggtagcct gtttgctaaa ggcatgaagt tggcgcttgg tggtgcgcg    8700
```

```
atgatgggtg ccatcaatgt tgctaagaag ggcctcaagt ctatctatga tgtgactatt   8760
ggtggcggta ttgctcgcgc tatggctatt gatgaggctc aggctaaact gactggtttg   8820
ggtcacacgt cttctgatac gtcttcgatt atgaattcgg ctattgaggc tgtgactggt   8880
acgtcgtatg cgttggggga tgcggcgtct acggcggcgg cgttgtctgc ttcgggtgtg   8940
aagtctggcg gtcagatgac ggatgtgttg aagactgtgc ggatgtgtc ttatatttcg   9000
ggtaagtcgt ttcaggatac gggcgctatt tttacgtctg tgatggctcg cggtaagttg   9060
cagggcgatg acatgttgca gcttacgatg gctggtgttc ctgtgctgtc tttgcttgcc   9120
aggcagacgg gtaaaacctc ggctgaggtt tcgcagatgg tgtcgaaggg cagattgat   9180
tttgccacgt ttgcggctgc gatgaagctt ggcatgggtg gtgctgcgca ggcgtctggt   9240
aagacgtttg agggcgctat gaagaatgtt aagggcgctt tgggctattt gggtgctacg   9300
gctatggcgc cgtttcttaa cggcctgcgg cagattttg ttgcgttgaa tccggttatt   9360
aagtctatca cggattctgt gaagccgatg tttgctgccg tcgatgctgg tatccagcgg   9420
atgatgccgt ctattttggc gtggattaac cgtatgccgg ctatgatcac gagaatgaat   9480
gcacagatgc gcgccaaggt ggagcagttg aagggcatt ttgcgagaat gcatttgcct   9540
gttcctaaag tgaatttggg tgccatgttt gctggcggca ccgcagtgtt tggtattgtt   9600
gctgcgggtg tggggaagct tgttgcaggg tttgctccgt tggcggttgc gttgaagaat   9660
ctgttgccgt cgtttggtgc tttgaggggt gccgccgggg ggcttggtgg cgtgttcgc   9720
gccctgggtg gccctgtcgg gattgtgatc gcttgtttg cggcaatgtt tgccacgaac   9780
gcccagttcc gtgccgctgt tatgcagctg gtgctgtgg ttggtcaggc gttgggccag   9840
attatgcag ctgtgcagcc gctgtttggt ttggttgctg gcgtggttgc caggttggcg   9900
ccggtgttcg gccagattat cggtatggtt gctggttgg ctgcccggct ggtgcctgtt   9960
attggtatgc ttattgcccg gctggttcct gttatcaccc agattattgg tatggtaacc  10020
caggttgctg ccatgttgtt gcctatgctg atgccggtta ttcaggctgt tgttgctgtg  10080
atacggcagg ttattggtgt cattatgcag ttgatacctg ttttgatgcc ggttgtgcag  10140
cagatttttg gtgctgtcat gtctgttttg ccgccgattg ttggtttgat acggtcgctg  10200
ataccggtga tcatgtcgat tatgcgtgtg gtggtgcagg ttgttggtgc tgtgctacag  10260
gtggtggccc gtattattcc ggttgttatg ccgattatg tttcggtgat tggattcatt  10320
gccaagattt atgctgcggt tatcgttttt gaggctaagg ttattggcgc tattcttcgt  10380
actattacgt ggattgtgaa tcattcagtg tctggcgtga gtctatggg cacggccatc  10440
cagaatggct ggaatcatat taaatcgttt acgtctgcgt ttattaacgg ttttaagtcg  10500
atcatttctg gcggcgtgaa cgcggttgtg gggtttttta cgcggcttgg ttttgtcggt  10560
gcttcccatg tgaggtccgg ttttaacgct gcgaggggtg ctgttctc cgccatgaat  10620
gctattcgga gtgttgtgtc ttcggtgcg tctgctgttg gcgggttttt cagttcgatg  10680
gcgtctcgtg ttcggaatgg tgctgtgcgc gggtttaatg gtgcccggag tgcggcttct  10740
tctgctatgc atgctatggg gtccgctgtg tctagtggtg tgcatggtgt gctgggtttt  10800
ttccggaatt tgcctgacaa tattcggcgt cgcttggta atatgggtc cctgttggtg  10860
tcggctggcc gtgatgtggt gtccggttta ggtaatggta tcaagaatgc tttgagtggc  10920
ctgttggata cggtgcgtaa tatgggttct caggttgcta atgcggcgaa gtcggtgttg  10980
ggtattcatt ccccgtctcg ggtgtttcgt gacgaggttg gccggcaggt tgttgccggt  11040
ttggctgagg gtattactgg taatgctggt ttggcgttgg atgcgatgtc gggtgtggct  11100
gggaggctgc ctgatgcggt tgatgcccgg tttggtgtgc gatcgtctgt gggttcgttt  11160
accccgtatg gcaggtatca gcgcatgaat gataagagtg ttgtggtgaa tgtgaatggg  11220
cctacttatg gggatcctgc cgagtttgcg aagcggatg agcggcagca gcgtgacgct  11280
ttgaacgcgt tggcttacgt gtgatttgg gggtgtggtg catgtttatt cctgaccgt  11340
ctgatcgttc tggtttgact gtgacttggt ctatgttgcc gttgattggt aatgatccgg  11400
agcgtgtgct tcatttgacg gattatacgg ggtcgtctcc gataatgttg ttgaatgatt  11460
cgttgcggg tttgggtgtt cctgaggtgg agcattttc tcaaactcat gttggggtgc  11520
atggctcgga gtggcgcggg tttaatgtga agcctcgcga ggtgacgcta ccggtgttgt  11580
tgtcgggtgt tggcccggat ccggtgggcg gttttcgtga cggttttttg aaggcgtatg  11640
acgagttgtg gtctgctttt cctcctgcg aggtgggga gttgtctgtg aagactcctg  11700
ccggtcgtga gcgtgtgttg aagtgccgct ttgattcggt ggatgacacg tttacggtgg  11760
atccggtgaa caggggttat gcgcgttatc tgttgcattt gacggcttat gacccgtttt  11820
ggtatgggga tgagcagaag tttcgtttca gtaacgctaa gttgcaggat ggttgggtg  11880
gcggccctgt cgacggtaag ggtaccgcgt ttccggtggt gttgacgcct ggtgttggtt  11940
cgggttggga taatcgtct aataagggtg atgtgcctgc gtggcctgtg attcgtgttg  12000
aggggccgtt gtcgtcgtgg tctgtgcaga ttgatggttt gcgtgtgtcc tcggattggc  12060
cggtggagga gtatgattgg atcactattg atacggatcc tcgtaagcag tctgcgttgt  12120
tggacgggtt tgaggatgtg atggatcgtt tgaaggagtg ggagtttgcg cctatcccgc  12180
ctggcggttc tcggagtgtg aatattgaga tggttgggtt gggtgccatt gttgtgtcgg  12240
tgcagtacag gttttgagg gcttggtgaa tagttgatgg ctggtttttgt tccgcatgta  12300
acattgttta caccggatta tcgccgtgtg gcgcctatca atttttttga gtcgttgaag  12360
ttgtcgttga agtggaatgg tttgtccact ttggagttgg tggtgtctgg tgatcattct  12420
aggcttgacg ggttgactag gccgggtgcg cggcttgtgg ttgattatgg tggtggccaa  12480
attttttctg ggcctgtgcg tcgggtgcat ggtgtgcgtc ttcgcgtgtg  12540
actatcacgt gtgaggatga tattcgtctg ttgtggcgta tgttgatgg cctgtgaat  12600
tatcgtcctg gtatggttgg tatggagtgg cgtgcggatc gggattatgc ccattattcg  12660
ggtgcggcgg agtcggtggc taagcgggtg ttgggggata atgcttggcg ttttccgtct  12720
ggtttgttta tgaacgatga tgagagtcgt ggccgctata ttaaggattt tcaggtgcgg  12780
tttcacgtgt ttgccgataa gttgttgccg gtgttgtcgt cgttgtccgg at gactgtcacg  12840
gtgaaccagt ttgagaatgc gaagtttgat cagcgtggtt tggtgtttga ttgtgtgcct  12900
gctgtgaccc ggaaacatgt gttgactgcc agtcgggtt cgattgtgtc gtgggagtat  12960
gtgcgtgacg ccccgaaggc gacatctgtg gtggttggtg gccgtggcga gggtaaggat  13020
cggctgtttt gtgaggatgt tgattcggcg gccgaggatg attggtttga tcgtgtcgag  13080
gtgtttaagg atgccgtaa cacggattcc gagaaggtgt ctctcttcga tgaggctgag  13140
cgggtgttgt ccgagtcggg ggctacgtcg ggtttaaga ttgagttggc tgagtcggat  13200
gtgttgcggt ttggtcccgg caatctgatg cctgggggatt tgatctatgt ggatgtgggt  13260
tctgggccta ttgcggagat tgtgcggcag attgatgtgg agtgtgtatc gcctggtgat  13320
ggttggacga aggtgactcc ggttgcgggg gattatgagg ataatccgtc ggccctgttg  13380
gctcgccgtg tggctggttt ggctgcgggt gtgcgggatt tgcaaaagtt ttagtaagtg  13440
```

```
attgggtttt gttgtgggta ttgtgtgtaa agggtttgat ggtgtgttga ccgagtatga  13500
ttgggctcaa atgtctggtc tgatgggtaa tatgccgtct gtgaaggggc ctgacgattt  13560
tcgtgtcggc acgacgattc agggttctac ggtgttgtgt gagatcctgc cggggcaggc  13620
ttgggctcac ggggtgatgt gcacgtcgaa tagtgttgag acggtgacgg gtcagcttcc  13680
gggcccgggt gagactcgat acgactatgt ggtgttgctt cgggattggc aggagaaatac 13740
ggccaagttg gagattgttc ccggtgggcg tgcggagcgt gccagggatg tgttgagggc  13800
tgagcctggc gtgtttcatc agcagctact ggcgactttg gtgttgtcgt ctaacgggtt  13860
gcagcagcag ttggataggc gtgctgtggc ggctagggtt gcgtttgggg agtctgctgc  13920
gtgtgatcct acccctgtgg agggtgaccg tgtgatggtt ccttcggggg ctgtgtgggc  13980
taaccatgcc ggcgagtgga tgttgttgtc tcccaggatt gagacgggtt cgaagtcgat  14040
catgtttggt ggttctgctg tgtatgctta cacgatcccg tttgagcgcc agttcagtag  14100
tccgcctgtt gtggtggcgt ctatggctac ggcggctggg ggcacggcac agattgatgt  14160
gaaagcctac aatgtgactg cccaaaattt tagtttggcg tttattacga atgatggttc  14220
gaagccgaat ggtgtgcctg cggtggcgaa ttggattgct gtcggcgtgt gactgcacgg  14280
gtgttgtggc ggatggtgtg atgttggggg gctgtggtgt cgtggtttac tcctgcactg  14340
gtggcctcta tttgtaccgc gttggccacg gttttgggtt ctgttcaggc tgtcacatcc  14400
cggtctagga agcgtttacg caggctgtcg gctcaggtgg atgcgatgga agagtatacg  14460
tggggtgtgc ggcgcgaggt gcgaaaggttt aacgccgggc ttcctgatga tgtgagccg  14520
atgcatcttc ctgatttgcc cgagttttt aaagatactg ttgatggtgg aggtgagtag  14580
ggttgaggga gttggaggag gagaagcggc agcgccgcaa ttttgagaag gcttcactgg  14640
tgttgttgtt tttgtcgctt gtgttgttgg cggtggttgc tgcgggtgct ttgcgtttcg  14700
gggctgtatc ctctgagcgg gattcggagc aggcgaggc ccagtcgaat ggtacggccg  14760
ccagggggttt ggctgccgt gtgaagcagg cgtgtgcttc gggtggggtg gagtctgtgc  14820
gtcttcaccg ttctgttttg tgtgtggatg ctgtgcgtgt tgagcagcgt gttcagggtg  14880
tgccgggtcc tgccggtgag cgcggccgc aaggcccttc aggtcctgcc ggccgggatg  14940
gtgttaatgg ttcggctggg ctggttggcc tgttggtcg gcaagggttct ccgggtttga  15000
atggtgtgaa aggtcctgac ggcttgcctg gcgctaacgg ttcggatggc cgtgatggtg  15060
ttccaggtcg tgcaggtgct gacggtgtga acggcgttga cggcgctgat ggtcgggatg  15120
gttctgccgg tgagcgcggc ccgcaaggcc cttcaggtcc tgccgcccg caaggtgcac  15180
agggtgaacg gggtgagcgt ggtcccgccg gtgcgaatgg atccgatggc catgatggta  15240
aggatgggcg ctcggtggtg tctgtgtact gttccggggg ccgcctggtt gtgaaatata  15300
gtgacggtgt ggcttccacg atatcgggtt cggcggcctg ccagggtgtg aaaccgtcgc  15360
ctctagtgac tatatcatcc cacaaataga aggagtggc tgtgatggtg gtgtttggtg  15420
gtggtgtgtt gtgagatata ttcctgcggc gcatcattct gccggctcga atagtccggt  15480
gaatagggtt gtgattcatg cgacgtgccc ggatgtgggg tttccgtccg cctcgcgtaa  15540
aggacgggct gtgtccacgg caaactattt cgcttcccca tcgtctggtg gttcggcgca  15600
ttatgtgtgt gatattgggg agacggtgca atgcttgtcg gagtctacga ttgggtggca  15660
tgccccgccg aatccgcata gtttgggtat agagatttgc gcggatgggg gttcgcacgc  15720
ctcgttccgg gtgccgggg atgcttacac tcgtgagcag tgctgtagcc ctcgcgtgtg  15780
gcctgccggtt gagcgtgccg ccatcctgtg tagacgtttg tgtgacaagc atggtgttcc  15840
gaaaaggaaa ctgtctgtgg ccgatttgaa ggccggtaaa cggggtgttt gcgggcatgt  15900
ggatgttacg gatgcgtggc atcagtcgga tcatgacgat ccggggccgt ggtttccgtg  15960
ggacaaattt atggctgtgg ttaatggcca cggcggcggt tcaagtagtg aggagttgag  16020
tatggctgat gtacaagcgt tacataatca gattaaacag ttgtcggcac aggtggccca  16080
gtcggtgaat aagctgcatc acgatgttgg tgtggttcag gttcagaatg gtgatttggg  16140
taaacgtgtt gatgccttgt cgtgggtgaa gaatcctgtg acggggaagc tgtggcgcac  16200
taaggatgct ttgtggagtg tctggtatta cgtgttggag tgtcgtagcc gtcttgacag  16260
gctcgagtct gctgtcaacg atttgaaaaa gtgatggtgg tttgttgtgg gtaaacagtt  16320
ttggttaggt ttgctggagc gtgccctgaa aactttttgtt caaacgtttg ttgccgtgtt  16380
gggggttact gcgggtgtca cctatactgc ggagtcgttt cgtggtttgc cgtgggaatc  16440
cgcgctgatc acggcaacgt ttgctgctgt cctgtccgtt gctacctcgt ttggtagccg  16500
gtcgtttgtg gccggcaagc ccggcaagca gccccaggtg gatgcgggtt tggttccacc  16560
ggatgatggg ggcttggttg agccgcatat ggtggatgtg tcggatcctg gcatgatcga  16620
gccgacggat gatgcggatc ttgccggcta tgagcctcgg cgtgcagccg agtcggaggt  16680
tggcaggta gagtctactg ttgcataatt gaatatagat gtgtgcccca gcggtgctgc  16740
cacgattgtg tggtggcggc tgctgggggca ctatttttgt atatgcggtg tggctatgat  16800
tcgttgctgt cgatggtgtc ttcgagcatc tgatacaggt ggaggcaggt agagatagtt  16860
tcgctggcct gatcgagaac gttccggccg ataacgtttt tgtggttgtc gcggtggcgg  16920
atgatagccc acatgatctc gtcggctgcc gcctgtaata gtttggcctg gtatgcgatt  16980
ccggcgagcc agtctagtgc ttcctggctt gtatagggc tctggtcctc gctgttgccg  17040
cgggtgttgc tgttgtttgt ggggtgtcct gcactgtcgc atagccacag gatttcgctg  17100
cactcgtcta gcgtgtcttg gtcgatagcg agatcgtcga ggctgacatt gttgacggta  17160
aggttcacgt tgtcgaggga gatgggtaca ccgtactggt tttcgacact gtcaacaatg  17220
ttttccagct gttgcatgtt ggtggactga tacggtgtat cgctggttg  17280
agggtggtgt aggtgatgtt gtgtgtgttg tccatggttt ttatgccatt ccttcgttat  17340
cgtctggcat gtagtatgtg ctgttttcgt actcggttaa cgtcatcagt gtttggtctg  17400
cccactgttt cacggtttgc cgggtgactc cgagtcgttg ggcggctgtg gcgtaggttt  17460
gatcatacc gtatacttcc cggaatgctg ccaacctagc taggtgtttc tctcgtttgg  17520
atggttcaca ggtgagggtg tagtcgtcga tggctagctg tgatcgatc atggagacga  17580
tgttgttgcc gtgtgttgt ggcgcggttg gtggggtgg cattcctggc tccacggagg  17640
gtttccaggg gccgccgttc cagatccatt gggcagcttg gatgatgtcg gcggtggtgt  17700
aggttcggtt cactggtcac cccctgaaca ggtcgttggt gttgttggtg tcgaatcgtc  17760
cgacgcagtg gcagtagtcg tacatgagtt taataatgtg ttggtggtct cccaaatagg  17820
tgtttccgct gatgctgtat gtgcctgtgc cgtcttttcgc tggtgtgtat ttggcggtga  17880
tggtttcggg gttttcggtg tcggtgatga ttgctgtggt ggtggcgcct actgtttgga  17940
gtatggtggt ttgggttccg tcgtcgatgg tggttttaac catggtgtgt gttttcccctt  18000
ttgttagtta cttgttttggt tgtcggctag atgaataata tcgggtaaag gtttcggctg  18060
gtctaggtgt tgtatggttt tgttggctag ccgtttggct accctgtaac acattttggt  18120
gtagtgtttg ttgtctaggt tgtggtattg ttcccgcacc gcaatatata gcaggagtc  18180
```

```
ttggtacagg tcgtctgcac tgattgcggg gtagtgtgcg gctgttttgg tgcatgcccg   18240
gttgagtgtg cgaagatgat ggtctgtggc ccacacccac gatgcggtgg tggccaggtc   18300
ggcttttgtt ggtcgtctgc tcatggcact atttcatctc gctatctgat agttgtttgg   18360
tgttttgttg tggatagtgt agcacactag tcctgggtgg ccggtggtgc ctgtgcggtg   18420
acggaaccat gtggattcgc cttccatgga tgggcattgg atgaaggtgc gttgtccttg   18480
ctcggagatt tctaggtggt gccggtgccc ggccatgaga atattagata cggtgccgtt   18540
gtggaattct tggccgcgcc accaatcata gtgtttaccg gtgcgccatt ggtgcccgtg   18600
ggcgtgcagt atccgtgtgc ctgccacatc aacggtggtg gtcatttcgt ctcggctggg   18660
gaagtggaag tgtaggttgg ggtattggtt attgagctgg taggcttctg cgatggcccg   18720
gcagcagtcc acgtcgaatg agtcatcgta ggtggtgact cctttaccga agcgcacggc   18780
ttcaccatgg ttgccgggga tggatgtgat ggtcacattt ttgcagtggt cgaattggtg   18840
gatgagttgc atcatggcca tgcgggtgag cctgatttgt tcggtgaggg gtgtttgtgt   18900
tcgccaggcg ttgttgcctc cttgtgacac gtatccttcg atcatgtcgc cggatgaaggc   18960
ggtgtggact cgttcgggtt tgcctgcttg ttgccagcag tgttttgcga ctatgaggga   19020
gtgtaggtag ttgtcggcga agtgtgctgt ttctccgccg gggatgcctt tgccgatttg   19080
gaagtctcct gccccgatga cgaaggctgc ggtgctgtag tcggtgtggg tgtcttgttc   19140
gggttttggg ggtgtccatt cggctagttt atcgacgagt tcgtctaccg ggtaggggtt   19200
tgttgcgggt tggtggtcga tgattttttg tatggatcgg cctgttttctc ccttggggag   19260
tgtccattcg gagatgcgtg tgcggcgcac ggtgccgttg gctagattgt cgtcgatggt   19320
gtcgatggcg ttgtcgtggt tggctagctg tgtgagtagc cggtcaatat tgtctatcac   19380
tgggtatcct cctcttgcgg ggtggtgctg gcttgtttgc ggcgatagtc tttaataacg   19440
gtggcggaga tggggtatcc tgcctggtgt agctgttttg ctagccatga ggcggggata   19500
gacctgtcgg cgagcacgtc ggcggctttg ttgccgtagc gttgaataag ggtttcagtt   19560
ttggttgcca tgatgtccta tcggttgtgt ggtgggctgc catcctgtgc ggcagtcgcc   19620
gtcgtgtcct ggtttgcgtg tgcaccacga tacggttccg tctgtgtggt tgagtgtttt   19680
accgcacatg acgtttcgga gatgctccgg cagctgatca tcctggttgc tggttttgtg   19740
gtcgaagagt gttttctggt tggtgaaatg ttctgacacg gtgccgttat gcacgggtag   19800
tatccatgtt ttccattgtt gttgtagcct ggtgttccag tggaattgtt tggcggcgtt   19860
ttcggcctgt tttaaggttt tgtggtagcc gactagtatg cgttgatgct gctggtctgg   19920
aggggtttggg cctcgccagt atttgccgc cacggcgtgg ctgttgctgt ctgtgaaggc   19980
gtcccagcag tattcgataa tgtgttgcaa catactgtct ggcaggctgt caggggttgat   20040
gttgatgttt tgggtgataa tgtcacggat ggcttgccgg tttttggtgg tgggtttgaa   20100
cgagatgctc acgatagtac cggctggtcg tcttgcatga actggttgaa ggtgttgttc   20160
ccggcgtgtt gggcttgtgt tatttgttgg tcggtccagt ctgggtgttg ctgttttcaga   20220
tagtgccagt ggcacgcatt gtaggtttcg tcttgtagcc gtgtgagatg gttttcggtg   20280
atgatttgtt tccacatggc ccatgacacg tcgagccggt cgaggatttc gagggctggg   20340
atgttgaatt ggttcaggaa gaggatttcg tgggtgtagt agttttttctc gtaggcgtcc   20400
catccgcttc ggtgcctgtt gggctggttt ttggggtagg cttcccggca tactttgtgt   20460
aaacgcttgg ccatgtcgtc gggtagttta atgtcgggat tggcgcggat catgatcgc   20520
atcccatcat aggtggtgcc ccaggtgtgc atgatgtagg tggggtcttc tccgtcggcc   20580
catttttctg cacagatggc gaggcggata cgcctcctgg cagcttggct ggtgttgcgc   20640
cggttgggga ttgggcacgt gtcgagggga tccatgatgt tttagtgtac cttctggtt   20700
tcgtgttgtt gacaggttt actgtagcac agtgtctagt gcgtgtgtca accctgtttt   20760
tccggcttga aggtaggtgt ctgtgacatc ccctagggtg agggggcacgt gcacagcttg   20820
ggggagtgcc gcctggaggg tttgggccat ctggtcgcct gcggggtctg ggtctgacca   20880
gatgtagatg tggtcgtagc cttcaaaaaa tttggtccaa aaaatttgcc acgaggttgc   20940
gccgggtagg gcgacggccg accatccgca ttgttcgagg atcatggagt cgaattcgcc   21000
ttcgcaaatg tgcatttcgg ctgccgggtt ggccatggcg gccatgttgt agatggagcc   21060
tgtgtctcct gccgggggtta ggtatttggg gtggttgtgg gttttgcagt cgtgcgggag   21120
tgagcagcgg aaacgcattt ttcttatttc ggctgggccg ccccaaacgg ggtacatgta   21180
tgggatggtg atgcactggt tgtagttttc gtggcctggg atggggtcat tgtcgatgta   21240
tccaaggtgg tggtagcggg ctgtttcttc gctgatgcct cttgctgaga gcaggtcgag   21300
tatgttttcg aggtgggttt cgtagcgggc tgaggctttc tggattcggc ggcgttccgc   21360
aatgttgtat gggcgtatgc tgtcgtacat ttgggttttc ttcttctaat cgttgttgta   21420
gcttggcgag tccgcctccg acaccgcatg tgtggcagta ccagacgccc ttgtcgaggt   21480
tgatgctcat ggagggctgg tggtcgtcgt ggaacgggca gagtatgtgt tgctcgttcc   21540
tggacggatt gtaccgtatc tgataatggt cgaggaggcg gcaggtgtca gaggtgtggg   21600
aggagctcgt tgagggttga taccacatag gcttcactcc atggcttgtt gcgctgtttc   21660
atcactacga gtccgatggt ggaattgttt tgtttgtttc ggtgtgttc gtagttgcgt   21720
gcctcccggc tggcttgttt cacgaattgg gctaggtgtg gttgcccggc tttcgcctgg   21780
ataatgtagg ttttatgcc ggttgtgagg atgaggtcgc cttcgtcttc gcggccgttg   21840
aggtggaggc gttcgatatt gtgtccggtg tcgcgtagct ggtggaggag tcttgtttcc   21900
cattcggctc cggcccgccg gttgcgtgcc tgctgtgtgg ccatagtttt ttagagtcct   21960
ttgtgtgttg tggtcatgtt ccagggctgt tttcggcgtg ggcccgaa gaatgtgtat   22020
tcggggtatg ctctgagtcg ttcgtatcgg gtgccgtcgg ggctggattt gcctgtgcgc   22080
tgtttgagta cggcgatgcg tgcctctgcc ggtatcgata gcccgttgcc gttatcctcg   22140
ccaccataca atgagactcc gaggatgagt tgtggttttt cggagaggcc gttttttgatt   22200
tctcgccgtg ctgcgggtg ttcgatgtcg gttccggttt tgtcggttgc gtggtgtgtg   22260
acaataatgg tggagccagt atccctgccc aatgctgtga tccattgcat ggcttcttgc   22320
tgtgcctggt agtcggattc gcagtcttga atgtccatca ggttgtcgat aacaatgagt   22380
ggtgggaagg tgttccacat ttccatgtag gcttgtaact ccatggtgat gtctgtccat   22440
gtgatgggtg actggaatga gaatgtgatg tgttggccgt ggtggatgct gtctcgatag   22500
tattctggcc cgtagtcgtc gatgtttgt tgtatttgtt gggtggtgtg ttgtgtgttg   22560
agggagatga ttcgtgtgga ggcctcccag gctgcagtct ccctgatat gtagagggcg   22620
ggctggttga gcatcgctgt gatgaacatg gctagccctg attttggct gccgaccgc   22680
cccgcgatca tcaccaagtc gcccttatgg atgtgcaaat cttggttatc atatagtggt   22740
gcgagttgtg gtatgcgggg tagttcggct gcggtttggg aggctctctc gaaggatcgt   22800
tgtagagaga gcatcgggac cttaatctat ctgtctgttg gttgtgtggc tggtcagatg   22860
gagtcgatat cgatatcagc atcagcagag gctgaagtgt catctagctg accattatcg   22920
```

```
cgcttgtcta cgtattcggc aaccttatcg tagatggcgt cgtccaatgt ttttgagcacg  22980
accgcgttga aaccgttttt ggtgcgcacg gtgctagtt tgaaggcctg ctcctcgcca    23040
aggtatgcct ctagttcgcg gatcatggag tgtgggcggt cgttattgcc gcgggctttc   23100
tcaataatag cgttggggat ggtttctggg gtgccgttgt tgagatcgtc tagggtgtgg   23160
aagatggtga catcagcgta gatgcggtct gcgacctgtc caccgtagcc ttcagtgttg   23220
tgctggacgt cgtgcacttt gaaggcgatg gccgtggcgt cctggtttcg ggaggggttg   23280
aagaaggtgc tgttgctgtt gttgcggtag tttgcgagtc ccataactat tgtttccttt   23340
tactgttgtg tctgtttttg ttggcttata ttggtttatc gggtgaggct gtttcgctta   23400
gtgcggaaag cgtcggaaac atcactgtta ctggtgatga tcttcttgta ctgttttaga   23460
aggtctgcta gctgtgcctt gcttgttgca ttgttgattt tgttgatgac gatggtgttt   23520
tctttggatg cgattttgtt gacgtagtct ttggctgcct ggttgtatcg gtcttggagg   23580
atgattgatg cgctcgctac gagtgttgct agatcccagt ctttggacac gtcatcgttt   23640
ttgagtccgc ctagcaggtc gatgatggcc tgttttgtct gctctgctgt gtctcctcgg   23700
atgaccgccc atggtgcagc atagtctcca ccatatttga gtgtgatcgt gagtcgatca   23760
ttgtcgatct tgtctttatc tgtcatttgg tgtcctttc tttattgtct gtttctggtg    23820
gctgtacggt ggattctacc gggtatctgt acgagttttt gccgttgacg gcccagcagg   23880
cgtctcgtac ggggcatcct ttacagagtg ttgtgacgtg ggggacgaag atgccttcgc   23940
tgattccttt cattgcttga ctgtacatgg atgatacatg ccggtaggtg ttgttgtcaa   24000
ggtcgtagag ttcggtggat gtgccttgtg tcggggactt gtcgtcgttg cggctggtgt   24060
ctggcgtcca aaacatgcct tcgtgacat ggatgtcgtg ttggttgagc atgtaccggt    24120
atgtgtgcag ctgcatactg tcggcgggta ggcgtccggt tttgaggtcg aggatgaagg   24180
tttcgccggt gtcggtgtcg gtgaaaacac ggtcgatgta tttgtgtcat             24240
cgtcgaggat ggtttctacc gggtattcga tgcctggttt accgtccagg attgcggtga   24300
tgtattctgg gtgttgcgc ctccatgttt tccagcggtc cacaaggtg gggccgtaaa     24360
ccatccacca gtcgtagtct ttcttgtgtg gtccgcctga ctcgcacatg ttttttgcata  24420
ttctgccgga gggtttgatt tctgtgcctt cggattcggc gagggctacc tgggtgtcga   24480
aaatgttttt gaaggatgag agtttgtctg gcagtgcagg gtattcggcg ggattgtaca   24540
ggtgtaggtc gtattgttcg gtgatgtggt gtatggcgct tccggcgatg gtggcgtacc   24600
aggtgtggtg ttgggcgtga tagccgtggg ataggcgcca tttttctccg cattcggccc   24660
actgggtgag tgaactgtag gagatgtgtc ctgggtggct gatggttttc gggtattgtg   24720
ctagaggcat tacttgtcgc ttgtgttcca tgtgttgcgg gtgtcttggc cggcgtggtg   24780
ttgctggtag gcgaggagtg cgaggcagtg ccaggctgcg tgtgctagat ggggtagccc   24840
ggattcgtgg tcgaggttgt tgccttgctg ccatgatagt agatgcctgt agagggcgtc   24900
gacactgtgg ctccacgggt atcctccggt ccagttgttg tcgccatatt tggtggcacc   24960
gtatccggct acttcgccta gggcgtgaag ggatgctggg tcgatgaggg agagcctgca   25020
gagtttcaat tcttttcggg caccgctgtt ggggtcggtg tacatgcggg tgggctcatc   25080
catggggtgt gtgctcctta agggtgggtt actggttgtt gttgtgggct agggcggcgg   25140
cgagaataat gatggcgagg gtttcggcta tcagtatggg tgttgtgatc atttggttgc   25200
tcggggattg ttggtgagtg ttgaggcacc caggagggtg gcgagggcgc atgcggcaat   25260
aatggcgagg gctgccttgt gtggggtgcc ggttgcgtac atccatgtga tgatggcacc   25320
ttggatccag gctaggctgg tgaagaaggt tcgtagctg tgcagctcaa tgttgttgtt    25380
gggtgtgttc atgcttgctc ctgaagaatg tgttgatga tttataaat gttgtacagg     25440
tcggtttcga tagataacag ttggttgatt tggtggtcga gatcaatgtc tgggttgagt   25500
gtgttgatgc gggaggcaat atcggtggct gtgcgtagtg tgccgccggt gtggtgaata   25560
atgtgtgccg tgtcggcgag tccggtggtg acgcgtagt gggataggag aggcatagcg    25620
gggatgctcc ttggcgggtt actgttgcgg gttgatgttg aggtcggtga cgtgcggtga   25680
gttttctgtt ccggtgacga ggcagtggac ggtgacgggt agtttggatg ctcccggctg   25740
gcggacggtg gcgccgtaga cgatgctgaa tgtgtctttta ccgatggttt tgtggagttga 25800
gaggtcgatg tcggggttgc cgttccagtt gacaccttgc gctgcggcct gttgttcggc   25860
tttgtggttg caggtgtgtg ctgccgtgat catggtgagt ccggtggcgg tttcttcacc   25920
ccttgcttgg gcttgcttgt gggctttggc ctgctcggct tgtagggatc gggtggcggc   25980
tgcctgccgt gccgctttct cggctttgcg ctgttgggta gtcttggggg tccatgtggt   26040
gttggctgtg gttgcctgtg gggctggctg tgaggtgagt ggcggggttgt cgtctggtgc   26100
tggcatgaat gaggcggcgg caatgatggc ggctgtgatg cctgcgatgg tgtagccgtt   26160
tttcttgttc atgttttgtg tccccttttcc ggggtgttgt tcgttgctga catggttaat   26220
actttcagcg gctgggccca ctgtcaaggc tgcgctcagt ttgtgtgagc gtttggtgtg   26280
tggctagggg ttttgtcatg taagcgtgac atgtcactac cttgcgtcca gtatccatgg   26340
cggttgcgag ccatcccttt ggcgagcatc tcgtccacag tgaggcacct gcggcgattg   26400
gggccttcct tgaccccgtg atcgcctatc cggtgcatgt ccccggcata agtgccatta   26460
aatgtttcgt ggcagactgt gcagtgttct ggtcggtatc cgatgattgt gctatcgcac   26520
ttgtggcatg tccattgcat gattggtcct tctttcgtgt tttaagcttg tgctctgagg   26580
attagagcga ctttcagccc ttgggggtag gattatatag gtcaggtatt tctaggcgat   26640
tctaggctca ttgtgtgtgg ttgggggtttt atcgggcgca tagggttagc aggtggccca   26700
cattggtgcg gctcacattc cagtagagtt gcgtggcttc cttactggtg agcggcttcc   26760
actcgtcatg gctgaacacg gtgccatcgg atgcgatgaa cgtgttgggg cgtagccttgc  26820
gaagctcggc ttccacatgc tgccggtagg cttcggcgag gctctcaaaa tccatgtggt   26880
cgcaggagag gttttcgagg cgtgtcaggt cgaaaggctc cgggcagtcg tagctggctg   26940
gagtgtagag ctgggtgaag tggtcggcga tcttctgcat ggcgggttcc tttctggtgt   27000
gtggatggtt tttatcgtgt ggatgcgaca aggatgcgt ctacgtcgat catgtcgatc    27060
atgtcgttga gttcctcggc ctcattctcg gagaggtcgg gccagtcggg tggcccgtat   27120
acggcgccgt cgagggtgac agtccacagg ggccggatga gtcgtatggc ttcttcgact   27180
ttggcgtggt acatgcggcg caccatatcc agatcgatgt cgtctgaatg gtttccggtg   27240
aggctgtgga ggctgagcgg gtcgatttct gtctgcctgt agaggctggt gaatgatggt   27300
gtgatgagtg tgcatccat gagtgtgctc ttttctaggg gttgttgtgg ttctagagt     27360
gtgtgggctg tgaccccaca gtcaaggcta cgctcatttg gattgagcgt ttcatatggg   27420
tgtggcatga aatctacacc ctcatactgt gtgagatgta tcatatcccc ctggcttggt   27480
gtgcacccct caagactact ctgccgacct ggcgtggagg gtgtagccca gaaatgccgt   27540
ttaaagcttc aggggtacgc ctaggagcgc cttacagggt gggggctagg tatttatacc   27600
cccagcatat tctgatcgat tctagacgac tcccagagcc cgatacacga tcaaccatct   27660
```

```
cgacatagac catcagcccc tatcctggtt agctaagcct caactatgtg gacagtgtgg    27720
gacactgtgg gggaagaagg acacggtaca agaaagaggg gggagcatca gccttaaagc    27780
cttaagatct tagcgcttag caccgatggt cttagcagtt agcaccgagc ccttgagggg    27840
gctcggcatc agcctcatcg ggctcagctc atcaggcaca gccctgaaaa gggtacacgc    27900
catcagggaa ggcttgagag tacgaggagc cctagcgacg agtactcgaa agcctgaggg    27960
aacaccctca gtactgatga gcctagcgta ttcggaaagg acgcaagagt aaagtgtgac    28020
agctatccgg gagtgaaacc cgttccgact aggggtttca gccttaacca ccctcaaagg    28080
ttacaagact ctaagaaaat ttaagaaact tcttaggaag aaagttgtgt tcatatcccc    28140
ctaaaaacac ccaaaatagt cctcaaaccc gcctataga ccaaacagtc aagtttgact    28200
cgtctagacg gcgtatgata ggctggacag gtagccagct ggacgcaagg ccagaaagtg    28260
ctgacgcact tcccgacctc gcttaccatc agtctaccaa acactttaaa gcttcaaggc    28320
ttagcgctaa gcccttaaga tcttaacgct tagcaccgag ccccctcaa gggctcgaca    28380
tcagtcttaa agtcttaaac actttaagta actttaaagc ttcaaggctt agcccttaag    28440
gatctaagtt actataaaag ctttaaacac ttaaagtaac tataaagctt taagagctta    28500
acatttaagg atataaataa acattaaagc tttaaagtct taaagtaaat ataaccttt    28560
aacacttaag ttaagtataa aaccttaaag gcttagcact taaggatata aacttaacat    28620
cagtgtttaa gacttaaaga gttaaagtaa ctattaagac ttaaaggctt ataagcttta    28680
atactttaag tagctataag actttaaaaa cctgaagtac ttaaagttaa ccatcagtct    28740
taaactttaa tattataagt attaaagctt ataagttata aaagttttta gaagagttaa    28800
agggttaact tctttacttc tcttctctct ttggttcttt ctctcttctc ttcttttctt    28860
catcagggga gaagaggaac ctttaaccgt caacgctgat ggacttttca ccgtgtgact    28920
cgtgtgcttc tggtcgcaag ctcccatcgc acactcccca cactcttca ccccgtgcccc   28980
tttacggctt agcgtgttcg tcggaaggcg tacggcgtgt cacgcttaaa cccttaacac    29040
caggtaagac ttaaagtgca tattataagt agaagacttt aaaacctata aggtgttccc    29100
gcttagcccg tgttccttta acgctaggcg ctcagcgcta agatgtgaaa cgtgaacacc    29160
catccaccc cattttttctt ccgtgtcctt ctccttttga caccgctggg gggcgatgtg    29220
atatttctca catgccaggg ggtagtggag aaaacaacca ccccggaacg tttaagacac    29280
cccctcaaac gaacaaaaca gggcctagaa tcgatcagca gggcaccggt aggggtattcc    29340
tacccccaga cgattcaagg ccattacagg agcaatgaga ggctcacagg ggccatggga    29400
gattggggg cgtgatggca cacaccaacc gcacagccag ccaagcccac cggcgctggc    29460
gggcaaggct catcacccaa gcccgacaac aaggccaaac cgaatgccca ctctgcggag    29520
tcaccatcac ctggaacacc cacgacctgc caaccagccc cgaagccgac cacatcacac    29580
ccgtcagccg gggaggactc aacaccctcg acaacgggca aatcatctgc agaacatgca    29640
acagaagcaa aggcaacaga acacaaccaa acatcaaatt ccaacaacaa accacaaaaa    29700
cattgattcc atggtgaaaa acccgccaac ccccaccggg cacaccccct gcacaccgt    29760
gcaagacc                                                            29768

SEQ ID NO: 24          moltype = DNA  length = 11979
FEATURE                Location/Qualifiers
source                 1..11979
                       mol_type = other DNA
                       note = pANS514 plasmid
                       organism = synthetic construct
SEQUENCE: 24
catggttgcg ccatgcagca caggccaagc gtgaggccca agcacgagga ctcgcccgct    60
gcccactgtg cggcgtctgg atggactacg aggtcggcaa gcgacccaac tcggccgaag    120
cagaccacat cagaccgcat tcgcttggtg gttcagacga catcgacaac attcgcgtca    180
tttgtcgtcg ttgcaatcaa tcgcgcgaaa acgccgaaa gcgaccaggg cgccaacgtc    240
agcgtccaat caagcgcatc gagctggccc aaccggcccg cagtgggca tttcctgccc    300
cgccggcatg aatggaaggg cagtgcggat ggtgcggtcg ggcattcgat cgtgcccgga    360
cgggtcgccc gcgacgcttc tgctcggccc gctgtcgggt cgccgcgtcc cggtgtgcga    420
tcccgctggc catgaggtcc cgcactgcgt gggtccgctg cgacggcaag cgccccatca    480
ccctggctgg cgctccggcc tcatccacgg acccgggcac atggtctggc tggtcgcagg    540
tgcgacgcgc cacggccggc gatggcttcg ggaccatgct cggtgacggg ctgggtgct    600
gggatctcga ccacttcgac gatcagggcg cccgggcct catcgaccgg atcgataagc    660
cgatcatctt cgccgagcgg tcggtgtcgg ggcatggctt ccacatcttc gtccggactg    720
acgaggcccc cggacgccgc accggaaaca tcgagttcta ctcacgccat cggttcatca    780
gggtcacagg agaccagttc gtctgaaggt cgtgccgggt tgtgtctga tgaggagtgg    840
ttgtttctca tggatgctgc ggtgattcat gatgtggtgt ggcgtgaggg tcgcgcggat    900
ttggtggctt cgttgcgtgc tcatgtgaag gctttttatg gtatgttgga taggtattcg    960
gttgatgtgg cgtctggtgg ccgtggtggg ggttctgcgg tagcgatgat tgaccggtat    1020
aggaagcgta gggggcttg agtaggtgtc tggtgttgtt gggtctcagg ttcctcgtca    1080
ccgggtggct gtggcgtatt cggtgtctgc tggcgggat gctggggagc ttggtagggc    1140
ttatgggttg acgcctgatc cgtggcagca caggtgttg gatgattggc ttgctgtgga    1200
tggtaatggc aggcttgctt cgggtgtgtg tggggtgttt gttccgcggc agaatggcaa    1260
gaatgctatt ttggagattg tggagttgtt taaggcgact attcagggtc gccgtatttt    1320
gcatacggct cacgagttga agtcggctcg taaggctttt atgcggttgc ggtcgttttt    1380
tgagaatgag cggcagtttc ctgacttgta tcgtatggtg aagtcgattc gtgcgacgaa    1440
tggccaggag gctattgtgt tgcatcatcc ggattgtgcc acgtttgaga agaagtgtga    1500
ttgtccgggt tggggttcgg ttgagtttgt ggctcgtagc cggggttctg ctcgcgggtt    1560
tacggttgat gatttggtgt gtgatgaggc tcaggagttg tcggatgagc agttggaggc    1620
tttgcttcct accgtgagcg ctgccccgtc tggtgatcct cagcagattt ttttgggtac    1680
gccgccgggg ccgttggctg acgggtctgt ggtgttgcgt cttcgcggc aggctttgtc    1740
gggtggtaaa cggttcgtg gacggagtt ttcgattcgt gacgagtcgt atcgtgatga    1800
tgtgtcgcgg cagtggcgga agttggcggg tgacactaat ccggcgttgg ggcgccgcct    1860
gaatttcggg acagtctcgg atgagcatga tcgatgtct gctgccgggt ttgctcggga    1920
gcggcttggc tggtgggatc gtggccagtc tgcttcgtct gtgattccgg cggataagtg    1980
ggttcagtcg gctgtggttg aggcggctct ggttggcggg aagttttttg gtgtctcgtt    2040
ttctcgctcg ggggatcgtg tcgcgttggc tggtgctggt aaaacggatt ctggtgtgca    2100
```

```
tgttgaggtt attgatggcc tgtctgggac gattgttgat ggtgtgggcc agctggctga  2160
ttggttggcg ttgcgttggg gtgacactga aaaggttatg gttgcagggt ctggtgcggt  2220
gttgttgcag aaggctttga cggatcgtgg tgttccgggt cgtggcgtga ttgtggctga  2280
tactggggtg tatgtggagg cgtgtcaagc cttcctggag ggtgtcaggt ctgggagcgt  2340
gtctcatcct cgtgccgatt cgaggcgtga catgttggat attgctgtga ggtcggctga  2400
gcagaagaag aagggttctg cgtggggttg gggttcctcg tttaaggatg gttctgaggt  2460
tcctttggag gctgtgtctt tggctatct  tggtgcaaag atggcgaaag cgaagcggcg  2520
tgaacggtct ggtaggaagc gggtgtctgt ggtatgaact cggatgagtt ggctctgatt  2580
gagggcatgt acgatcgtat tcaagggttg tcttcgtggc attgccgtat tgagggctac  2640
tatgagggct ctaatcgggt gcgtgatttg ggggttgcta ttccttcgga gttgcagcgg  2700
gtgcagacgg tggtgtcatg gcctgggatt gcggtggatg ctttggagga gcgtctggat  2760
tggcttggct ggactaatgg tgacggctac ggtttggatg tgtgtatgc  tgcgaatcgg  2820
cttgctacgg cgtcgtgtga tgttcacctt gatgcactga ttttgggtt  gtcgtttgtg  2880
gcgatcattc cccaagagga tgggtcggtg ttggttcgtc ctcagtcgcc gaagaattgt  2940
actggccggt tttctgccga tgggtcttgt ttggatgctg gccttgtggt gcagcagacg  3000
tgtgatcctg aggttgttga ggcggagttg ttgcttcctg atgtgattgt tcaggtggag  3060
cggcggggtt cgcgtgagtg ggttgagacg ggccgtatcg agaatgtgtt gggtgcggtt  3120
ccgttggtgc ctgttgtgaa tcgtcgccgt acttctagga ttgatggccg ttcggagatt  3180
acgaggtcta ttagggctta cacgatgag  gctgttcgca cactgttggg gcagtctgtg  3240
aatcgtgatt tttatgcgta tcctcagcgt tgggtgactg gcgtgagcgc ggatgagttt  3300
tcgcagccgg gttgggttct gtcgatggct tctgtgtggg ctgtggataa ggatgatgat  3360
ggtgacactc cgaatgtggg gtcgtttcct gtgaattctc ctacaccgta ttctgatcag  3420
atgcgtttgt tggcgcagtt gactgcgggt gaggcggctc ttccggaacg ctatttcggg  3480
tttatcactt ctaacccgcc ttctggggag gctttggctg cggaggagtc tcggcttgtg  3540
aagcgtgctg aacgcaggca gacgtcgttt ggtcagggct ggctgtcggt tggtttcctg  3600
gctgcccggg cgttggattc gagtgttgat gaggccgcgt tttttggtga tgttggtttg  3660
cgttggcgtg atgcgtcgac gccgactcgg gcggctacgg ctgatgctgt gacgaagctt  3720
gtgggtgctg gtattttgcc tgctgattct cggacggtgt tggagatgtt gggtttggat  3780
gatgtgcagg ttgaggctgt gatgcgtcat cgtgccgagt cttcggatcc gttggcggca  3840
ctggctgggg ctatttcccg tcaaactaac gaggtttgat aggcgatggc ttcgggtgct  3900
gtgtcgaggc ttgctgcgac tgagtatcag cgtgaggctg tcaggtttgc tgggaagtat  3960
gcgggctatt atgccgagtt gggtcgtttg tggcgtgccg gcaggatgag tgacacgcag  4020
tatgtgcgtt tgtgtgtgga gttggagcgt gccggccatg acggttcagc agctatggcg  4080
ggcaaattcg tttcagattt tcgccggttg aatggtgtcg atcctggttt gatcgtgtat  4140
gacgagtttg atgctgcggc ggcttttggc aggtcgtttt cgactatgaa gattatgaat  4200
agtgacccgg ataggcgaa  tgatacgatt gatgcgatgg ctgcgggtgt taatcgggct  4260
gttatgaatg ctggtcgtga cacgttgag  tggtcggcgg gtgcgcaggg taggtcgtgg  4320
cgtcgggtga ctgatggtga tccgtgtgct ttttgtgcca tgttggctac gaggtcggat  4380
tatacgacta aagagcgggc gcttactact ggtcatacgc ggtgccggt  cataagctgc  4440
aggcgtccgt ttggttcgaa gtatcatgat cattgtggtt gtacggtggt tgaggttgtt  4500
ggtccttggg aaccgaatag ggctgatgcc gagtatcaga ggacgtatga gaaggctcgt  4560
gagtggggttg atgatcatgg gttgcagcag tcgtctggca atattttgaa ggctatgcgt  4620
actgttggtg gcatgagata atttgatgtg gtttccggtt gtgtgccgcc ggttatcgat  4680
gcacagggtt gtctcccgca cggggtcaa  caatgttgtg ttgttttccg caaggagtgt  4740
agggttaggc tatggccgat cagagtattg aggaacagaa tgttgacaat gatgttgtgg  4800
agtccggaaa ggataacggc attgttgata cagtaaaaga cgatggcggg caggaggtag  4860
ccgacaatca gttgaagaat gaaggcgagg gtaaatcgcc gggggactgat tggaaggcgg  4920
aggcccgtaa gtgggagtct cgtgctaaaa gtaatttcgc cgagttggag aagcttcgta  4980
catcgagtga cgattctgga tctactattg atgagcttcg ccgcaagaat gaggaactcg  5040
aagaccggat taacgggttt gttcttgagg gtgtgaagcg cgaggtggct gccgagtgtg  5100
gcctgtcggg tgatgcgatc gcttttcttc acggtagcga taaggagtcg cttgccgagt  5160
ctgctaaggc tttgaagggt ttgatcgacc atagtagtgg tggtggcgcg ggtgtgcgcc  5220
gtcttgcggg gagtgccccc gttgatgatg ttaaacgacg tgagggtgtc gcgtttgtgg  5280
atgctcttgt caataattct aggagatgat ttatcatggc tgacgatttt ctttctgcag  5340
ggaagcttga gcttcctggt tctatgattg gtgccgtgct tgaccgtgct atcgattctg  5400
gtgttcttgc taaactgtca ccggagcagc cgactatttt cgggcctgtt aagggcgccg  5460
tttttagtgg tgttccgcgc gctaagattg ttggcgaggg cgatgttaag ccttccgcta  5520
gcgttgatgt ttctgcgttt actgcgcagc ctatcaaggt tgtgactcag cagcgtgtct  5580
cggacgagtt tatgtgggct gacgccgatt accgtctggg tgtgcttcag gatctgattt  5640
cccccggccct gggtgcttct attggtcgcg ccgttgatct tattgctttc catggtattgt  5700
atcctgctac gggtaagcct gctgcggctg tcaaggtgtc gctggataag acgaataaga  5760
cggttgatgc caccgattcc gctacggctg atcttgttaa ggctgttggt ctgattgctg  5820
gtgctggttt gcaggttcct aacggtgttg ctttggatcc ggcgttctcg tttgctctgt  5880
caactgaggt gtatccgaag ggttcgccgc ttgccgtca  gccaatgtat cctgccgccg  5940
ggttcgccgg cctggataat tggcgcggcc taaatgttgg ttcttcttcg actgtttctg  6000
gtgccccgga gatgtcgcct gcttctggtt ttaaggctat tgttggtgat ttctctcgtg  6060
tccattgggg gttccagcgt aacttcccga ttgagctgat cgagtatggt gacccggatc  6120
agacggggcg tgacttgaag ggccataatg aggttatggt tcgtgccgag gctgtgctgt  6180
atgttgcgat tgagtcgctt gattcgtttg ctgtcgtgaa ggagaaggct gccccgaagc  6240
ctaatccgcc ggccggtaac tgattcattt gttgcgataa tgtttatgct gtgtgcaggg  6300
ggtggtgttg atgggtatca ttttgaagcc tgaggatatt gagcctttcg ccgatattcc  6360
tagagagaag cttgaggcga tgattgccga tgtggaggct gtggctgtca gtgtcgcccc  6420
ctgtatcgct aaaccggatt tcaaatatag ggatgccgct aaggctattc tgcgtagggc  6480
tttgttgcgc tggaatgata ctggcgtgtc gggtcaggtg cagtatgagt ctgcgggccc  6540
gtttgctcag actacacggt cgaatactcc tacgaatttg ttgtggcctt ctgagattgc  6600
cgcgttgaag aagttgtgtg agggtgatag tggggctggt aaggcgttca ctattacacc  6660
gaccatgagg agtagtgtga atcattctga ggtgtgttcc acggtgtggg gtgagggttg  6720
ctcgtgcggg tcgaatatta acggctatgc tggcccgttg tgggagatat gatatgaccg  6780
gttttcctta cggtgaaacg gttgtgatgc ttcagccgac tgttcgtgtc gatgatcttg  6840
```

```
gtgacaaggt ggaggattgg tctaagcctg tcgagactgt gtaccataac gtggccatct  6900
atgcttccgt ttcgcaggag gatgaggccg cggggcgtga ctcggattat gagcattgga  6960
cactgctgtt caagcagcct gtcaaggctg ctggttatcg gtgtcgttgg cgtattcggg  7020
gtgttgtgtg ggaggctgac gggtctccta tggtgtggca tcatccgatg tctggctggg  7080
atgctggtac gcaggttaat gtgaagcgta agaagggcgt atgggttgtg gcacgtgatg  7140
ttgatgtgaa gctgaacttg ccgggtattc gtgaggtgtt gaagtcttct ggggtgcagg  7200
gcatgttggc tgagcgtggt gagcgtgtca agcgtgcggc ctcggcgaat gtgggcggta  7260
acgcttacga tagggcccag tatcgtgccg ggttgtcgtc tgaggtgcag gttcaccgtg  7320
ttgaggctgt ggcgcgtatt ggcaccacct ataaggtgg taaaaggatt gaggctaagc  7380
atggcacgtt ggcgaggtcg attggggctg cgtcgtgatc gtttacggtg atcctcgaat  7440
atgggctaaa cgtgtgttgg cggatgatgg ttggctgtct gatgtaccgt gcacgggtac  7500
tgtgccggat acatttgagg gtgatctgat ttggttggcg ttggatggtg gcccggagtt  7560
gcatgttcgt gagcgtgttt ttttgcgtgt gaatgtgttt tcggatacgc cggatcgtgc  7620
tatgtctttg gctcgccggg ttgaggctgt gctggctggt ggtgtggatg gtgatccggt  7680
ggtgttttgc aggcgttcga ctgggcctga tttgctggtg gatggtgcac gttttgatgt  7740
gtattcgctt tttgagctga tatgtaggcc tgcggagtct gaataagctt attgtttttg  7800
ttttaatgta attgtttgat atttaatggg ggttgtgatg gctgctacac gtaaagcgtc  7860
taatgttcgt tcagcggtta ctggcgacgt ttatattggt gacgcgcacg cgggtgattc  7920
tattaagggt gtggaggcgg ttccttccgg gcttacagct ttggggtatc tgtctgatga  7980
cgggtttaag attaagcctg agcgtaaaac ggatgatttg aaggcttggc agaatgcgga  8040
tgttgttcgc actgtggcta cggagtcgtc tatcgagatt tctttccagc tgattgagtc  8100
gaagaaggag gttatcgaac tgttttggca gtcgaaggtt actgccggat ctgattcggg  8160
ttcgttcgat atttctcctg gtgccacaac aggtgttcac gccctgttga tggatattgt  8220
tgatggcgat caggttattc gctactattt ccctgaggtt gagctcattg atcgtgacga  8280
gattaagggc aagaatggcg aagtgtacgg gtatggtgtg acgttgaagg cgtatccctg  8340
ccagattaat aagactggta atggcggtgtc gggtcggggg tggatgacgg ctttaaaagc  8400
tgatactcct ccgactcctc cgccggcccc ggttcctccg aagcctcagc cggatccgaa  8460
tccgccgtcc ggtaactgat acacgatttt aggggattgt taatagatga gtgacactgg  8520
tttcacgttg aagattggtg atcgtagctg ggtgttggcg gatgcggagg agacggctca  8580
ggctgttcct gcccgcgttt tccgtcgtgc cgccaggatt gccagtcgg ggggagtctgc  8640
ggatttcgcc caggttgagg tgatgttttc tatgttggag gctgccgccc cagctgacgc  8700
ggtggaggcc ctgaaggggc ttccatatgg t tcgtgtggcg gaggttttcc gtgagtggat  8760
ggaatacaag cctgacggta agggtgcctc gctgggggaa tagtttggct ccacggcctg  8820
attgatgatt atcgtgggc catcgaatac gattccgca ccaagtttgg tgtttcgttt  8880
tatagtgttg gtgcccgca gatgtgttgg ggtgaggctg tccggctgtg tggcgttgtg  8940
tgtaccgata cgtctagcca gttggcggcc caccttaatg gttggcagcg cccgtttgag  9000
tggtgcgagt gggctgtgtt ggacatgttg gatcattaca ggtctgctaa tagtgagggg  9060
cagccggagc ctgtggcgag gccgactgat gagcgtcggg caaggtttac gtctgggcag  9120
gtggacgata tttttggcgcg tgttcgtgcc ggtggcgggg tgtctccgca gattgatatt  9180
atggggtgaa tagtgtatgt ctggtgagat tgcttccgca tatgtgtcgt tgtatacgaa  9240
gatgcctggc cttaaaagtg atgttggtaa acagttgtcg ggtgttatgc ctgctgaggg  9300
gcagcgttcg ggtagcctgt ttgctaaagg catgaagttg gcgcttggtg gtgcggcgat  9360
gatgggtgcc atcaatgttg ctaagaaggg cctcaagtct atctatgatg tgactattgg  9420
tggcggtatt gctcgcgcta tggctattga tgaggctcag gctaaactga ctggtttggg  9480
tcacacgtct tctgatacgt cttcgattat gaattcggct attgaggctg tgactggtac  9540
gtcgtatgcg ttggggatg cggcgtctac ggcggcggcg ttgtctgctt cgggtgtgaa  9600
gtctgcgggt cagatgacgg atgtgttgaa gactgtccgg gatgtgtctt atatttcggg  9660
taagtcgttt caggatacgg gcgctatttt tacgtctgtg atggctcgcg gtaagttgca  9720
gggcgatgac atgttgcagc ttacgatggc tggtgttcct gtgctgtctt tgcttgccag  9780
gcagacgggt aaaacctcgg ctgaggtttc gcagatggtg tcgaagggc agattgattt  9840
tgccacgttt gcggctgcga tgaagcttgg catgggtggt gctgcgcagg cgtctggtaa  9900
gacgtttgag ggcgctatga agaatgttaa gggcgctttg gctatttggg gtgctacggc  9960
tatggcgccg tttcttaacg gcctgcggca gattttttgtt gcgttgaatc cggttattaa 10020
gtctatcacg gattctgtga agccgatgtt tgctgccgtc gatgctggta tccagccggat 10080
gatgccgtct attttggcgt ggattaaccg tatgccggct atgatcacga gaatgaatgc 10140
acagatgcgc gccaaggtgg agcagttgga gggcattttt gcgagaatgc atttgcctgt 10200
tcctaaagtg aatttgggtg ccatgtttgc tggcggcacc gcagtgtttg gtattgttgc 10260
tgcgggtgtg gggaagcttg ttgcaggggtt tgctccgttg gcggttgcgt gaagaatct 10320
gttccgtcg tttggtgctt tgaggggtgc cgccgggggg cttggtggcg tgtttcgcgc 10380
cctgggtggc cctgtcggga ttgtgatcgg cttgtttgcg gcaatgtttg ccacgaacgc 10440
ccagttccgt gccgctgtta tgcagtcggt ggctgtggct ggtcaggcgt tgggccagat 10500
tatgcagct gtgcagccgc tgtttggttt ggttgctggc gtggttgcca ggttggcgcc 10560
ggtgttcggc cagattatcg gtatggttgc tggtttggct gcccggctgg tgcctgttat 10620
tggtatgctt attgcccggc tggttcctgt tatcacccga attattggta tggtaaccca 10680
ggttgctgcc atgttgttgc ctatgctgat gccggttatt caggctgttg ttgctgtgat 10740
acggcaggtt attggtgtca ttatgcagtt gatacctgtt tgatgccgg ttgtgcagca 10800
gattttgggt gctgtcatgt ctgttttgcc gccgattgtt ggtttgatac ggtcgctgat 10860
accggtgatc atgtcgatta tgcgtgtggt ggtgcaggtt gttggtgctg tgctacaggt 10920
ggtggcccgt attattccgg ttgttatgcc gatttatgtt tcggtgattg gattcattgc 10980
caagatttat gctgcggtta tcgtttttga ggctaaggtt attggcgcta ttcttcgtac 11040
tattacgtgg attgtgaatc attcagtgtc tggcgtgagg tctatgggca cggccatcca 11100
gaatggctgg aatcatatta aatcgtttac gtctgcgttt attaacggtt ttaagtcgat 11160
catttctggc ggcgtgaacg cggttgtggg gtttttacg cggcttggtt tgtcggttgc 11220
tcccatgtg aggtccggtt taacgctgc gagggtgcgt gtttcttccg ccatgaatgc 11280
tattcggagt gttgtgtctt cggtggcgtc tgctgttggc gggttttcca gttcgatggc 11340
gtctcgtgtt cggaatggtg ctgtgcgcgg gtttaatggt gcccgagtg cggcttcttc 11400
tgctatgcat gctatggggt ccgctgtgtc tagtggtgtg catggtgtgc tgggttttt 11460
ccggaatttg cctgacaata ttcggcgtgc gcttggtaat atgggtcccc tgttggtgtc 11520
ggctggccgt gatgtggtgt ccggtttagg taatggtatc aagaatgctt tgagtggcct 11580
```

```
gttggatacg gtgcgtaata tgggttctca ggttgctaat gcggcgaagt cggtgttggg   11640
tattcattcc ccgtctcggg tgtttcgtga cgaggttggc cggcaggttg ttgccggttt   11700
ggctgagggt attactggta atgctggttt ggcgttggat gcgatgtcgg gtgtggctgg   11760
gaggctgcct gatgcggttg atgcccggtt tggtgtgcga tcgtctgtgg gttcgtttac   11820
cccgtatggc aggtatcagc gcatgaatga taagagtgtt gtggtgaatg tgaatgggcc   11880
tacttatggg gatcctgccg agtttgcgaa gcggattgag cggcagcagc gtgacgcttt   11940
gaacgcgttg gcttacgtgt gattttgggg gtgtggtgc                          11979

SEQ ID NO: 25           moltype = DNA  length = 83
FEATURE                 Location/Qualifiers
source                  1..83
                        mol_type = other DNA
                        note = PAC7 cos of pAN594
                        organism = synthetic construct
SEQUENCE: 25
acaaaaggga ggtatttcac taagccgtac gaggtcttgc acgggtgtgc aggggggtgtg   60
cccggtgggg gttggcgggt ttt                                            83

SEQ ID NO: 26           moltype = DNA  length = 4670
FEATURE                 Location/Qualifiers
source                  1..4670
                        mol_type = other DNA
                        note = operon of gp15-gp19+gp45
                        organism = synthetic construct
SEQUENCE: 26
cgacgcggcg gtctgccgac ccggcaacga ccaactcccc gacgggcgct gacaccggcc   60
cggcagcgtg catgcgtgca tttccaccct caagaaccat tgactggcga cgcgcaggtg   120
ggagaattga actgaacgct tgaacgcgct tggcttacgt gtgatttggg gggtgtggtg   180
catgtttatt cctgacccgt ctgatcgttc tggtttgact gtgacttggt ctatgttgcc   240
gttgcaggat aatgatccgg agcgtgtgct tcatttgacg gattatacgg ggtcgtctc    300
gataatgttg ttgaatgatt cgttgcgcgg tttgggtgtt cctgaggtgg agcattttc    360
tcaaactcat gttggggtgc atggctcgga gtggcgcggg tttaatgtga agcctcgcga   420
ggtgacgcta ccggtgttgg tgtcgggtgt tggcccggat ccggtggggcg gttttcgtga   480
cggttttttg aaggcgtatg acgagttgtg gtctgctttt cctcctggcg aggtggggga   540
gttgtctgtg aagactcctg ccggtcgtga gcgtgtgttg aagtgccggt ttgattcggt   600
ggatgacacg tttacggtgg atccggtgaa caggggttat gcgcgttatc tgttgcattt   660
gacgcttat gacccgtttt ggtatgggga tgagcagaag tttcgtttca gtaacgctaa   720
gttgcaggat tggttgggtg gcggcccctg cgacggtaag ggtaccgcgt ttccggtggt   780
gttgacgcct ggtgttggtt cgggttggga taatctgtct aataagggtg atgtgcctgc   840
gtggcctgtg attcgtgttg aggggccgtt gtcgtcgtgg tctgtgcaga ttgatgtttt   900
gcgtgtgtcc tcggattggc cggtggagga gtatgattgg atcactattg atacggatcc   960
tcgtaagcag tctgcgttgt tggacgggtt tgaggatgtg atggatcgtt tgaaggagtg   1020
ggagtttgcg cctatcccgc ctggccgttc tcggagtgtg aatattgaga tggttggttt   1080
gggtgccatt gttgtgtcgg tgcagtacag gttttttgagg gcttggtgaa tagttgatgg   1140
ctggttttgt tccgcatgta acattgttta caccggatta tcgccgtgtg gcgcctatca   1200
attttttga gtcgttgaag ttgtcgttga agtggaatgc tttgtccact ttggagttgg   1260
tggtgtctgg tgatcattct aggctgtgacg ggttgactag gccgggtgcg ccgcttgtgg   1320
ttgattatgg tggtgccag attttttctg ggcctgtgcg tcgggtgcat ggtgtgggtc   1380
cgtggcgttc ttcgcgtgtg actatcacgt gtgaggatga tattcgtctg ttgtggcgta   1440
tgttgatgtg gcctgtgaat tatcgtcctg gtatggttgg tatggagtgg cgtgcggatc   1500
gggattatgc ccattattcg ggtgcggcgg agtcggtggc taagcgggtg ttggggggata   1560
atgcttggcg tttccgtct ggtttgttta tgaacgatga tgagagtcgt ggccgctata   1620
ttaaggattt tcaggtgcgg tttcacgtgt ttgccgataa gttgttgccg gtgttgtcgt   1680
gggctcggat gactgtcacg gtgaaccagt ttgagaatgc gaagtttgat cagcgtggtt   1740
tggtgtttga ttgtgtgcct gctgtgaccc ggaaacatgt gttgactgcc gagtcgggtt   1800
cgattgtgtc gtgggagtat gtgcgtgacg ccccgaaggc gacatctgtg gtggttggtg   1860
gccgtggcga gggtaaggat cggctgtttt gtgaggatgt tgattcggcg gccgaggatg   1920
attggtttga tcgtgtcgag gtgtttaagg atgcccgtaa cacggattcc gagaaggtgt   1980
ctctcttcga tgaggctgag cgggtgttgt ccgagtcggg ggctacgtcg gggtttaaga   2040
ttgagttgac tgagtcggat gttgcggt ttggtcccgg caatctgatg cctggggatt   2100
tgatctatgt ggatgtgggt tctgggccta ttgcggagat tgtgcggcag attgatgtgg   2160
agtgtgtatc gcctggtgat ggttggacga aggtgactcc ggttgcgggg gattatgagg   2220
ataatccgtc ggccctgttg gctcgccgtg tggctggttt ggctgcgggt gtgcgggatt   2280
tgcaaaagtt ttagtaagtg attgggtttt gttgtggta ttgtgtgtaa agggtttgat   2340
ggtgtgttga ccgagtatga ttgggctcaa atgtctggtc tgatgggtaa tatgccgtct   2400
gtgaaggggc ctgacgattt tcgtgtcggg acgacgattc agggttctac ggtgttgtgt   2460
gagatcctgc cggggcaggc ttgggctcac ggggtgatgt gcacgtcgaa tagtgttgag   2520
acggtgacgg gtcagcttcc gggccgggt gagactcgat acgactatgt ggtgttgtct   2580
cgggattggc aggagaatac ggccaagttg gagattgtga tgcggggagc gt           2640
gccagggatg tgttgagggc tgagcctggc gtgtttcatc agcagctact ggcgactttg   2700
gtgttgtcgt ctaacgggtt gcagcagcag ttggataggc gtgctgtggc ggctagggtt   2760
gcgtttgggg agtctgctgc gtgtgatcct accctgtgg agggtgaccg tgtgatggtt   2820
ccttcggggg ctgtgtgggc taaccatgcc ggcgagtgga tgttgttgtc tcccaggatt   2880
gagacggtt cgaagtcgat catgtttggt ggtctgctta tgtatgctta cacgatccccg   2940
tttgagcgcg agttcagtag tccgcctgtt gtggtggcgt ctatggctac ggcggctggg   3000
ggcacggcac agattgatgt gaaagcctac aatgtgactg cccaaaatt tagttttggcg   3060
tttattacga atgatggttc gaagccgaat ggtgtgcctg cggtgcgaa ttggattgct   3120
gtcgcgtgtg gactgcacgg gtgttgtggc ggatggtgtg atgttggggg gctgtggtgt   3180
cgtggtttac tcctgcactg gtggcctcta tttgtaccgc gttggccacg gttttgggtt   3240
```

```
ctgttcaggc tgtcacatcc cggtctagga agcgtttacg caggctgtcg gctcaggtgg   3300
atgcgatgga agagtatacg tggggtgtgc ggcgcgaggt gcgaaggttt aacgccgggc   3360
ttcctgatga tgtggagccg atgcatcttc ctgatttgcc cgagtttttg aaagatactg   3420
ttgatggtgg aggtgagtag ggttgaggga gttggaggag gagaagcggc agcgccgcaa   3480
ttttgagaag gcttcactgg tgttgttgtt tttgtcgctt gtgttgttgg cggtggttgc   3540
tgcgggtgct ttgcgtttcg gggctgtatc ctctgagcgg gattcggagc aggcgagggc   3600
ccagtcgaat ggtacggctg ccaggggttt ggctgcccgt gtgaagcagg cgtgtgcttc   3660
gggtggggtg gagtctgtgc gtcttcaccg ttctggtttg tgtgtggatg ctgtgcgtgt   3720
tgagcagcgt gttcagggtg tgccgggtcc tgccggtgag cgcggcccgc aaggcccttc   3780
aggtcctgcc ggccgggatg gtgttaatgg ttcggctggg ctggttggcc ctgttggtcc   3840
gcaaggttct ccgggtttga atggtgtgaa aggtcctgac ggcttgcctg gcgctaacgg   3900
ttcggatggc cgtgatggtg ttccaggtcg tgcaggtgct gacggtgtga acggcgttga   3960
cggcgctgat ggtcgggatg gttctgccgg tgagcgcggc ccgcaaggcc cttcaggtcc   4020
tgccggcccg caaggtgcac agggtgaacg gggtgagcgt ggtcccgccg gtgcgaatgg   4080
atcggatggc catgatggta aggatgggcg ctcggtggtg tctgtgtact gttccggggg   4140
ccgcctggtt gtgaaatata gtgacggtgt ggcttccacg atatcgggtt cggcggcctg   4200
ccagggtgtg aaaccgtcgc ctctagtgac tatatcatcc cacaaataga ggctcacagg   4260
ggccatggga gattggggg cgtgatggca cacaccaacc gcacagccag ccaagcccac   4320
cggcgctggc gggcaaggct catcacccaa gcccgacaac aaggccaaac cgaatgccca   4380
ctctgcggag tcaccatcac ctggaacacc cacgacctgc caaccagccc cgaagccgac   4440
cacatcacac ccgtcagccg gggaggactc aacaccctcg acaacgggca aatcatctgc   4500
agaacatgca acagaagcaa aggcaacaga acacaaccaa acatcaaatt ccaacaacaa   4560
accacaaaaa cattgattcc atggtgagga tatccacgag ctgcgttcgg ctaaacccaa   4620
aagtaaaaac ccgccgaagc gggttttaac gtaaaacagg tgaaactgac              4670

SEQ ID NO: 27         moltype = DNA  length = 1910
FEATURE               Location/Qualifiers
source                1..1910
                      mol_type = other DNA
                      note = pAN241 vector
                      organism = synthetic construct
SEQUENCE: 27
caagtggccc atcgaagagg acggcaccac catctcgccg ggcaagctca aggacgtgtc    60
caggctgacg ctcacggtgc tgctgcaccc ctcgtgcgcc atcatcgtgg atccccaaga   120
ttgtccggac ggcggttgag cgcggcctga taggcgccgc agctcctgct cccgggccgc   180
cccggtcggc ggtttactcc tttcctgccg gccggggcac tcaagacaac cgggggcccct  240
cgcgaaattg aggggccccg cctgattgca aggggtgcc catgaagcaa cccgggcccc   300
accaaagaat gcgggctacc ttcaaggccg acaggggctg gcgagtggca tgcccacggt   360
gcgcctggca tgccaccagc acccaccttg catggctcat ggatcaggcc agcacacaca   420
cctgtgcacc cctgctgttg tcgcccacgc caccccgacgt ggagctggca ccggcaggcg   480
acgggctgtc cgtcctgtgg cccgaggtgg acggtgacgt gcagttcacc tgcatccaca   540
ccagcaccgc cacgtgcagg caggacgcac catgagcacc agtcgcaccg gcacggccac   600
atggttgcgc catgcagcac aggccaagcg tgaggcccaa gcacgaggac tcgcccgctg   660
cccactgtgc ggcgtctgga tggactacga ggtcggcaag cgacccaact cggccgaagc   720
agaccacatc agaccgcatt cgcttggtgg ttcagacgac atcgacaaca ttcgcgtcat   780
ttgtcgtcgt tgcaatcaat cgcgcggaaa cggcctgaag cgaccagggc gccaacgtca   840
ggtccaatc aagcgcatcg agctgcccca accggcccgc agtggggcat ttcctgcccc   900
gccggcatga atggaagggc agtgcggatg gtgcggtcgg gcattcgatc gtgcccggac   960
gggtcgcccg cgacgcttct gctcggcccg ctgtcgggtc gccgcgtccc ggtgtgcgat  1020
cccgctggcc atgaggtccc gcactgcgtg gtccgctgc gacggcaagc gccccatcac  1080
cctggctggc gctccggcct catccacgga cccgggcaca tggtctggct ggtcgcaggt  1140
gcgacgcgcc acggccggcg atggcttcgg gaccatgctc ggtgacgggc tggggtgctg  1200
ggatctcgac cacttcgacg atcagggcgc ccgggccttc atcgaccgga tcgataagcc  1260
gatcatcttc gccgagcgt cggtgtcggg gcatggcttc cacatcttcg tccggactga   1320
cgaggccccc ggacgccgca ccggaaacat cgagttctac tcacgccatc ggttcatcag  1380
ggtcacagga gaccagttcg tctgaagaag ggggtgcgcc atggctgcac aggtcagggc  1440
cgtggacccc gatgagcgcc cacccgcccg caagcgggcc aagaccatca cccaggccgc  1500
gaagtccggc actgaggttg aactgttgga ggcactgcag gctcgcgtgg cccgcgccgt  1560
gcaggaccgt gacactccgc cgcgcgatct ggcagcgctg acgaagcggc tgatggacat  1620
cacccgggag ctcgagggg cccgggtcaa ggatcaggag gcgggatctg atggtgccgt  1680
caccgcagac gaaacatggc gaccgcaagc tctctgaggt cgccaagcac ctgatccttc  1740
ctgaagggat cgtctcgacg ggctggccgg ccgtgcgtga ccggtgtggc gagtggggtg  1800
tggtcttcga ccgttggcag gacggcatgg gccgggtgat cctgtcgaag cgcggcagcg  1860
gcctgttcgc cgctggtgtg ggcggggtcg gcatgtcgat cccgcgccag              1910
```

PRODUCTION OF LYTIC PHAGES

CROSS REFERENCE TO RELATED APPLICATIONS

This application is a divisional of U.S. application Ser. No. 17/742,693 filed on May 12, 2022, which claims the benefit of U.S. application 63/187,531 filed May 12, 2021, and U.S. application 63/187,532 filed May 12, 2021, which are incorporated herein by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Oct. 3, 2023, is named EB2021-04b_US-_Div.xml and is 179,370 bytes in size.

FIELD OF THE INVENTION

The present invention concerns bacterial cells for producing lytic phage particles and methods using such bacterial cells.

BACKGROUND

Lytic bacteriophages (phages) are self-replicating viruses, which are capable of infecting and lysing their specific host bacteria. Because of their host specificity and nontoxicity, lytic phages are considered to be an alternative solution to combat antimicrobial-resistant pathogens.

However, lytic phages are naturally incapable of being stably maintained in the genome and/or as episomes of/in a strain, which drastically complicates their production at an industrial scale.

Moreover, most current phage or phage-derived delivery vehicle production methods imply the use, as production cell, of the bacterial species or strain which is the natural host of said phages. Such methods can turn out to be dangerous when such bacterial cells are pathogenic, for example when they produce toxins. Moreover, many bacterial species cannot be easily manipulated, for instance because of their growth conditions or because there is no efficient genetic tool for those bacteria.

There is thus a need for a method enabling the safe, easier and efficient production of a lytic phage or lytic phage-derived particle.

The present inventors considered that phages can be viewed as more or less large genetic circuits, the final output of which is the generation of more phage particles. To do this, no matter if the phage is lytic, temperate or chronic (for instance filamentous phages such as M13), the present inventors considered that the information encoded in their genomes can be roughly categorized depending on the function it performs:
  Genes devoted to insertion/excision (for temperate phages).
  Genes devoted to DNA replication, RNA transcription, etc. Indeed, some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.
  Genes devoted to packaging of the newly synthesized phage genome into the newly synthesized phage capsids: terminases and accessory proteins, ligases, etc.
  Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).
  Genes related to defense from host's anti-phage mechanisms, degradation/modification of host's elements to complete the lytic cycle, super-exclusion mechanisms or genes that are advantageous for the host.

The DNA packaging and structural genes categories are deeply connected, since the packaging machinery recognizes the pre-assembled heads and the DNA to be packaged in these heads, initiates and terminates DNA packaging.

The present inventors hypothesized that by abstracting and differentiating all the modules defined above, a system could be built that contains all excision/insertion, replication and regulation elements from a non-lytic phage and encodes the packaging/structural elements for a lytic phage, since, as considered by the inventors, they could be viewed as independent genetic modules.

Treating them as independent genetic modules could also allow for the construction of a system that contains only the desired structural and/or regulatory elements of the lytic phage to be produced under the control of a master regulatory element (an inducible repressor, for example) that may not be derived from a phage. For instance, only the structural operon and the DNA packaging machinery of a lytic phage could be placed under the control of a repressor that responds to a small molecule or a physical/chemical signal (LacI, AraC, PhlF, Lambda cI, etc.), triggering the production of all the elements necessary to generate pure mature lytic phage delivery particles (phages or packaged phagemids). This "trimmed down" version of a phage genome could be stably maintained in a bacterial production strain.

SUMMARY OF THE INVENTION

The present invention arises from the unexpected finding by the inventors that it is possible, by exchanging the structural operon of an *Escherichia coli* production strain encoding a system to generate pure Lambda packaged phagemids with the structural elements of a strictly lytic phage (such as T7 phage), to drive the assembly and packaging of pure heterologous lytic phagemid particles when supplemented with a plasmid containing the correct packaging signals (LTR for T7 phage). The present inventors thus here showed that packaged phagemids can be produced structurally based on a T7 lytic phage, but regulated and maintained in a lysogenic state by the Lambda prophage machinery in an *Escherichia coli* production strain.

The inventors also showed that the structural operon of a *P. freudenreichii* prophage can be exchanged with the structural operon of a lytic phage of a *C. acnes* strain. With this approach, the inventors showed that it is possible, by exchanging the structural operon of a *P. freudenreichii* prophage with the structural operon of a lytic phage of a *C. acnes* strain, to drive the assembly and packaging of pure *C. acnes* phagemids.

The present invention thus concerns a production bacterial cell for producing lytic phage particles or lytic phage-derived delivery vehicles, said production bacterial cell stably comprising at least one phage structural genes and at least one phage DNA packaging genes, said phage structural gene(s) and phage DNA packaging gene(s) being derived from a lytic bacteriophage, wherein the expression of at least one of said phage structural genes and/or at least one of said phage DNA packaging gene(s) in said production bacterial cell is controlled by an induction mechanism.

The present invention also concerns a method for producing lytic phage particles or lytic phage-derived delivery vehicles, comprising:
  (a) providing the production bacterial cell of the invention, and
  (b) inducing, in said production bacterial cell, expression of said at least one of said phage structural gene(s) and said at least one of said phage DNA packaging gene(s), and assembly of the products expressed by said at least one phage structural gene(s) and said at least one phage DNA packaging gene(s), thereby producing lytic phage particles or lytic phage-derived delivery vehicles.

Another object of the invention concerns a hybrid helper phage system comprising:
  (i) at least one phage DNA packaging gene(s) derived from a lytic bacteriophage,
  (i') at least one phage structural gene(s) derived from said lytic bacteriophage,
  (i") optionally, at least one phage gene(s) involved in phage regulation derived from said lytic bacteriophage, and
  (ii) at least one gene, derived from a non-lytic bacteriophage, involved in phage excision/insertion, phage DNA replication, and/or phage regulation,
wherein said genes (i), (i'), (i") and (ii) are comprised in a unique nucleic acid molecule or in separate nucleic acid molecules, and
wherein said hybrid helper phage system does not comprise any expressed phage structural gene derived from said non-lytic bacteriophage.

DETAILED DESCRIPTION OF THE INVENTION

Production Bacterial Cell

The present invention concerns a production bacterial cell for producing lytic phage particles or lytic phage-derived delivery vehicles, said production bacterial cell stably comprising at least one phage structural gene(s) and at least one phage DNA packaging gene(s) derived from a lytic bacteriophage, wherein the expression of at least one of said phage structural gene(s) and at least one of said phage DNA packaging gene(s) in said production bacterial cell is controlled by an induction mechanism.

As used herein, the term "phage particle" refers to a functional or non-functional (for example non-reproductive and/or replicative) virion.

As used herein, the term "lytic phage particle" refers to particles derived from phages which are naturally incapable of being stably maintained in the genome and/or as episomes of/in a strain and thus have a strictly lytic (as opposed to lysogenic) lifestyle, i.e. the infection process always ends with the lysis of the target strain.

As used herein, the term "lytic phage-derived delivery vehicle" refers to any means that allows the transfer of a payload into a bacterium and which is derived from a lytic bacteriophage. In the context of the invention, the term "lytic phage-derived delivery vehicle" further encompasses lytic bacteriophage-derived particles which do not comprise any payload but are able to target bacterial cells.

The lytic phage-derived delivery vehicle can refer to a lytic bacteriophage derived scaffold and can be obtained from a natural, evolved or engineered lytic bacteriophage.

Bacterial Cell

The production bacterial cell of the invention may be of any bacterial species or strain, in particular defined below under the section "Targeted bacteria".

However, the production bacterial cell is preferably a non-pathogen bacterial cell. Still preferably, the production bacterial cell is a bacterial cell which can be easily manipulated.

By "easily manipulated" is meant herein that the bacterial cell can be cultured and/or modified using well-known techniques.

In a particular preferred embodiment, said production bacterial cell is an *E. coli* bacterial cell. Alternatively, said production bacterial cell may be a *Bacteroides* bacterial cell, more particularly a *Bacteroides* thetaiotaomicron bacterial cell, a *P. freudenreichii* bacterial cell, a *Fusobacterium* bacterial cell, or a *Streptococcus* bacterial cell. In a particular embodiment, said production bacterial cell is a *P. freudenreichii* bacterial cell.

The production bacterial cell of the invention can be obtained by any technique well-known from the skilled person, in particular by introducing into a bacterial cell, said phage structural gene(s) and phage DNA packaging gene(s) derived from a lytic bacteriophage, by any technique well-known in the art.

The production bacterial cell of the invention can typically be obtained by homologous recombination or recombineering including for example MAGE (Wannier et al. Recombineering and MAGE. Nat Rev Methods Primers 1, 7 (2021)), using CRISPR, TALEN, meganucleases and/or Zn-finger technologies for instance or using site specific recombination with phage integrase, PASTE (Ioannidi et al. Drag-and-drop genome insertion without DNA cleavage with CRISPR-directed integrases. Biorxiv 2021.11.01.466786 (2021) doi:10.1101/2021.11.01.466786) or Transposon-Associated CRISPR-Cas System (Ma et al. Trends Microbiol 29, 565-568 (2021)).

Phage DNA Packaging Genes and Phage Structural Genes

The production bacterial cell of the invention stably comprises at least one phage structural gene(s) and at least one phage DNA packaging gene(s) derived from a lytic bacteriophage.

By "stably comprise" or "stably comprising" is meant herein that the production bacterial cell retains said phage structural gene(s) and phage DNA packaging gene(s) either incorporated into its chromosome, or on an episome that is maintained in the cell typically through selection (e.g., with a nutritional, auxotrophic, or drug resistance marker). Each gene stably comprised by the production bacterial cell can independently be on a plasmid, on a helper phage, or is integrated into the production bacterial cell chromosome.

In a particular embodiment, said production bacterial cell stably comprises at least two, 3, 4, or all phage structural genes derived from said lytic bacteriophage, and at least one phage DNA packaging gene(s) derived from said lytic bacteriophage.

In a particular embodiment, said production bacterial cell stably comprises at least one phage structural gene(s) derived from said lytic bacteriophage, and at least two or all phage DNA packaging genes derived from said lytic bacteriophage.

In a particular embodiment, said production bacterial cell stably comprises at least two, 3, 4, or all phage structural genes derived from said lytic bacteriophage, and at least two or all phage DNA packaging genes derived from said lytic bacteriophage.

In a particular embodiment, said production bacterial cell stably comprises all phage structural genes derived from said lytic bacteriophage, and all phage DNA packaging genes derived from said lytic bacteriophage.

By "phage structural genes" is meant herein genes from a bacteriophage which are involved in the building of the bacteriophage protein capsid. Phage structural genes include genes encoding phage structural elements; genes encoding phage proteins involved in the assembly of the phage structural elements; and genes encoding phage proteins packaged inside the capsid as scaffold or as pilot proteins to be injected into a targeted bacterial cell.

Phage structural elements are well-known from the skilled person and depend on the type of bacteriophage from which they are derived. Phage structural elements can be proteins but also RNAs (for example some phages like phi29 from *Bacillus subtilis* encode a structural scaffold made of RNA). Phage structural elements typically include capsid proteins, tape measure proteins, fibers, baseplate proteins, tail sheath proteins, whisker proteins, decoration proteins, etc . . .

Phage proteins involved in the assembly of the structural elements are well-known from the skilled person and depend on the type of bacteriophage from which they are derived, and optionally on the structural elements encoded by the other phage structural genes. Phage proteins involved in the assembly of the structural elements typically include phage chaperone proteins and phage proteases.

Phage proteins packaged inside the capsid as scaffold or as pilot proteins to be injected into a target host cell are well-known from the skilled person and depend on the type of bacteriophage from which they are derived. Examples of such phage proteins are RNA polymerase from phage N4 or minor pilot proteins.

As will be understood by the skilled person, the presence of a particular phage structural gene in the production bacterial cell of the invention will depend on the bacteriophage from which said phage structural genes are derived.

By "phage DNA packaging genes" is meant herein genes from a bacteriophage which are involved in the packaging of the bacteriophage genome into the bacteriophage capsid. Phage DNA packaging genes are well-known from the skilled person and include genes encoding phage terminases, genes encoding phage accessory proteins, genes encoding phage ligases, genes encoding phage exonucleases involved in DNA packaging and genes encoding phage endonucleases involved in DNA packaging.

In a particular embodiment, said production bacterial cell further stably comprises at least one gene involved in phage regulation derived from said lytic bacteriophage.

By "gene involved in phage regulation" is meant herein phage genes involved in the interaction of the phage with the host. Examples of genes involved in phage regulation include phage genes encoding master repressors, phage genes encoding anti-termination proteins, phage genes involved in transcription such as phage genes encoding RNA polymerases, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In a particular embodiment, said production bacterial cell stably comprises phage gene(s) involved in defense against host's anti-phage mechanisms derived from said lytic bacteriophage.

In another particular embodiment, said production bacterial cell stably comprises phage gene(s) involved in transcription such as phage genes encoding RNA polymerases, derived from said lytic bacteriophage.

In a particular embodiment, said phage structural gene(s) and phage DNA packaging gene(s) derived from said lytic bacteriophage, and optionally said gene(s) involved in phage regulation derived from said lytic bacteriophage are comprised in at least one plasmid, chromosome and/or helper phage. In a particular embodiment, said phage structural gene(s) and phage DNA packaging gene(s) derived from said lytic bacteriophage, and optionally said gene(s) involved in phage regulation derived from said lytic bacteriophage are comprised in at least two separate nucleic acid molecules, in particular at least two plasmids, chromosomes, helper phages or combinations thereof.

In a particular embodiment, said phage structural gene(s) and phage DNA packaging gene(s) derived from said lytic bacteriophage, and optionally said gene(s) involved in phage regulation derived from said lytic bacteriophage are comprised in a hybrid helper phage system as defined below.

In a particular embodiment, said phage structural gene(s) and phage DNA packaging gene(s) derived from said lytic bacteriophage, and optionally said gene(s) involved in phage regulation derived from said lytic bacteriophage are comprised in a helper phage.

Induction Mechanism

In the context of the invention, the expression of at least one of said phage structural gene(s) and/or at least one of said phage DNA packaging genes, as defined in the section "Phage DNA packaging genes, and phage structural genes" above, in said production bacterial cell is controlled by at least one induction mechanism.

In a particular embodiment, the expression of at least one of said phage structural gene(s), in particular at least two, at least three, or all said phage structural genes, in said production bacterial cell is(are) controlled by at least one induction mechanism, in particular by one induction mechanism.

In a particular embodiment, the expression of at least one of said phage DNA packaging gene(s), in particular at least two, at least three, or all said phage DNA packaging genes, in said production bacterial cell is(are) controlled by at least one induction mechanism, in particular by one induction mechanism.

In a particular embodiment, the same induction mechanism controls the expression of the at least one of said phage structural gene(s) and the at least one of said phage DNA packaging gene(s).

In an alternative embodiment, the expression of the at least one of said phage structural gene(s) and the expression of the at least one of said phage DNA packaging gene(s) are controlled by different induction mechanisms.

By "induction mechanism" is meant herein a mechanism, encoded by a gene or group of genes comprised, in particular stably comprised, in said production bacterial cell, able to induce the expression of the genes they control, in response to a given trigger.

In a particular embodiment, said induction mechanism further controls the copy number of said at least one of said phage structural gene(s) and/or said at least one of said phage DNA packaging gene(s). In other words, in a particular embodiment, said induction mechanism further controls the replication of said at least one of said phage structural gene(s) and/or of said at least one of said phage DNA packaging gene(s), in particular the replication of the nucleic acid molecule(s) carrying said at least one of said phage structural gene(s) and/or said at least one of said phage DNA packaging gene(s).

In a particular embodiment, said induction mechanism further controls the assembly of the products expressed by said at least one of said phage structural gene(s) and said at least one of said phage DNA packaging gene(s).

Examples of Such Induction Mechanism Include

Protein repressor or activator-based induction systems responding to small molecules (for example sugars, quorum-sensing molecules, gases, synthetic molecules, peptides, amino acids, metabolites, etc), physical signals (temperature, pressure, etc.), chemical signals (osmolarity, pH, etc.), biological signals (cell density, DNA damage, etc.); these systems may be activated by a secondary protein such as an orthogonal RNA polymerase or sigma factor.

Protein degradation systems to activate or repress transcription from a promoter.

RNA-based induction systems such as aptamers responding to the signals stated above, such as RNAi, CRISPRi, toehold systems, riboswitches, etc.

One or more nucleic acids comprising at least one gene, derived from a non-lytic bacteriophage, involved in phage excision/insertion, phage DNA replication, and/or phage regulation.

In a particular embodiment, said induction mechanism comprises at least one gene, derived from a non-lytic bacteriophage, involved in phage excision/insertion, phage DNA replication, and/or phage regulation.

Therefore, in particular embodiment, said production bacterial cell further comprises at least one gene, derived from a non-lytic bacteriophage, involved in phage excision/insertion, phage DNA replication, and/or phage regulation.

Genes Involved in Phage Excision/Insertion, Phage DNA Replication, and/or Phage Regulation By "gene involved in phage excision/insertion" is meant herein genes from lysogenic phages involved in the excision of the phage, present as a prophage, from the genome or episome of a bacterial cell and/or the insertion of the phage, as a prophage, in the genome or episome of a bacterial cell.

By "gene involved in phage DNA replication" is meant herein genes from lysogenic phages, involved in the mechanism of replication of the phage DNA. Examples of genes involved in phage DNA replication include genes encoding DNA polymerase and genes involved in the segregation of the prophage sequence if it exists in a plasmid or linear plasmid form.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In the context of the invention, said gene(s) involved in phage excision/insertion, phage DNA replication, and/or phage regulation, is(are) not DNA packaging gene(s) nor structural gene(s), as defined above.

In a preferred embodiment, the production bacterial cell of the invention comprises at least one gene, preferably all the genes, involved in phage excision/insertion derived from a second type of bacteriophage; at least one gene, preferably all the genes, involved in phage DNA replication derived from a non-lytic bacteriophage; and/or at least one gene, preferably all the genes, involved in phage regulation derived from a non-lytic bacteriophage.

In the context of the invention, said production bacterial cell does not comprise genes derived from the lytic bacteriophage which are involved in phage excision/insertion and/or phage DNA replication.

In a particular embodiment, said gene(s) involved in phage excision/insertion, phage DNA replication, and/or phage regulation derived from said non-lytic bacteriophage, are comprised in at least one plasmid, chromosome and/or helper phage. In a particular embodiment, said gene(s) involved in phage excision/insertion, phage DNA replication, and/or phage regulation derived from said non-lytic bacteriophage are comprised in at least two separate nucleic acid molecules, in particular at least two plasmids, chromosomes, helper phages or combinations thereof.

In a particular embodiment, said gene(s) involved in phage excision/insertion, phage DNA replication, and/or phage regulation derived from said non-lytic bacteriophage are comprised in a hybrid helper phage system as defined below.

In a particular embodiment, said gene(s) involved in phage excision/insertion, phage DNA replication, and/or phage regulation derived from said non-lytic bacteriophage, are comprised in a helper phage system, more particularly on the same helper phage system as said said phage structural gene(s) and phage DNA packaging gene(s) derived from said lytic bacteriophage, and optionally said gene(s) involved in phage regulation derived from said lytic bacteriophage.

In a particular embodiment, said production bacterial cell is from the same bacterial species or strain as the bacterial species or strain from which said non-lytic bacteriophage comes and/or that said non-lytic bacteriophage targets.

In a more particular embodiment, said production bacterial cell is an *E. coli* bacterial cell. In another particular embodiment, said production bacterial cell is a *P. freudenreichii* bacterial cell.

Other Elements

In a particular embodiment, the production bacterial cell of the invention further comprises at least one gene involved in phage RNA transcription.

By "gene involved in phage RNA transcription" is meant genes from temperate or lytic phages, involved in the mechanism of transcription of the phage RNA. Examples of such genes include genes encoding phage RNA polymerase and phage genes encoding proteins modifying the host's RNA polymerases, typically to be able to work past terminators.

Bacteriophage and Gene Derived from a Bacteriophage

By "gene derived from a bacteriophage" is meant herein that the sequence of the gene is obtained from a bacteriophage, said sequence being optionally modified, recoded and/or optimized compared to the sequence initially present in the bacteriophage. For example, said sequence may be recoded for codon exchange or optimization or preventing recombination.

Bacteriophages are obligate intracellular parasites that multiply inside bacteria by co-opting some or all of the host biosynthetic machinery. Alternatively, some bacteriophages (lytic bacteriophages) are naturally incapable of being stably maintained in the bacterial genome and/or as episomes in bacteria and cause lysis of the bacteria. Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

By "lytic phage" is meant herein a bacteriophage which infects bacteria or archaea, and which is naturally incapable of being stably maintained in the genome and/or as episomes of/in a strain and thus has a strictly lytic (as opposed to lysogenic) lifestyle and causes lysis and destruction of the bacterial or microorganism cell after replication of the phage. As soon as the cell is destroyed, the phage progeny can find new host cells (e.g., bacteria) to infect. It is well-known from the skilled person which bacteriophages, in the bacteriophages listed below, are lytic phages.

In a particular embodiment, said non-lytic bacteriophage is a temperate bacteriophage, filamentous phage, or pseudo-lysogenic phage.

By "temperate bacteriophage" or "lysogenic bacteriophage" is meant herein a bacteriophage which infects bacteria or achaea, which can be stably maintained in the genome and/or as episomes of/in a strain, and which replicates with cells without, in their lysogenic state, producing virions. It is well-known from the skilled person which bacteriophages, in the bacteriophages listed below, are temperate phages.

By "filamentous phage" is meant herein a bacteriophage characterized by having a single-stranded DNA genome that is encased by a long protein capsid cylinder. Typically, bacteria infected by filamentous phages are not lysed during the life cycle and replication of the phage, but rather experience a reduced rate of growth as the phage particles are secreted from the membrane. It is well-known from the skilled person which bacteriophages, in the bacteriophages listed below, are filamentous phages.

By "pseudo-lysogenic phage" is meant herein a bacteriophage being at a stage of stalled development in a host cell without either multiplication of the phage genome (as in lytic development) or its replication synchronized with the cell cycle and stable maintenance in the cell line (as in lysogenization), which proceeds with no viral genome degradation, thus allowing the subsequent restart of virus development.

In a particular embodiment, the lytic bacteriophage is selected from the lytic bacteriophages of Order Caudovirales and/or the non-lytic bacteriophage is selected from the non-lytic bacteriophages of Order Caudovirales, said Order Caudovirales consisting of, based on the taxonomy of Krupovic et al. (Krupovic et al. Arch Virol. 2016 January; 161(1):233-47):

family Myoviridae (such as, without limitation, genus Cp220 virus, Cp8 virus, Ea214 virus, Felixo1 virus, Mooglevirus, Suspvirus, Hp1 virus, P2 virus, Kayvirus, P100 virus, Silviavirus, Spo1 virus, Tsarbombavirus, Twortvirus, Cc31 virus, Jd18 virus, Js98 virus, Kp15 virus, Moonvirus, Rb49 virus, Rb69 virus, S16 virus, Schizot4 virus, Sp18 virus, T4 virus, Cr3 virus, Se1 virus, V5 virus, Abouovirus, Agatevirus, Agrican357 virus, Ap22 virus, Arv1 virus, B4 virus, Bastillevirus, Bc431 virus, Bcep78 virus, Bcepmuvirus, Biquartavirus, Bxz1 virus, Cd119 virus, Cp51 virus, Cvm10 virus, Eah2 virus, Elvirus, Hapunavirus, Jimmervirus, Kpp10 virus, M12 virus, Machinavirus, Marthavirus, Msw3 virus, Muvirus, Myohalovirus, Nit1 virus, P1 virus, Pakpunavirus, Pbunavirus, Phikzvirus, Rheph4 virus, Rsl2 virus, Rslunavirus, *Secunda*5 virus, Sep1 virus, Spn3 virus, Svunavirus, Tg1 virus, Vhmlvirus and Wphvirus)

family Podoviridae (such as, without limitation, genus Fri1 virus, Kp32 virus, Kp34 virus, Phikmvvirus, Pradovirus, Sp6 virus, T7 virus, Cp1 virus, P68 virus, Phi29 virus, Nona33 virus, Pocjvirus, T12011 virus, Bcep22 virus, Bpp1 virus, Cba41 virus, Dfl12 virus, Ea92 virus, Epsilon15 virus, F116 virus, G7 cvirus, Jwalphavirus, Kf1 virus, Kpp25 virus, Lit1 virus, Luz24 virus, Luz7 virus, N4 virus, Nonanavirus, β22 virus, Pagevirus, Phieco32 virus, Prtbvirus, Sp58 virus, Una961 virus and Vp5 virus)

family Siphoviridae (such as, without limitation, genus Camvirus, Likavirus, R4 virus, Acadianvirus, Coopervirus, Pg1 virus, Pipefishvirus, Rosebushvirus, Brujitavirus, Che9 cvirus, Hawkeyevirus, Plotvirus, Jerseyvirus, K1gvirus, Sp31 virus, Lmd1 virus, Una4 virus, Bongovirus, Reyvirus, Buttersvirus, Charlievirus, Redivirus, Baxtervirus, Nymphadoravirus, Bignuzvirus, Fishburnevirus, Phayoncevirus, Kp36 virus, Rogue1 virus, Rtpvirus, T1 virus, Tlsvirus, Ab18 virus, Amigovirus, Anatolevirus, Andromedavirus, Attisvirus, Barnyardvirus, Bernal13 virus, Biseptimavirus, Bronvirus, C2 virus, C5 virus, Cba181 virus, Cbastvirus, Cecivirus, Che8 virus, Chivirus, Cjw1 virus, Corndogvirus, Cronusvirus, D3112 virus, D3 virus, Decurrovirus, Demosthenesvirus, Doucettevirus, E125 virus, Eiauvirus, Ff47 virus, Gaiavirus, Gilesvirus, Gordonvirus, Gordtnkvirus, Harrisonvirus, Hk578 virus, Hk97 virus, Jenstvirus, Jwxvirus, Kelleziovirus, Korravirus, L5 virus, Lambdavirus, Laroyevirus, Liefievirus, Marvinvirus, Mudcatvirus, N15 virus, Nonagvirus, Np1 virus, Omegavirus, P12002 virus, P12024 virus, P23 virus, P70 virus, Pa6 virus, Pamx74 virus, Patiencevirus, Pbi1 virus, Pepy6 virus, Pfr1 virus, Phic31 virus, Phicbkvirus, Phietavirus, Phifelvirus, Phijl1 virus, Pis4avirus, Psavirus, Psimunavirus, Rdjlvirus, Rer2 virus, Sap6 virus, Send513 virus, Septima3 virus, Seuratvirus, Sextaecvirus, Sfi11 virus, Sfi21dt1 virus, Sitaravirus, Sk1 virus, Slashvirus, Smoothievirus, Soupsvirus, Spbetavirus, Ssp2 virus, T5 virus, Tankvirus, Tin2 virus, Titanvirus, Tm4 virus, Tp21 virus, Tp84 virus, Triavirus, Trigintaduovirus, Vegasvirus, Vendettavirus, Wbetavirus, Wildcatvirus, Wizardvirus, Woesvirus, Xp10 virus, Ydn12 virus and Yuavirus)

family Ackermannviridae (such as, without limitation, genus Ag3 virus, Limestonevirus, Cba120 virus and Vi1 virus)

In a particular embodiment, the lytic bacteriophage and/or the non-lytic bacteriophage is not part of the Order Caudovirales but from families with Unassigned order such as, without limitation, family Tectiviridae (such as genus Alphatectivirus, Betatectivirus), family Corticoviridae (such as genus Corticovirus), family lnoviridae (such as genus Fibrovirus, Habenivirus, Inovirus, Lineavirus, Plectrovirus, Saetivirus, Vespertiliovirus), family Cystoviridae(such as genus Cystovirus), family Leviviridae(such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

In a particular embodiment, the lytic bacteriophage and/or the non-lytic bacteriophage is targeting Archea not part of the Order Caudovirales but from families with Unassigned order such as, without limitation, Ampullaviridae, Fusello-Viridae, Globuloviridae, Guttaviridae, Lipothrixviridae, Pleolipoviridae, Rudiviridae, Salterprovirus and Bicauda-viridae.

In a particular embodiment, said lytic bacteriophage comes from a given bacterial species or strain. In another particular embodiment, said non-lytic bacteriophage comes from a same or different given bacterial species or strain.

By "bacteriophage coming from a given bacterial species or strain" is meant herein a bacteriophage specifically targeting a particular bacterial species or strain and/or a bacteriophage hosted by a particular bacterial species or strain.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-1, Av-2, Av-3, BF307, CTI, CT2, CT3, CT4, CT6, CT7, CT8 and 1281.

Bacteria of the genus *Aeromonas* can be infected by the following phages: AA-, Aeh2, N, PMI, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, A1-K-1, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-1, Coll, Corl, CP-53, CS-1, CSi, D, D, D, D5, entl, FP8, FP9, FSi, FS2, FS3, FS5, FS8, FS9, G, GH8, GT8, GV-1, GV-2, GT-4, g3, g12, g13, g14, g16, g17, g21, g23, g24, g29, H2, kenl, KK-88, Kuml, Kyul, J7W-1, LP52, (syn=LP-52), L7, MexI, MJ-1, mor2, MP-7, MPIO, MP12, MP14, MP15, Neol, N°2, N5, N6P, PBCI, PBLA, PBPI, P2, S-a, SF2, SF6, Shal, Sill, SP02, (syn=CDSPP1), SPp, STI, STi, SU-II, t, Tbl, Tb2, Tb5, TblO, Tb26, Tb51, Tb53, Tb55, Tb77, Tb97, Tb99, Tb560, Tb595, Td8, Td6, Tdl5, Tgl, Tg4, Tg6, Tg7, Tg9, TgIO, Tgll, Tg13, Tg15, Tg21, Tinl, Tin7, Tin8, Tin13, Tm3, Tocl, Togl, toll, TP-1, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yunl, α, γ, pl 1, φmed-2, φT, pp-4, φ3T, φ75, φIO5, (syn=φIO5), IA, IB, 1-97A, 1-97B, 2, 2, 3, 3, 3, 5, 12, 14, 20, 30, 35, 36, 37, 38, 41C, 51, 63, 64, 138D, 1, 11, IV, NN-*Bacillus* (13), alel, ARI, AR2, AR3, AR7, AR9, Bace-11, (syn=11), Bastille, BLI, BL2, BL3, BL4, BL5, BL6, BL8, BL9, BP124, BS28, BS80, Ch, CP-51, CP-54, D-5, darl, denl, DP-7, entl, FoSi, FoS2, FS4, FS6, FS7, G, gall, gamma, GEl, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-1, No. 1, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subl, SW, Tg8, Tg12, Tg13, Tg14, thu/\, thuA, thuS, Tin4, Tin23, TP-13, TP33, TP50, TSP-1, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, 111, 4 (*B. megaterium*), 4 (*B. sphaericus*), AR13, BPP-lO, BS32, BS107, BI, B2, GA-1, GP-lO, GV-3, GV-5, g8, MP20, MP27, MP49, Nf, PP5, PP6, SF5, Tgl8, TP-1, Versailles, φ15, φ29, 1-97, 837/IV, mi-*Bacillus* (1), BatlO, BSLIO, BSLI 1, BS6, BSI 1, BS16, BS23, BSIOI, BS102, g18, morl, PBLI, SN45, thu2, thu3, Tml, Tm2, TP-20, TP21, TP52, type F, type G, type IV, HN-BacMus (3), BLE, (syn=ec), BS2, BS4, BS5, BS7, EIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and µ.

Bacteria of the genus *Bacteroides* can be infected by the following phages: crAss-phage, ad 12, Baf-44, Baf-48E, Baf-64, Bf-1, Bf-52, B40-8, F1, β1, φAI, φEBrO, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOI), (syn=FQI), D, FP2, (syn=FP2), (syn=FD2), Fz, (syn=Fz75/13), (syn=Firenze 75/13), (syn=Fi), Fi, (syn=FI), Fim, (syn=Flm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=25), F25U, (syn=F25u) (syn=F25U), (syn=F25V), F44, (syn- F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=FiO), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chpl.

Bacteria of the genus *Clostridium* can be infected by the following phages: CAKI, CA5, Ca7, CEβ, (syn=1C), CEγ, Cldl, c-n71, c-203 Tox-, DEP, (syn=ID), (syn=IDtOX+), HM3, KMI, KT, Ms, NAI, (syn=Naltox+), PA1350e, Pf6, PL73, PL78, PL81, PI, P50, P5771, P19402, ICtOX+, 2CtOX 2D3 (syn=2DtOX+), 3C, (syn=3Ctox+), 4C, (syn=4CtOX+), 56, Ill-I, NN-*Clostridium* (61), NBItOX+, a1, CAI, HMT, HM2, PFI5 P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cl, c4, c5, HM7, H1 1/A1, H18/Ax, FWS23, Hi58ZA1, K2ZA1, K21ZS23, ML, NA2tOX; Pf2, Pf3, Pf4, S9ZS3, S41ZA1, S44ZS23, a2, 41, 112ZS23, 214/S23, 233/Ai, 234/S23, 235/S23, ll-1, II-2, II-3, NN-*Clostridium* (12), CAI, F1, K, S2, 1, 5 and NN-*Clostridium* (8).

Bacteria of the genus *Corynebacterium* can be infected by the following phages: CGKI (defective), A, A2, A3, AIOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, li/31, J, K, K, (syn="Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γ toχ-), γ19, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, F1, F2, 1, 2, 4, 14, 41, 867, DI, SB24, 2BV, 182, 225, C2, C2F, E3, E62, DS96, H24, M35, P3, P9, SBIOI, S2, 2B11, 5, 182a, 705, 873, 881, 940, 1051, 1057, 21096C, NN-*Enterococcus* (1), PEI, F1, F3, F4, VD13, 1,200,235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, El, E24, E41, FI-2, FI-4, FI-5, HI8A, Ffl8B, i, MM, Mu, (syn=mu), (syn=Mul), (syn=Mu-I), (syn=MU-I), (syn=Mul), (syn=μ), 025, Phl-5, Pk, PSP3, PI, PID, P2, P4 (defective), SI, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, F13, H, HI, H3, H8, K3, M, N, ND-2, ND-3, ND4, ND-5, ND6, ND-7, Ox-I (syn=OXI), (syn=HF), Ox-2 (syn=0x2), (syn=OX2), Ox-3, Ox-4, Ox-5, (syn=OX5), Ox-6, (syn=66F), (syn= (φ66t), (syn=(φ66t-)5 0111, Phl-1, RB42, RB43, RB49, RB69, S, Sal-I, Sal-2, Sal-3, Sal-4, Sal-5, Sal-6, TC23, TC45, Tull*-6, (syn=Tull*), TuIP-24, Tull*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, α1, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, )Φ4-CF, Φ05, Φ06, Φ07, φl, φ1.2, φ20, φ95, φ263, ΦIO92, φl, φll, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, ECI, EC2, E21, E29, F1, F26S, F27S, Hi, HK022, HK97, (syn=ΦHK97), HK139, HK253, HK256, K7, ND-I, no.D, PA-2, q, S2, TI, (syn=a), (syn=P28), (syn=T-l), (syn=Tx), T3C, T5, (syn=T-5), (syn=T5), UC-I, w, β4, γ2, λ (syn=lambda), (syn=Φλ), ΦD326, φγ, Φ6, Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J, 933H, 0157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HPI, S2 and N3.

Bacteria of the genus *Helicobacter* are infected by the following phage: HPI and ˆˆ *Helicobacter* (1).

Bacteria of the genus *Klebsiella* are infected by the following phage: AIO-2, K14B, K16B, K19, (syn=K19), K114, K115, K121, K128, K129, K132, K133, K135, K1106B, K1171B, K1181B, K1832B, AIO-1, AO-I, AO-2, AO-3, FC3-10, K, KI1, (syn=KII), K12, (syn=K12), K13, (syn=K13), (syn=KI 70/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, 1l, VI, IX, C1-I, K14B, K18, KI11, K112, K113, K116, K117, K118, K120, K122, K123, K124, K126, K130, K134, K1106B, KIi65B, K1328B, KLXI, K328, P5046, 11, 380, Ill, IV, VII, VIII, FC3-11, K12B, (syn=K12B), K125, (syn=K125), K142B, (syn=K142), (syn=K142B), K1181B, (syn=KII 81), (syn=K1181B), K1765/!, (syn=K1765/1), K1842B, (syn=K1832B), K1937B, (syn=K1937B), LI, (P28, 7, 231, 483, 490, 632 and 864/100.

Bacteria of the genus *Lepitospira* are infected by the following phage: LEI, LE3, LE4 and -NN-Leptospira (1).

Bacteria of the genus *Listeria* are infected by the following phage: A511, 01761, 4211, 4286, (syn=B054), A005, A006, A020, A500, A502, A511, A1 18, A620, A640, B012, B021, B024, B025, B035, B051, B053, B054, B055, B056, BIOI, BI 10, B545, B604, B653, C707, D441, HS047, HIOG, H8/73, H19, H21, H43, H46, H107, H108, HI 10, H163/84, H312, H340, H387, H391/73, H684/74, H924A, PSA, U153, pMLUP5, (syn=P35), Φ0241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/ 11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phage: 13, AGI, ALi, ATCC 11759, A2, B.C3, BG2, BKI, BK5, butyricum, B-I, B5, B7, B30, B35, Clark, C1, C2, DNAIII, DSP1, D4, D29, GS4E, (syn=GS4E), GS7, (syn=GS-7), (syn=GS7), Pa, lacticola, Legendre, Leo, L5, (syn=ΦL-5), MC-I, MC-3, MC-4, minetti, MTPHI I, Mx4, MyF3P/59a, *phlei*, (syn=*phlei* 1), *phlei* 4, Polonus II, rabinovitschi, *smegmatis*, TM4, TM9, TMIO, TM20, Y7, YIO, φ630, IB, IF, IH, 1/1, 67, 106, 1430, BI, (syn=Bol), B24, D, D29, F—K, F—S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPl.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, Pml, Pm3, Pm4, Pm6, Pm7, Pm9, PmlO, Pml I, Pv2, rl, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, r2600, cpX7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/ 9402 and 9213/921 Ia.

Bacteria of the genus *Pseudomonas* are infected by the following phage: Pfl, (syn=Pf-I), Pf2, Pf3, PP7, PRRI, 7s, im-*Pseudomonas* (1), A1-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PBI), pfl6, PMN17, PPI, PP8, Psal, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PY029, PY032, PY033, PY035, PY036, PY037, PY038, PY039, PYO41, PY042, PY045, PY047, PY048, PY064, PY069, PYO103, PIK, SLPI, SL2, S2, UNL-I, wy, Yai, Ya4, Yan, PBE, PCTX, (φC17, φKZ, (syn=ΦKZ), φ-LT, Φmu78, φNZ, φPLS-1, (φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, C1-I, CI-2, C5, D, gh-1, FI 16, HF, H90, K5, K6, KI 04, K109, K166, K267, N4, N5, 06N-25P, PE69, Pf, PPN25, PPN35, PPN89, PPN91, PP2, PP3, PP4, PP6, PP7, PP8, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, ΦKf77, φ-MC, OmnF82, φPLS27, φPLS743, φS-1, 1,2, 2, 3,4, 5,6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-1, C22, D3, D37, D40, D62, D3112, F7, FIO, g, gd, ge, gξ, Hwl2, Jb 19, KFI, L°, OXN-32P, 06N-52P, PCH-1, PC13-1, PC35-1, PH2, PH51, PH93, PH132, PMW, PM13, PM57, PM61, PM62, PM63, PM69, PM105, PMI 13, PM681, PM682, P04, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, SDI, SLI, SL3, SL5, SM, φC5, φCI 1, φCI I-1, φC13, φC15, φMO, φX, φ04, φl 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GIOI, M6, M6a, LI, PB2, Pssyl5, Pssy4210, Pssy4220, PYO12, PY034, PYO49, PYO50, PYO51, PYO52, PYO53, PYO57, PYO59, PYO200, PX2, PX5, SL4, φ03, φ06 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, Fels 2, GI, GUI, GVI, GVIII, k, K, i, j, L, 01, (syn=0-1), (syn=01), (syn=0-1), (syn=7), 02, 03, P3, P9a, PIO, Sab3, Sab5, SanIS, San17, SI, Taunton, Vil, (syn=Vil), 9, imSalmonella (1), N-1, N-5, N-1O, N-17, N-22, 11, 12, 16-19, 20.2, 36, 449C/C178, 966A/C259, a, B.A.O.R., e, G4, GUI, L, LP7, M, MG40, N-18, PSA68, β4, P9c, β22, (syn=β22), (syn=PLT22), (syn=PLT22), β22al, β22-4, β22-7, β22-11, SNT-I, SNT-2, SP6, Villi, ViIV, ViV, ViVI, ViVII, Worksop, Sj5, ε34, 1,37, 1(40), (syn=φI[40]), 1,422, 2, 2.5, 3b, 4, 5, 6,14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, β22-1, β22-3, β22-12, Sabl, Sab2, Sab2, Sab4, Sanl, San2, San3, San4, San6, San7, San8, San9, San13, Sanl4, San16, San18, San19, San20, San21, San22, San23, San24, San25, San26, SasLI, SasL2, SasL3, SasL4, SasL5, SIBL, SII, Vill, φ1, 1, 2, 3a, 3al, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, ΦCP-3, ΦCP-6, 3M, 10/la, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, ΦCP6-1, ΦCP6-2, ΦCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/1Oa, L.359 and SMBI.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PE5, P90, Sfll, Sh, SHm, SHrv, (syn=HIV), SHvi, (syn=HVI), SHVvm, (syn=HVIII), SKy66, (syn=gamma 66), (syn=ypp), (syn=γ66b), SKm, (syn=Slllb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVfI-A, (syn=SvmA), (syn=VIIIA), STvi, STK, STx1, STxn, S66, W2, (syn=D2c), (syn=D20), (l, (PVb 3-SO-R, 8368-SO-R, F7, (syn=FS7), (syn=K29), FIO, (syn=FSIO), (syn=K31), 11, (syn=alfa), (syn=FSa), (syn=KI 8), (syn=α), 12, (syn=α), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=Ssll), (syn=II), SKrv, (syn=Sm), (syn=SslV), (syn=IV), SK1Va, (syn=Swab), (syn=SslVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssy66), φ2, Bl1, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-SO-S, SG36, (syn=SO-36/G), (syn=G36), SG3204, (syn=SO-3204/G), SG3244, (syn=SO-3244/G), SHi, (syn=HI), SHvrr, (syn=HVII), SHK, (syn=HIX), SHx1, SHxrr, (syn=HXn), SKI, KI, (syn=S1), (syn=Ssl), SKVII, (syn=KVII), (syn=Svrr), (syn=SsVll), SKIX, (syn=KIX), (syn=S1x), (syn=SslX), SKXII, (syn=KXII), (syn=Sxn), (syn=SsXII), STi, STffl, STrv, STVi, STvrr, S70, S206, U2-SO-S, 3210-SO-S, 3859-SO-S, 4020-SO-S, φ3, φ5, φ7, φ8, φ9, φ1O, φl I, φ13, φ14, φ18, SHm, (syn=Hrri), SHχi, (syn=HXt) and SKx, (syn=KXI), (syn=Sχi), (syn=Ssχl), (syn=χI).

Bacteria of the genus *Staphylococcus* are infected by the following phage: A, EW, K, Ph5, Ph9, PhIO, Ph13, PI, P2, P3, β4, P8, P9, PIO, RG, SB-i, (syn=Sb-I), S3K, Twort, ΦSK311, φ812, 06, 40, 58, 119, 130, 131, 200, 1623, STCI, (syn=stcl), STC2, (syn=stc2), 44AHJD, 68, ACI, AC2, A6"C", A9"C", b581, CA-1, CA-2, CA-3, CA-4, CA-5, DI 1, L39x35, L54a, M42, NI, N2, N3, N4, N5, N7, N8, NIO, Ni I, N12, N13, N14, N16, Ph6, Phl2, Phl4, UC-18, U4, U15, SI, S2, S3, S4, S5, χ2, Z1, φB5-2, φD, ω, 11, (syn=φl 1), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155,157, 157A, 165,187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, pRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-1, NN-Streptococais (1), a, Cl , FLOThs, H39, Cp-I, Cp-5, Cp-7, Cp-9, Cp-lO, AT298, A5, alO/JI, alO/J2, alO/J5, alO/J9, A25, BTI 1, b6, CAI, c20-1, c20-2, DP-I, Dp-4, DTI, ET42, elO, FA101, FETHs, FK, FKKIOI, FKLIO, FKP74, FKH, FLOThs, FylOI, fl, F10, F20140/76, g, GT-234, HB3, (syn=HB-3), HB-623, HB-746, M102, 01205, pO1205, PST, PO, PI, P2, P3, P5, P6, P8, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfil 1, (syn=SFil 1), (syn=φSFil1), (syn=ΦSfil 1), (syn=φSfil 1), sfil9, (syn=SFil9), (syn=φSFil9), (syn=φSfil9), Sfi21, (syn=SFi21), (syn=φSFi21), (syn=φSfi21), ST0, STX, st2, ST2, ST4, S3, (syn=pS3), s265, Φ17, φ42, φ57, φ80, φ81, φP82, φ83, φ84, φ85, φ86, φ87, φ88, φ89, φ90, φ91, φ92, φ93, φ94, φ95, φ96, φ97, φ98, φ99, φ1OO, φ0, φ102, φ227, 07201, ω1, ω2, ω3, ω4, ω5, ω6, ω8, wlO, 1, 6, 9, 1° F., 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, Vfl2, Vf33, VPIΦ, VSK, v6, 493, CP-TI, ET25, kappa, K139, Labol, )XN-69P, OXN-86, 06N-21P, PB-I, P147, rp-1, SE3, VA-1, (syn=VcA-1), VcA-2, VPI, VP2, VP4, VP7, VP8, VP9, VPIO, VP17, VP18, VP19, χ29, (syn=29 d'Herelle), ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHCl-1, ΦHCl-2, ΦHCl-3, ΦHC1-4, ΦHC2-1, >HC2-2, ΦHC2-3, ΦHC2-4, ΦHC3-1, ΦHC3-2, ΦHC3-3, 0HD1S-1, 0HD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, 00139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, OPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, 016, φ138, 1- II, 5, 13, 14, 16, 24, 32, 493, 6214, 7050, 7227, 1l, (syn=group II), (syn=φ2), V, VIII,-m-*Vibrio* (13), KVP20, KVP40, nt-1, 06N-22P, P68, e1, e2, e3, e4, e5, FK, G, I, K, nt-6, NI, N2, N3, N4, N5, 06N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, 1 (syn=group 1), Ill (syn=group Ill), VI, (syn=A-Saratov), VII, IX, X, HN-*Vibrio* (6), pAl, 7, 7-8, 70A-2, 71A-6, 72A-5, 72A-8, 108A-10, 109A-6, 109A-8, I IOA-1, 110A-5, 110A-7, hv-1, OXN-52P, P13, P38, P53, P65, P108, Pill, TP13 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VP5, VPII, VP15, VP16, α1, α2, α3a, α3b, 353B and HN-*Vibrio* (7).

Bacteria of the genus *Yersinia* are infected by the following phage: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In a particular embodiment, the lytic bacteriophage is selected from the group consisting of the lytic bacteriophages listed above, and the non-lytic bacteriophage is selected from the group consisting of the non-lytic bacteriophages listed above.

In a particular embodiment, the lytic bacteriophage and/or the non-lytic bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus Phaxl, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HYO2, *Escherichia* virus JH2, *Escherichia* virus TP1, *Escherichia* virus VpaE1, *Escherichia* virus wV8, *Salmonella* virus Felix01, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HYO1, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, *Cronobacter* virus CR3, *Cronobacter* virus CR8, *Cronobacter* virus CR9, *Cronobacter* virus PBESO2, *Pectobacterium* virus phiTE, *Cronobacter* virus GAP31, *Escherichia* virus 4MG, *Salmonella virus SE1, Salmonella virus SSE121, Escherichia virus FFH2, Escherichia virus FV3, Escherichia virus JES2013, Escherichia virus V5, Brevibacillus virus Abouo, Brevibacillus virus Davies, Bacillus virus Agate, Bacillus virus Bobb, Bacillus virus Bp8pC, Erwinia virus Deimos, Erwinia virus Ea35-70, Erwinia virus RAY, Erwinia virus Simmy50, Erwinia virus SpecialG, Acinetobacter virus AB1, Acinetobacter virus AB2, Acinetobacter virus AbC62, Acinetobacter virus AP22, Arthrobacter virus ArV1, Arthrobacter virus Trina, Bacillus virus AvesoBmore, Bacillus virus B4, Bacillus virus Bigbertha, Bacillus virus Riley, Bacillus virus Spock, Bacillus virus Troll, Bacillus virus Bastille, Bacillus virus CAM003, Bacillus virus Bc431, Bacillus virus Bcp1, Bacillus virus BCP82, Bacillus virus BM15, Bacillus virus Deepblue, Bacillus virus JBP901, Burkholderia virus Bcep1, Burkholderia virus Bcep43, Burkholderia virus Bcep781, Burkholderia virus BcepNY3, Xanthomonas virus OP2, Burkholderia virus BcepMu, Burkholderia virus phiE255, Aeromonas virus 44RR2, Mycobacterium virus Alice, Mycobacterium virus Bxz1, Mycobacterium virus Dandelion, Mycobacterium virus HyRo, Mycobacterium virus 13, Mycobacterium virus Nappy, Mycobacterium virus Sebata, Clostridium virus phiC2, Clostridium virus phiCD27, Clostridium virus phiCD119, Bacillus virus CP51, Bacillus virus JL, Bacillus virus Shanette, Escherichia virus CVM10, Escherichia virus ep3, Erwinia virus Asesino, Erwinia virus EaH2, Pseudomonas virus EL, Halomonas virus HAP1, Vibrio virus VP882, Brevibacillus virus Jimmer, Brevibacillus virus Osiris, Pseudomonas virus Ab03, Pseudomonas virus KPP10, Pseudomonas virus PAKP3, Sinorhizobium virus M7, Sinorhizobium virus M12, Sinorhizobium virus N3, Erwinia virus Machina, Arthrobacter virus Brent, Arthrobacter virus Jawnski, Arthrobacter virus Martha, Arthrobacter virus Sonny, Edwardsiella virus MSW3, Edwardsiella virus PEi21, Escherichia virus Mu, Shigella virus SfMu, Halobacterium virus phiH, Bacillus virus Grass, Bacillus virus NIT1, Bacillus virus SPG24, Aeromonas virus 43, Escherichia virus P1, Pseudomonas virus CAb1, Pseudomonas virus CAb02, Pseudomonas virus JG004, Pseudomonas virus PAKP1, Pseudomonas virus PAKP4, Pseudomonas virus PaP1, Burkholderia virus BcepF1, Pseudomonas virus 141, Pseudomonas virus Ab28, Pseudomonas virus DL60, Pseudomonas virus DL68, Pseudomonas virus F8, Pseudomonas virus JG024, Pseudomonas virus KPP12, Pseudomonas virus LBL3, Pseudomonas virus LMA2, Pseudomonas virus PB1, Pseudomonas virus SN, Pseudomonas virus PA7, Pseudomonas virus phiKZ, Rhizobium virus RHEph4, Ralstonia virus RSF1, Ralstonia virus RSL2, Ralstonia virus RSL1, Aeromonas virus 25, Aeromonas virus 31, Aeromonas virus Aes12, Aeromonas virus Aes508, Aeromonas virus AS4, Stenotrophomonas virus IME13, Staphylococcus virus IPLAC1C, Staphylococcus virus SEP1, Salmonella virus SPN3US, Bacillus virus 1, Geobacillus virus GBSV1, Yersinia virus R1RT, Yersinia virus TG1, Bacillus virus G, Bacillus virus PBS1, Microcystis virus Ma-LMM01, Vibrio virus MAR, Vibrio virus VHML, Vibrio virus VP585, Bacillus virus BPS13, Bacillus virus Hakuna, Bacillus virus Megatron, Bacillus virus WPh, Acinetobacter virus AB3, Acinetobacter virus Abp1, Acinetobacter virus Fri1, Acinetobacter virus IME200, Acinetobacter virus PD6A3, Acinetobacter virus PDAB9, Acinetobacter virus phiAB1, Escherichia virus K30, Klebsiella virus K5, Klebsiella virus K11, Klebsiella virus Kp1, Klebsiella virus KP32, Klebsiella virus KpV289, Klebsiella virus F19, Klebsiella virus K244, Klebsiella virus Kp2, Klebsiella virus KP34, Klebsiella virus KpV41, Klebsiella virus KpV71, Klebsiella virus KpV475, Klebsiella virus SU503, Klebsiella virus SU552A, Pantoea virus Limelight, Pantoea virus Limezero, Pseudomonas virus LKA1, Pseudomonas virus phiKMV, Xanthomonas virus f20, Xanthomonas virus f30, Xylella virus Prado, Erwinia virus Era103, Escherichia virus K5, Escherichia virus K1-5, Escherichia virus K1E, Salmonella virus SP6, Escherichia virus T7, Kluyvera virus Kvp1, Pseudomonas virus gh1, Prochlorococcus virus PSSP7, Synechococcus virus P60, Synechococcus virus Syn5, Streptococcus virus Cp1, Streptococcus virus Cp7, Staphylococcus virus 44AHJD, Streptococcus virus C1, Bacillus virus B103, Bacillus virus GA1, Bacillus virus phi29, Kurthia virus 6, Actinomyces virus Av1, Mycoplasma virus P1, Escherichia virus 24B, Escherichia virus 933W, Escherichia virus Min27, Escherichia virus PA28, Escherichia virus Stx2 II, Shigella virus 7502Stx, Shigella virus POCJ13, Escherichia virus 191, Escherichia virus PA2, Escherichia virus TL2011, Shigella virus VASD, Burkholderia virus Bcep22, Burkholderia virus Bcepil02, Burkholderia virus Bcepmigl, Burkholderia virus DC1, Bordetella virus BPP1, Burkholderia virus BcepC6B, Cellulophaga virus Cba41, Cellulophaga virus Cba172, Dinoroseobacter virus DFL12, Erwinia virus Ea9-2, Erwinia virus Frozen, Escherichia virus phiV10, Salmonella virus Epsilon15, Salmonella virus SPN1S, Pseudomonas virus F116, Pseudomonas virus H66, Escherichia virus APEC5, Escherichia virus APEC7, Escherichia virus Bp4, Escherichia virus EC1UPM, Escherichia virus ECBP1, Escherichia virus G7C, Escherichia virus IME11, Shigella virus Sb1, Achromobacter virus Axp3, Achromobacter virus JWAlpha, Edwardsiella virus KF1, Pseudomonas virus KPP25, Pseudomonas virus R18, Pseudomonas virus Ab09, Pseudomonas virus LIT1, Pseudomonas virus PA26, Pseudomonas virus Ab22, Pseudomonas virus CHU, Pseudomonas virus LUZ24, Pseudomonas virus PAA2, Pseudomonas virus PaP3, Pseudomonas virus PaP4, Pseudomonas virus TL, Pseudomonas virus KPP21, Pseudomonas virus LUZ7, Escherichia virus N4, Salmonella virus 9NA, Salmonella virus SP069, Salmonella virus BTP1, Salmonella virus HK620, Salmonella virus P22, Salmonella virus ST64T, Shigella virus Sf6, Bacillus virus Page, Bacillus virus Palmer, Bacillus virus Pascal, Bacillus virus Pony, Bacillus virus Pookie, Escherichia virus 172-1, Escherichia virus ECB2, Escherichia virus NJ01, Escherichia virus phiEco32, Escherichia virus Septima11, Escherichia virus SU10, Brucella virus Pr, Brucella virus Tb, Escherichia virus Pollock, Salmonella virus FSL SP-058, Salmonella virus FSL SP-076, Helicobacter virus 1961P, Helicobacter virus KHP30, Helicobacter virus KHP40, Hamiltonella virus APSE1, Lactococcus virus KSY1, Phormidium virus WMP3, Phormidium virus WMP4, Pseudomonas virus 119X, Roseobacter virus SIO1, Vibrio virus VpV262, Vibrio virus VC8, Vibrio virus VP2, Vibrio virus VP5, Streptomyces virus Amela, Streptomyces virus phiCAM, Streptomyces virus Aaronocolus, Streptomyces virus Caliburn, Streptomyces virus Danzina, Streptomyces virus Hydra, Streptomyces virus Izzy, Streptomyces virus Lannister, Streptomyces virus Lika, Streptomyces virus Sujidade, Streptomyces virus Zemlya, Streptomyces virus ELB20, Streptomyces virus R4, Streptomyces virus phiHau3, Mycobacterium virus Acadian, Mycobacterium virus Baee, Mycobacterium virus Reprobate, Mycobacterium virus Adawi, Mycobacterium virus Bane1, Mycobacterium virus BrownCNA, Mycobacterium virus Chrisnmich, Mycobacterium virus Cooper, Mycobacterium virus JAMaL, Mycobacterium virus Nigel, Mycobacterium virus Stinger, Mycobacterium virus Vincenzo, Mycobacterium virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wksl3, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LNO3, *Leuconostoc* virus LNO4, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, Cronobacter virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus blL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, Cellulophaga virus Cba121, Cellulophaga virus Cba171, Cellulophaga virus Cba181, Cellulophaga virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSL-SPO30, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, Edwardsiella virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, Sodalis virus S01, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobac-* terium virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071 NO5, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151 N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PB11, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus clP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus blL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus Sl4, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sal2, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phil7, *Xanthomonas* virus Xop411, *Xanthomonas* virus Xp10, *Streptomyces* virus TP1604, *Streptomyces* virus YDN12, Alphaproteobacteria virus phiJI001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, Spiroplasma virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, Spiroplasma virus C74, Spiroplasma virus R8A2B, Spiroplasma virus SkV1CR23x, *Escherichia* virus F1, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, Bdellovibrio virus MAC1, Bdellovibrio virus MH2K, *Chlamydia* virus Chp1, *Chlamydia* virus Chp2, *Chlamydia* virus CPAR39, *Chlamydia* virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, , based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus EC026_P06, *Escherichia* virus EC0103_P15, *Escherichia* virus EC0103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Sp5; the first bacteriophage being different from the second bacteriophage.

In one embodiment, the first bacteriophage is selected in the group consisting of BW73, B278, D6, D108, E, El, E24, E41, FI-2, FI-4, FI-5, HI8A, Ff18B, i, MM, Mu, 025, Phl-5, Pk, PSP3, PI, PID, P2, β4, SI, Wφ, φK13, φ1, φ2, φ7, φ92, 7 A, 8p, 9p, 18, 28-1, 186, 299, HH-*Escherichia* (2), AB48, CM, C4, C16, DD-VI, E4, E7, E28, FII, F13, H, HI, H3, H8, K3, M, N, ND-2, ND-3, ND4, ND-5, ND6, ND-7, Ox-I, Ox-2, Ox-3, Ox-4, Ox-5, Ox-6, Phl-I, RB42, RB43, RB49, RB69, S, Sal-I, Sal-2, Sal-3, Sal-4, Sal-5, Sal-6, TC23, TC45, Tull*-6, TuIP-24, Tull*46, TuIP-60, T2, T4, T6, T35, α1, 1, IA, 3, 3A, 3T+, 5p, 9266Q, CF0103, HK620, J, K, KIF, m59, no. A, no. E, no. 3, no. 9, N4, sd, T3, T7, WPK, W31, ΔH, φC3888, φK3, φK7, φK12, φV-1, 004-CF, Φ05, 006, 007, P1, φ1.2, φ20, φ95, φ263, φ1092, pl, pll, 08, 1, 3, 7, 8, 26, 27, 28-2, 29, 30, 31, 32, 38, 39, 42, 933W, NN-*Escherichia* (1), Esc-7-11, AC30, CVX-5, C1, DDUP, ECI, EC2, E21, E29, F1, F26S, F27S, Hi, HK022, HK97, HK139, HK253, HK256, K7, ND-I, PA-2, q, S2, TI, ), T3C, T5, UC-I, ω, β4, γ2, A, ΦD326, φγ, Φ6, Φ7, Φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

In a preferred embodiment, said lytic bacteriophage is T7 bacteriophage. In another preferred embodiment, said lytic bacteriophage is a *C. acnes* lytic bacteriophage.

In a preferred embodiment, said non-lytic bacteriophage is lambda bacteriophage. In another preferred embodiment, said non-lytic bacteriophage is a *P. freudenreichii* bacteriophage.

In a preferred embodiment, said lytic bacteriophage is T7 bacteriophage and said non-lytic bacteriophage is a lambda bacteriophage. In another preferred embodiment, said lytic bacteriophage is a *C. acnes* lytic bacteriophage and said non-lytic bacteriophage is a *P. freudenreichii* bacteriophage.

Additional bacterial gene

As well-known from the skilled person, some phages use products produced by their bacterial host for folding and/or assembly of their structural elements, and/or for proper packaging of their DNA.

Therefore, in a particular embodiment, said production bacterial cell further comprises at least one bacterial gene, derived from a bacterial species or strain from which the lytic bacteriophage comes, involved in folding and/or assembly of phage structural elements and/or involved in DNA packaging.

As will be understood by the skilled person, bacterial genes involved in folding and/or assembly of phage structural elements depend on the particular bacteriophage from which said phage structural elements are obtained. They typically include bacterial genes encoding chaperones.

Similarly, bacterial genes involved in phage DNA packaging depend on the particular bacteriophage from which the phage DNA packaging genes are obtained. Examples of such bacterial genes include genes encoding IHF proteins.

Payload

In a particular embodiment, said production bacterial cell further comprises a payload to be packaged into said phage particles or phage-derived delivery vehicles.

As used herein, the term "payload" refers to any nucleic acid sequence (DNA and/or RNA) or amino acid sequence, or a combination of both (such as, without limitation, peptide nucleic acid or peptide-oligonucleotide conjugate) transferred into a bacterium with a delivery vehicle. In a particular embodiment, the payload is a nucleic acid payload, more particularly a DNA and/or RNA payload, still particularly a DNA payload.

The term "payload" may also refer to a plasmid, a vector or a cargo.

The payload can be a phagemid or phasmid obtained from a natural, evolved or engineered bacteriophage genome. The payload can also be composed only in part of a phagemid or phasmid obtained from a natural, evolved or engineered bacteriophage genome.

As used herein, the term "phagemid" or "phasmid" are equivalent and refer to a recombinant DNA vector comprising at least one sequence of a bacteriophage genome and is able to permit packaging in a capsid, and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise an origin of replication and thus cannot replicate by itself once injected into a bacterium. Alternatively, the phagemid comprises a plasmid origin of replication, in particular a bacterial and/or phage origin of replication.

In a particular embodiment, said payload is to be packaged in the form of a packaged phagemid.

As used herein, the term "packaged phagemid" refers to a phagemid which is encapsidated in a bacteriophage scaffold, phage-derived delivery particle or capsid. Particularly, it refers to a bacteriophage scaffold, phage delivery particle or capsid devoid of a bacteriophage genome. The packaged phagemid may be produced with a helper phage strategy, well known from the man skilled in the art. The helper phage typically comprises all the genes coding for the structural and functional proteins that are indispensable for the phagemid according to the invention to be encapsidated.

In a particular embodiment, said payload is to be delivered into targeted bacterial cells, as defined below.

In a more particular embodiment, said payload is stably maintained in said targeted bacterial cells. In an alternative embodiment, said payload does not replicate in said targeted bacterial cells.

Sequence of Interest Under the Control of a Promoter

In a particular embodiment, the payload comprises a sequence of interest, in particular under the control of a promoter.

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species.

Also, methods of prokaryotic promoter prediction exist, and can be based on DNA stability analysis as described in Kanhere and Bansal (BMC Bioinformatics 2005, 6:1). The choice of promoter on the payload used in the context of the present invention can thus be made based on the bacteria to target.

In some embodiments, the nucleic acid of interest may be positioned under the control of a recombinant or heterologous promoter, which refers to a promoter that is not normally associated with the nucleic acid of interest in its natural environment.

Examples of bacterial promoters for use in accordance with the present invention include, without limitation, positively regulated E. coli promoters such as positively regulated a 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(Rhl), Pu, FecA, pRE, cadC, hns, pLas, pLux), a "s" promoter (e.g., Pdps), a 32 promoters (e.g., heat shock) and a 54 promoters (e.g., glnAp2); negatively regulated E. coli promoters such as negatively regulated a 70 promoters (e.g., Promoter (PRM+), modified lambda Prm promoter, TetR-TetR-4C P(Las) TetO, P(Las) CIO, P(Lac) IQ, RecA_DlexO_D-Lac01, dapAp, FecA, Pspac- hy, pel, plux-cl, plux-lac, CinR, CinL, glucose controlled, modified Pr, modified Prm+, FecA, Pcya,rec A (SOS), Rec A (SOS), EmrRregulated, Betl_regulated, pTetLac, pLac_lux, pLac/Mnt,pTet/Mnt, LsrAlcl, pLux/cl, Lacl, LaclQ, pLaclQl, pLas/cl, pLas/Lux, pLux/Las, pRecA with LexA binding site, reverse BBa_R0011, pLacl/ara-1, pLaclq, rrnB PI, cadC, hns, PfhuA, pBad/araC, nhaA, OmpF, RcnR), a S promoters (e.g., Lutz-Bujard LacO with alternative sigma factor a 38), a 32 promoters (e.g., Lutz-Bujard LacO with alternative sigma factor a 32), a 54 promoters (e.g., glnAp2); negatively regulated B. subtilis promoters such as repressible B. subtilis a A promoters (e.g., Gram-positive IPTG-inducible, Xyl, hyper-spank), a promoters, and the BioFAB promoters disclosed in Mutalik V K et al (Nature Methods, 2013, 10: 354-360, see in particular the supplementary data) as well as on the BioFAB website (biofab synberc org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by a 70 such as the promoters of the Anderson collection (parts igem org/Promoters/Catalog/Anderson): BBa_J23100, BBa_J23101, BBa_J23102, BBa_J23103, BBaJ23104, BBa_J23105, BBa_J23106, BBaJ23107, BBaJ23108, BBaJ23109, BBaJ23110, BBaJ23111, BBaJ23112, BBa_J23113, BBa_J23114, BBa_J23115, BBaJ23116, BBa_J23117, BBa_J23118, and BBa_J23119.

Other preferred bacterial promoters are the promoters disclosed in Stanton et al. (2014) Nat. Chem. Biol. 10:99-105, incorporated herein by reference, including in particular TetR, IcaR(A), AmtR, Betl, SrpR, Orf2, BM3R1, ButR, PhIF, PsrA, HIyIIR, AmeR, LmrA, QacR, ScbR, McbR, LitR, HapR, SmcR, TarA and variants thereof. In a particular embodiment, said promoter is SrpR and/or PhIF, or a variant thereof.

In some embodiments of the present invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

In some embodiments, the payload may comprise a terminator sequence, or terminator.

A "terminator," as used herein, is a nucleic acid sequence that causes transcription to stop. A terminator may be unidirectional or bidirectional. It consists of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated.

A terminator may be necessary in vivo to achieve desirable gene/protein expression levels.

The most commonly used type of terminator is a forward terminator. When placed downstream of a nucleic acid of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of a palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, lambda TI and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

In one embodiment, the sequence of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the payload so as to be delivered to targeted bacteria. Preferably, the sequence of interest added to the payload leads to cell death of the targeted bacteria. For example, the nucleic acid sequence of interest added to the payload may encode holins, endolysins, restriction enzymes or toxins affecting the targeted bacteria.

Alternatively, the sequence of interest circuit added to the payload does not lead to death of targeted bacteria. For example, the sequence of interest may encode reporter genes leading to a luminescence or fluorescence signal. Alternatively, the sequence of interest may comprise proteins and enzymes achieving a useful function such as modifying the metabolism of the targeted bacteria, the composition of its environment or affecting the host subject. More specifically the sequence of interest can be an antigen triggering a host subject's immune response. The specific antigen can be released in the environment after induction of the lysis of the target cell or can be secreted by the target cell. (Costa et al. Nat Rev Microbiol. 2015 Jun;13(6):343-59; Anne et al. Curr Top Microbiol Immunol. 2017;404:267-308)

In a particular embodiment, the nucleic acid sequence of interest is selected from the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a transposase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

In a particular embodiment, the nucleic acid sequence of interest encodes a guide RNA-assisted targeting (INTEGRATE) system, typically as disclosed in Vo et al. Nat Biotechnol. 2021 Apr;39(4):480-489, said INTEGRATE system including for example a Type I-F *V. cholerae* CRISPR-transposon or a Type V-K S. hofmanii CRISPR-transposon. In a particular embodiment, said nucleic acid sequence of interest includes a nucleic acid encoding a crRNA, a nucleic acid encoding TniQ cascade, cas8, cas7 and cas6 proteins, a nucleic acid encoding tnsA, tnsB and tnsC proteins, and further including a donor DNA, said donor DNA encoding a protein of interest to be added into the targeted bacteria genome. In a particular embodiment, said nucleic acids encoding TniQ cascade, cas8, cas7 and cas6 proteins, and encoding tnsA, tnsB and tnsC proteins, are in the form of a single polycistronic nucleic acid. In another particular embodiment, said nucleic acid sequence of interest includes a nucleic acid encoding a guide RNA, a nucleic acid encoding cas12k protein, tnsB and tnsC proteins and TniQ cascade, and further including a donor DNA, said donor DNA encoding a protein of interest to be added into the targeted bacteria genome.

In a particular embodiment, the payload used in the context of the invention comprises a sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class Ill or Class IV bacteriocins).

In one embodiment, the payload used in the context of the invention further comprises a sequence of interest encoding a toxin selected in the group consisting of microcins, colicin-like bacteriocins, tailocins, Class I, Class II, Class Ill and Class IV bacteriocins. The circuit may also encode the transporter needed to secrete the toxin to the extracellular space.

In a particular embodiment, the corresponding immunity polypeptide (i.e. anti-toxin) may be used to protect bacterial cells (see review by Cotter et al., Nature Reviews Microbiology 11: 95, 2013) for payload production and encapsidation purpose but is absent in the pharmaceutical composition and in the targeted bacteria in which the payload used in the context of the invention is delivered.

In a particular embodiment, the payload used in the context of the invention comprises a sequence of interest that encodes a CRISPR-Cas system.

The CRISPR system contains two distinct elements, i.e. i) an endonuclease, in this case the CRISPR associated nuclease (Cas or "CRISPR associated protein") and ii) a guide RNA.

Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al. Science. 2012 Aug. 17; 337(6096):816-21). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified.

The modification may be guided by a repair matrix.

The CRISPR system includes two main classes depending on the nuclease mechanism of action:
  Class 1 is made of multi-subunit effector complexes and includes type 1, Ill and IV;
  Class 2 is made of single-unit effector modules, like Cas9 nuclease, and includes type II (II-A,11-B,11-C,11-C variant), V (V-A,V-B,V-C,V-D,V-E,V-U1,V-U2,V-U3, V-U4,V-U5) and VI (VI-A,VI-B1,VI-B2,VI-C,VI-D).

The sequence of interest according to the present invention may comprise a nucleic acid sequence encoding Cas protein. A variety of CRISPR enzymes are available for use as a sequence of interest on the payload used in the context of the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type Ill CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host subject.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al. Nucleic Acids Res. 2014 February;42(4):2577-90; Koonin et al. Curr Opin Microbiol. 2017 June;37:67-78).

Examples of Cas9 proteins useful in the present invention include, but are not limited to, Cas9 proteins of *Streptococcus pyogenes* (SpCas9), *Streptococcus* thermophiles (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al. Curr Opin Microbiol. 2017 June;37:67-78). Examples of Cpf1(Cas12a) proteins useful in the present invention include, but are not limited to, Cpf1(Cas12a) proteins of Acidaminococcus sp, Lachnospiraceae bacteriu and *Francisella novicida*.

The sequence encoding Cas13a (the entire protein or a fragment thereof) as used in the context of the invention can be obtained from any known Cas13a (C2c2) protein (Abudayyeh et al. Nature. 2017 Oct. 12; 550(7675):280-284). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al. Mol Cell. 2018 Apr. 19; 70(2):327-339.e5.). Examples of Cas13d proteins useful in the present invention include, but are not limited to, Cas13d proteins of *Eubacterium* siraeum and Ruminococcus sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In a particular embodiment, the nucleic sequence of interest is a CRISPR/Cas9 system for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host subject.

In one embodiment, the CRISPR system is used to target and inactivate a virulence factor.

A virulence factor can be any substance produced by a pathogen that alter host subject-pathogen interaction by increasing the degree of damage done to the host subject. Virulence factors are used by pathogens in many ways, including, for example, in cell adhesion or colonization of a niche in the host subject, to evade the host subject's immune response, to facilitate entry to and egress from host subject's cells, to obtain nutrition from the host subject, or to inhibit other physiological processes in the host subject. Virulence factors can include enzymes, endotoxins, adhesion factors, motility factors, factors involved in complement evasion, scavenging factors and factors that promote biofilm formation. For example, such targeted virulence factor gene can be E. coli virulence factor gene such as, without limitation, EHEC-HIyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be Cutibacterium *acnes* porphyrins genes, CAMP-factors (CAMP1, CAMP2, CAMP3, CAMP4), Hyaluronate lyase (HYL-IB/1l, HYL-IA), Lipases (GehA, GehB), Haemolysins, Sialidases, Endoglycoceramidases, Endo-B9-N-acetylglucosaminidase, Dermatan sulfate adhesin (DsA1, DsA2), Proline-Threonine Repeats (PTRs) or any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al. mBio. 2013 Apr. 30; 4(3):e00003-13.

In another embodiment, the CRISPR/Cas system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA p-lactamase, mecA,Omp36, OmpF, PIB, bla (blal, blaR1) and mec (mec, mecR1) operons, Chloramphenicolacetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta- subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FoIP, Tetracycline inactivation enzyme TetX, TetA, TetB, TetC, Tet30, Tet31, TetM, TetO, TetQ, Tet32, Tet36, MacAB-ToIC, MsbA, MsrA,VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD, card mcmaster ca/).

In another embodiment, the CRISPR/Cas system is used to target and inactivate a bacterial toxin gene. Bacterial toxins can be classified as either exotoxins or endotoxins.

Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

In a particular embodiment, the payload used in the context of the invention comprises a sequence of interest that encodes a base editing system.

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

In some embodiments, the base editing system comprises one or more of the following enzymes and systems:

A) Cytosine base editors (CBE) and Adenosine base editors (ABE), as described in Rees, H. A. & Liu, D. R. *Nat Rev Genet* 19, 770-788 (2018).

So far there are seven types of DNA base editors described:
- Cytosine Base Editor (CBE) that convert C:G into T:A (Komor, A et al. Nature 533:420-4. (2016))
- Adenine Base Editor (ABE) that convert A:T into G:C (Gaudelli, N. M. et al. Nature 551(7681) 464-471 (2017))
- Cytosine Guanine Base Editor (CGBE) that convert C:G into G:C (Chen, L et al. Precise and programmable C:G to G:C base editing in genomic DNA. Biorxiv (2020).; Kurt, I et al. CRISPR C-to-G base editors for inducing targeted DNA transversions in human cells. Nature Biotechnology (2020))
- Cytosine Adenine Base Editor (CABE) that convert C:G into A:T (Zhao, D et al. New base editors change C to A in bacteria and C to G in mammalian cells. Nature Biotechnology (2020))
- Adenine Cytosine Base Editor (ACBE) that convert A:T into C:G (WO2020181180)
- Adenine Thymine Base Editor (ATBE) that convert A:T into T:A (WO2020181202)
- Thymine Adenine Base Editor (TABE) that convert T:A into A:T (WO2020181193; WO2020181178; WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:
- the addition of one or two uracil DNA glycosylase inhibitor domain (UGI) to prevent base excision repair mechanism to revert base edition
- the addition of Mu-GAM that decrease insertion-deletion rate by inhibiting Non-homologous end joining mechanism in the cell (NHEJ)
- the use of nickase active Cas9 (nCas9 D10A) that, by creating nicks on the non-edited strand favors its repair and consequently the fixation of the edited base.
- the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, ABE, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
- A cytosine deaminase (rAPOBEC) and base excision repair proteins (e.g. rXRCC1) (Chen, L et al. Precise and programmable C:G to G:C base editing in genomic DNA. Biorxiv (2020).; Chen et al. Nature Communications 12:1384 (2021))
- A rat APOBEC1 variant (R33A) protein and an *E. coli*-derived uracil DNA N-glycosylase (eUNG) (Kurt, I et al. CRISPR C-to-G base editors for inducing targeted DNA transversions in human cells. Nature Biotechnology (2020))

Cytosine Adenine Base Editors (CABE) consist of a Cas9 nickase, a cytidine deaminase (e.g. AID), and a uracil-DNA glycosylase (Ung) (Zhao, D et al. New base editors change C to A in bacteria and C to G in mammalian cells. Nature Biotechnology (2020)).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020)).

In a particular embodiment, the base editing system comprises a Cytosine base editor (CBE) and/or an Adenosine base editor (ABE) as defined above.

B) Prime editors (PE), as described in Anzalone, A. V. et al. Nature 576, 149-157 (2019), consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime Editing Systems Include:
 a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
 a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

Cas9 Retron preclSe Parallel Editing via homologY ('CRISPEY'), a retron RNA fused to the sgRNA and expressed together with Cas9 and the retron proteins including at least the reverse transcriptase (Sharon, E. et al. Cell 175, 544-557.e16 (2018)).

The SCRIBE strategy: a retron system expressed in combination with a recombinase promoting the recombination of single stranded DNA, also known as single stranded annealing proteins (SSAPs) (Farzadfard, F. & Lu, T. K. Science 346, 1256272 (2014)). Such recombinases include but are not limited to phage recombinases such as lambda red, recET, Sak, Sak4, and newly described SSAPs described in Wannier, T. M. et al. Improved bacterial recombineering by parallelized protein discovery. Biorxiv 2020.01.14.906594 (2020) doi:10.1101/2020.01.14.906594.

The targetron system based on group II introns described in Karberg, M. et al. *Nat Biotechnol* 19, 1162-7 (2001) which has been adapted to many bacterial species.

Other retron based gene targeting approaches are described in Simon, A. J., Ellington, A. D. & Finkelstein, I. J. *Nucleic Acids Res* 47, 11007-11019 (2019).

C) CRISPR/Cas. In various embodiments, the sequence of interest encodes fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al..

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a DNA sequence or gene of interest such as, for example, a toxin gene, a virulence factor gene, an antibiotic resistance gene, a remodeling gene or a modulatory gene (cf. WO2014124226 and US2015/0064138).

In one embodiment, the base editing system or base editor is used to inactivate the expression of a gene by editing one or several nucleotides involved in transcription or translation.

More specifically the base editor is targeting one or several nucleotides of a promoter, a RBS, a start codon.

In one embodiment, the base editing system or base editor is used to introduce a premature stop codon.

In one embodiment, the base editing system or base editor is used to introduce one or several rare codons.

In another embodiment, the base editing system or base editor is used to modulate the expression of genes by editing one or several nucleotides involved in transcription or translation.

More specifically the base editor is targeting one or several nucleotides of a promoter, a RBS, a start codon. leading to an increase or decrease of gene expression.

In another embodiment, the base editing system or base editor is used to revert a mutation that leads to the inactivation, decrease or increase in activity of a gene or pathway.

In another embodiment, the base editing system or base editor is used to revert a mutation that leads to an increase of pathogenicity.

In one embodiment, the base editing system or base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

In some embodiments, the sequence of interest encodes a RNA base editing system.

RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain (ADAR2nn-E488Q for REPAIRv1 and ADAR2nn-E488Q-T375G for REPAIRv2), Cox et al improved specificity and efficiency compare to previous RNA editing strategies (Cox, D. B. T. et al. Science 358, 1019-1027 (2017)).

Non-limiting examples of RNA based editor proteins include REPAIRv1, REPAIRv2.

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

In a preferred embodiment, said sequence of interest only generates an effect in said targeted bacterial cells. More preferably, said sequence of interest is only expressed in said targeted bacterial cells.

Origins of Replication

In a particular embodiment, the copy number of said payload is controlled, in said production bacterial cell, by said at least one induction mechanism defined above. In an alternative embodiment, another induction mechanism controls the copy number of said payload in said production bacterial cell.

Origins of replication known in the art have been identified from species-specific plasmid DNAs (e.g. ColE1, RI, pT181, pSC101, pMB1, R6K, RK2, φ15a and the like), from bacterial virus (e.g. φX174, M13, F1 and P4) and from bacterial chromosomal origins of replication (e.g. oriC).

In one embodiment, the payload used in the context of the invention comprises a bacterial origin of replication that is functional in the targeted bacteria.

Alternatively, the payload used in the context of the invention does not comprise any functional bacterial origin of replication or contains an origin of replication that is inactive in the targeted bacteria. In such embodiment, the payload used in the context of the invention cannot replicate by itself once it has been introduced into a bacterium by the phage particle or phage-derived delivery particle.

In one embodiment, the origin of replication on the payload to be packaged is inactive in the targeted bacteria, meaning that this origin of replication is not functional in the bacteria targeted by the phage particle or phage-derived delivery vehicle, thus preventing unwanted plasmid replication.

In one embodiment, the payload comprises a bacterial origin of replication that is functional in the production bacterial cell of the invention.

Bacteria-specific origins of replication

Plasmid replication depends on host bacteria enzymes and on plasmid-controlled cis and trans determinants. For example, some plasmids have determinants that are recognized in almost all gram-negative bacteria and act correctly in each host bacteria during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. These replication origins contain sites that are required for interactions of plasmid and/or host encoded proteins.

Origins of replication used on the payload used in the context of the invention may be moderate copy number, such as ColE1 on from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), φ15a, ColA, ColE2, pOSAK, pSC101, R6K, IncW(pSaetc), IncFll, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, plJ101, pSN22, pAMbeta1, pIP501, plP407, ZM6100(Sa), pCU1, RA3, pMOL98, RK2/RP4/RP1/R68, φB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), φ15a, ColA, ColE2, pOSAK, pSC101, R6K, IncW (pSa etc), IncFll, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, plJ101, pSN22, pAMbeta1, pIP501, plP407, ZM6100(Sa), pCU1, RA3, pMOL98, RK2/RP4/RP1/R68, φB10, R300E, pRO1614, pRO1600, pECE2, pCM1, pFA3, RepFIA, RepFIB, RepFIC, pYVE439-80, R387, phasyl, RA1, TF-FC2, pMV158 and pUE113.

Even more preferably, the bacterial origin of replication are ColE1 and p15a.

In one embodiment, the bacterial origin of replication is functional in *Propionibacterium* and *Cutibacterium*, more specifically in *Propionibacterium freudenreichii* and *Cutibacterium acnes* and is selected from the group consisting of pLME108, pLME106, φ545, pRGO1, pZGX01, pPG01, pYS1, FRJS12-3, FRJS25-1, pIMPLE-HL096PA1 A_15_1_R1. In a particular embodiment, the bacterial origin of replication is selected from the bacterial origins of replication disclosed in US applications US2022/135986 and US2022/135987.

Phage Origin of Replication

The payload used in the context of the invention may comprise a phage origin of replication which can initiate, with complementation of a complete phage genome, the replication of the payload for later encapsulation into the different capsids.

A phage origin of replication can also be engineered to act as a bacterial origin of replication without the need to package any phage particles.

A phage origin of replication comprised in the payload used in the context of the invention can be any origin of replication found in a phage.

Preferably, the phage origin of replication can be the wild-type or non-wild type sequence of the M13, f1, pX174, β4, Lambda, P2, 186, Lambda-like, HK022, mEP237, HK97, HK629, HK630, mEPO43, mEP213, mEP234, mEP390, mEP460, mEPx1, mEPx2, phi80, mEP234, T2, T4, T5, T7, RE49, phiX174, R17, PRD1 PI-like, P2-like, β22, β22-like, N15 and N15-like bacteriophages.

More preferably, the phage origin of replication is selected in the group consisting of phage origins of replication of M13, f1, pX174, β4, and Lambda.

In a particular embodiment, the phage origin of replication is the P4 origin of replication.

In a particular embodiment, the phage origin of replication is from *Propionibacterium* phages: BW-like phages such as Doucette, E22, E6, G4; BV-like phages such as Anatole, E1, E3; BX-like phages such as PFR1 and PFR2; filamentous E5 phage; BU-like phages (Cutibacterium *acnes* phages). In a particular embodiment, the phage origin of replication is selected from the phage origins of replication disclosed in US applications US2022/135986 and US2022/135987, incorporated herein by reference.

Conditional Origin of Replication

In a particular embodiment, the payload comprises a conditional origin of replication which is inactive in the targeted bacteria but is active in the production bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication involving said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said production bacterial cell because said production bacterial cell expresses said given protein, peptid, RNA, nucleic acid, molecule or any combination thereof. In a particular embodiment, said protein, peptid, RNA nucleic acid, molecule or any combination thereof is expressed in trans in said production bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid.

In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, β4, lambda, phi82, phi80.

In a particular embodiment, said conditional origin of replication is selected from the group consisting of the R6KA DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host subject's microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host subject's microbiome, in particular of the bacteria representing more than 50%, more particularly more than 60%, more than 70%, more than 80%, more than 90% or more than 95% of the host subject's microbiome.

As used herein, the term "phage-inducible chromosomal islands" or "PICIs" refers to mobile genetic elements having a conserved gene organization, and encode a pair of divergent regulatory genes, including a *PICI* master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors, in particular based on the primase-helicase and origin of replication from PICIs. These origins may be relatively rare in target strains, and more advantageously the primase-ori pair may be unique for each *PICI*, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) The ISME Journal 12:2114-2128.

In a particular embodiment, said conditional origin of replication is the primase on from the PICI of the *Escherichia coli* strain CFT073, typically of sequence SEQ ID NO: 1.

In another particular embodiment, said conditional origin of replication is the primase on from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase on from the PICI of the *Escherichia coli* strain CFT073, devoid of the restriction site GAAABCC. Preferably, said conditional origin of replication is of sequence SEQ ID NO: 3.

In another particular embodiment, said conditional origin of replication is the primase on from the PICI of the *Escherichia coli* strain CFT073 devoid of the restriction sites GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 4.

In a particular embodiment, wherein said origin of replication is derived from phage-inducible chromosomal islands (PICIs), said conditional origin of replication is active in said production bacterial cell because said production bacterial cell expresses a rep protein, in particular a primase-helicase, in particular a primase-helicase of sequence SEQ ID NO: 5, typically encoded by a nucleic acid comprising or consisting of the sequence SEQ ID NO: 6.

It was demonstrated that these specific conditional origins of replication were particularly compatible with lambda-based packaging, leading to sufficiently high titers ($>10^{10}/$ mL) required for microbiota-related applications.

Preferably, said production bacterial cell stably comprises said payload and is able to replicate said payload.

In a particular embodiment, when the conditional origin of replication of said payload is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined above.

In a particular embodiment, said production bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 5.

In a particular embodiment, said production bacterial cell stably comprises a nucleic acid encoding said rep protein, in particular said primase-helicase, said nucleic acid typically comprising or consisting of the sequence SEQ ID NO: 6.

Packaging Site

In a particular embodiment, said payload is a nucleic acid payload comprising a packaging site derived from said lytic bacteriophage.

By "packaging site" is meant herein the DNA sequence on the phage genome that is required for genome packaging into the virion. Host-specific bacteriophages (and their packaging sites) include but are not limited to SPP1 (SPP1 pac site), P1 (P1 pac site), T1 (T1 pac site), T7 (T7 concatamer junction), lambda (cos site), mu (mu pac site), P22 (P22 pac site), P8 (P8 pac site), Sf6 (Sf6 pac site), 149 (149 pac site), and A1122 (A1122-concatamer junction). For most bacteriophages, the packaging site is termed the pac site. In some cases, the packaging site is referred to as a concatamer junction (e.g. T7 concatamerjunction). In every case, the packaging site is substantially in isolation from sequences naturally occurring adjacent thereto in the bacteriophage genome.

For some bacteriophages, the packaging site may be unknown. In these cases, pac sites can be determined by taking advantage of the property that plasmids containing a functional bacteriophage pac site are packaged. For example, the DNA sequences necessary for packaging of bacteriophage A were determined by incorporating small restriction fragments of the A phage genomic DNA into a plasmid (Hohn 1983 PNAS USA 80:7456-7460). Following introduction into an in vivo packaging strain, the efficiency of packaging/transduction was quantitatively assessed.

Using a similar strategy, the pac sites for a number of bacteriophages have been determined: A (Miwa 1982 Gene 20:267-279); Mu (Croenen et al. 1985 Virology 144:520-522); filamentous bacteriophages including f1, fd, M13, and Ike (Russel et al. 1989J Virol 1989 63:3284-3295); P22 (Petri et al. 1990 Gene 88:47-55; Wu et al. 2002 Molec Microbiol 45:1631-1646); T7 (Chung et al. 1990 J Mol Biol 216:927-938), and T3 (Hashimoto et al. 1992 Virology 187:788-795).

In a particular embodiment, said packaging site is as disclosed in US applications US2022/135986 and US2022/135987.

Other Components of the Payload

The payload used in the context of the invention is preferably devoid of antibiotic resistance marker.

Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

In a particular embodiment, the payload used in the context of the invention comprises an auxotrophic marker. Auxotrophic markers in bacteria have previously been described, for example, in U.S. Pat. Nos. 4,920,048, 5,691, 185, 6,291,245, 6,413,768, and 6,752,994; U.S.

Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111 118, and typically include DapA and ThyA. In a particular embodiment, said auxotrophic marker is ThyA.

In a particular embodiment, said payload does not comprise any restriction site recognized by restriction enzymes which are frequently encoded by said targeted bacterial cell. In another particular embodiment, said payload comprises no more than 40, 30, 20, 10, 9, 8, 7, 6, 5, 4, 3, 2 or 1 restriction site(s) recognized by restriction enzymes which are frequently encoded by said targeted bacterial cell or a population or a group of targeted bacterial cell(s).

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme.

The payload according to the invention preferably comprises no more than 100 restriction sites. In a preferred embodiment, the payload according to the invention comprises no more than 10 restriction sites. In a most preferred embodiment, the payload according to the invention does not comprise any restriction site.

Targeted Bacteria

The bacteria targeted by the phage particles or phage-derived delivery particles of the invention can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the first type of bacteriophage as defined in the section "Bacteriophage and gene derived from a bacteriophage" above. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Francisella* spp., *Corynebacterium* spp., Citrobacterspp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., Erysipelothrix spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., Selnomonas spp., *Shigella* spp., Zymonas spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., Parvimonas spp., *Fusobacterium* spp., *Actinomyces* spp., *Porphyromonas* spp., *Micrococcus* spp., *Bartonella* spp., *Borrelia* spp., Brucelia spp., *Campylobacter* spp., Chlamydophilia spp., Cutibacterium spp., *Propionibacterium* spp., *Gardnerella* spp., *Ehrlichia* spp., *Haemophilus* spp., Leptospira spp., *Listeria* spp., *Mycoplasma* spp., *Nocardia* spp., *Rickettsia* spp., *Ureaplasma* spp., *Lactobacillus* spp., *Faecalibacterium* spp., Ruminococcus spp. and a mixture thereof.

Thus, phage particles, phage delivery particles and/or phages may target (e.g., specifically target) a bacterial cell from any one or more of the foregoing genus of bacteria in particular to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., Cutibacterium spp., *Propionibacterium* spp., *Fusobacterium* spp., *Porphyromonas* spp. and *Gardnerella* spp.

In some embodiments, the targeted bacteria are anaerobic bacterial cells (e.g., cells that do not require oxygen for growth). Anaerobic bacterial cells include facultative anaerobic cells such as but not limited to *Escherichia coli, Shewanella oneidensi, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromonas* species. In humans, anaerobic bacteria are most commonly found in the gastrointestinal tract. In some particular embodiments, the targeted bacteria are thus bacteria most commonly found in the gastrointestinal tract. Bacteriophages used for preparing the hybrid helper phage, and then the phage particles, phage delivery vehicles and/or phages, may target (e.g., to specifically target) anaerobic bacterial cells according to their specific spectra known by the person skilled in the art to specifically deliver the plasmid.

In some embodiments, the targeted bacterial cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus* actinobycetemcomitans, cyanobacteria, *Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis strain PCC6803, Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aeruginosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes (formerly Propionibacterium acnes), Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aeruginosa, and a mixture thereof, preferably the bacteria of interest are selected from the group consisting of Escherichia coli, Enterococcus faecium, Staphylococcus aureus, Klebsiella pneumoniae, Acinetobacter baumanii, Pseudomonas aeruginosa, Enterobacter cloacae, and Enterobacter aerogenes, and a mixture thereof.

In some embodiments, the targeted bacterial cells are, without limitation, Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter, Weisella, Clostridium, Bacteroides, Ruminococcus, Faecalibacterium, Treponema, Phascolarctobacterium, Megasphaera, Faecalibacterium, Bifidobacterium, Lactobacillus, Sutterella, and/or Prevotella.

In other embodiments, the targeted bacteria cells are, without limitation, Achromobacter xylosoxidans, Acidaminococcus fermentans, Acidaminococcus intestini, Acidaminococcus sp., Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides sp., Bacteroides stercoris, Bacteroides thetaiotaomicron, Bacteroides uniformis, Bacteroides vulgatus, Bacteroides xylanisolvens, Bacteroides pectinophilus ATCC, Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Bryantella formatexigens, butyrate-producing bacterium, Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter sp., Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium sp, Clostridium sp., Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella *tarda*, Eggerthella *lenta*, Eisenbergiella tayi, Enorma *massiliensis*, Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus sp., Enterovibrio *nigricans*, Erysipelatoclostridium ramosum, Escherichia coli, Escherichia sp., *Eubacterium* biforme, *Eubacterium* dolichum, *Eubacterium hallii*, *Eubacterium limosum*, *Eubacterium ramulus*, *Eubacterium rectale*, *Eubacterium siraeum*, *Eubacterium ventriosum*, *Exiguobacterium marinum*, *Exiguobacterium undae*, *Faecalibacterium* cf. *Faecalibacterium prausnitzii*. Faecalitalea cylindroides, Ferrimonas *balearica*, *Finegoldia magna*, Flavobacterium daejeonense, Flavonifractor plautii, Fusicatenibacter *saccharivorans*, *Fusobacterium gonidiaformans*, *Fusobacterium mortiferum*, *Fusobacterium necrophorum*, *Fusobacterium nucleatum*, *Fusobacterium periodonticum*, *Fusobacterium* sp., *Fusobacterium ulcerans*, *Fusobacterium varium*, Gallibacterium *anatis*, Gemmiger formicilis, Gordonibacter pamelaeae, Hafnia alvei, *Helicobacter bilis*, *Helicobacter bills*, *Helicobacter canadensis*, *Helicobacter canis*, *Helicobacter cinaedi*, *Helicobacter macacae*, *Helicobacter pametensis*, *Helicobacter pullorum*, *Helicobacter pylori*, *Helicobacter rodentium*, *Helicobacter winghamensis*, Herbaspirillum massiliense, Holdemanella *biformis*, Holdemania fdiformis, Holdemania *filiformis*, *Holdemania massiliensis*, *Holdemania filiformis*, *Hungatella hathewayi*, *Intestinibacter bartlettii*, *Intestinimonas butyriciproducens*, *Klebsiella oxytoca*, *Klebsiella pneumoniae*, *Kurthia massiliensis*, *Lachnospira pectinoschiza*, *Lactobacillus acidophilus*, *Lactobacillus amylolyticus*, *Lactobacillus animalis*, *Lactobacillus antri*, *Lactobacillus brevis*, *Lactobacillus buchneri*, *Lactobacillus casei*, *Lactobacillus curvatus*, *Lactobacillus delbrueckii*, *Lactobacillus fermentum*, *Lactobacillus gasseri*, *Lactobacillus helveticus*, *Lactobacillus hilgardii*, *Lactobacillus iners*, *Lactobacillus intestinalis*, *Lactobacillus johnsonii*, *Lactobacillus murinus*, *Lactobacillus paracasei*, *Lactobacillus plantarum*, *Lactobacillus reuteri*, *Lactobacillus rhamnosus*, *Lactobacillus ruminis*, *Lactobacillus sakei*, *Lactobacillus salivarius*, *Lactobacillus ultunensis*, *Lactobacillus vaginalis*, *Lactobacillus plantarum* subsp., *Leuconostoc mesenteroides*, *Leuconostoc pseudomesenteroides*, *Listeria grayi*, *Listeria innocua*, *Mannheimia granulomatis*, Marvinbryantia formatexigens, Megamonas *funiformis*, Megamonas hypermegale, Methanobrevibacter *smithii*, Methanobrevibacter smithiiFl, *Micrococcus luteus*, Microvirgula aerodenitrificans, Mitsuokella jalaludinii, Mitsuokella multacida, Mollicutes bacterium, Murimonas intestini, *Neisseria macacae*, *Nitriliruptor alkaliphilus*, *Oceanobacillus massiliensis*, Odoribacter laneus, Odoribacter splanchnicus, Ornithobacterium rhinotracheale, Oxalobacter formigenes, *Paenibacillus* barengoltzii, *Paenibacillus chitinolyticus*, *Paenibacillus lautus*, *Paenibacillus motobuensis*, *Paenibacillus senegalensis*, Paenisporosarcina quisquiliarum, Parabacteroides *distasonis*, Parabacteroides goldsteinii, Parabacteroides *gordonii*, *Parabacteroides johnsonii*, Parabacteroides merdae, Paraprevotella xylaniphila, Parasutterella excrementihominis, Parvimonas micra, *Pediococcus acidilactici*, *Peptoclostridium difficile*, *Peptoniphilus harei*, Peptoniphilus obesi, Peptoniphilus *senegalensis*, *Peptoniphilus timonensis*, Phascolarctobacterium succinatutens, *Porphyromonas asaccharolytica*, *Porphyromonas uenonis*, *Prevotella baroniae*, *Prevotella bivia*, *Prevotella copri*, *Prevotella dentalis*, *Prevotella micans*, *Prevotella multisaccharivorax*, *Prevotella oralis*, *Prevotella salivae*, *Prevotella stercorea*, *Prevotella veroralis*, *Propionibacterium acnes*, *Propionibacterium avidum*, *Propionibacterium freudenreichii*, *Propionimicrobium lymphophilum*, *Proteus mirabilis*, *Proteus penneri* ATCC, *Providencia alcalifaciens*, *Providencia rettgeri*, *Providencia rustigianii*, *Providencia stuartii*, *Pseudoflavonifractor capillosus*, *Pseudomonas aeruginosa*, *Pseudomonas luteola*, *Ralstonia pickettii*, Rheinheimera perlucida, Rheinheimera *texasensis*, Riemerella columbina, Romboutsia lituseburensis, *Roseburia* faecis, *Roseburia intestinalis*, *Roseburia inulinivorans*, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi, Sellimonas intestinalis, Senegalimassilia anaerobia, *Shigella sonnei*, *Slackia piriformis*, *Staphylococcus epidermidis*, *Staphylococcus lentus*, *Staphylococcus nepalensis*, *Staphylococcus pseudintermedius*, *Staphylococcus xylosus*, *Stenotrophomonas maltophilia*, *Streptococcus agalactiae*, *Streptococcus anginosus*, *Streptococcus australis*, *Streptococcus caballi*, *Streptococcus castoreus*, *Streptococcus didelphis*, *Streptococcus equinus*, *Streptococcus gordonii*, *Streptococcus henryi*, *Streptococcus hyovaginalis*, *Streptococcus infantarius*, *Streptococcus infantis*, *Streptococcus lutetiensis*, *Streptococcus merionis*, *Streptococcus mitis*, *Streptococcus mutans*, *Streptococcus oralis*, *Streptococcus ovis*, *Streptococcus parasanguinis*, *Streptococcus plurextorum*, *Streptococcus porci*, *Streptococcus pyogenes*, *Streptococcus salivarius*, *Streptococcus sobrinus*, *Streptococcus thermophilus*, *Streptococcus thoraltensis*, *Streptomyces albus*, *Subdoligranulum variabile*, Succinatimonas hippei, Sutterella parvirubra, Sutterella wadsworthensis, Terrisporobacter glycolicus, Terrisporobacter *mayombei*, Thalassobacillus devorans, Timonella *senegalensis*, *Turicibacter sanguinis*, unknown sp, unknown sp., Varibaculum cambriense, *Veillonella atypica*, *Veillonella dispar*, *Veillonella parvula*, *Vibrio cincinnatiensis*, *Virgibacillus salexigens* and/or Weissella paramesenteroides.

In other embodiments, the targeted bacteria cells are those commonly found on the skin microbiota and are without limitation Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans subsp. *xylosoxidans*, Acidovorax konjaci, Acidovorax radicis, Acinetobacter johnsonii, Actinomadura citrea, Actinomadura coerulea, Actinomadura fibrosa, Actinomadura *fulvescens*, Actinomadura *jiaoheensis*, Actinomadura luteofluorescens, Actinomadura *mexicana*, Actinomadura nitritigenes, Actinomadura verrucosospora, Actinomadura yumaensis, *Actinomyces odontolyticus*, *Actinomycetospora atypica*, *Actinomycetospora corticicola*, *Actinomycetospora rhizophila*, *Actinomycetospora rishiriensis*, Aeromonas australiensis, Aeromonas bestiarum, Aeromonas bivalvium, Aeromonas encheleia, Aeromonas eucrenophila, Aeromonas hydrophila subsp. *hydrophila*, Aeromonas piscicola, Aeromonas popoffii, Aeromonas rivuli, Aeromonas salmonicida subsp. pectinolytica, Aeromonas salmonicida subsp. smithia, Amaricoccus kaplicensis, Amaricoccus veronensis, Aminobacter aganoensis, Aminobacter ciceronei, Aminobacter lissarensis, Aminobacter niigataensis, Ancylobacter *polymorphus*, Anoxybacillus flavithermus subsp. *yunnanensis*, *Aquamicrobium aerolatum*, Archangium gephyra, Archangium gephyra, Archangium minus, Archangium *violaceum*, Arthrobacter viscosus,

*Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis,* Buttiauxella gaviniae, Caenimonas *terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium* afermentans subsp. lipophilum, *Corynebacterium minutissimum, Corynebacterium sundsvallense, Cupriavidus metallidurans, Cupriavidus nantongensis, Cupriavidus necator, Cupriavidus pampae, Cupriavidus* yeoncheonensis, Curtobacterium *flaccumfaciens,* Devosia epidermidihirudinis, Devosia *riboflavina, Devosia riboflavina, Diaphorobacter oryzae,* Dietzia psychralcaliphila, Ensifer *adhaerens, Ensifer americanus, Enterococcus malodoratus, Enterococcus pseudoavium, Enterococcus viikkiensis, Enterococcus xiangfangensis, Erwinia rhapontici,* Falsirhodobacterhalotolerans, *Flavobacterium* araucananum, *Flavobacterium* frigidimaris, *Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum,* Herbaspirillum frisingense, Herbaspirillum hiltneri, Herbaspirillum huttiense subsp. putei, Herbaspirillum *lusitanum, Herminiimonas fonticola, Hydrogenophaga intermedia, Hydrogenophaga pseudoflava, Klebsiella oxytoca, Kosakonia sacchari, Lactobacillus delbrueckii* subsp. *bulgaricus, Lactobacillus modestisalitolerans, Lactobacillus plantarum* subsp. argentoratensis, *Lactobacillus* xiangfangensis, Lechevalieria roselyniae, Lentzea *albida, Lentzea californiensis, Leuconostoc carnosum, Leuconostoc citreum, Leuconostoc gelidum* subsp. *gasicomitatum, Leuconostoc mesenteroides* subsp. suionicum, Luteimonas *aestuarii, Lysobacter antibioticus, Lysobacter koreensis, Lysobacter oryzae,* Magnetospirillum moscoviense, Marinomonas alcarazii. Marinomonas primoryensis, Massilia *aurea, Massilia jejuensis,* Massilia kyonggiensis, Massilia timonae, *Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium* subsp. silvaticum, *Mycobacterium* colombiense, *Mycobacterium* conceptionense, *Mycobacterium* conceptionense, *Mycobacterium farcinogenes, Mycobacterium* fortuitum subsp. fortuitum, *Mycobacterium* goodii, *Mycobacterium* insubricum, *Mycobacterium* llatzerense, *Mycobacterium* neoaurum, *Mycobacterium* neworleansense, *Mycobacterium obuense, Mycobacterium peregrinum, Mycobacterium saopaulense, Mycobacterium septicum, Mycobacterium setense, Mycobacterium smegmatis,*

*Neisseria subflava, Nocardia lijiangensis, Nocardia* thailandica, Novosphingobium barchaimii, Novosphingobium lindaniclasticum, *Novosphingobium lindaniclasticum,* Novosphingobium mathurense, Ochrobactrum pseudogrignonense, Oxalicibacterium solurbis, Paraburkholderia *glathei, Paraburkholderia* humi, *Paraburkholderia phenazinium, Paraburkholderia phytofirmans, Paraburkholderia sordidicola, Paraburkholderia terricola, Paraburkholderia xenovorans,* Paracoccus laeviglucosivorans, Patulibacter ginsengiterrae, Polymorphospora *rubra, Porphyrobacter colymbi, Prevotella jejuni, Prevotella melaninogenica, Propionibacterium acnes* subsp. *elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis,* Pseudonocardia alaniniphila, Pseudonocardia ammonioxydans, Pseudonocardia *autotrophica,* Pseudonocardia kongjuensis, Pseudonocardia *yunnanensis, Pseudorhodoferax soli, Pseudoxanthomonas daejeonensis,* Pseudoxanthomonas indica, Pseudoxanthomonas kaohsiungensis, *Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis,* Ramlibacter ginsenosidimutans, *Rheinheimera japonica,* Rheinheimera muenzenbergensis, Rheinheimera *soli,* Rheinheimera tangshanensis, Rheinheimera *texasensis,* Rheinheimera *tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus* enclensis, Rhodoferax saidenbachensis, *Rickettsia canadensis, Rickettsia heilongjiangensis, Rickettsia honei, Rickettsia* raoultii, Roseateles *aquatilis,* Roseateles *aquatilis,* Salmonella *enterica* subsp. salamae, *Serratia ficaria, Serratia myotis, Serratia vespertilionis, Shewanella aestuarii, Shewanella decolorationis,* Sphingobium amiense, Sphingobium baderi, Sphingobium barthaii, Sphingobium *chlorophenolicum,* Sphingobium cupriresistens, Sphingobium czechense, Sphingobium fuliginis, Sphingobium indicum, Sphingobium indicum, Sphingobium *japonicum,* Sphingobium *lactosutens, Sphingomonas dokdonensis, Sphingomonas* pseudosanguinis, Sphingopyxis *chilensis,* Sphingopyxis fribergensis, Sphingopyxis granuli, Sphingopyxis indica, Sphingopyxis witflariensis, *Staphylococcus agnetis, Staphylococcus aureus* subsp. *aureus, Staphylococcus epidermidis, Staphylococcus hominis* subsp. novobiosepticus, *Staphylococcus nepalensis, Staphylococcus saprophyticus* subsp. *bovis, Staphylococcus sciuri* subsp. carnaticus, *Streptomyces* caeruleatus, *Streptomyces* canarius, *Streptomyces capoamus, Streptomyces ciscaucasicus, Streptomyces griseorubiginosus, Streptomyces olivaceoviridis, Streptomyces pana-* ciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii subsp. anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibactersegnis, Agrococcus baldri, Albibactermethylovorans, Alcaligenes faecalis subsp. faecalis, Algoriphagus ratkowskyi, Alkalibacterium olivapovliticus, Alkalibacterium pelagium, Alkalibacterium pelagium, Alloprevotella rava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas sulfidaeris, Herpetosiphon aurantiacus, Hydrocarboniphaga effusa, Idiomarina maris, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevaniformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacterterrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacteruvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis subsp. novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter *sanguinis*, Undibacterium oligocarboniphilum, Undibacterium squillarum, Vagococcus salmoninarum, Varibaculum cambriense, Vibrio *metschnikovii*, Xanthobacter tagetidis, Xenophilus aerolatus, Xenophilus arseniciresistens, Yimella *lutea*, Zimmermannella alba, Zimmermannella *bifida* and/or Zoogloea caeni.

In other embodiments, the targeted bacteria cells are those commonly found in the vaginal microbiota and are, without limitation, Acinetobacter antiviralis, Acinetobacter *baumannii*, Acinetobacter calcoaceticus, Acinetobacter johnsonii, Actinobaculum massiliense, Actinobaculum schaalii, *Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis*, Aliivibrio wodanis, Alistipes finegoldii, Alloiococcus otitis, Alloprevotella *tannerae*, Alloscardovia omnicolens, Altererythrobacter epoxidivorans, Ammoniphilus *oxalaticus*, Amnibacterium kyonggiense, Anaerococcus *hydrogenalis, Anaerococcus lactolyticus*, Anaerococcus murdochii, Anaerococcus obesiensis, Anaerococcus *prevotii, Anaerococcus tetradius, Anaerococcus vaginalis*, Anaeroglobus geminatus, Anoxybacillus pushchinoensis, Aquabacterium *parvum*, Arcanobacterium phocae, Arthrobacter *aurescens*, Asticcacaulis excentricus, Atopobium *minutum, Atopobium parvulum*, Atopobium rimae, Atopobium vaginae, Avibacterium gallinarum, Bacillus acidicola, *Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis*, Bacteroides *barnesiae*, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella vischericola, Bhargavaea cecembensis, *Bifidobacterium adolescentis, Bifidobacterium bifidum, Bifidobacterium breve, Bifidobacterium dentium, Bifidobacterium logum* subsp. *infantis, Bifidobacterium longum, Bifidobacterium pseudocatenulatum, Bifidobacterium scardovii*, Bilophila wadsworthia, Blautia hydrogenotrophica, Blautia obeum, Blautia *producta*, Brachybacterium *faecium*, Bradyrhizobium japonicum, Brevibacterium *mcbrellneri*, Brevibacterium otitidis, Brevibacterium *paucivorans*, Bulleidia extructa, Burkholderia fungorum, Burkholderia phenoliruptix, Caldicellulosiruptor saccharolyticus, Caldimonas *taiwanensis*, Campylobacter gracilis, Campylobacter hominis, Campylobacter sputorum, Campylobacter ureolyticus, Capnocytophaga *ochracea*, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudogenitalium, Corynebacterium pyruviciproducens, Corynebacterium singulare, Corynebacterium striatum, Corynebacterium tuberculostearicum, Corynebacterium xerosis, Cryobacterium *psychrophilum*, Curtobacterium *flaccumfaciens*, Cutibacterium acnes, Cutibacterium *avidum*, Cytophaga xylanolytica, Deinococcus radiophilus, Delftia tsuruhatensis, *Desulfovibrio desulfuricans*, Dialister invisus, Dialister micraerophilus, Dialister pneumosintes, Dialister propionicifaciens, Dickeya *chrysanthemi*. Dorea longicatena, Eggerthella *lenta*, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella *asaccharolytica*, Gemella bergeri, Gemella haemolysans, Gemella *sanguinis*, Geobacillus stearothermophilus, Geobacillus thermocatenulatus, Geobacillus thermoglucosidasius, Geobacter grbiciae, Granulicatella *elegans*, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium *lividum*, Jonquetella *anthropi*, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter *orientalis*, Marinomonas protea, Marinospirillum *insulare*, Massilia timonae, Megasphaera elsdenii, Megasphaera micronuciformis, *Mesorhizobium* amorphae, *Methylobacterium radiotolerans*, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella *asaccharolytica*, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia *ramosa*, Nevskia soli, Nitriliruptor alkaliphilus, Odoribacter splanchnicus, Oligella urethralis, Olsenella uli, *Paenibacillus amylolyticus, Paenibacillus humicus, Paenibacillus pabuli, Paenibacillus pasadenensis, Paenibacillus pini, Paenibacillus validus*, Pantoea agglomerans, Parabacteroides merdae, Paraburkholderia *caryophylli*, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium et/i, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae and/or Zoogloea ramigera.

In one embodiment, the targeted bacteria are Escherichia coli.

In one embodiment, the targeted bacteria are Cutibacterium acnes more specifically the acne related Cutibacterium acnes from the phylogroup IA1 or RT4, RT5, RT8, RT9, RT10 or Clonal Complex(CC) CC1, CC3, CC4, more specifically the ST1, ST3, ST4.

Thus, the first type of bacteriophage disclosed herein, and therefore the phage particles or phage-derived delivery particles of the invention, may target (e.g., specifically target) a bacterial cell from any one or more of the foregoing genus and/or species of bacteria in particular to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) Escherichia coli, ESBL Klebsiella pneumoniae, vancomycin-resistant Enterococcus (VRE), methicillin-resistant Staphylococcus aureus (MRSA), multidrug-resistant (MDR) Acinetobacter baumannii, MDR Enterobacter spp., and a combination thereof. Preferably, the targeted bacteria can be selected from the group consisting of extended-spectrum beta-lactamase-producing (ESBL) Escherichia coli strains.

Alternatively, the targeted bacterium can be a bacterium of the microbiome of a given species, preferably a bacterium of the human microbiota.

In a particular embodiment, said targeted bacterial cells are from a species or strain different from the production bacterial cell.

Hybrid helper phage system and hybrid helper phage

The present invention also concerns a hybrid helper phage system comprising:
(i) at least one phage DNA packaging gene(s), as defined in the section "Production bacterial cell" above, derived from a lytic bacteriophage, as defined in the section "Bacteriophage and gene derived from a bacteriophage" above,
(i') at least one phage structural gene(s), as defined in the section "Production bacterial cell" above, derived from said lytic bacteriophage,
(i") optionally, at least one phage gene(s) involved in phage regulation, as defined in the section "Production bacterial cell" above, derived from said lytic bacteriophage, and
(ii) at least one gene, derived from a non-lytic bacteriophage, as defined in the section "Bacteriophage and gene derived from a bacteriophage" above, involved in phage excision/insertion, phage DNA replication, and/or phage regulation, as defined in the section "Production bacterial cell" above, wherein said genes (i), (i'), (i") and (ii) are comprised in a unique nucleic acid molecule or in separate nucleic acid molecules, and wherein said hybrid helper phage system does not comprise any expressed phage structural gene derived from said non-lytic bacteriophage.

In the context of the invention, the term "hybrid helper phage system" is meant a group of at least one nucleic acid molecule, preferably of at least two separate nucleic acid molecules, comprising the genes (i), (i'), optionally (i"), and (ii) defined above, which enables the production of lytic phage particles and/or lytic phage-derived delivery vehicles by the production bacterial cell comprising said system, wherein when the system comprises at least two separate nucleic acid molecules, said genes (i), (i'), optionally (i"), and (ii) are distributed on said at least two separate nucleic acid molecules.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Weigele et al. Chem Rev. 2016 Oct 26;116(20):12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present invention.

In a particular embodiment, said genes (i), (i'), optionally (i"), and (ii) are comprised in a bacterial chromosome, in particular in a production bacterial cell chromosome. In a more particular embodiment, said genes (i), (i'), optionally (i"), and (ii) are comprised in a bacterial chromosome in a same region. In an alternative embodiment, said genes (i), (i'), optionally (i"), and (ii) are comprised in a bacterial chromosome in distinct regions.

In an alternative embodiment, said genes (i), (i'), optionally (i"), and (ii) are comprised in separate plasmids. In another particular embodiment, said genes (i), (i'), optionally (i"), and (ii) are all comprised in a same plasmid.

In another particular embodiment, said genes (i), (i'), optionally (i"), and (ii) are each independently comprised in a bacterial chromosome or in a plasmid.

In a more particular embodiment, said genes (i), (i'), optionally (i"), and (ii) are comprised in a hybrid helper phage.

Therefore, in a particular embodiment, said hybrid helper phage system consists of a hybrid helper phage comprising:
(i) at least one phage DNA packaging gene(s), as defined in the section "Production bacterial cell" above, at least one phage structural gene(s), as defined in the section "Production bacterial cell" above, and optionally at least one phage gene(s) involved in phage regulation, as defined in the section "Production bacterial cell" above, derived from a lytic bacteriophage, as defined in the section "Bacteriophage and gene derived from a bacteriophage" above, and
(ii) at least one gene, derived from a non-lytic bacteriophage, as defined in the section "Bacteriophage and gene derived from a bacteriophage" above, involved in phage excision/insertion, phage DNA replication, and/or phage regulation, as defined in the section "Production bacterial cell" above, wherein said hybrid helper phage does not comprise any phage structural gene derived from said non-lytic bacteriophage.

By "helper phage" is meant herein an engineered phage providing all the necessary gene products for particle formation when using phagemid vectors. Helper phages typically have a defective origin of replication or packaging signal, and hence, are inefficient in self-packaging.

By "hybrid helper phage" is meant herein an engineered helper phage which is constituted of elements derived from at least a lytic bacteriophage and a non-lytic bacteriophage.

In a particular embodiment, the hybrid helper phage of the invention is integrated in the genome of the production bacterial cell as a prophage.

Production Method

The present invention further concerns a method for producing lytic phage particles or lytic phage-derived delivery vehicles, comprising:
(a) providing the production bacterial cell of the invention, and
(b) inducing, in said production bacterial cell, expression of said at least one of said phage structural gene(s) and at least one of said phage DNA packaging gene(s), and assembly of the products expressed by said at least one phage structural gene(s) and said at least one phage DNA packaging gene(s), thereby producing lytic phage particles or lytic phage-derived delivery vehicles.

The inducing step (b) can be carried out by any technique well-known from the skilled person. In particular, as will be understood by the skilled person, said inducing step will depend on the particular induction mechanism controlling the expression of said at least one of said phage structural genes and phage DNA packaging genes, in said production bacterial cell.

More particularly, it will be understood by the skilled person that, when said induction mechanism comprises at least one gene, derived from a non-lytic bacteriophage, involved in phage excision/insertion, phage DNA replication, and/or phage regulation, said inducing step will depend on the bacteriophage from which said sequences are derived. Typically, said inducing step can be a thermal induction (for phages that are naturally triggered by this signal or engineered repressors such as lambda cl), small molecule inducers (depending on the phage), any signal triggering SOS response (for instance addition of mitomycin), etc.

Unless defined otherwise, all technical and scientific terms used herein have the same meaning as commonly understood by one of ordinary skills in the art to which this invention belongs.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

Although the invention has been described in conjunction with specific embodiments thereof, many alternatives, modifications and variations will be apparent to those skilled in the art. Accordingly, it is intended to embrace all such alternatives, modifications and variations to fall within the spirit and broad scope of the appended claims.

All publications, patents and patent applications mentioned in this specification are herein incorporated in their entirety by reference into the specification, to the same extent as if such individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The following examples are given for the purpose of illustrating various embodiments of the invention and are not meant to limit the present invention in any fashion.

Sequences

| SEQ ID NO: | Description | Type |
|---|---|---|
| 1 | primase ori from the PICI of the Escherichia coli strain CFT073 | DNA |
| 2 | Restriction site | DNA |
| 3 | Primase ori deltaGAAABCC | DNA |
| 4 | Primase ori devoid of restriction sites | DNA |
| 5 | PICI primase-helicase | Protein |
| 6 | PICI primase-helicase | DNA |
| 7 | Lambda prophage structural operon | DNA |
| 8 | Complete edited structural "operon" | DNA |
| 9 | Payload pJ23115-GFP T7 cos 2.0 | DNA |
| 10 | p1884 plasmid | DNA |
| 11 | p1885 plasmid | DNA |
| 12 | T7 RNA polymerase version AAV | DNA |
| 13 | T7 RNA polymerase version AAV | Protein |
| 14 | T7 RNA polymerase version LVA | DNA |
| 15 | T7 RNA polymerase version LVA | Protein |
| 16 | AD1334 primer | DNA |
| 17 | AD1335 primer | DNA |
| 18 | AD1336 primer | DNA |
| 19 | AD1337 primer | DNA |
| 20 | AD1322 primer | DNA |
| 21 | AD1323 primer | DNA |
| 22 | BW4 genome | DNA |
| 23 | PAC7 genome | DNA |
| 24 | pANS514 plasmid | DNA |
| 25 | PAC7 cos of pAN594 | DNA |
| 26 | operon of gp15-gp19 + gp45 | DNA |
| 27 | pAN241 vector | DNA |

EXAMPLES

Figure 1:
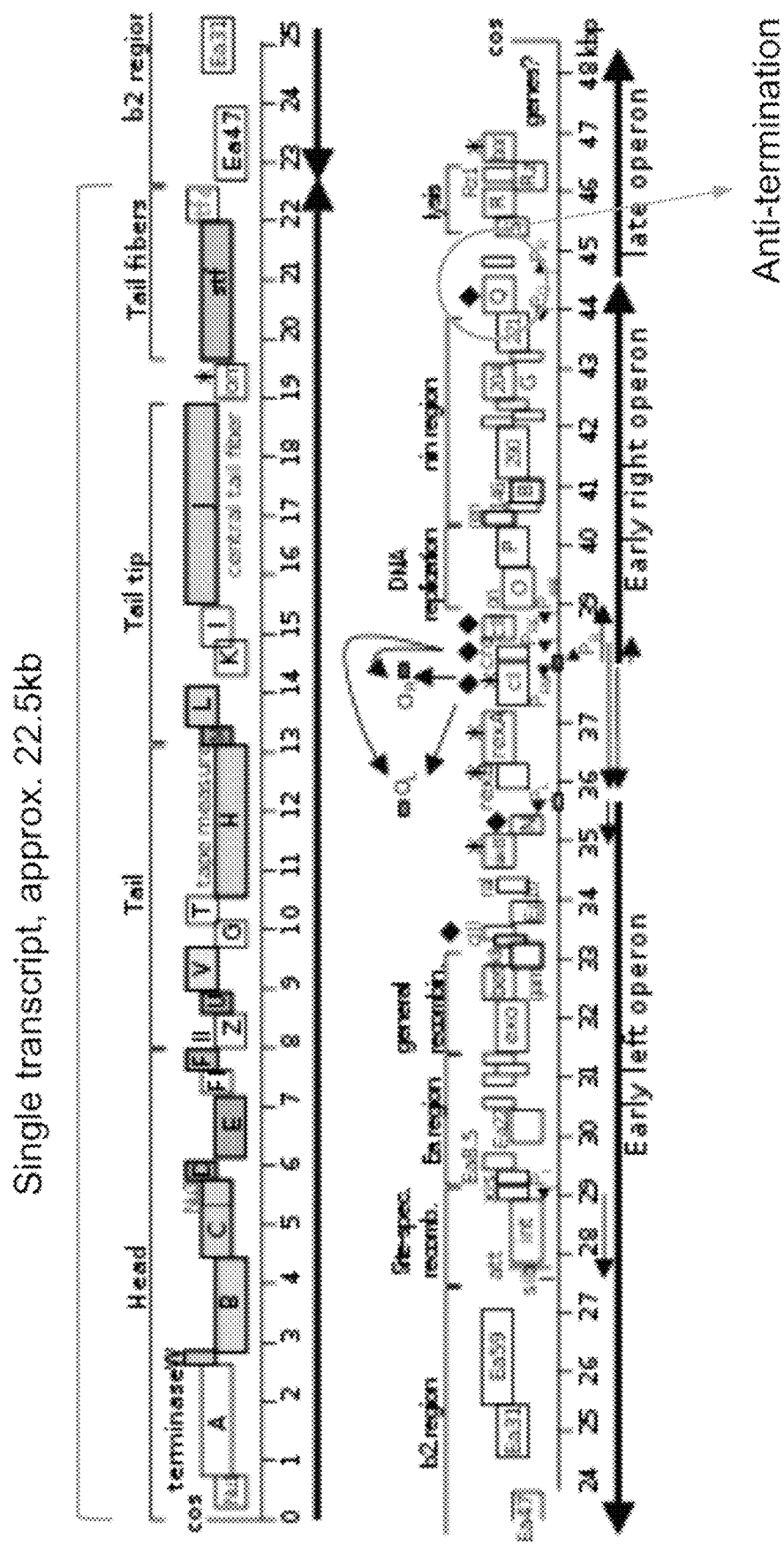
FIG. 1: Lambda genome organization (packaged variant). The structural operon is marked with a red line as well as the antitermination protein Q that allows transcription of the late structural operon. Figure adapted from Rajagopala et al. BMC Microbiol 11, 213 (2011).

Example 1: Exchange of the Structural Operon of Lambda for Elements of a Lytic Phage The inventors considered that phages can be viewed as more or less large genetic circuits whose final output is the generation of more phage particles. To do this, no matter if the phage is lytic, temperate or chronic (for instance filamentous phages such as M13), the information encoded in their genomes can be roughly categorized depending on the function it performs:

Genes devoted to insertion/excision (for temperate phages).

Genes devoted to DNA replication, RNA transcription, etc. . . . . Some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.

Genes related to defense from host's anti-phage mechanisms, degradation/modification of host's elements to complete the lytic cycle, super-exclusion mechanisms or genes that are advantageous for the host.

Genes devoted to DNA packaging: terminases and accessory proteins, ligases, etc.

Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).

The last two categories (DNA packaging and structural genes) are deeply connected, since the packaging machinery recognizes the pre-assembled heads and the DNA to be packaged, initiates and terminates DNA packaging.

The inventors hypothesized that by abstracting and differentiating all the modules defined above, in principle a system could be built that contains all excision/insertion, replication and regulation elements from one phage, in particular a non-lytic phage, and encodes the packaging/structural elements from another phage, in particular from a lytic phage, since, in principle, they could be viewed as independent genetic modules.

In the present example, it is referred to "structural elements" for proteins needed for DNA packaging and structural proteins needed to assemble a mature virion.

Such a "hybrid structural phage" could be very advantageous for different approaches, because:
 a species which is more amenable for laboratory work/large scale production/safer could be used to produce such particles where the structural genes come from another species;
 pure phagemid producing strains could be constructed using the regulatory elements of a well-characterized phage (for instance, Lambda) driving the production of capsids of a different phage, etc., and
 and finally, structural hybrid prophages (i.e. carried in the genome) driving the production of lytic phage capsids could be constructed.

This is the approach that was developed herein. Using a production strain encoding a system to generate pure Lambda phagemids, its structural operon has been exchanged (from the small terminase to the STF gene, about 23 kb) with the structural elements of a strictly lytic E. coli phage, T7. A schematic diagram shows the lambda genome organization (FIG. 1).

In this system, the thermolabile version of the prophage Lambda contains all regulatory elements needed to excise the prophage, replicate the circularized excised genome and drive the expression of the long, late operon, including the presence of the antitermination protein Q. This should drive the assembly and packaging of pure phagemid particles completely based on other phages when supplemented with a plasmid containing the correct packaging signals (LTR for T7)

Construction of the Hybrid

The Lambda prophage structural operon (SEQ ID NO: 7) was exchanged with the structural "operon" of the lytic phage T7, from gp6.5 to gp19.5 (not strictly an operon since the T7 RNA polymerase drives the transcription of different mRNAs within this region), using the lambda red recombineering system, starting from a production strain containing a Lambda prophage without the cos site (s1965). Several changes were further made:
 Removal of putative holin and lysis genes in T7 (gp17.5 and gp18.5)
 Recoding of the 3' part of the gp19 DNA maturation protein and the intergenic region between this gp19 and the next one, gp19.5 (explained below)
 All T7 RNA polymerase promoters were left intact but no T7 RNA polymerase was added to the system.

The complete edited structural "operon" spans about 20 kb (SEQ ID NO: 8). The final production was named CY-L7 and was built without any specific remarks.

Production and Titrations

A payload was built that should be packaged by T7 as described in Auster et al. RNA Biol. 2019 Apr;16(4):595-599, called pJ23115-GFP T7 cos 2.0 (p1883, SEQ ID NO: 9). This payload contains the 5' LTR necessary to be efficiently packaged by T7. The putative packaging region of this plasmid contains the 3' part of gp19 and the intergenic region between gp19 and gp19.5. It is for this reason that the 3' part of gp19 was recoded before inserting it into the genome of the production strain, so recombination is prevented.

Next, the CY-L7 strain was transformed with the p1883 payload and productions carried out as described below.

Overnight cultures were diluted 1:6 in a final volume of LB+5 mM $CaCl_2$ supplemented with chloramphenicol and grown for 30 min at 30° C. with shaking. After that, a 45-minute-long heat shock at 42° C. was performed. Finally the cultures were grown at 37° C. for 3 hours with shaking. After this period, cells were recovered by centrifugation and lysed using 3 mL of B-PER™ protein extraction reagent, 600 mg of detergent removal bio-beads were added and an incubation at room temperature with mild shaking performed for 1 hour. After that, the lysates were centrifuged for 10 min at 10,000 g and the supernatants filtered through a 0.2 micron pore-size membrane.

The lysates were titrated in E. coli MG1655 and KEIO-waaG (a derivative with a deletion of the waaG gene, which has been shown to be necessary for T7 binding, (Qimron et al. Proc Natl Acad Sci USA. (2006) 103(50):19039-19044)). If phagemids are produced, colonies should only be detected in the MG1655 strain, since the KEIO-waaG does not contain the receptor for T7.

Figure 2:
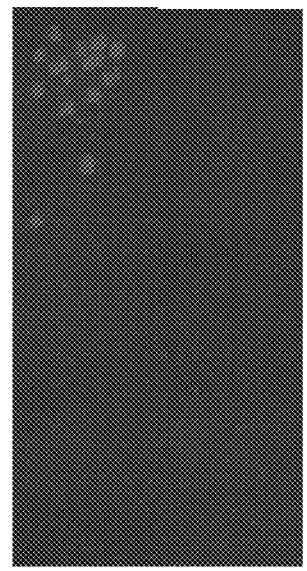
FIG. 2: Titration of T7 phagemids produced in a Lambda-T7 hybrid prophage system. Production strain CY-L-7 contains the payload p1883. Left panel, titration on MG1655; right panel, titration on KE10-waaG.

As can be seen in FIG. 2, a small number of colonies could be detected only in the MG1655 columns. This result is the first proof that a strictly lytic phage can be "tamed" and its structural and packaging genes controlled by a lysogenic one (lambda) to yield pure phagemid particles based on T7.

The titers obtained were very low, although pure T7-based phagemids were produced.

The inventors sought to improve the titers by applying different rational approaches. For instance, it is known that for T7 plasmid or genome packaging, transcription by the T7 RNA polymerase from a promoter within the 5' LTR is needed (Chung et al. J Mol Biol. 1990 Dec. 20; 216(4):927-38). Additionally, the T7 genome is transcribed by its cognate RNA polymerase and many different T7 promoters are found, even within the region encoding the different structural elements (Dunn et al. J Mol Biol. 1983 Jun. 5; 166(4):477-535). This produces different mRNAs that are then processed by the E. coli RNAse III (Studier et al. "Processing of bacteriophage T7 RNAs by RNase III" Ed: Thomas R. Russell, Keith Brew, Harvey Faber, Julius Schultz, From Gene to Protein: Information Transfer in Normal and Abnormal Cells, Academic Press, 1979, p. 261-269).

For these two reasons, the production strain was complemented with the T7 RNA polymerase in trans, in an inducible plasmid under the control of the PhIF repressor.

Initially, the transformation of the T7 RNA polymerase plasmid in the CY-L7 strain containing the p1883 payload gave no colonies, presumably due to toxicity coming from leakiness of the inducible pphlF promoter (data not shown). For this reason, two alternative plasmids encoding the T7 RNA polymerase with two different degradation tags of different strengths were built (p1884, SEQ ID NO: 10; and p1885, SEQ ID NO: 11). The sequences of the T7 RNA polymerase encoded in these two plasmids are disclosed (SEQ ID NO: 12 and SEQ ID NO: 13 for version AAV; SEQ ID NO: 14 and SEQ ID NO: 15 for version LVA). It has been demonstrated that by adding a degradation tag to a protein, the potential effects of leaky expression from a repressible promoter are improved (Fernandez-Rodriguez et al. Nucleic Acids Res. (2016) 44(13):6493-6502).

Productions were carried out from strain CY-L7 harboring the payload p1883 and supplemented with the T7 RNA polymerase variants encoded in plasmids p1884 or p1885, with the same protocol specified above. The lysates were then titrated on MG1655 or on KEIO-waaG.

Figure 3:
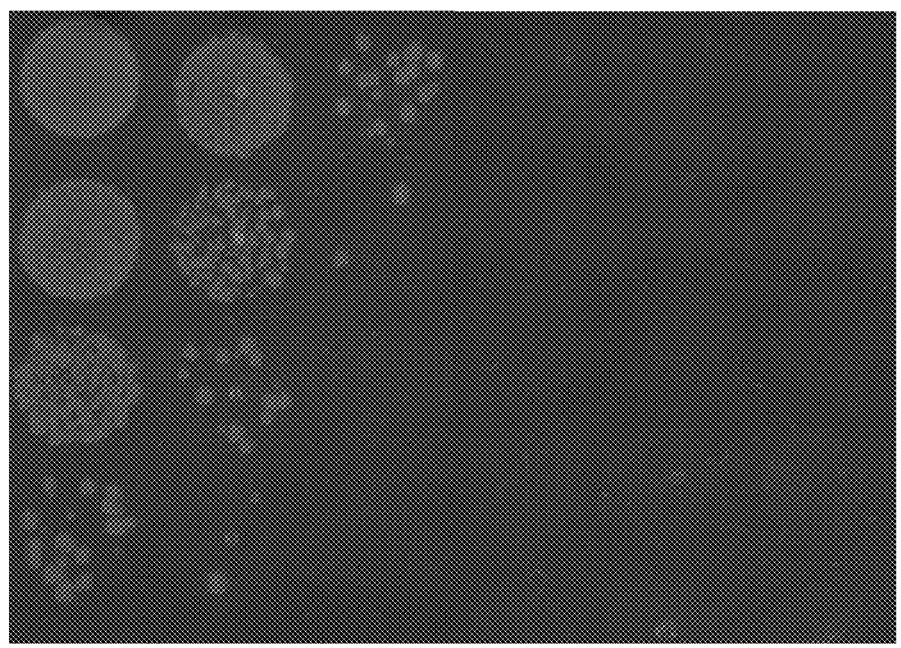
FIG. 3: Titration of T7 phagemids produced in a Lambda-T7 hybrid prophage system. Left panel, titration on MG1655. Right panel, titration on KE10-waaG. From left to right: left) payload p1883+p1885 (T7 RNA polymerase with fast degradation); middle) payload p1883 +p1884 (T7 RNA polymerase with medium strength degradation); right) payload p1883 only.

As can be seen on FIG. 3, the introduction of the T7 RNA polymerase increases the titers obtained by a factor of 100× (for the medium degradation tag) or by 1000X (for the fast degradation tag) as compared to productions harboring the p1883 payload only. The titers obtained in this system are about $2 \times 10^6$ TU/mL.

These experiments show that, for certain types of phages, a regulatory protein not belonging strictly to the structural categories defined above may be needed, in this case the T7 RNA polymerase, either to improve or promote the packaging reaction or to control the amount or processing of the mRNAs encoding the structural components.

Example 2: Production of Cutibacterium *Acnes* Phage-Derived Particles

Cutibacterium *acnes* is one of the most prevalent and abundant species of the skin (Kashaf et al. *Nat Microbiol* 7, 169-179 (2022)) where it colonizes the pilosebaceous unit (PSU).

Unlike on the stratum corneum, bacteria present in the PSU are surrounded by living cells notably keratinocytes, sebocytes and different immune cells (Kabashima et al. *Nat Rev Immunol* 19, 19-30 (2019)). Close contact between C. *acnes* and these cells might lead to either beneficial or detrimental interactions. (BrQaggemann et al. *Front Microbiol* 12, 673845 (2021)). Being able to genetically modify C. *acnes* was notoriously challenging before the applicant's' new tools as disclosed in US applications US2022/135986 and US2022/135987. In these patent applications, the inventors described, for the first time, the production of C. *acnes* phage-derived particles using C. *acnes* as a production strain.

In the present example, the inventors used *P. freudenreichii* strain to produce C. *acnes* phage-derived particles by swapping the structural genes from a *P. freudenreichii* prophage for the structural genes of a C. *acnes* phage.
Results
Isolation of BW4 Phage

*P. freudenreichii* and associated bacteriophages are known to be present in some dairy products (Gautier et al. (1995) Lait 75:427-434; Gautier et al. (1995) *Appl. Environ. Microbiol.* 61:2572-2576; Cheng et al. (2018) *BMC Microbiology* 18:19). The inventors therefore screened for the presence of both *Propionibacterium* phages or *P. freudenreichii* lysogens in cheese samples.

Different types of cheese samples were grinded, resuspended in Reinforced Clostridial Medium (RCM) and incubated at 30° C. in anaerobic conditions for 2 days. After incubation, a dilution of the culture was performed in lithium glycerol broth, a media selective for Propionibacteria (WO1994017201), and incubated for 6 days at 30° C. A final dilution in RCM+mitomycin C was incubated for 1 day at 30° C. in order to induce potential prophages. The induced cultures were filtered (0.2 pm) and spotted on different indicator strains. One of the samples led to turbid plaque formation on top agar of the *P. freudenreichii* strain Pf0s2841. Three individual plaques were isolated by two successive picking and streaking on Pf0s2841 and amplification was performed on top agar of Pf0s2841. For the three different plaques, amplification led to phage suspension ·$10^{10}$ PFU/mL.

Two clusters of temperate dsDNA *P. freudenreichii* phages (BW and BV) have been previously identified (Cheng et al. (2018) BMC Microbiology 18:19). Using PCRs, designed on BW genome from Doucette phage (KX620751), two different fragments were extracted:
ORF3 with AD1334 (SEQ ID NO: 16)/AD1335 (SEQ ID NO: 17)
ORF5 with AD1336 (SEQ ID NO: 18)/AD1337 (SEQ ID NO: 19).

Figure 4:
FIG. 4: Identification of P. freudenreichii phages with PCR. PCR on ORF3 and ORF5 was performed on all phage suspensions. BW4 from plaques 1-3 give a band at the expected size for both orf3 and orf5. Ladder is GENERULER 1 kb plus.
Figure 4:
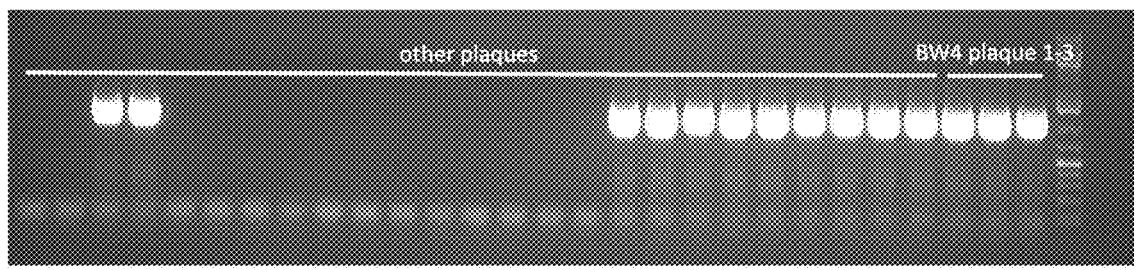

The inventors could classify the isolated phages as BW-like (FIG. 4). Sequencing of ORF5 revealed that all phages were most probably identical and therefore were coming from the same BW-like phage that was named BW4.
Isolation of Pf0s2841 Lysogen Carrying the BW4 Phage The inventors then isolated *P. freudenreichii* lysogen carrying the BW4 phage as a prophage. For that, BW4 phage suspension was spotted on strain Pf0s2841 and incubated for 3 days. Turbid plaques were picked, resuspended and streaked. After 5 days, single colonies were obtained, several colonies were streaked and incubated a second and third time and presence of the phage genes was checked, at each streaking, by PCR, after DNAse treatment, across the cohesive ends (AD1322 (SEQ ID NO: 20)/AD1323 (SEQ ID NO: 21)) to ensure presence of the phage but absence of phage particles.

Figure 5:
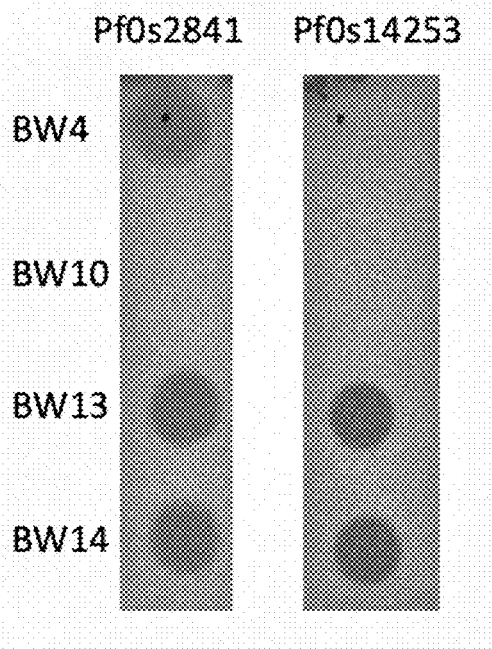
FIG. 5: Immunity to superinfection of lysogen Pf0s14253. Left panel: Top agar of Pf0s2841 with spots of 4 different BW-like phage suspensions. Right panel: Top agar of Pf0s14253 with spots of 4 different BW-like phage suspensions.
Figure 6:
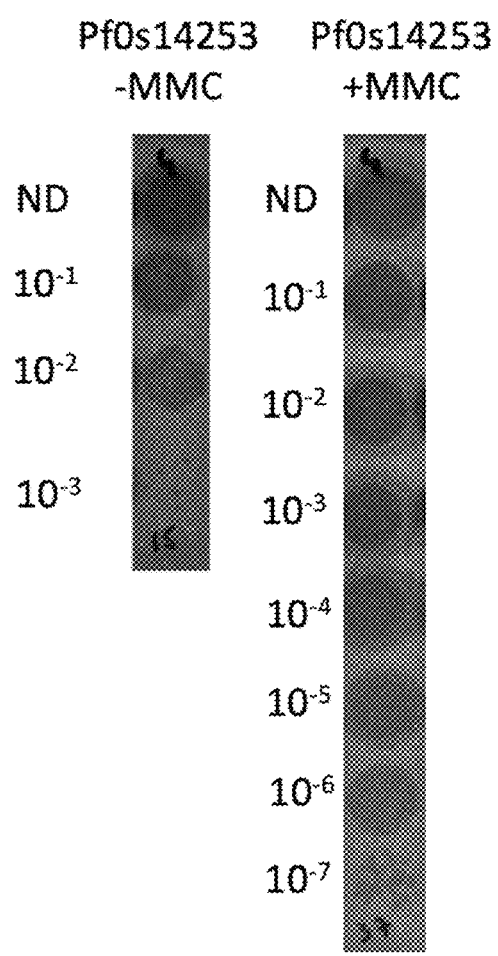
FIG. 6: High induction of BW4 phage after mitomycin C treatment. Left panel: Top agar of Pf0s2841 with spots of culture supernatant from Pf0s14253 without mitomycin C (MMC) induction (ND: non diluted to dilution 10-3). Right panel: Top agar of Pf0s2841 with spots of culture supernatant from Pf0s14253 with 0.5 pg/ml of mitomycin C induction (ND: non diluted to dilution 10-7).

After the third streak, colonies were grown as a top agar and a spot of non diluted BW-like phages suspensions were spotted on the putative lysogenic strain (Pf0s14253) and on the ancestor strain (Pf0s2841). After incubation, clearance was observed for both strains for BW13 and BW14 spots whereas clearance was only observed for Pf0s2841 in the case of BW4 spot (FIG. 5). This indicates that the strain Pf0s14253 is immune to BW4 phage superinfection and carries the BW4 prophage. The absence of immunity for BW14 and BW13 indicates that these phages have likely a different immunity repressor.
BW4 Prophage Induction In order to use the BW4 lysogen strain as a production strain for phage-derived particles the inventors first had to test the ability to produce high concentration of the BW4 phage upon induction of the lytic cycle. To do so, Pf0s14253 was grown in absence or presence of mitomycin C (MMC), an antibiotic known to induce prophages, and the culture supernatant was titered for the presence of BW4 phage particles on the indicator strain Pf0s2841. A high amount of BW4 phage particles was observed in the condition supplemented with mitomycin C (FIG. 6) with $7.4 \times 10^7$ PFU/μL against 3.0x103 PFU/μL for the condition without mitomycin C. This indicates a high dynamic range between lytic and lysogenic cycle for BW4 prophage under such conditions and confirmed the potential of BW4 for the production of phage-derived particles.
Sequencing and Annotation of BW4 Phage To engineer the BW4 prophage towards production of C. *acnes* phage-derived particles, the BW4 phage was sequenced. DNA isolation (PROMEGA™ WIZARD® DNA Clean-Up System) followed by ILLUMINA™ sequencing was performed on BW4 phage suspension. Raw reads were assembled into a single contig using Spades and termini were corrected by sanger sequencing (SEQ ID NO: 22). Annotation was performed using PHASTER and manually curated based on homologies with other BW-like phages (Cheng et al. (2018) BMC Microbiology 18:19).

As described in Cheng et al. (2018) BMC Microbiology 18:19, BW-like phages have typical genomic architecture of other temperate phages with a large putative structural operon (also called lytic operon) organized in different functional modules with, in order of transcription: packaging, head, tail, and lysis module. Surprisingly, the first gene of the putative operon (gp1) appears to be related to DNA replication based on HHpred as it contains a domain similar to bifunctional primase and polymerase proteins. Other parts of the BW4 phage genome contain the genes necessary for prophage integration/excision, DNA replication, DNA recombination, regulation of the lytic/lysogenic cycle and other accessory proteins. This modular architecture confirms the possibility to swap the genes necessary for the production of BW4 phage capsid and the packaging of the phage genome by their equivalent from a C. acnes phage genome.

Isolation of C. Acnes PAC7 Phage

C. acnes phages were isolated from skin of healthy volunteers. Briefly a patch (BIORE™) was applied to the nose allowing to extract comedones that were resuspended in RCM, plated on MRS and incubated at 37° C. in anaerobic conditions. For some of the plates, plaques could be observed in the dense lawn of C. acnes. DPBS (Dulbecco's Phosphate Buffered Saline) was poured on the plate to resuspend potential phages and filtered to remove bacteria. This phage suspension was streaked on plate and a top agar of strain Ca0s2345 was added. Plates were incubated for 2 days and plaques were reisolated by three successive picking, streaking and top agar plating. Finally a plaque was amplified on top agar with Ca0s2345 strain and the resulting phage suspension was PEG precipitated. High titer (>10$^6$ PFU/μL) phage suspension was obtained when titered on Ca0s2345.

Sequencing and Annotation of PAC7 Phage

Figure 7:
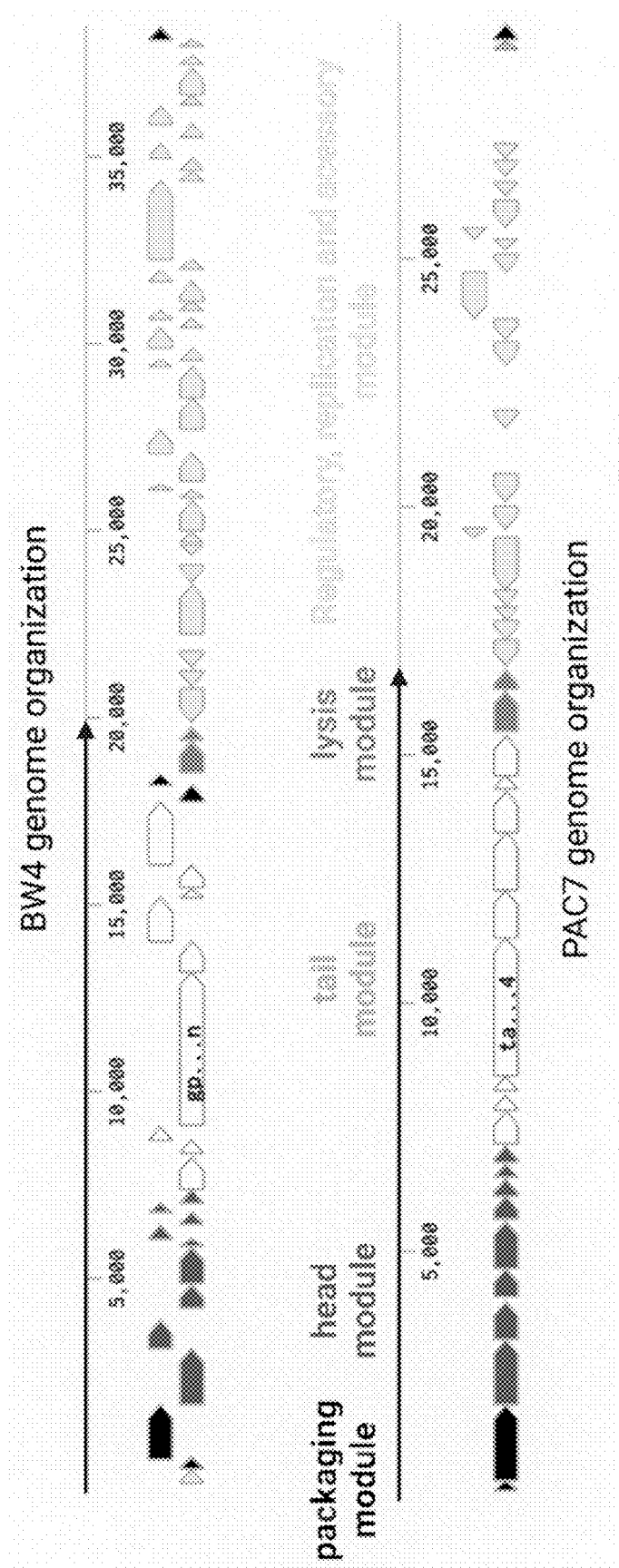
FIG. 7: Genome organization of BW4 and PAC7 bacteriophages. BW4 and PAC7 genome organization is similar with both putative structural operons (represented by the arrows) containing the packaging, head, tail and lysis modules.

DNA isolation (PROMEGA™ WIZARD® DNA Clean-Up System) followed by ILLUMINA™ sequencing was performed on PAC7 phage suspension. Raw reads were assembled into a single contig using Spades and termini were corrected by sanger sequencing (SEQ ID NO: 23). Annotation was performed using PHASTER and manually curated based on homologies with other C. acnes phages (Marinelli et al. (2012) *mBio* 3:e00279-12). Similar to the *P. freudenreichii* BW4 phage, a structural operon comprising modules for packaging, head and tail assembly and cell lysis was identified (FIG. 7). An HNH endonuclease was identified as the last gene of the phage (gp45). Such endonuclease has already been shown to be essential for efficient packaging (Quiles-Puchalt et al. (2014) *Proc Nat. Acad. Sci.* 111:6016-6021).

Construction of lysogen strain with a chimeric BW4-PAC7 prophaqe

Figure 8:
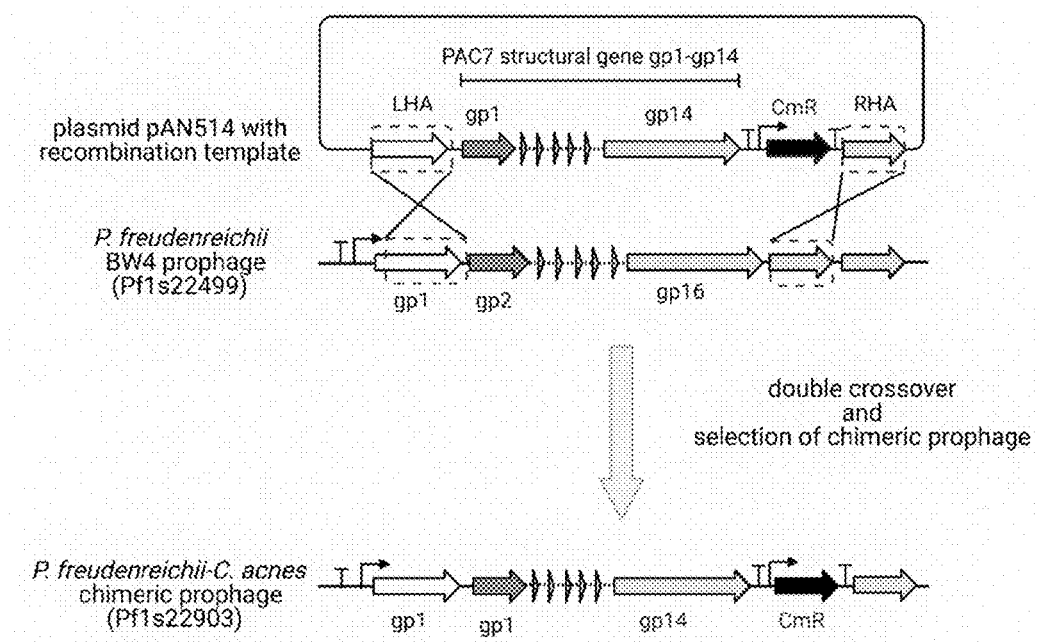
FIG. 8: Construction of chimeric BW4-PAC7 prophage. Transformation of the pAN514 suicide plasmid into strain Pf1s22499 containing the BW4 prophage. Selection on chloramphenicol was used to select for double crossover at the Left Homology Arm (LHA) and Right Homology Arm (RHA). The prophage obtained is a chimer containing a structural operon with first BW4 gp1 followed by gp1-gp14 of PAC7 and after the chloramphenicol selection cassette (CmR) the leftover of BW4 structural genes (gp15-gp25).

The genes in the structural operon of BW4 prophage, from the small terminase gp2 to the tape-measure protein gp16 included, were replaced by the structural PAC7 genes from gp1 to gp14 (FIG. 8). This was performed by homologous recombination using plasmid pAN514 (SEQ ID NO: 24), a *P. freudenreichii* suicide vector that was cloned in *E. coli* DH10B. After transformation of the vector, a double crossing over event was selected in *P. freudenreichii* (Pf1s22499) by selection on chloramphenicol. The chimeric BW4-PAC7 structural operon integrity was globally confirmed by PCR and sanger sequencing of the entire chimeric structural operon.

Figure 9:
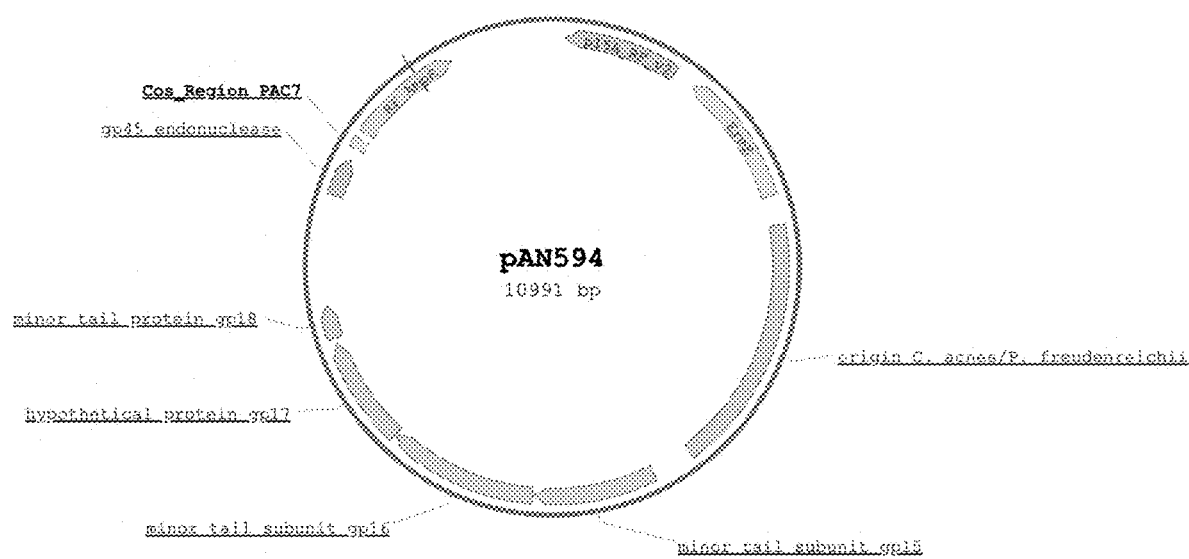
FIG. 9: Plasmid map of cosmid pAN594.

Production and titration of PAC7 derived particles from a lysogen strain carrying a chimeric BW4-PAC7 propaae In order to produce C. acnes phage-derived particles from a *P. freudenreichii* BW4-PAC7 chimeric lysogen, the pAN594 cosmid (FIG. 9) containing the packaging signal of the PAC7 phage (SEQ ID NO: 25), an operon expressing five genes of the PAC7 tail module (gp15-gp19) and the gp45 endonuclease (SEQ ID NO: 26) and an origin of replication functional in *P. freudenreichii* and C. acnes (as disclosed in US applications US2022/135986 and US2022/135987) were transformed into Pf1s22903. Transformants were streaked and grown in presence of both chloramphenicol (1 pg/ml) to select for the presence of the prophage and erythromycin (2.5 μg/ml) to select for the presence of pAN594. At $OD_{600}$~~0.4, culture was supplemented with 0.5 μg/ml of mitomycin C and grown overnight at 30° C. in anaerobic conditions.

After incubation, cells were collected by centrifugation, lysed by bead beating (2×20 min at 30 Hz with 0.1 mm glass beads), supernatant was filtered and the presence of phage derived particles was titered on C. acnes Ca0s2258.

Figure 10:
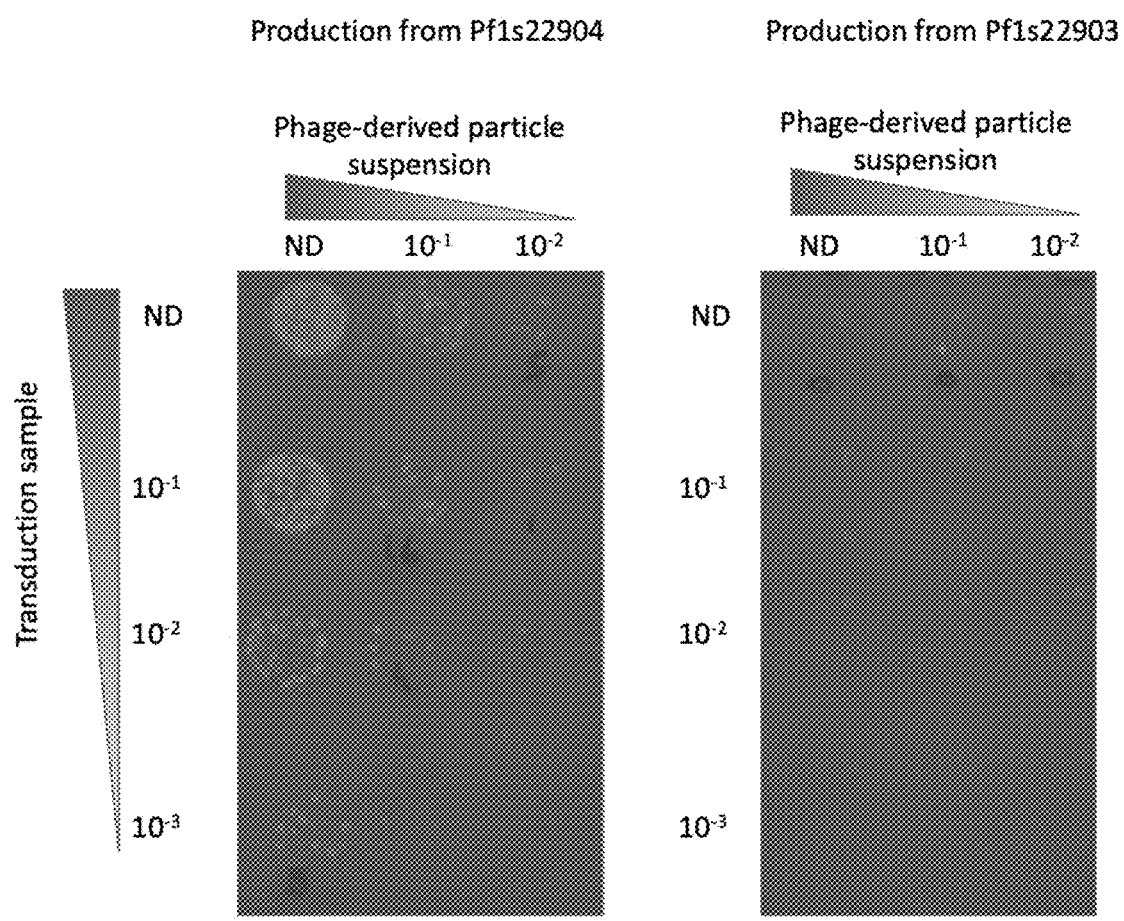
FIG. 10: Titration of PAC7 phage-derived particles. Left Panel: Titration from Pf1s22904 plated on erythromycin. Right Panel: Titration from control suspension of strain Pf1s22903 that does not carry any cosmid plated on erythromycin.
Figure 11:
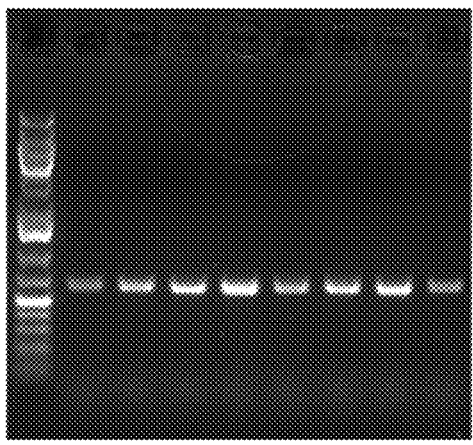
FIG. 11: Confirmation for 8 colonies streaked from phage-derived particles titration of Pf1s22904 production by PCR. Top Panel: SLTS PCR (Scholz 2014) on 8 colonies streaked from the phage derived titration assay. Expected size is 612 bp. Bottom Panel: pAN594 specific PCR on 8 colonies. Expected size is 769 bp. Ladder is generuler 1 kb plus.
Figure 11:
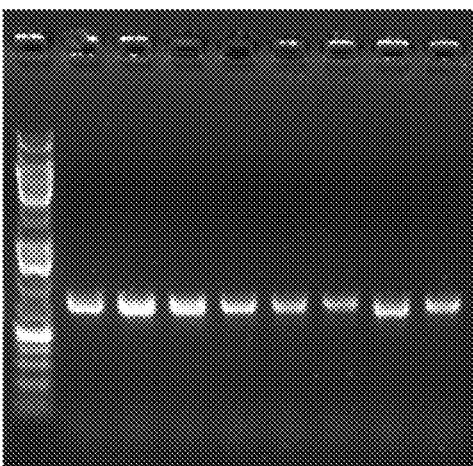

Up to ~$10^2$ potential transductants per μL were obtained (FIG. 10). 8 colonies were streaked on Brain Heart Infusion (BHI) erythromycin (5 μg/mL) and confirmed to be C. acnes and transductants carrying pAN594 using PCR (FIG. 11).

The inventors thus demonstrated for the first time that C. acnes phage-derived particles able to deliver DNA into Cutibacterium acnes can be produced by swapping structural genes of a *P. freudenreichii* prophage for the structural genes of a Cutibacterium acnes phage.

Material and Methods

Strain Used and Generated

TABLE 1

Strains used and generated

| Eligo ID | Description |
| --- | --- |
| Pf0s2841 | Indicator strain for *P. freudenreichii* BW4 phage (CIRM-BIA 509, TL110 belonging to INRAE) |
| Pf0s14253 | Strain Pf0s2841 with a BW4 prophage |
| Pf1s22499 | Strain Pf0s14253 with the packaging signal of BW4 deleted |
| Pf1s22903 | Strain Pf1s22499 with the BW4 genes gp2-gp16 replaced by PAC7 gp1-gp14 |
| Pf1s22904 | Strain Pf1s22903 with pAN594 |
| Ca0s2345 | Indicator strain for C. acnes PAC7 phage |
| Ca0s2258 | Cutibacterium acnes ATCC 11828 |

Culture Conditions

All incubations of *P. freudenreichii* strains were performed at 30° C. in anaerobic conditions (THERMO SCIENTIFIC™ SACHET OXOID™ ANAEROGEN™).

All incubations of C. acnes strains were performed at 37° C. in anaerobic chamber.

Construction of Strain Pf1s22499

Deletion of the packaging signal from BW4 prophage was performed by homologous recombination and CRISPR-Cas selection of the recombinant using the pAN241 *P. freudenreichii* vector that was cloned in *E. coli* and then transformed into Pf0s14253 strain. The pAN241 vector contains a template for homologous recombination (SEQ ID NO: 27) and a FnCpf1 transcriptional cassette with a crRNA targeting the cos of the BW4 prophage.

Transformation Protocol for *P. freudenreichii*

Transformation of *P. freudenreichii* was adapted from Brede, D. A. et al. *Appl Environ Microb* 71, 8077-8084 (2005), replacing SLB (sodium lactate broth) media for BHI.

Phage-derived particles titration

Strain Ca0s2258 was streaked on BHI agar plate. Once dense growth on plate was obtained, a liquid culture was set up in BHI. After overnight incubation, the turbid culture was concentrated 10× in BHI. 90 μl of cells were mixed with pure, diluted 1/10 and diluted 1/100 solutions of 10 μL of phage-derived particles produced from either Pf1s22904 or Pf1s22903 as negative control. Samples were incubated 2 hours at room temperature and then 1/10 serial dilutions were performed in BHI, samples were incubated 2 h at 37° C. in anaerobic conditions before spotting 4 μL on BHI+5 μg/mL erythromycin. Plates were incubated for 7 days at 37° C. in anaerobic conditions.

The invention claimed is:

1. A method for producing lytic phage particles or lytic phage-derived delivery vehicles, comprising:
   (a) providing a production bacterial cell stably comprising phage structural genes and phage DNA packaging genes of a lytic bacteriophage,
      wherein the expression of said phage structural genes and phage DNA packaging genes in said production bacterial cell is controlled by an induction mechanism comprising phage excision/insertion genes, phage DNA replication genes, and phage regulation genes of a second, non-lytic bacteriophage, wherein said phage excision/insertion genes, phage DNA replication genes and phage regulation genes are neither phage DNA packaging genes nor phage structural genes,
   wherein said production bacterial cell does not comprise phage excision/insertion genes and/or phage replication genes of the lytic bacteriophage,
   wherein said production bacterial cell is a *P. freudenreichii* bacterial cell, wherein the lytic bacteriophage is a *C acnes* phage and wherein the second, non-lytic bacteriophage is a *P. freudenreichii* phage; and (b) inducing, in said production bacterial cell, expression of said phage structural genes and phage DNA packaging genes, and assembly of the products expressed by said phage structural genes and phage DNA packaging genes, thereby producing lytic phage particles or lytic phage-derived delivery vehicles.

2. The method according to claim 1, wherein said production bacterial cell further comprises a payload to be packaged into said lytic phage particles or lytic phage-derived delivery vehicles.

3. The method according to claim 2, wherein said payload is a nucleic acid payload comprising a packaging site derived from said lytic bacteriophage.

4. The method according to claim 2, wherein said payload is to be delivered into targeted bacterial cells.

5. The method according to claim 2, wherein said payload comprises a sequence of interest.

6. The method according to claim 5, wherein said sequence of interest only generates an effect in said targeted bacterial cells.

7. The method according to claim 4, wherein said targeted bacterial cells are from a species or strain different from the production bacterial cell.

8. The method according to claim 5, wherein said sequence of interest encodes a CRISPR-Cas system.

9. The method according to claim 5, wherein said sequence of interest comprises a nucleic acid sequence encoding Cas protein.

10. The method according to claim 9, wherein said Cas protein is selected from the group consisting of Cas1, Cas1B, Cas2, Cas3, Cas4, Cas5, Cas6, Cas7, Cas8, Cas9, Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, and modified versions thereof.

11. The method according to claim 5, wherein said sequence of interest comprises a nucleic acid sequence encoding a guide RNA or sgRNA.

12. The method according to claim 5, wherein said sequence of interest encodes a base editing system.

13. The method according to claim 2, wherein said payload is devoid of antibiotic resistance marker.

14. The method according to claim 2, wherein said payload comprises a conditional origin of replication which is inactive in the targeted bacterial cells but is active in the production bacterial cell.

15. The method according to claim 2, wherein said payload comprises a bacterial origin of replication that is functional in the production bacterial cell.

16. The method according to claim 2, wherein said payload comprises an origin of replication which is inactive in the targeted bacterial cells.

17. The method according to claim 1, wherein said production bacterial cell is from the same bacterial strain as the bacterial strain from which said non-lytic bacteriophage comes and/or that said non-lytic bacteriophage targets.

18. The method according to claim 1, wherein said phage structural genes and phage DNA packaging genes of said lytic bacteriophage are comprised in at least one plasmid, chromosome and/or helper phage.

19. The method according to claim 1, wherein the production bacterial cell comprises the entire structural operon of the lytic bacteriophage.

* * * * *